United States Patent
Chabrier de Lassauniere et al.

(10) Patent No.: US 6,586,454 B2
(45) Date of Patent: *Jul. 1, 2003

(54) DERIVATIVES OF 2-(IMINOMETHYL) AMINO-PHENYL, THEIR PREPARATION, THEIR USE AS MEDICAMENTS AND THE PHARMACEUTICAL COMPOSITIONS CONTAINING THEM

(75) Inventors: Pierre Etienne Chabrier de Lassauniere, Paris (FR); Serge Auvin, Mauchamps (FR); Dennis Bigg, Gif-sur-Yvette (FR); Michel Auguet, Palaiseau (FR); Jeremiah Harnett, Gif-sur-Yvette (FR)

(73) Assignee: Societe de Conseils de Recherches et d'Applications Scientifiques (S.C.R.A.S.) (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/953,682

(22) Filed: Sep. 17, 2001

(65) Prior Publication Data

US 2002/0042511 A1 Apr. 11, 2002

Related U.S. Application Data

(60) Division of application No. 09/882,264, filed on Jun. 15, 2001, which is a division of application No. 09/456,205, filed on Dec. 7, 1999, now Pat. No. 6,335,445, which is a continuation-in-part of application No. 09/381,749, filed on Sep. 22, 1999, now Pat. No. 6,340,700.

(30) Foreign Application Priority Data

Mar. 24, 1997 (FR) .......................................... 97 03528
Jun. 20, 1997 (FR) .......................................... 97 07701

(51) Int. Cl.[7] ..................... A61K 31/425; A61K 31/35; A61K 31/335; C07D 277/62; C07D 277/20
(52) U.S. Cl. ........................ 514/365; 514/449; 514/456; 548/100; 548/146; 548/202
(58) Field of Search ............................... 548/100, 146, 548/202; 514/365, 449, 456

(56) References Cited

U.S. PATENT DOCUMENTS 3,652,645 A * 3/1972 Deitrich et al. ............. 544/358
6,335,445 B1 * 1/2002 Lassauniere et al. ........ 544/358
6,340,700 B1 * 1/2002 Lassunier et al. ........... 514/438

FOREIGN PATENT DOCUMENTS

| DE | 1912847 | * | 3/1972 |
| EP | 388809 | * | 9/1990 |
| JP | 51110586 | * | 9/1976 |
| WO | 9505363 | * | 2/1995 |

* cited by examiner

Primary Examiner—Richard L. Raymond
Assistant Examiner—Sudhaker B. Patel
(74) Attorney, Agent, or Firm—Muserlian, Lucas and Mercanti

(57) ABSTRACT

A compound of the formula XXV(H) wherein the substituents are defined as set forth in the specification which are useful intermediates for the production of derivatives of 2-(iminomethyl)-amino-phenyl having inhibitory activity on NO-synthase enzymes.

7 Claims, No Drawings

DERIVATIVES OF 2-(IMINOMETHYL) AMINO-PHENYL, THEIR PREPARATION, THEIR USE AS MEDICAMENTS AND THE PHARMACEUTICAL COMPOSITIONS CONTAINING THEM

PRIOR APPLICATIONS

This application is a division of U.S. patent application Ser. No. 09/882,264 filed Jun. 15, 2001 which is a division of U.S. patent application Ser. No 09/456,205 filed Dec. 7, 1999, now U.S. Pat. No. 6,335,445 which is a continuation-in-part of U.S. patent application Ser. No 09/381,749 filed Sep. 22, 1999, now U.S. Pat. No. 6,340,700 which is a 371 of PCT/FR98/00288 filed Feb. 16, 1998.

A subject of the present invention is new derivatives of 2-(iminomethyl)amino-phenyl which have an inhibitory activity on NO-synthase enzymes producing nitrogen monoxide NO and/or an activity which traps the reactive oxygen species (ROS). The invention relates to the derivatives corresponding to general formula (I) defined below, their preparation methods, the pharmaceutical preparations containing them and their use for therapeutic purposes, in particular their use as NO-synthase inhibitors and selective or non selective traps for reactive oxygen species.

Given the potential role of NO and the ROS's in physiopathology, the new derivatives described corresponding to general formula (I) may produce beneficial or favourable effects in the treatment of pathologies where these chemical species are involved. In particular:

- cardio-vascular and cerebro-vascular disorders including for example artherosclerosis, migraine, arterial hypertension, septic shock, ischemic or hemorragic cardiac or cerebral infarctions, notably those related with complications of coronary artery bypass grafting, ischemias and thromboses.
- disorders of the central or peripheral nervous system such as for example neurodegenerative diseases where there can in particular be mentioned cerebral infarctions, sub-arachnoid haemorrhaging, ageing, senile dementias including Alzheimer's disease, Huntington's chorea, Parkinson's disease, Creutzfeld Jacob disease and prion diseases, amyotrophic lateral sclerosis but also pain, cerebral and bone marrow traumas, addiction to opiates, alcohol and addictive substances, erective and reproductive disorders, cognitive disorders, encephalopathies, encephalopathies of viral or toxic origin.
- disorders of the skeletal muscle and neuromuscular joints (myopathy, myosis) as well as cutaneous diseases.
- proliferative and inflammatory diseases such as for example artherosclerosis, pulmonary hypertension, respiratory distress, glomerulonephritis, portal hypertension, psoriasis, arthrosis and rheumatoid arthritis, fibroses, amyloidoses, inflammations of the gastro-intestinal system (colitis, Crohn's disease) or of the pulmonary system and airways (asthma, sinusitis, rhinitis).
- organ transplants.
- auto-immune and viral diseases such as for example lupus, AIDS, parasitic and viral infections, diabetes, multiple sclerosis.
- cancer.
- neurological diseases associated with intoxications (Cadmium poisoning, inhalation of n-hexane, pesticides, herbicides), associated with treatments (radiotherapy) or disorders of genetic origin (Wilson's disease).
- all the pathologies characterized by an excessive production or dysfunction of NO and/or ROS's.

In all these pathologies, there is experimental evidence demonstrating the involvement of NO or ROS's (*J. Med. Chem.* (1995) 38, 4343–4362; *Free Radic. Biol. Med.* (1996) 20, 675–705; *The Neuroscientist* (1997) 3, 327–333).

Furthermore, NO Synthase inhibitors, their use and more recently the combination of these inhibitors with products having antioxidant or antiradicular properties have already been described in previous Patents (respectively U.S. Pat. Nos. 5,081,148; 5,360,925 and an unpublished Patent Application).

A subject of the present invention is the derivatives of 2-(iminomethyl)amino-phenyl, their preparation and their therapeutic use.

The compounds of the invention correspond to general formula (I):

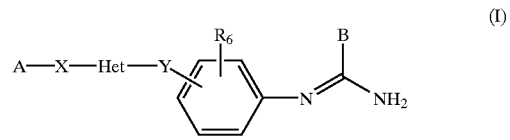

in which:

A represents a hydrogen atom or:

either a

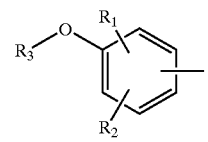

radical in which $R_1$ and $R_2$ represent, independently, a hydrogen atom, a halogen, the OH group, a linear or branched alkyl or alkoxy radical having from 1 to 6 carbon atoms, $R_3$ represents a hydrogen atom, a linear or branched alkyl radical having from 1 to 6 carbon atoms or a —$COR_4$ radical, $R_4$ represents a linear or branched alkyl radical having from 1 to 6 carbon atoms, or a

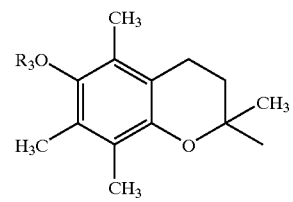

radical in which $R_3$ represents a hydrogen atom, a linear or branched alkyl radical having from 1 to 6 carbon atoms or a —$COR_4$ radical, $R_4$ represents a linear or branched alkyl radical having from 1 to 6 carbon atoms, or a

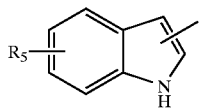

radical in which R$_5$ represents a hydrogen atom, the OH group or a linear or branched alkyl or alkoxy radical having from 1 to 6 carbon atoms;

B represents a linear or branched alkyl radical having from 1 to 6 carbon atoms, carbocyclic or heterocyclic aryl with 5 or 6 members containing from 1 to 4 heteroatoms chosen from O, S, N and in particular the thiophene, furan, pyrrole or thiazole radicals, the aryl radical being optionally substituted by one or more groups chosen from the linear or branched alkyl, alkenyl or alkoxy radicals having from 1 to 6 carbon atoms;

X represents —Z$_1$—, —Z$_1$—CO—, —CH=, —CH=CH—CO—, —Z$_1$—NR$_3$—CO—Z'$_1$—, —CO—NR$_3$—Z'$_1$—, —Z$_1$—NR$_3$—CS—, —Z$_1$—NR$_3$—SO$_2$— or a single bond;

Het does not exist or represents a heterocycle containing from 1 to 5 heteroatoms chosen from O, N, S which can be substitued by one or more substituents X'—OR$_3$, X'—NR$_3$, X'—S—R$_3$ and such as for example:
oxetane, pyrrole, pyrrolidine, furan, tetrahydrofuran, thiophene, tetrahydrothiophene, sulpholane, imidazole, imidazoline, dihydroimidazole-2-one, dihydroimidazole-2-thione, oxazole, isoxazole, oxazoline, isoxazoline, oxazolidine, oxazolidinone, thiazole, thiazoline, thiazolidine, thiazolidinone, hydantoine, 1,2,4-triazole, 1,3,4-oxadiazole, 1,3,4-thiadiazole, 1,1-dioxyde-1,2,5-thiadiazolidine, 1,2,4-triazole-3-one, tetrazole, tetrahydropyridine, piperazine, homopiperazine, 2-methylpiperazine, 2,5-dimethyl-piperazine or 4-aminopiperidine;

Y represents a radical chosen from the —Z$_2$—Q—, —Z$_2$—CO—, —Z$_2$—NH—CO—, —Z$_2$—CH$_2$—NR$_3$—CO—, —NR$_3$—Z$_2$—Q—, —NR$_3$—CO—Z$_2$—Q—, —NR$_3$—NH—CO—Z$_2$—, —NH—NH—Z$_2$—, —NR$_3$—O—Z$_2$—, —NR$_3$—SO$_2$—NR$_3$—Z$_2$—, —O—Z$_2$—Q—, —O—CO—Z$_2$—Q— or —S—Z$_2$—Q— radicals,
in which Q represents a single bond, O—Z$_3$, R$_3$—N—Z$_3$ or S—Z$_3$;

Z$_1$, Z'$_1$, Z$_2$ and Z$_3$ represent independently a single bond or a linear or branched alkylene radical having from 1 to 6 carbon atoms; preferably, Z$_1$, Z'$_1$, Z$_2$ and Z$_3$ represent —(CH$_2$)$_m$—, m being an integer comprised between 0 and 6;

R represents a hydrogen atom or an OH group;

it being understood that when Het is absent, then A is not a hydrogen atom and that when A is hydrogen then Het does not represent a piperidine, pyrrolidine or morpholine radical;

or are salts of the latter.

The compounds of general formula (I) containing an asymmetrical centre are of isomeric form. The racemic and enantiomeric forms of these compounds also form part of this invention.

The compounds of the invention can exist in the state of bases or of addition salts in particular with organic or inorganic acids or with bases, and in particular in the state of hydrates, hydrochlorides, dihydrochlorides, fumarates or hemifumarates.

By linear or branched alkyl having from 1 to 6 carbon atoms is meant in particular the methyl, ethyl, propyl, isopropyl, butyl, isobutyl, sec-butyl and tert-butyl, pentyl, neopentyl, isopentyl, hexyl, isohexyl radicals. By linear or branched alkoxy having from 1 to 6 carbon atoms is meant radicals the alkyl radical of which has the meaning indicated previously. By halogen is meant fluorine, chlorine, bromine or iodine atoms.

Preferably, the compounds of general formula (I) are such that they include at least one of the following features:

A represents a

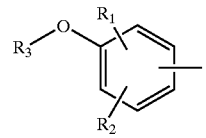

radical in which R$_1$ and R$_2$ represent, independently, a branched alkyl radical having from 3 to 6 carbon atoms,
R$_3$ represents a hydrogen atom, a linear or branched alkyl radical having from 1 to 6 carbon atoms or a —COR$_4$ radical,
R$_4$ represents a linear or branched alkyl radical having from 1 to 6 carbon atoms, or A represents a

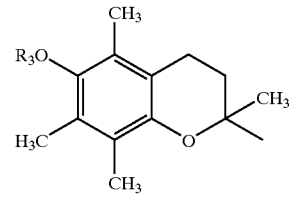

radical in which R$_3$ represents a hydrogen atom or a linear or branched alkyl radical having from 1 to 6 carbon atoms;

B represents a thiophene or phenyl radical;

X represents —Z$_1$—CO— or —CO—NR$_3$—Z'$_1$—;

Het is absent or represents a piperazine or tetrahydropyridinyl radical;

Y represents —Z$_2$—Q— or —NR$_3$—Z$_2$—Q—;

R$_6$ represents a hydrogen atom.

A particular subject of the invention is the following compounds of general formula (I), described in the examples (in the form of salts in certain cases):

3,5-bis-(1,1-dimethylethyl)-4-hydroxy-N-{4-[(2-thienyl(imino)methyl)amino]phenyl}-benzamide;
3,5-bis-(1,1-dimethylethyl)-4-hydroxy-N-{4-[[(2-thienyl(imino)methyl)amino]phenyl]methyl}-benzamide;
4-acetoxy-3,5-dimethoxy-N-{4-[[(2-thienyl(imino)methyl)amino]phenyl]methyl}-benzamide;
3,5-dimethoxy-4-hydroxy-N-{4-[[(2-thienyl(imino)methyl)amino]phenyl]methyl}-benzamide;
3,5-bis-(1,1-dimethylethyl)-4-hydroxy-N-{4-[2-[(2-thienyl-(imino)methyl)amino]phenyl]ethyl}-benzamide;
4-acetoxy-3,5-dimethoxy-N-{4-[2-[(2-thienyl-(imino)methyl)-amino]phenyl]ethyl}-benzamide;
3,5-dimethoxy-4-hydroxy-N-{4-[2-[(2-thienyl-(imino)methyl)-amino]phenyl]ethyl}-benzamide;
3,4,5-trihydroxy-N-{4-[2-[(2-thienyl(imino)methyl)-amino]phenyl]ethyl}-benzamide;

N-{4-[4-[3,5-bis-(1,1-dimethylethyl)-4-hydroxybenzoyl]-1-piperazinyl]-phenyl}-2-thiophenecarboximidamide;

N-{4-[4-[3,5-bis-(1,1-dimethylethyl)-4-hydroxybenzyl]-1-piperazinyl]phenyl}-2-thiophenecarboximidamide;

N-{4-[4-[3,5-dimethoxy-4-hydroxybenzoyl]-1-piperazinyl]-phenyl}-2-thiophenecarboximidamide;

3,4-dihydro-6-hydroxy-2,5,7,8-tetramethyl-N-{4-[(2-thienyl(imino)methyl)amino]phenyl}-2H-1-benzopyran-2-carboxamide;

N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

N-{4-[4-[(5-methoxy-1H-indol-3-yl)methylcarbonyl]-1-piperazinyl)phenyl]-2-thiophenecarboximidamide;

N-[4-[4-[{3-[3,5-bis-(1,1-dimethylethyl)-4-hydroxyphenyl]-1-oxo-2-propenyl}-1-piperazinyl]-phenyl]]-2-thiophenecarboximidamide;

3,5-bis-(1,1-dimethylethyl)-4-hydroxy-N-{3-[[(2-thienyl-(imino)methyl)amino]phenyl]methyl}-benzamide;

N-[3,5-bis-(1,1-dimethylethyl)-4-hydroxyphenyl]-N'-{{4-[(2-thienyl(imino)methyl)amino]phenyl}methyl}-urea;

N-[5-[{3-(3,5-bis-(1,1-dimethylethyl)-4-hydroxyphenyl)-1-oxo-2-propenyl}amino]-2-hydroxyphenyl]-2-thiophenecarboximidamide;

N-[3-[{3-(3,5-bis-(1,1-dimethylethyl)-4-hydroxyphenyl)-1-oxo-2-propenyl}-amino]-4-hydroxyphenyl]-2-thiophenecarboximidamide;

N-{4-[4-[3,4,5-trihydroxybenzoyl]-1-piperazinyl]phenyl}-2-thiophenecarboximidamide;

N-[3,5-bis-(1,1-dimethylethyl)-4-hydroxyphenyl]-N'-{{4-[(2-thienyl(imino)methyl)amino]phenyl}carbonylamino}-urea;

N-[3,5-bis-(1,1-dimethylethyl)-4-hydroxyphenyl]-N'-{{4-[(2-thienyl(imino)methyl)amino]phenyl}methyl}-thiourea;

N-[3,5-bis-(1,1-dimethylethyl)-4-hydroxyphenyl]-N'-{2-{4-[(2-thienyl(imino)methyl)amino]phenyl}ethyl}-urea;

N-(4-{4-[(3,4-dihydro-6-methoxy-2,5,7,8-tetramethyl-2H-1-benzopyran-2-yl)carbonyl]-1-piperazinyl}phenyl)-2-thiophenecarboximidamide;

N-[4-{4-[(3,4-dihydro-6-hydroxy-2,5,7,8-tetramethyl-2H-1-benzopyran-2-yl)carbonyl]-1H-1,4-diazepin-1-yl}phenyl]-2-thiophenecarboximidamide;

(R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

(S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

3,5-bis-(1,1-dimethylethyl)-4-hydroxy-N-{2-[3-[(2-thienyl(imino)methyl)amino]phenyl]ethyl}-benzamide;

N-{4-(4-[2-(3,5-bis-(1,1-dimethylethyl)-4-hydroxyphenyl)-1-oxo-ethyl]-1-piperazinyl)phenyl}-2-thiophenecarboxamide;

2-{4-[(2-thienyl(imino)methyl)amino]phenyl}ethyl 3,5-bis-(1,1-dimethylethyl)-4-hydroxy-benzoate;

2-{3-[(2-thienyl(imino)methyl)amino]phenyl}ethyl 3,5-bis-(1,1-dimethylethyl)-4-hydroxy-benzoate;

2-{2-[(2-thienyl(imino)methyl)amino]phenyl}ethyl 3,5-bis-(1,1-dimethylethyl)-4-hydroxy-benzoate;

N-[4-(1H-imidazol-1-yl)phenyl]-2-thiophenecarboximidamide.

N-[4-(3-thiazolidinylmethyl)phenyl]-2-thiophenecarboximidamide;

N-[4-(1,2,3,6-tetrahydropyridin-1-yl)phenyl]-2-thiophenecarboximidamide;

N-[4-(1H-imidazol-1-yl methyl)phenyl]-2-thiophenecarboximidamide;

N-[4-{2-(3-thiazolidinyl)ethyl}phenyl]-2-thiophenecarboximidamide;

N-{4-[2-(1H-imidazol-1-yl)ethyl]phenyl}-2-thiophenecarboximidamide;

N-{4-[2-(1,2,3,6-tetrahydropyridin-1-yl)ethyl]phenyl}-2-thiophenecarboximidamide;

N-[4-(3-thiazolidinylcarbonylmethyl)phenyl]-2-thiophenecarboximidamide;

N-(4-{[2-thiazolidinyl]carbonylaminomethyl}phenyl)-2-thiophenecarboximidamide;

N-(3,5-di-t-butyl-4-hydroxyphenyl)-5-[4-{imino(2-thienyl)-methylamino}phenyl]-2-furan carboxamide;

3-(3,5-di-t-butyl-4-hydroxyphenyl)-1-[4-{imino(2-thienyl)-methylamino}phenyl]-2,5-imidazolidinedione;

2-(3,5-di-t-butyl-4-hydroxyphenyl)-3-[4-{imino(2-thienyl)-methylamino}phenyl]-4-thiazolidinone;

5-[(3,5-di-t-butyl-4-hydroxyphenyl)methylene]-1-methyl-3-[4-{imino(2-thienyl)methylamino}phenyl]-2,4-imidazolidinedione;

2-(S)-4-(S)-N-[4-hydroxy-3,5-bis-(1,1-dimethylethyl)-phenyl]-4-{4-[(imino(2-thienyl)methyl)amino]phenoxy}-prolinamide;

5,6-dihydro-N-{4-[(imino(2-thienyl)methyl)amino]phenyl}-1-(2H)-pyridinecarboxamide;

N-[4-hydroxy-3,5-bis-(1,1-dimethylethyl)phenyl]-2-(R.S)-{4-[(imino(2-thienyl)methyl)arino]phenyl}-4-(R)-thiazolidine carboxamide;

N-[3,5-bis(1,1-dimethylethyl)-4-hydroxyphenyl]-2-{4-[(imino(2-thienyl)methyl)amino]phenyl}-4-thiazolecarboxamide;

N-[3,5-bis(1,1-dimethylethyl)-4-hydroxyphenyl]-4-(S)-{4-[(imino(2-thienyl)methyl)amino]phenoxy}-pyrrolidine-2-(R)-carboxamide;

methyl 1-[(3,4-dihydro-6-hydroxy-2,5,7,8-tetramethyl-2-H-[1]-benzopyran-2-yl)carbonyl]-4-(S)-{4-[(imino(2-thienyl)methyl)amino]-phenoxy}-pyrrolidine-2-(S)-carboxylate;

1-[(3,4-dihydro-6-hydroxy-2,5,7,8-tetramethyl-2H-[1]-benzopyran-2-yl)carbonyl]-3-(S)-{4-[(imino(2-thienyl)methyl)amino]phenoxy}-pyrrolidine;

3-{[(3,4-dihydro-6-hydroxy-2,5,7,8-tetramethyl-2H-[1]-benzopyran-2-yl)-carbonyl]amino}-1-{4-[(imino(2-thienyl)methyl)amino]phenyl}pyrrolidine;

4-[3,5-bis-(1,1-dimethylethyl)-4-hydroxyphenyl]-N-{4-[(imino(2-thienyl)methyl)amino]benzoyl}-N-methyl-1H-imidazole-2-methanamine;

N-[3,5-bis-(1,1-dimethylethyl)-4-hydroxyphenyl]-1-{4-[(imino(2-thienyl)methyl)amino]phenyl}-1H-pyrrole-2-carboxamide;

1-[3,5-bis(1,1-dimethylethyl)-4-hydroxyphenyl]-3-{[4-[(imino(2-thienyl)methyl)amino]phenyl]carbonyl}-2-imidazolidinone;

3-[3,5-bis(1,1-dimethylethyl)-4-hydroxyphenyl]-4,5-dihydro-N-{4-[(imino(2-thienyl)methyl)amino]phenyl}-5-isoxazoleacetamide;

4-[3,5-bis(1,1-dimethylethyl)-4-hydroxyphenyl-N-{4-[(imino(2-thienyl)methyl)amino]phenyl}-N-methyl-2-thiazolemethanamine;

4-[3,5-bis(1,1-dimethylethyl)-4-hydroxyphenyl]-N-{4-[(imino(2-thienyl)methyl)amino]phenyl}-N-methyl-1H-imidazole-2-methanamine;

3-[3,5-bis(1,1-dimethylethyl)-4-hydroxyphenyl]-4,5-dihydro-5-{2-{4-[(imino(2-thienyl)methyl)amino]phenoxy}ethyl}isoxazole;

1-{[3,5-bis(1,1-dimethylethyl)-4-hydroxyphenyl]amino}-carbonyl}-3-{4-[(imino(2-thienyl)methyl)amino]phenoxy}azetidine;

1-(2-hydroxy-5-methoxybenzoyl)-3-{4-[(imino(2-thienyl)methyl)amino]phenoxy}azetidine;

1-[(3,4-dihydro-6-hydroxy-2,5,7,8-tetramethyl-2H-[1]-benzopyran-2-yl)carbonyl]-4-[4-[(imino(2-thienyl)methyl)amino]phenoxy}-piperidine;

1-[(3,4-dihydro-6-hydroxy-2,5,7,8-tetramethyl-2H-[1]-benzopyran-2-yl)carbonyl]-3-{4-[(imino(2-thienyl)methyl)amino]-phenoxy}azetidine;

as well as their salts, in particular their hydrochlorides, dihydrochlorides, fumarates or hemi-fumarates.

In a preferential manner, the compounds according to the invention will be one of the following compounds:

3,5-bis-(1,1-dimethylethyl)-4-hydroxy-N-{4-[2-[(2-thienyl-(imino)methyl)amino]phenyl]ethyl}-benzamide;

3,4,5-trihydroxy-N-{4-[2-[(2-thienyl(imino)methyl)-amino]phenyl]ethyl}-benzamide;

N-{4-[4-[3,5-bis-(1,1-dimethylethyl)-4-hydroxybenzoyl]-1-piperazinyl]phenyl}-2-thiophenecarboximidamide;

N-{4-[4-[3,5-bis-(1,1-dimethylethyl)-4-hydroxybenzyl]-1-piperazinyl]phenyl}-2-thiophenecarboximidamide;

3,4-dihydro-6-hydroxy-2,5,7,8-tetramethyl-N-{4-[(2-thienyl(imino)methyl)amino]phenyl}-2H-1-benzopyran-2-carboxamide;

N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

N-{4-[4-[(5 methoxy-1H-indol-3-yl)methylcarbonyl]-1-piperazinyl]phenyl}-2-thiophenecarboximidamide;

3,5-bis-(1,1-dimethylethyl)-4-hydroxy-N-{3-[[(2-thienyl-(imino)methyl)amino]phenyl]methyl}-benzamide;

N-[3,5-bis-(1,1-dimethylethyl)-4-hydroxyphenyl]-N'-{{4-[(2-thienyl(imino)methyl)amino]phenyl}methyl}-urea;

N-[5-[{3-(3,5-bis-(1,1-dimethylethyl)-4-hydroxyphenyl)-1-oxo-2-propenyl}-amino]-2-hydroxyphenyl]-2-thiophenecarboximidamide;

N-[3-[{3-(3,5-bis-(1,1-dimethylethyl)-4-hydroxyphenyl)-1-oxo-2-propenyl}-amino]-4-hydroxyphenyl]-2-thiophenecarboximidamide;

N-{4-[4-[3,4,5-trihydroxybenzoyl]-1-piperazinyl]phenyl}-2-thiophenecarboximidamide;

N-[3,5-bis-(1,1-dimethylethyl)-4-hydroxyphenyl]-N'-{{4-[(2-thienyl(imino)methyl)amino]phenyl}carbonylamino}-urea;

or a salt of one of the latter, in particular a hydrochloride, dihydrochloride, fumarate or hemi-fumarate of one of the latter.

Other preferred compounds for the invention will be the following compounds:

4-acetoxy-3,5-dimethoxy-N-{4-[2-[(2-thienyl-(imino)methyl)-amino]phenyl]ethyl}-benzamide;

3,5-dimethoxy-4-hydroxy-N-{4-[2-[(2-thienyl-(imino)methyl)-amino]phenyl]ethyl}-benzamide;

or a salt of one of the latter, in particular a hydrochloride, dihydrochloride, fumarate or hemi-fumarate of one of the latter.

Particularly preferred compounds of the invention will be as follows:

N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

N-{4-[4-[(5 methoxy-1H-indol-3-yl)methylcarbonyl]-1-piperazinyl]phenyl}-2-thiophenecarboximidamide;

(R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

(S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

N-[4-(1,2,3,6-tetrahydropyridin-1-yl)phenyl]-2-thiophenecarboximidamide;

or a salt of one of the latter, in particular a hydrochloride, dihydrochloride, fumarate or hemi-fumarate of one of the latter.

More particularly preferred compounds of the invention will be as follows:

N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

(R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

(S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide;

or a salt of one of the latter, in particular a hydrochloride, dihydrochloride, fumarate or hemi-fumarate of one of the latter.

The invention also offers useful new synthesis intermediates of general formula (Σ)

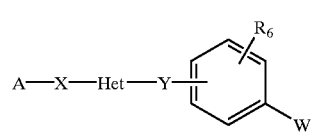

in which:

A, X, Het, Y and $R_6$ have the same meaning as in general formula (I); and

W represents an amino or nitro radical;

with the exception however of 3,5-bis-(1,1-dimethylethyl)-4-hydroxy-N-(4-nitrophenyl)-benzamide.

The invention further comprises a process for preparing a compound of general formula, (I) as defined earlier, characterized in that a compound of general formula (Σ)

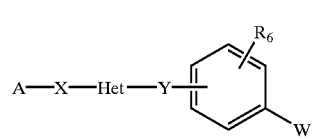

in which:

A, X, Het, Y and $R_6$ have the same meaning as in general formula (I); and

W represents an amino radical;

is reacted in a lower alcohol, such as methanol, ethanol, isopropyl alcohol or t-butanol, preferably in isopropyl alcohol, at a temperature between 20 and 90° C., for example at 50° C., and for one to 48 hours, preferably for 15 to 24 hours, optionally in the presence of DMF, with a compound of general formula (IV)

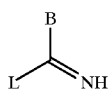

said compound of general formula (IV) being optionally salified by a mineral acid G, B having the same meaning as in general formula (I) and L representing a leaving group and in particular an alkoxy, thioalkyl, sulphonic acid, halide, aryl alcohol or tosyl radical (other leaving groups well known to a person skilled in the art which can optionally be used for the invention are described in the following work: *Advanced Organic Chemistry*, J. March, 3rd Edition (1985), Mc Graw-Hill, p. 315). Preferably, G represents HCl, HBr or HI.

According to a particular variant of the invention, the compounds of the invention correspond to general formula $(I)_L$:

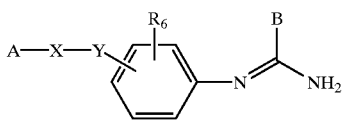

in which:

A represents:
either a

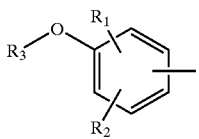

radical in which $R_1$ and $R_2$ represent, independently, a hydrogen atom, a halogen, the OH group, a linear or branched alkyl or alkoxy radical having from 1 to 6 carbon atoms, $R_3$ represents a hydrogen atom, a linear or branched alkyl radical having from 1 to 6 carbon atoms or a —$COR_4$ radical, $R_4$ represents a linear or branched alkyl radical having from 1 to 6 carbon atoms, or a

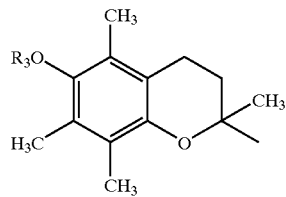

radical in which $R_3$ has the meaning indicated above or a

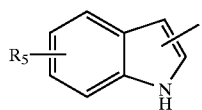

radical in which $R_5$ represents a hydrogen atom, the OH group or a linear or branched alkyl or alkoxy radical having from 1 to 6 carbon atoms;

B represents a linear or branched alkyl radical having from 1 to 6 carbon atoms, carbocyclic or heterocyclic aryl with 5 or 6 members containing from 1 to 4 heteroatoms chosen from O, S, N and in particular the thiophene, furan, pyrrole or thiazole radicals, the aryl radical being optionally substituted by one or more groups chosen from the linear or branched alkyl, alkenyl or alkoxy radicals having from 1 to 6 carbon atoms;

X represents —$Z_1$—, —$Z_1$—CO—, —CH=CH—CO—, —$Z_1$—$NR_3$—CO—, —$Z_1$—$NR_3$—CS—, —$Z_1$—$NR_3$—$SO_2$— or a single bond;

Y represents a radical chosen from the —$Z_2$—Q, piperazine, homopiperazine, 2-methylpiperazine, 2,5-dimethyl-piperazine, 4-aminopiperidine, —$NR_3$—$Z_2$—Q—, —$NR_3$—CO—$Z_2$—Q—, —$NR_3$—NH—CO—$Z_2$—, —NH—NH—$Z_2$—, —$NR_3$—O—$Z_2$—, —$NR_3$—$SO_2$—$NR_3$—$Z_2$—, —O—$Z_2$—Q—, —O—CO—$Z_2$—Q— or —S—$Z_2$— radicals, in which Q represents a single bond, O—$Z_3$, $R_3$—N—$Z_3$ or S—$Z_3$;

$Z_1$, $Z_2$ and $Z_3$ represent independently a single bond or a linear or branched alkylene radical having from 1 to 6 carbon atoms; preferably, $Z_1$, $Z_2$ and $Z_3$ represent —$(CH_2)_m$—,m being an integer comprised between 0 and 6;

$R_6$ represents a hydrogen atom or an OH group;

or are salts of the latter.

There will generally be preferred the compounds of general formula $(I)_L$ for which:

X represents a linear or branched alkylene radical having from 1 to 6 carbon atoms and Y represents a piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$— or —$NR_3$—O—$Z_2$— radical; or X represents —$Z_1$—CO— or —CH=CH—CO— and Y represents a piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$—, —$NR_3$—O—$Z_2$—, —O—$Z_2$—Q— radical or —$NR_3$—CO—Q'— radical with Q'=$R_3$—N—$Z_3$; or X represents —$Z_1$—$NR_3$—CO— and Y represents —$Z_2$—Q—, —NH—$Z_2$—Q—, —NH—CO—$Z_2$'Q"— with Q"=O—$Z_3$—, $R_3$—N—$Z_3$— or S—$Z_3$—, or Y represents —$NR_3$—$SO_2$—$NR_3$—$Z_2$— or —O—$Z_2$—Q—; or X represents —$Z_1$—NH—CO— and Y represents a piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$— or —$NR_3$—O—$Z_2$— radical; or X represents —$Z_1$—$NR_3$—$SO_2$— and Y represents —$Z_2$—Q"— with Q"=O—$Z_3$—, $R_3$—N—$Z_3$— or S—$Z_3$—, or Y represents —$NR_3$—$Z_2$—Q—; or X represents —$Z_1$— and Y represents —O—CO—$Z_2$—Q—; or X represents —$Z_1$—$NR_3$—CS— and Y represents —NH—$Z_2$—Q—, or a piperazine, homopiperazine, 2-methylpiperazine, 2,5-dimethyl-piperazine, 4-aminopiperidine, —$NR_3$—$Z_2$—Q—, —NH—NH—$Z_2$— or —$NR_3$—O—$Z_2$— radical; or X represents a bond and Y represents —O—$Z_2$—NH—, —S—$Z_2$—NH—.

Moreover, the X—Y group will preferably be chosen from the following radicals:

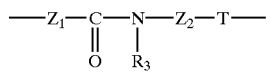

in which T represents a single bond, the —$NR_3$— radical or the —CO—$NR_3$— radical, or

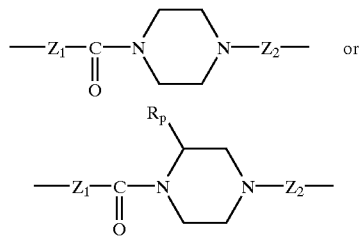

in which $R_p$ represents a hydrogen atom or a methyl radical, or

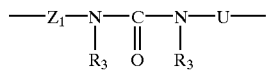

in which U represents a —$Z_2$, —$NR_3$—CO—, —CO—$Z_2$—O—, —CO—, —$NR_3$— radical or an oxygen atom,

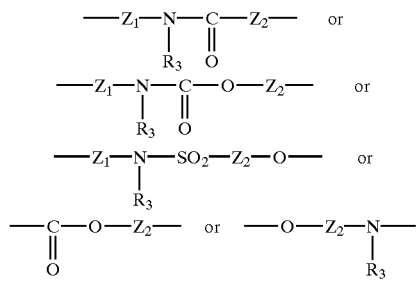

the $Z_1$, $Z_2$ and $R_3$ radicals having the meaning indicated above.

Finally, there will be particularly preferred for the invention the compounds of general formula $(I)_L$ presenting the following characteristics:

either:

A represents:

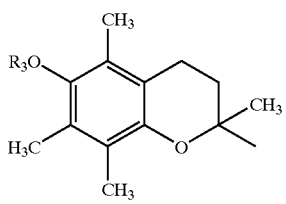

or

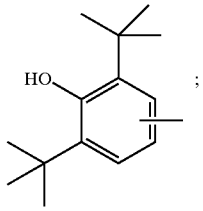

X represents —CO— or —NH—CO—;

and Y represents an —NH—$Z_2$—Q— or piperazine radical, Q representing a single bond or an O—$Z_3$, $R_3$—N—$Z_3$ or S—$Z_3$ radical, and $Z_2$ and $Z_3$ representing independently a bond or a linear or branched alkylene radical having from 1 to 6 carbon atoms and $R_3$ represents a hydrogen atom or a linear or branched alkyl radical having from 1 to 6 carbon atoms.

or: $R_6$ is an OH group.

The invention also offers, as new industrial products, the synthetic intermediates of the products of general formula $(I)_L$, namely the products of general formula $(II)_L$:

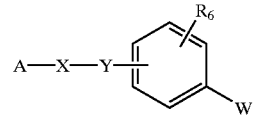

$(II)_L$ in which:

W represents an amino or nitro radical,

A represents:

either a

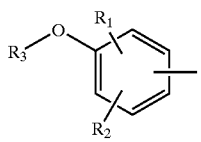

radical in which $R_1$ and $R_2$ represent, independently, a hydrogen atom, a halogen, the OH group, a linear or branched alkyl or alkoxy radical having from 1 to 6 carbon atoms, $R_3$ represents a hydrogen atom, a linear or branched alkyl radical having from 1 to 6 carbon atoms or a —$COR_4$ radical, $R_4$ representing a linear or branched alkyl radical having from 1 to 6 carbon atoms, or a

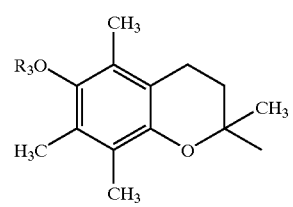

radical in which $R_3$ has the meaning indicated above or a

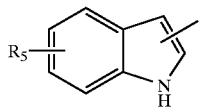

radical in which R₅ represents a hydrogen atom, the OH group or a linear or branched alkyl or alkoxy radical having from 1 to 6 carbon atoms;

X represents —Z₁—, —Z₁—CO—, —CH=CH—CO—, —Z₁—NR₃—CO—, —Z₁—NR₃—CS—, —Z₁—NR₃—SO₂— or a single bond;

Y represents a radical chosen from the —Z₂—Q, piperazine, homopiperazine, 2-methyl-piperazine, 2,5-dimethylpiperazine, 4-aminopiperidine, —NR₃—Z₂—Q—, —NR₃—CO—Z₂—Q—, —NR₃—NH—CO—Z₂—, —NH—NH—Z₂—, —NR₃—O—Z₂—, —NR₃-SO₂—NR₃—Z₂—, —O—Z₂—Q—, —O—CO—Z₂—Q— or —S—Z₂—Q— radicals, in which Q represents a single bond, O—Z₃, R₃—N—Z₃ or S—Z₃;

Z₁, Z₂ and Z₃ represent independently a single bond or a linear or branched alkylene radical having from 1 to 6 carbon atoms; preferably, Z₁, Z₂ and Z₃ represent —(CH₂)ₘ—, m being an integer comprised between 0 and 6;

R₆ represents a hydrogen atom or an OH group;

with the exception however of 3,5-bis-(1,1-dimethylethyl)-4-hydroxy-N-(4-nitrophenyl)-benzamide;

or the salts of the latter.

Moreover, the invention offers in particular, as new industrial products, the following compounds, which are synthetic intermediates of products of general formula (I):

3,5-bis-(1,1-dimethylethyl)-4-hydroxy-N-(4-aminophenyl)-benzamide;
3,5-bis-(1,1-dimethylethyl)-4-hydroxy-N-[(4-nitrophenyl)methyl]-benzamide;
3,5-bis-(1,1-dimethylethyl)-4-hydroxy-N-[(4-aminophenyl)methyl]-benzamide;
4-acetoxy-3,5-dimethoxy-N-[(4-nitrophenyl)methyl]-benzamide;
4-acetoxy-3,5-dimethoxy-N-[(4-aminophenyl)methyl]-benzamide;
3,5-bis-(1,1-dimethylethyl)-4-hydroxy-N-[2-(4-nitrophenyl)ethyl]-benzamide;
3,5-bis-(1,1-dimethylethyl)-4-hydroxy-N-[2-(4-aminophenyl)ethyl]-benzamide;
4-acetoxy-3,5-dimethoxy-N-[2-(4-nitrophenyl)ethyl]-benzamide;
4-acetoxy-3,5-dimethoxy-N-[2-(4-aminophenyl)ethyl]-benzamide;
3,4,5-trihydroxy-N-[2-(4-nitrophenyl)ethyl]-benzamide;
3,4,5-trihydroxy-N-[2-(4-aminophenyl)ethyl]-benzamide;
2,6-bis-(1,1-dimethylethyl)-4-{[4-(4-nitrophenyl)-1-piperazinyl]-carbonyl}-phenol;
2,6-bis-(1,1-dimethylethyl)-4-{[4-(4-aminophenyl)-1-piperazinyl]-carbonyl}-phenol;
2,6-bis-(1,1-dimethylethyl)-4-{[4-(4-nitrophenyl)-1-piperazinyl]-methyl}-phenol;
2,6-bis-(1,1-dimethylethyl)-4-{[4-(4-aminophenyl)-1-piperazinyl]-methyl}-phenol;
2,6-dimethoxy-4-{[4-(4-nitrophenyl)-1-piperazinyl]carbonyl}-phenol;
2,6-dimethoxy-4-{[4-(4-aminophenyl)-1-piperazinyl]carbonyl}-phenol;
3,4-dihydro-6-hydroxy-2,5,7,8-tetramethyl-N-(4-nitrophenyl)-2H-1-benzopyran-2-carboxamide;
3,4-dihydro-6-hydroxy-2,5,7,8-tetramethyl-N-(4-aminophenyl)-2H-1-benzopyran-2-carboxamide;
3,4-dihydro-2,5,7,8-tetramethyl-2-{4-[(4-nitrophenyl)-1-piperazinyl]-carbonyl}-2H-1-benzopyran-6-ol;
3,4-dihydro-2,5,7,8-tetramethyl-2-{4-[(4-aminophenyl)-1-piperazinyl]-carbonyl}-2H-1-benzopyran-6-ol;
1-[(5 methoxy-1H-indol-3-yl)methylcarbonyl]-4-(4-nitrophenyl)-piperazine;
1-[(5 methoxy-1H-indol-3-yl)methylcarbonyl]-4-(4-aminophenyl)-piperazine;
2,6-bis-(1,1-dimethylethyl)-4-{3-[4-(4-nitrophenyl)-1-piperazinyl]-3-oxo-2-propenyl}-phenol;
2,6-bis-(1,1-dimethylethyl)-4-{3-[4-(4-aminophenyl)-1-piperazinyl]-3-oxo-2-propenyl}-phenol;
3,5-bis-(1,1-dimethylethyl)-4-hydroxy-N-[(3-nitrophenyl)methyl]-benzamide;
3,5-bis-(1,1-dimethylethyl)-4-hydroxy-N-[(3-aminophenyl)methyl]-benzamide;
N-[3,5-bis-(1,1-dimethylethyl)-4-hydroxyphenyl]-N'-[(4-nitrophenyl)methyl]-urea;
N-[(4-aminophenyl)methyl]-N'-[3,5-bis-(1,1-dimethylethyl)-4-hydroxyphenyl]-urea;
3-[(3,5-bis-(1,1-dimethylethyl)-4-hydroxyphenyl]-N-(4-hydroxy-3-nitrophenyl)-2-propenamide;
3-[(3,5-bis-(1,1-dimethylethyl)-4-hydroxyphenyl]-N-(4-hydroxy-3-aninophenyl)-2-propenamide;
3-[(3,5-bis-(1,1-dimethylethyl)-4-hydroxyphenyl]-N-(2-hydroxy-5-nitrophenyl)-2-propenamide;
3-[(3,5-bis-(1,1-dimethylethyl)-4-hydroxyphenyl]-N-(2-hydroxy-5-aminophenyl)-2-propenamide;
5-{[4-(4-nitrophenyl)-1-piperazinyl]carbonyl}-benzene-1,2,3-triol;
5-{[4-(4-aminophenyl)-1-piperazinyl]carbonyl}-benzene-1,2,3-triol;
N-[3,5-bis-(1,1-dimethylethyl)-4-hydroxyphenyl]-N'-[(4-nitrophenyl)-carbonylamino]-urea;
N-[(4-aminophenyl)carbonylamino]-N'-[3,5-bis-(1,1-dimethylethyl)-4-hydroxyphenyl]-urea;
N-[3,5-bis-(1,1-dimethylethyl)-4-hydroxyphenyl]-N'-[(4-nitrophenyl)methyl]-thiourea;
N-[(4-aminophenyl)methyl]-N'-[3,5-bis-(1,1-dimethylethyl)-4-hydroxyphenyl]-thiourea;
N-[3,5-bis-(1,1-dimethylethyl)-4-hydroxyphenyl]-N'-[2-(4-nitrophenyl)ethyl]-urea;
N-[2-(4-aminophenyl)ethyl]-N'-[3,5-bis-(1,1-dimethylethyl)-4-hydroxyphenyl]-urea;
1-{[3,4-dihydro-6-methoxy-2,5,7,8-tetramethyl-2H-1-benzopyran-2-yl]carbonyl}-4-(4-nitrophenyl)piperazine;
1-{[3,4-dihydro-6-methoxy-2,5,7,8-tetramethyl-2H-1-benzopyran-2-yl]carbonyl}-4-(4-aminophenyl)piperazine;
hexahydro4-(4-nitrophenyl)-1H-1,4-diazepine;
1-[(3,4-dihydro-6-hydroxy-2,5,7,8-tetramethyl-2H-1-benzopyran-2-yl)carbonyl]hexahydro-4-(4-nitrophenyl)-1H-1,4-diazepine;
1-(4-aminophenyl)-4-[(3,4-dihydro-6-hydroxy-2,5,7,8-tetramethyl-2H-1-benzopyran-2-yl)carbonyl]hexahydro-1H-1,4-diazepine;
hydrochloride du N-[4-{4-[(3,4-dihydro-6-hydroxy-2,5,7,8-tetramethyl-2H-1-benzopyran-2-yl)carbonyl]-1H-1,4-diazepin-1-yl)phenyl]-2-thiophenecarboximidamide hydrochloride;
(R)-3,4-dihydro-2,5,7,8-tetramethyl-2-(4-[(4-nitrophenyl)-1-piperazinyl]-carbonyl}-2H-1-benzopyran-6-ol;
(R)-3,4-dihydro-2,5,7,8-tetramethyl-2-{4-[(4-aminophenyl)-1-piperazinyl]-carbonyl}-2H-1-benzopyran-6-ol;

(S)-3,4-dihydro-2,5,7,8-tetramethyl-2-{4-[(4-nitrophenyl)-1-piperazinyl]-carbonyl}-2H-1-benzopyran-6-ol;

(S)-3,4-dihydro-2,5,7,8-tetramethyl-2-{4-[(4-aminophenyl)-1-piperazinyl]-carbonyl}-2H-1-benzopyran-6-ol;

3,5-bis-(1,1-dimethylethyl)-4-hydroxy-N-[2-(3-nitrophenyl)ethyl]-benzamide;

3,5-bis-(1,1-dimethylethyl)-4-hydroxy-N-[2-(3-aminophenyl)ethyl]-benzamide;

2-(4-nitrophenyl)ethyl 3,5-bis-(1,1-dimethylethyl)-4-hydroxybenzoate;

2-(4-aminophenyl)ethyl 3,5-bis-(1,1-dimethylethyl)-4-hydroxy-benzoate;

or their salts.

Finally, this particular variant of the invention also comprises processes for the preparation of compounds of general formula (I)$_L$ as defined above and consisting, for example, of the reaction in a lower alcohol such as methanol, ethanol, isopropyl alcohol or t-butanol, preferably in isopropyl alcohol, at a temperature comprised between 20 and 90° C., for example at 50° C., and for 1 to 48 hours, preferably for 15 to 24 hours, optionally in the presence of DMF, of a compound of general formula (III)$_L$ as defined above with a compound of general formula (IV)$_L$

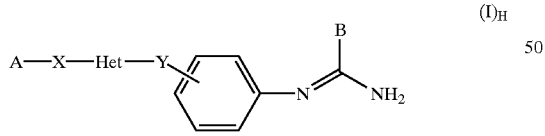

(IV)$_L$ said compound of general formula (IV)$_L$ being optionally salified by a mineral acid G, B having the meaning indicated above and L representing a leaving group and in particular an alkoxy, thioalkyl, sulphonic acid, halide, aryl alcohol or tosyl radical (other leaving groups well known to a person skilled in the art which can optionally be used for the invention are described in the following work: *Advanced Organic Chemistry*, J. March, 3rd Edition (1985), Mc Graw-Hill, p. 315). Preferably, G represents HCl, HBr or HI.

Other production processes can be envisaged and can be consulted in the literature (for example: The Chemistry of amidines and imidates, Vol. 2, Saul PATAI and Zvi RAPPOPORT, John Wiley & Sons, 1991).

According to another particular variant of the invention, the compounds of the invention correspond to general formula (I)$_H$:

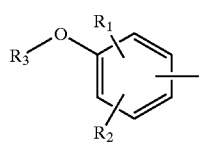

(I)$_H$ in which:

A is a hydrogen atom or an aromatic corresponding to structures:

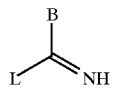

in which $R_1$ and $R_2$ represent, independently, a hydrogen atom, a halogen, the OH group, a linear or branched alkyl radical having from 1 to 6 carbon atoms, a linear or branched alkoxy radical having from 1 to 6 carbon atoms $R_3$ represents a hydrogen atom, a linear or branched alkyl radical having from 1 to 6 carbon atoms or a —COR$_4$ radical, R$_4$ representing an alkyl radical having from 1 to 6 carbon atoms, or

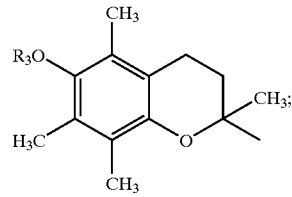

B represents a linear or branched alkyl radical having from 1 to 6 carbon atoms, phenyl, pyridinyl or a heterocycle with 5 members containing from 1 to 4 heteroatoms chosen from O, S, N and more particularly: thiophene, furan, pyrrole or thiazole, the carbons of which are optionally substituted by one or more groups chosen from a linear or branched alkyl radical having from 1 to 6 carbon atoms; an alkoxy radical having from 1 to 6 carbon atoms or a halogen;

X represents —CO—N(R$_3$)—X'—, —NH—CO—X'—, —CH=, —CO— or a bond, X' representing —(CH$_2$)$_n$— with n an integer from 0 to 6;

Y represents —Y'—, —CO—NH—Y', —Y'—NH—CO—, —CO—Y'—, —Y'—CO, —N(R$_3$)—Y'—, —Y'—N(R$_3$)—, Y'—CH$_2$—N(R$_3$)—CO—, —O—Y'—, —Y'—O—, —S—Y'—, —Y'—S—, —Y'—O—Y'—, —Y'—N(R$_3$)—Y'— or a bond, Y' representing —(CH$_2$)$_n$— with n an integer from 0 to 6;

Het represents a heterocycle containing from 1 to 5 heteroatoms chosen from O, N, S which can be substituted by one or more substituents X'—OR$_3$, X'—NR$_3$, X'—S—R$_3$ and such as for example:

oxetane, pyrrole, pyrrolidine, furan, tetrahydrofuran, thiophene, tetrahydrothiophene, sulpholane, imidazole, imidazoline, dihydroimidazole-2-one, dihydroimidazole-2-thione, oxazole, isoxazole, oxazoline, isoxazoline, oxazolidine, oxazolidinone, thiazole, thiazoline, thiazolidine, thiazolidinone, hydantoine, 1,2,4-triazole, 1,3,4-oxadiazole, 1,3,4-thiadiazole, 1,1-dioxyde-1,2,5-thiadiazolidine, 1,2,4-triazole-3-one, tetrazole, tetrahydropyridine, with the exception of the following heterocycles: piperazines, homopiperazines, 4-aminopiperidine;

it being understood that when A represents a hydrogen atom, Het does not represent a piperidine, pyrrolidine or morpholine radical.

The compounds of general formula (I)$_H$ containing one or more asymmetrical centres having isomer forms. The racemics and enantiomers of these compounds are also part of this invention. Similarly, the compounds of the invention can also exist in the state of bases or addition salts with acids.

More particularly the invention relates to the compounds of general formula (I)$_H$ in which:

A is a hydrogen atom or an aromatic corresponding to the structure:

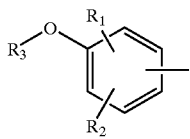

in which:
- $R_1$ and $R_2$ represent, independently a linear or branched alkyl radical having 1 to 6 carbon atoms or a linear or branched alkoxy radical having from 1 to 6 carbon atoms,
- $R_3$ represents a hydrogen atom or a linear or branched alkyl radical having from 1 to 6 carbon atoms;
- B represents a heterocycle with 5 members containing from 1 to 4 heteroatoms chosen from O, S, N and more particularly: thiophene, furan, pyrrole or thiazole, the carbons of which are optionally substitued by one or more groups chosen from a linear or branched alkyl having from 1 to 6 carbon atoms, an alkoxy radical having from 1 to 6 carbon atoms or a halogen;
- X represents —NH—CO—X'—, —CH=, —CO— or a bond, X' representing —(CH$_2$)$_n$— with n an integer from 0 to 6;
- Y represents —Y'—, —Y'—NH—CO—, —Y'—CO—, —Y'—O—, —Y'—O—Y'—, —Y'—N(R$_3$)—Y'— or a bond, Y' representing —(CH$_2$)$_n$— with n an integer from 0 to 6;
- Het represents a heterocycle containing from 1 to 5 heteroatoms chosen from O, N, S which can be substituted by one or more substituents X'—OR$_3$, X'—NR$_3$, X'—S—R$_3$ and such as for example:
  oxetane, pyrrole, pyrrolidine, furan, tetrahydrofuran, thiophene, tetrahydrothiophene, sulpholane, imidazole, imidazoline, dihydroimidazole-2-one, dihydroimidazole-2-thione, oxazole, isoxazole, oxazoline, isoxazoline, oxazolidine, oxazolidinone, thiazole, thiazoline, thiazolidine, thiazolidinone, hydantoin, 1,2,4-triazole, 1,3,4-oxadiazole, 1,3,4-thiadiazole, 1,1-dioxyde-1,2,5-thiadiazolidine, 1,2,4-triazole-3-one, tetrazole, tetrahydropyridine,
with the exception of the following heterocycles: piperazines, homopiperazines, 4-aminopiperidine.

Quite particularly the invention relates to the compounds of general formula (I)$_H$ in which:

A is a hydrogen atom or an aromatic corresponding to the structure:

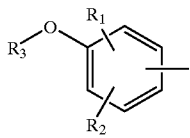

in which:
- $R_1$ and $R_2$ represent, independently a linear or branched alkyl radical having from 1 to 6 carbon atoms or a linear or branched alkoxy radical having from 1 to 6 carbon atoms,
- $R_3$ represents a hydrogen atom or a linear or branched alkyl radical having from 1 to 6 carbon atoms;
- B represents a thiophene ring, the carbons of which are optionally substituted by one or more groups chosen from a linear or branched alkyl having from 1 to 6 carbon atoms, an alkoxy radical having from 1 to 6 carbon atoms or a halogen;
- X represents —NH—CO—X'—, —CH=, —CO— or a bond, X' representing —(CH$_2$)$_n$— with n an integer from 0 to 6;
- Y represents —Y'—, —Y'—NH—CO—, —Y'—CO—, —Y'—O—, —Y'—O—Y'—, —Y'—N(R$_3$)—Y'— or a bond, Y' representing —(CH$_2$)$_n$— with n an integer from 0 to 6;
- Het represents a heterocycle containing from 1 to 5 heteroatoms chosen from O, N, S which can be substituted by one or more substituents X'—OR$_3$, X'—NR$_3$, X'—S—R$_3$ and such as for example:
  oxetane, pyrrole, pyrrolidine, furan, tetrahydrofuran, thiophene, tetrahydrothiophene, sulpholane, imidazole, imidazoline, dihydroimidazole-2-one, dihydroimidazole-2-thione, oxazole, isoxazole, oxazoline, isoxazoline, oxazolidine, oxazolidinone, thiazole, thiazoline, thiazolidine, thiazolidinone, hydantoin, 1,2,4-triazole, 1,3,4-oxadiazole, 1,3,4-thiadiazole, 1,1-dioxyde-1,2,5-thiadiazolidine, 1,2,4-triazole-3-one, tetrazole, tetrahydropyridine,
with the exception of the following heterocycles: piperazines, homopiperazines, 4-aminopiperidine.

Preferred compounds for this variant of the invention include the following compounds (described in the examples):

N-[4-(1H-imidazol-1-yl)phenyl]-2-thiophenecarboximidamide;
N-[4-(3-thiazolidinylmethyl)phenyl]-2-thiophenecarboximidamide;
N-[4-(1,2,3,6-tetrahydropynidin-1-yl)phenyl]-2-thiophenecarboximidamide;
N-[4-(1H-imidazol-1-yl methyl)phenyl]-2-thiophenecarboximidanide;
N-[4-{2-(3-thiazolidinyl)ethyl}phenyl]-2-thiophenecarboximidamide;
N-{4-[2-(1H-imidazol-1-yl)ethyl]phenyl}-2-thiophenecarboximidade;
N-{4-[2-(1,2,3,6-tetrahydropyridin-1-yl)ethyl]phenyl}-2-thiophenecarboximidamide;
N-[4-(3-thiazolidinylcarbonylmethyl)phenyl]-2-thiophenecarboximidamide;
N-(4-{[2-thiazolidinyl]carbonylaminomethyl)phenyl)-2-thiophenecarboximidamide;
N-(3,5-di-t-butyl-4-hydroxyphenyl)-5-[4-{imino(2-thienyl)-methylamino}phenyl]-2-furan carboxaniide;
3-(3,5-di-t-butyl-4-hydroxyphenyl)-1-[4-{imino(2-thienyl)-methylamino}phenyl]-2,5-imidazolidinedione;
2-(3,5-di-t-butyl-4-hydroxyphenyl)-3-[4-{imino(2-thienyl)-methylamino}phenyl]-4-thiazolidinone;
5-[(3,5-di-t-butyl-4-hydroxyphenyl)methylene]-1-methyl-3-[4-{imino(2-thienyl)methylamino}phenyl]-2,4-imidazolidinedione;
2-(S)-4-(S)-N-[4-hydroxy-3,5-bis-(1,1-dimethylethyl)-phenyl]-4-{4-[(imino(2-thienyl)methyl)amino]phenoxy}-prolinamide;
5,6-dihydro-N-(4-[(imino(2-thienyl)methyl)amino]phenyl}-1-(2H)-pyridinecarboxamide;
N-[4-hydroxy-3,5-bis-(1,1-dimethylethyl)phenyl]-2-(R.S)-{4-[(imino(2-thienyl)methyl)amino]phenyl}-4-(R)-thiazolidine carboxamide;
N-[3,5-bis(1,1-dimethylethyl)-4-hydroxyphenyl]-2-{4-[(imino(2-thienyl)methyl)amino]phenyl}-4-thiazolecarboxamide;
N-[3,5-bis(1,1-dimethylethyl)-4-hydroxyphenyl]-4-(S)-{4-[(imino(2-thienyl)methyl)amino]phenoxy}-pyrrolidine-2-(R)-carboxamide;

methyl 1-[(3,4-dihydro-6-hydroxy-2,5,7,8-tetramethyl-2-H-[1]-benzopyran-2-yl)carbonyl]-4-(S)-{4-[(imino(2-thienyl)methyl)amino]-phenoxy}-pyrrolidine-2-(S)-carboxylate;
1-[(3,4-dihydro-6-hydroxy-2,5,7,8-tetramethyl-2H-[1]-benzopyran-2-yl)carbonyl]-3-(S)-{4-[(imino(2-thienyl)methyl)amino]phenoxy}-pyrrolidine;
3-{[(3,4-dihydro-6-hydroxy-2,5,7,8-tetramethyl-2H-[1]-benzopyran-2-yl)-carbonyl]amino}-1-{4-[(imino(2-thienyl)methyl)amino]phenyl}pyrrolidine;
4-[3,5-bis-(1,1-dimethylethyl)-4-hydroxyphenyl]-N-{4-[(imino(2-thienyl)methyl)amino]benzoyl}-N-methyl-1H-imidazole-2-methanamine;
N-[3,5-bis-(1,1-dimethylethyl)-4-hydroxyphenyl]-1-{4-[(imino(2-thienyl)methyl)amino]phenyl}-1H-pyrrole-2-carboxamide;
1-[3,5-bis(1,1-dimethylethyl)-4-hydroxyphenyl]-3-{[4-[[imino(2-thienyl)methyl]amino]phenyl]carbonyl}-2-imidazolidinone;
3-[3,5-bis(1,1-dimethylethyl)-4-hydroxyphenyl]-4,5-dihydro-N-{4-[(imino(2-thienyl)methyl)amino]phenyl}-5-isoxazoleacetamide;
4-[3,5-bis(1,1-dimethylethyl)-4-hydroxyphenyl]-N-{4-[(imino(2-thienyl)methyl)amino]phenyl}-N-methyl-2-thiazolemethanamine;
4-[3,5-bis(1,1-dimethylethyl)-4-hydroxyphenyl]-N-{4-[(imino(2-thienyl)methyl)amino]phenyl}-N-methyl-1H-imidazole-2-methanamine;
3-[3,5-bis(1,1-dimethylethyl)-4-hydroxyphenyl]-4,5-dihydro-5-{2-{4-[(imino(2-thienyl)methyl)amino]phenoxy}ethyl}isoxazole;
1-{[3,5-bis(1,1-dimethylethyl)-4-hydroxyphenyl]amino}-carbonyl}-3-{4-[(imino(2-thienyl)methyl)amino]phenoxy}azetidine;
1-(2-hydroxy-5-methoxybenzoyl)-3-{4-[(imino(2-thienyl)methyl)amino]phenoxyl}azetidine;
1-[(3,4-dihydro-6-hydroxy-2,5,7,8-tetramethyl-2H-[1]-benzopyran-2-yl)carbonyl]-4-[4-[(imino(2-thienyl)methyl)amino]phenoxy}-piperidine;
1-[(3,4-dihydro-6-hydroxy-2,5,7,8-tetramethyl-2H-[1]-benzopyran-2-yl)carbonyl]-3-{4-[(imino(2-thienyl)methyl)amino]-phenoxy}azetidine;

as well as their salts, in particular their hydrochlorides, dihydrochlorides, fumarates or hemi-fumarates.

Preferred compounds for this variant of the invention are the following compounds:

N-[4-(1H-imidazol-1-yl)phenyl]-2-thiophenecarboximidamide hydroiodide;
N-[4-(3-thiazolidinylmethyl)phenyl]-2-thiophenecarboximidamide;
N-[4-(1,2,3,6-tetrahydropyridin-1-yl)phenyl]-2-thiophenecarboximidamide fumarate;
N-[4-(1H-imidazol-1-yl methyl)phenyl]-2-thiophenecarboximidamide hydrochloride;
N-[4-{2-(3-thiazolidinyl)ethyl}phenyl]-2-thiophenecarboximidamide;
N-{4-[2-(1H-imidazol-1-yl)ethyl]phenyl}-2-thiophenecarboximidamide hydroiodide;
N-{4-[2-(1,2,3,6-tetrahydropyridin-1-yl)ethyl]phenyl}-2-thiophenecarboximidamide fumarate
N-[4-(3-thiazolidinylcarbonylmethyl)phenyl]-2-thiophenecarboximidamide;
N-(4-{[2-thiazolidinyl]carbonylaminomethyl}phenyl)-2-thiophenecarboximidamide fumarate;
N-(3,5-di-t-butyl-4-hydroxyphenyl)-5-[4-{imino(2-thienyl)-methylamino}phenyl]-2-furan carboxamide hydroiodide;
3-(3,5-di-t-butyl-4-hydroxyphenyl)-1-[4-{imino(2-thienyl)-methylamino}phenyl]-2,5-imidazolidinedione hydrochloride;
2-(3,5-di-t-butyl-4-hydroxyphenyl)-3-[4-{imino(2-thienyl)-methylamino}phenyl]-4-thiazolidinone hydrochloride;
5-[(3,5-di-t-butyl-4-hydroxyphenyl)methylene]-1-methyl-3-[4-{imino(2-thienyl)methylamino}phenyl]-2,4-imidazolidinedione fumarate;
2-(S)-4-(S)-N-[4-hydroxy-3,5-bis-(1,1-dimethylethyl)-phenyl]-4-{4-[(imino(2-thienyl)methyl)aamino]phenoxy}-prolinamide hydrochloride;
5,6-dihydro-N-{4-[(imino(2-thienyl)methyl)amino]phenyl}-1-(2H)-pyridine carboxaride hydrochloride;
N-[4-hydroxy-3,5-bis-(1,1-dimethylethyl)phenyl]-2-(R,S)-{4-[(imino(2-thienyl)methyl)amino]phenyl}-4-(R)-thiazolidine carboxamide fumarate;
N-[4-(4-phenyl-1,2,3,6-tetrahydropyridine-1-yl)phenyl]-2-thiophenecarboximidamide hydroiodide;
N-[4-hydroxy-3,5-bis-(1,1-dimethyl)ethyl-phenyl]-2-{4-[(imino(2-thienyl)methyl)amino]phenyl}-4-thiazole carboxamide hydrochloride;

or their salts or enantiomers.

N-[4-(1,2,3,6-tetrahydropyridin-1-yl)phenyl]-2-thiophenecarboximidamide or its salts is the most preferred compound among the compounds of this variant of the invention.

The invention also offers, as new industrial products, the synthetic intermediates of the products of general formula $(I)_H$, namely the products of general formula $(II)_H$, $(III)_H$, $(V)_H$, $(VI)_H$ and $(VII)_H$

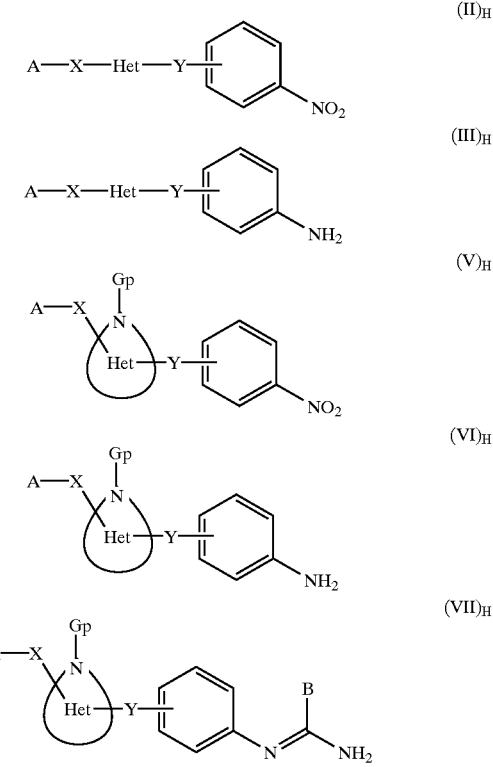

in which

A is a hydrogen atom or an aromatic corresponding to structures:

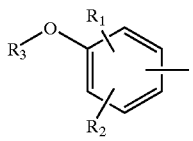

in which:

R₁ and R₂ represent, independently, a hydrogen atom, a halogen, the OH group, a linear or branched alkyl radical having from 1 to 6 carbon atoms, a linear or branched alkoxy radical having from 1 to 6 carbon atoms, R₃ represents a hydrogen atom, a linear or branched alkyl radical having from 1 to 6 carbon atoms or a —COR₄ radical R₄ representing an alkyl radical having from 1 to 6 carbon atoms, or

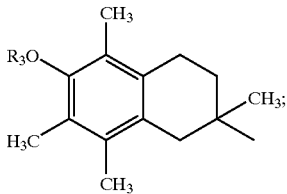

B represents a linear or branched alkyl radical having from 1 to 6 carbon atoms, phenyl, pyridinyl or a heterocycle with 5 members containing from 1 to 4 heteroatoms chosen from O, S, N and more particularly: thiophene, furan, pyrrole or thiazole, the carbons of which are optionally substituted by one or more groups chosen from a linear or branched alkyl having from 1 to 6 carbon atoms, an alkoxy radical having from 1 to 6 carbon atoms or a halogen;

X represents —CO—N(R₃)—X'—, —NH—CO—X'—, —CH=, —CO— or a bond, X' representing —(CH₂)ₙ— with n an integer from 0 to 6;

Y represents —Y'—, —CO—NH—Y', —Y'—NH—CO—, —CO—Y'—, —Y'—CO, —N(R₃)—Y'—, —Y'—N(R₃)—, Y'—CH₂—N(R₃)—CO—, —O—Y'—, —Y'—O—, —S—Y'—, —Y'—S—, —Y'—O—Y'—, —Y'—N(R₃)—Y'— or a bond, Y' representing —(CH₂)ₙ— with n an integer from 0 to 6;

Het represents a heterocycle containing from 1 to 5 heteroatoms chosen from O, N, S which can be substituted by one or more substituents X'—OR₃, X'—NR₃, X'—S—R₃ and such as for example:

oxetane, pyrrole, pyrrolidine, furan, tetrahydrofuran, thiophene, tetrahydrothiophene, sulpholane, imidazole, imidazoline, dihydroimidazole-2-one, dihydroimidazole-2-thione, oxazole, isoxazole, oxazoline, isoxazoline, oxazolidine, oxazolidinone, thiazole, thiazoline, thiazolidine, thiazolidinone, hydantoin, 1,2,4-triazole, 1,3,4-oxadiazole, 1,3,4-thiadiazole, 1,1-dioxyde-1,2,5-thiadiazolidine, 1,2,4-triazole-3-one, tetrazole, tetrahydropyridine, with the exception of the following heterocycles: piperazines, homopiperazines, 4-aminopiperidine;

Gₚ represents a protective group of the amine function preferably cleavable in an anhydrous acid medium, such as for example the carbamates of t-butyl, trichloroethyl or trimethylsilylethyl or also the trityl group.

Finally, the invention offers preparation processes for the compounds of general formula (I)ₕ as defined above and consisting of, for example, the reaction in a lower alcohol, such as methanol, ethanol, isopropyl alcohol or t-butanol, preferably in isopropyl alcohol, at a temperature between 20 and 90° C., for example at 50° C., and for one to 48 hours, preferably for 15 to 24 hours, optionally in the presence of DMF, of a compound of general formula (III)ₕ

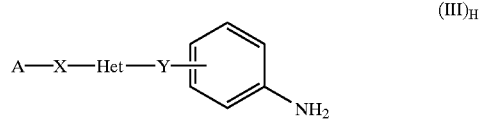

with a compound of general formula (IV)ₕ

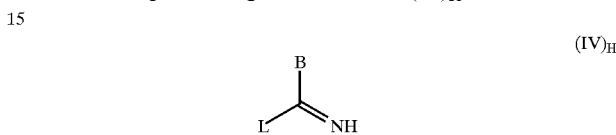

said compound of general formula (IV)ₕ optionally being able to be salified by a mineral acid G, B having the meaning indicated above and L representing a parting group and in particular an alkoxy, thioalkyl, sulphonic acid, halide, aryl alcohol or tosyl radical (other parting groups well-known to a person skilled in the art and being optionally able to be used for the invention are decribed in the following work: Advanced Organic Chemistry, J. March, 3rd Edition (1985), Mc Graw-Hill, p. 315). Preferably, G represents HCl, HBr or HI.

A subject of the invention is also, as medicaments, the compounds of general formula (I), (I)ₗ or (I)ₕ described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or inductible NO synthase, to inhibit lipidic peroxidation or to provide the double function of NO synthase inhibition and lipidic peroxidation.

More preferably, (S)-N-{4-[4-[(3,4-dihydro-6-hydroxy-2,5,7,8-tetramethyl-2H-1-benzopyran-2-yl)-carbonyl]-1-piperazinyl]-phenyl}-2-thiophenecarboximidamide or a pharmaceutically acceptable salt thereof, will be used in the pharmaceutical compositions of the invention. The same will also be preferred for producing medicaments according to the invention.

In a preferred manner, the compounds of general formula (I), (I)ₗ or (I)ₕ, or their pharmaceutically acceptable salts, and in particular (S)-N-{4-[4-[(3,4-dihydro-6-hydroxy-2,5,7,8-tetramethyl-2H-1-benzopyran-2-yl)-carbonyl]-1-piperazinyl]-phenyl}-2-thiophenecarboximidamide or a pharmaceutically acceptable salt thereof, will be used produce a medicament intended to treat stroke, neurodegenerative diseases or ischemic or hemorragic cardiac or cerebral infarctions, notably those related with complications of coronary artery bypass grafting.

The invention therefore provides a method of treating stroke or neurodegenerative diseases comprising administering to said warm-blooded animal a compound of general formula (I), (I)ₗ or (I)ₕ, or a pharmaceutically acceptable salt thereof, and in particular (S)-N-{4-[4-[(3,4-dihydro-6-hydroxy-2,5,7,8-tetramethyl-2H-1-benzopyran-2-yl)-carbonyl]-1-piperazinyl]-phenyl}-2-thiophenecarboximidamide or a pharmaceutically acceptable salt thereof, in an amount sufficient to inhibit stroke or neurodegenerative diseases.

The invention also provides a method of preventing or treating ischemic or hemorragic cardiac or cerebral infarctions related with complications of coronary artery bypass grafting in a warm-blooded animal comprising administering to said warm-blooded animal a compound of general formula (I), (I)$_L$ or (I)$_H$, or a pharmaceutically acceptable salt thereof, and in particular (S)-N-{4-[4-[(3,4-dihydro-6-hydroxy-2,5,7,8-tetramethyl-2H-1-benzopyran-2-yl)-carbonyl]-1-piperazinyl]-phenyl}-2-thiophenecarboximidamide or a pharmaceutically acceptable salt thereof, in an amount sufficient to inhibit said ischemic or hemorragic cardiac or cerebral infarctions.

By pharmaceutically acceptable salt is meant in particular addition salts of inorganic acids such as hydrochloride, sulphate, phosphate, diphosphate, hydrobromide and nitrate, or of organic acids, such as acetate, maleate, fumarate, tartrate, succinate, citrate, lactate, methane sulphonate, p-toluenesulphonate, pamoate, oxalate and stearate: The salts formed from bases such as sodium or potassium hydroxide also fall within the scope of the present invention, when they can be used. For other examples of pharmaceutically acceptable salts, reference can be made to "Pharmaceutical salts", *J. Pharm. Sci.* 66:1 (1977).

The pharmaceutical composition can be in the form of a solid, for example powders, granules, tablets, capsules, liposomes or suppositories. Appropriate solid supports can be for example calcium phosphate, magnesium stearate, talc, sugars, lactose, dextrin, starch, gelatin, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water.

A medicament according to the invention can be administered by topical, oral or parenteral route, by intramuscular injection, etc.

The envisaged administration dose for the medicament according to the invention is comprised between 0.1 mg and 10 g according to the type of active compound used.

According to the invention, the compounds of general formula (I)$_L$ can be prepared by the process described below.

Preparation of Compounds of General Formula (I)

The preparation of the compounds of general formula (I), corresponding to subformulae (I)$_L$ and (I)$_H$, is described hereafter.

A) Preparation of Compounds of General Formula (I)$_L$

The compounds of general formula (I)$_L$ can be prepared from intermediates of general formula (II)$_L$ according to diagram 1.

The reduction of the nitro function of the intermediates of general formula (II)$_L$ is generally carried out by catalytic hydrogenation in ethanol, in the presence of Pd/C, except when X=—CH=CH—CO— or Y=—O—CH$_2$—, the nitro group is selectively reduced using, for example, SnCl$_2$ (*J. Heterocyclic Chem.* (1987), 24, 927–930; *Tetrahedron Letters* (1984), 25, (8), 839–842). The reaction is then carried out by heating the mixture to approx. 70° C., for at least three hours, in ethyl acetate, sometimes with added ethanol.

The aniline derivatives of general formula (III)$_L$ thus obtained can be condensed on derivatives of general formula (IV)$_L$, for example derivatives of O-alkyl thioimidate or S-alkyl thioimidate type, in order to produce final compounds of general formula (I)$_L$ (cf. diagram 1). For example, for B=thiophene, the derivatives of general formula (III)$_L$ can be condensed on S-methylthiophene thiocarboxamide hydriodide, prepared according to a method in the literature (*Ann. Chim.* (1962), 7, 303–337). Condensation can be carried out by heating in an alcohol (for example in methanol or isopropanol), optionally in the presence of DMF at a temperature comprised between 0 and 100° C. for a duration generally comprised between a few hours and overnight.

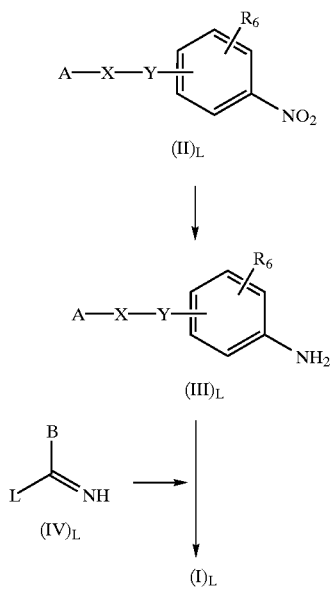

Diagram 1

Preparation of Intermediates of General Formula (II)$_L$

The intermediates of general formula (II)$_L$ can be prepared by different processes depending on the cherrical functions which are set up: amines, carboxamides, ureas, thioureas, sulphonamides, aminosulphonylureas, sulphamides, carbamates, ethers, esters, thioethers, acylureas, etc.:

When:

X=linear or branched alkylene radical having from 1 to 6 carbon atoms and

Y=piperazine, homopiperazine, 2-methylpiperazine, 2,5-dimethyl-piperazine, 4-aminopiperidine, —NR$_3$—Z$_2$—Q—, —NR$_3$—NH—CO—Z$_2$—, —NH—NH—Z$_2$—, —NR$_3$—O—Z$_2$—

The amines of general formula (II)$_L$, diagram 2, in which A, X, Y and R$_6$ are as defined above, can be obtained by nucleophile substitution of the halogenated derivatives of general formula (VI)$_L$ by an amine of general formula (VII)$_L$. The reaction is carried out, for example, in DMF in the presence of K$_2$CO$_3$ at 20° C. The halogenated derivatives of general formula (VI)$_L$ can be accessed, for example, by bromation of the primary alcohols of general formula (V)$_L$ using PBr$_3$, at 0° C., in anhydrous THF. The alcohols of general formula (V)$_L$ which are not commercially available can be prepared according to methods described in the literature (*Tetrahedron Lett.* (1983), 24, (24), 2495–2496).

Diagram 2

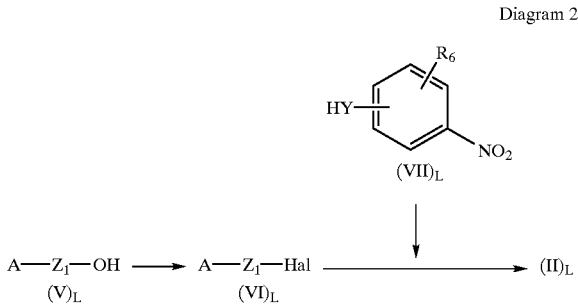

The amines of general formula (VII)$_L$ in which Y represents homopiperazine, 2,5-dimethylpiperazine, 4-aninopiperidine or more generally —NR$_3$—Z$_2$—NR$_3$— are synthesized in three stages from the corresponding commercial diamines. The diamines are selectively monoprotected in the form of the carbamate (*Synthesis* (1984), (12), 1032–1033; *Synth. Commun.* (1990), 20, (16), 2559–2564) before reaction by nucleophile substitution on a fluoronitrobenzene, in particular 4-fluoronitrobenzene. The amines, previously protected, are released at the last stage, according to methods described in the literature (T. W. Greene and P. G. M. Wuts, Protective Groups in Organic Synthesis, Second Edition (Wiley-Interscience, 1991)), in order to produce intermediates of general formula (VII)$_L$.

When:

X=—Z$_1$—CO—, —CH=CH—CO— and

Y=piperazine, homopiperazine, 2-methylpiperazine, 2,5-dimethyl-piperazine, 4-aminopiperidine, —NR$_3$—Z$_2$—Q—, —NR$_3$—NH—CO—Z$_2$—, —NH—NH—Z$_2$—, —NR$_3$—O—Z$_2$—

The carboxainides of general formula (II)$_L$, diagram 3, in which A, X, Y and R$_6$ are as defined above, are prepared by condensation of the commercial carboxylic acids of general formula (VIII)$_L$ for X=—Z$_1$—CO— and of general formula (IX)$_L$ for X=—CH=CH—CO— with amines of general formula (VII)$_L$. The non commercial acids can be synthesized according to methods similar to those described in the literature (*J. Org. Chem.* (1974), 39 (2), 219–222; *J. Amer. Chem. Soc.* (1957), 79, 5019–5023, and *CHIMIA* (1991), 45 (4), 121–123 when A represents a 6-alkoxy-2,5,7,8-tetramethylchromane radical). The amines of general formula (VII)$_L$ in which Y represents homopiperazine, 2,5-dimethylpiperazine, 4-aminopiperidine, or more generally —NR$_3$—Z$_2$—NR$_3$— are prepared according to methods similar to those described in the previous paragraph. The carboxamide bonds are formed under standard conditions for peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1.1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)).

Diagram 3

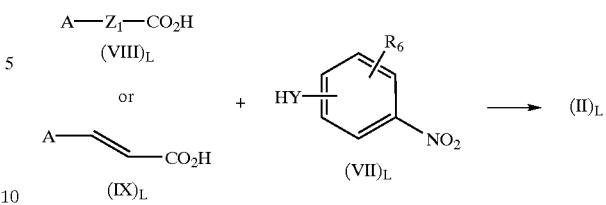

When:

X=—Z$_1$—NR$_3$—CO— and

Y=—Z$_2$—Q—

The carboxamides of general formula (II)$_L$ in which A, X, Y and R$_6$ are as defined above can also be prepared, as in diagram 4, by peptide condensation of an amine of general formula (X) with a commercial acid of general formula (XI)$_L$. When X=—NR$_3$—CO— and R$_3$=H, the compounds of general formula (X)$_L$ are anilines which are obtained by hydrogenation, in the presence of a catalytic quantity of Pd/C, the corresponding nitrobenzene derivatives, themselves synthesized according to a method described in the literature (*J. Org. Chem.* (1968), 33 (1), 223–226). When X≠—NR$_3$—CO— and R$_3$ is a linear or branched alkyl radical having from 1 to 6 carbon atoms, the monoalkylamines can be obtained according to a process described in the literature (U.S. Pat. Nos. 3,208,859 and 2,962,531). The non-commercial carboxylic acids of general formula (XI)$_L$ can be accessed using methods described in the literature (*Acta Chem. Scand.* (1983), 37, 911–916; *Synth. Commun.* (1986), 16 (4), 479–483; *Phophorus, Sulphur Silicon Relat. Elem.* (1991), 62, 269–273).

Diagram 4

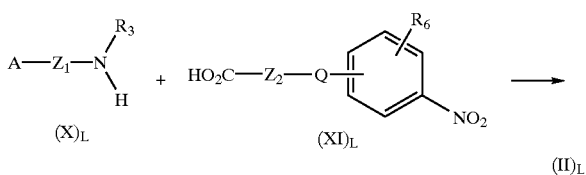

When:

X=—Z$_1$—NR$_3$—CO— and

Y=—NH—Z$_2$—Q—, —NH—CO—Z$_2$—Q— with Q=O—Z$_3$—, R$_3$—N—Z$_3$ or S—Z$_3$—,

The ureas of general formula (II)$_L$, diagram 5, in which A, X, Y and R$_6$ are as defined above, are prepared by the addition of an amine of general formula (X)$_L$ on an isocyanate of general formula (XII)$_L$, (XIII)$_L$ or (XIV)$_L$ in a solvent such as chloroform at 20° C. Synthesis of non-commercial isocyanates of general formula (XII)$_L$ is described in the literature (*J. Med. Chem.* (1992), 35 (21), 3745–3754). The halogenated intermediate ureas (XV)$_L$ and (XVII)$_L$ are then substituted by a derivative of general formula (XVI)$_L$, in which Q represents O—Z$_3$', R$_3$—N—Z$_3$— or S—Z$_3$—, in the presence of a base such as, for example, K$_2$CO$_3$ or NaH in an aprotic solvent such as THF or DMF in order to finally obtain ureas of general formula (II)$_L$.

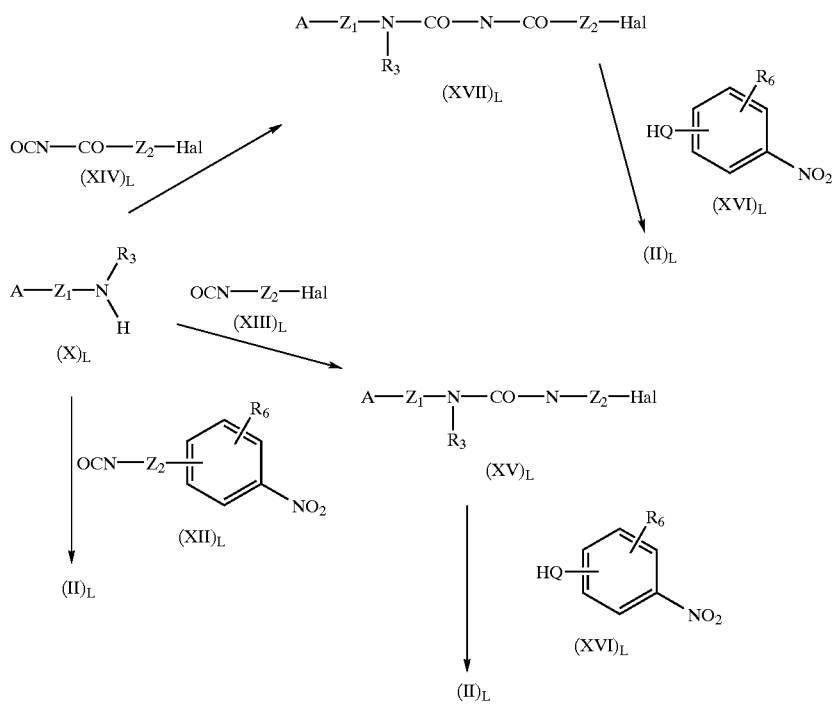

When:

X=—$Z_1$—NH—CO— and

Y=piperazine, homopiperazine, 2-methylpiperazine, 2,5-dimethylpiperazine, 4-aminopiperidine, —$NR_3$—$Z_2$—Q—, —$NR_3$—NH—CO—$Z_2$—, —NH—NH—$Z_2$—, —$NR_3$—O—$Z_2$—

The ureas of general formula (II)$_L$, diagram 6, in which A, X, Y and $R_6$ are as defined above, are prepared by the addition of an amine of general formula (VII)$_L$, described previously, onto an isocyanate of general formula (XVIII)$_L$ in the presence of a base such as diisopropylethylamine.

The isocyanates of general formula (XVII$^1$)$_L$ are synthesized from primary amines of general formula (X)$_L$, described previously, triphosgene and a tertiary amine (*J. Org. Chem.* (1994), 59 (7), 1937–1938).

The amines of general formula (VII)$_L$ in which Y≠—NH—O— are prepared according to a method described in the literature (*J. Org. Chem.* (1984), 49 (8), 1348–1352).

When:

X=—$Z_1$—$NR_3$—CO— and

Y=—$NR_3$—$SO_2$—$NR_3$—$Z_2$—

The aminosulphonylureas of general formula (II)$_L$, diagram 7, in which A, X, Y and $R_6$ are as defined above, are prepared by the addition of amines of general formula (X)$_L$, described previously, onto chlorosulphonylisocyanate (*J. Med. Chem.* (1996), 39(6), 1243–1252). The intermediate chlorosulphonylurea (XIX)$_L$ is then condensed on the amines of general formula (VII)$_L$, described previously, in order to produce the aminosulphonylureas of general formula (II)$_L$ which can optionally be alkylated by a halogenated derivative in the presence of a base such as, for example, NaH in order to produce other derivatives of general formula

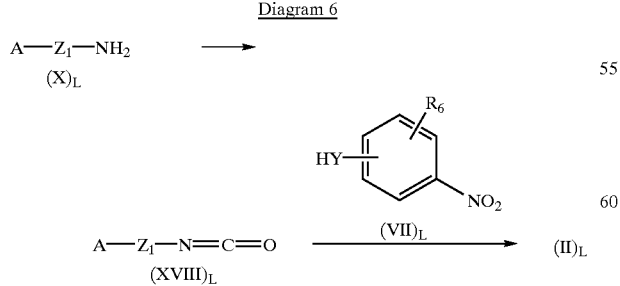

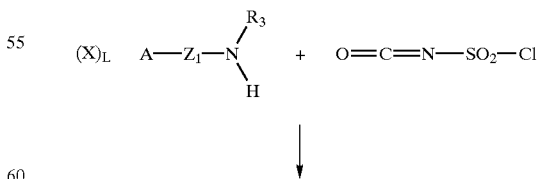

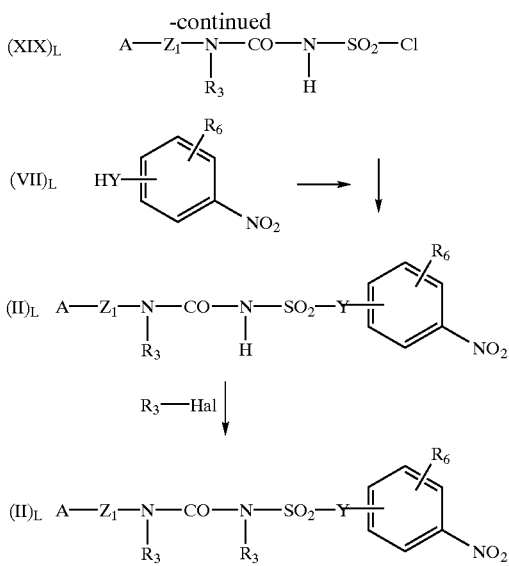

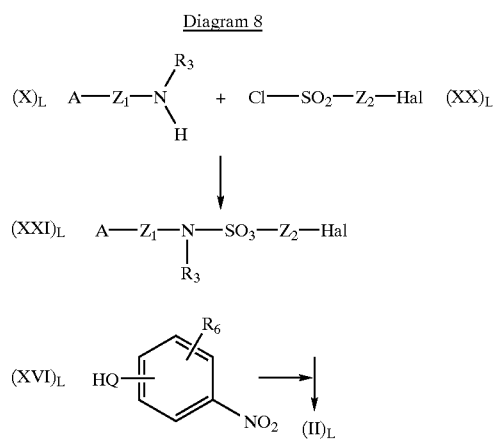

When:
X=—$Z_1$—$NR_3$—$SO_2$— and
Y=—$Z_2$—Q—, with Q=O—$Z_3$—, $R_3$—N—$Z_3$— or S—$Z_3$—, The sulphonamides of general formula $(II)_L$ diagram 8, in which A, X, Y and $R_6$ are as defined above, are prepared by the addition of amines of general formula $(X)_L$, described previously, onto halogenoalkylsulphonyl chlorides of general formula $(XX)_L$. The halogenoalkylsulphonamides of general formula $(XXI)_L$, obtained intermediately, are then condensed on an alcohol, an amine or a thiol of general formula $(XVI)_L$ in the presence of a base such as, for example, $K_2CO_3$ or NaH, in a polar solvent such as, for example, acetonitrile or DMF.

Diagram 8

When:
X=—$Z_1$—$NR_3$—$SO_2$— and
Y=—$NR_3$—$Z_2$—Q—

The sulphamides of general formula $(II)_L$, diagram 9, in which A, X, Y and $R_6$ are as defined above are prepared in three stages from amines of general formula $(X)_L$ and chlorosulphonylisocyanate. The reaction of an alcohol, such as tBuOH, on the isocyanate function of chlorosulphonylisocyanate (*Tetrahedron Lett.* (1991), 32 (45), 6545–6546) leads to an intermediate of chlorosulphonylcarbamate type, which reacts in the presence of an amine of general formula $(X)_L$ to produce a derivative of carboxylsulphamide type of general formula $(XXII)_L$. The treatment of this intermediate in a strong acid medium produces the sulphamide derivative of general formula $(XXIII)_L$. Alkylation of the compounds of general formula $(XXIII)_L$ by the halogenated derivatives of general formula $(XXIV)_L$ in the presence of a base such as, for example, NaH in a polar aprotic solvent allows sulphamide derivatives of general formula $(II)_L$ to be obtained.

Diagram 9

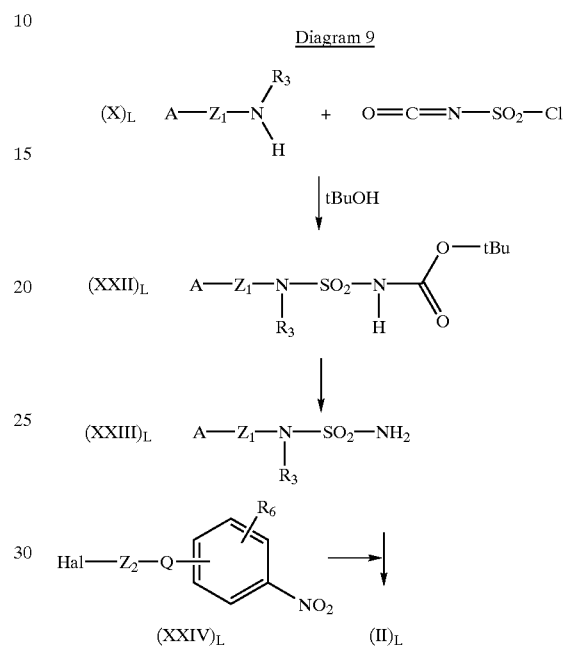

When:
X=—$Z_1$—$NR_3$—CO— and
Y=—O—$Z_2$—Q—

The carbamates of general formula $(II)_L$, diagram 10, in which A, X, Y and $R_6$ are as defined above, are prepared by the reaction of amines of general formula $(X)_L$, described previously, with chloroformate derivatives of general formula $(XXV)_L$ prepared according to a method described in the literature (*Tetrahedron Lett.* (1993), 34 (44), 7129–7132).

Diagram 10

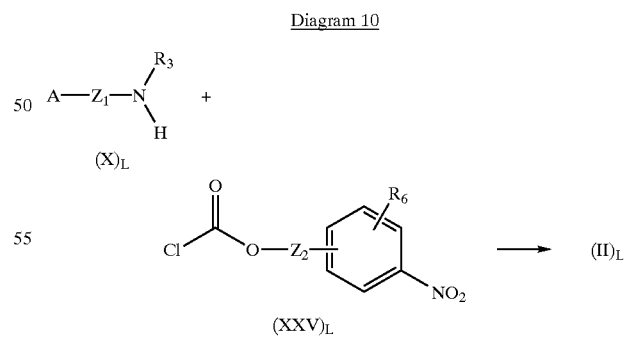

When:
X=—Zi—CO—, —CH=CH—CO— and
Y=—O—$Z_2$—Q—

The esters of general formula $(II)_L$, diagram 11, in which A, X, Y and $R_6$ are as defined above, are prepared by the reaction of acids of general formula $(VIII)_L$ or $(IX)_L$ and alcohols of general formula $(XXVI)_L$ in the presence de dicyclohexylcarbodiimide and of a catalytic quantity of 4-dimethylaminopyridine in a solvent such as, for example, THF or DMF at 20° C.

Diagram 11

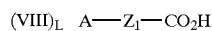

or +

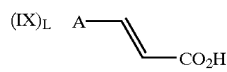

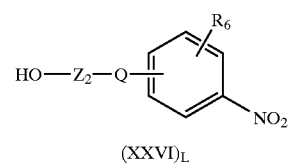

When:
X=—$Z_1$— and
Y=—O—CO—$Z_2$—Q—

The esters of general formula (II)$_L$, diagram 12, in which A, X, Y and $R_6$ are as defined above, can also be prepared by the reaction of acids of general formula (XI)$_L$, described previously, with the alcohols of general formula (V)$_L$ under the conditions described previously.

Diagram 12

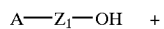

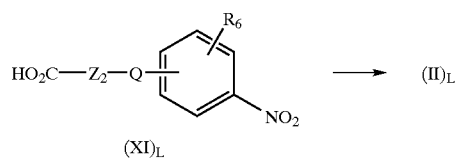

When:
X=—$Z_1$—$NR_3$—CS— and
Y=—NH—$Z_2$—Q—, piperazine, homopiperazine, 2-methylpiperazine, 2,5-dimethylpiperazine, 4-aminopiperidine, —$NR_3$—$Z_2$—Q—, —NH—NH—$Z_2$—, —$NR_3$—O—$Z_2$—

The thioureas of general formula (II)$_L$ in which A, X, Y and $R_6$ are as defined above, are prepared from the ureas described previously using Lawesson's reagent, following an experimental protocol described in the literature (*J. Med. Chem.* (1995), 38 (18), 3558–3565).

When:
X represents a bond
Y=—O—$Z_2$—Q—, —S—$Z_2$—Q— and
Q=—HN—

The etheroxides or thioetheroxides of general formula (II)$_L$, diagram 13, in which A, X, Y and $R_6$ are as defined above are prepared from dihydroquinones of general formula (XXVII)$_L$ (*J. Chem. Soc., Perkin Trans. I*, (1981), 303–306) or thiophenols of general formula (XXVIII)$_L$ (*Bio. Med. Chem. Letters*, (1993), 3 (12), 2827–2830) and an electrophile (E$^+$) such as, for example, bromoacetonitrile or 4-nitrophenyloxazolinone, in the presence of $K_2CO_3$ (*J. Heterocyclic Chem.*, (1994), 31, 1439–1443). The nitrites must be reduced (lithium hydride or catalytic hydrogenation) in order to produce intermediates of general formula (XXIX)$_L$ or (XXX)$_L$. The opening of the nitrophenyloxazolinones, accessible by reaction of the corresponding nitroanilines with chloroethylchloroformate as described in the literature (*J. Am. Chem. Soc.*,(1953), 75, 4596), by phenols or thiophenols leads directly to compounds of general formula (XXIX)$_L$ or (XXX)$_L$ which are then condensed on fluoronitrobenzene in order to produce intermediates of general formula (II)$_L$.

Diagram 13

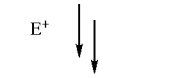

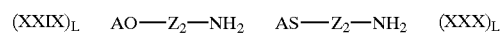

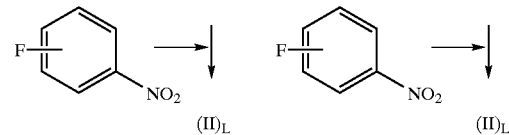

When:
X represents —$Z_1$—CO— or —CH=CH—CO—
Y=—$NR_3$—CO—Q— and
Q=$R_3$—N—$Z_3$

The acylureas of general formula (II)$_L$, diagram 14, in which A, X, Y and $R_6$ are as defined above are prepared by condensation of acids of general formula (VIII)$_L$ or (IX)$_L$, diagram 3, and ureas of general formula (XXXI)$_L$ in the presence of a coupling agent usually used in peptide synthesis, as described previously, in a solvent such as, for example, dichloromethane or DMF. The ureas of general formula (XXXI)$_L$ are accessible from isocyanates of general formula (XII)$_L$, diagram 5, according to a method in the literature (*J. Chem. Soc., Perkin Trans. I*, (1985), (1), 75–79).

Diagram 14

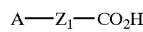

or +

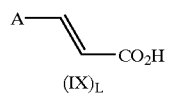

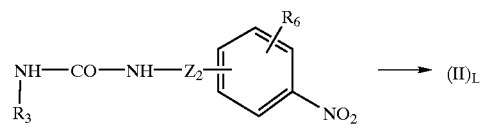

B) Preparation of Compounds of General Formula (I)$_H$

The compounds of general formula (I)$_H$ can be prepared starting from intermediates of general formula (II)$_H$, (II)$_H$ or (V)$_H$ according to diagram 15.

Diagram 15

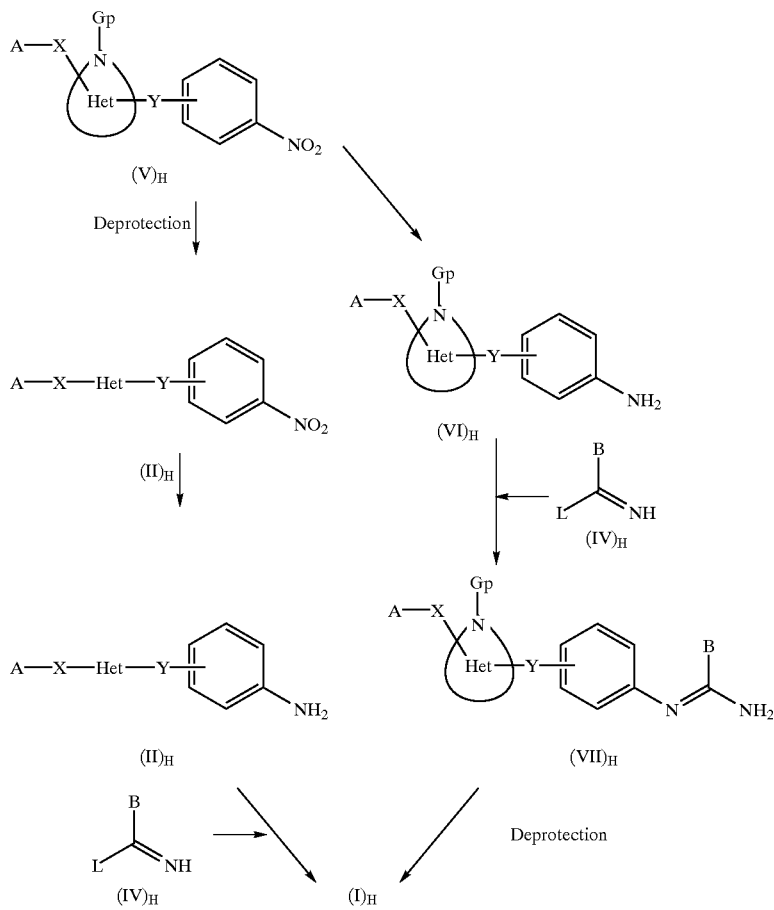

The reduction of the nitro function of the intermediates of general formula $(II)_H$ is generally carried out by catalytic hydrogenation in ethanol, in the presence of Pd/C, except when the molecules contain an unsaturation or a sulphur atom, this being a poison to the Pd/C. In this case, the nitro group is selectively reduced, for example, by heating the product in solution in ethyl acetate with a little ethanol in the presence of $SnCl_2$ (*J. Heterocyclic Chem.* (1987), 24, 927–930; *Tetrahedron Letters* (1984), 25, (8), 839–842) or by using Raney Ni with hydrazine hydrate added to it (*Monatshefte für Chemie,* (1995), 126, 725–732).

The aniline derivatives of general formula $(III)_H$ thus obtained can be condensed on derivatives of general formula $(IV)_H$, for example derivatives of O-alkyl thioimidate or S-alkyl thioimidate type, in order to produce final compounds of general formula $(I)_H$ (cf. diagram 15). For example, for B=thiophene, the derivatives of general formula $(III)_H$ can be condensed on S-methylethiophene thiocarboxamide hydriodide, prepared according to a method in the literature (*Ann. Chim.* (1962), 7, 303–337). Condensation can be carried out by heating in an alcohol (for example in methanol or isopropanol), optionally in the presence of DMF at a temperature generally comprised between 50 and 100° C. for a duration generally comprised between a few hours and overnight.

The final molecules of general formula $(I)_H$ are also accessible through another synthetic route passing through the intermediates of general formula $(V)_H$ which carry a heterocyclic amine function protected by a protective group "Gp", for example a 2-(trimethylsilyl)ethoxymethyl group (SEM) or by another protective group mentioned in: *Protective groups in organic synthesis,* 2d ed., (John Wiley & Sons Inc., 1991). The reduction and condensation stages which lead to intermediates $(VI)_H$ and $(VII)_H$ respectively are carried out under the same conditions as those described previously. The last stage of the synthesis consists in regenerating, for example in an acid medium or in the presence of a fluoride ion, the protected heterocyclic amine function.

Alternatively, the intermediates of general formula $(V)_H$ can be converted directly into the intermediate of general formula $(II)_H$ by release of the heterocyclic amine by treatment, for example, in an acid medium or in the presence of a fluoride ion.

Preparation of the Compounds of General Formula $(II)_H$, $(III)_H$ and $(V)_H$

The intermediates of general formula $(II)_H$, $(III)_H$ and $(V)_H$ can be prepared by the different synthetic routes illustrated below.

When:
  Het=nidazole, tetrahydropyridine, thiazolidine, dihydroimidazole-2-one and
  Y=—Y'—.

The amines of general formula $(II)_H$, diagram 16, in which A, X, Y and Het are as defined above, can be obtained by nucleophilic substitution of commercial halogenated derivatives of general formula $(IX)_H$ by a heterocyclic amine of general formula (VIII)$_H$. The reaction is carried out in acetonitrile, THF or DMF in the presence of a base such as K$_2$CO$_3$ at a temperature varying from 20 to 110° C. The synthesis of heterocyclic derivatives of general formula (VIII)$_H$, which are not commercially-available, is described below.

Diagram 16

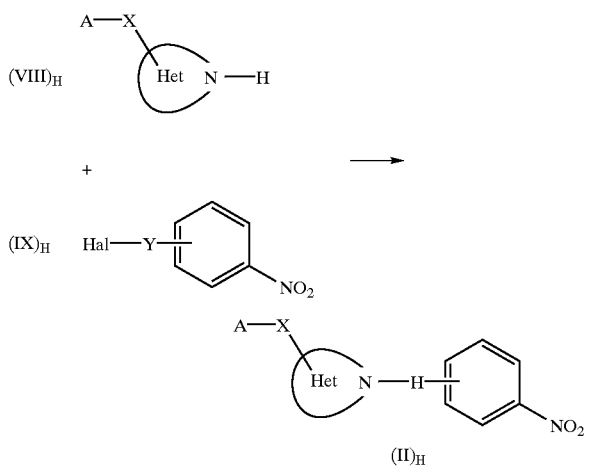

When:

Het=imidazole, thiazolidine, tetrahydropyridine and
Y=—Y'—.

The heterocyclic amines of general formula (III)$_H$, diagram 17, in which A, X, Y and Het are as defined above, are prepared in two stages starting from the amines of general formula (VIII)$_H$ (see below). The mixture of a brominated derivative of general formula (X)$_H$, the synthesis of which is explained in detail below, with an amine of general formula (VIII)$_H$ in a solvent such as acetonitrile or DMF in the presence of a base leads to intermediates of general formula (XI)$_H$. The deprotection of the amine function, in an organic acid medium, allows the compounds of general formula (III)$_H$ to be obtained.

Diagram 17

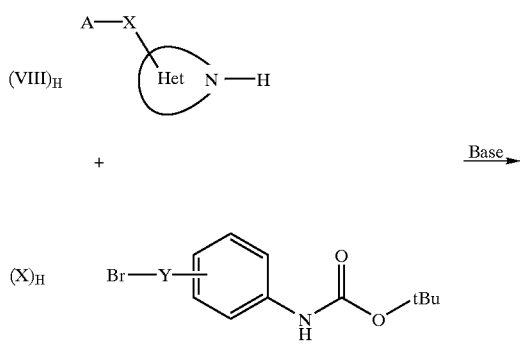

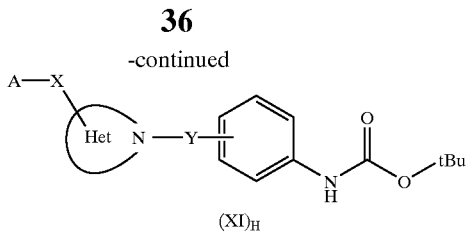

When:
Het thiazolidine and
Y=—CO—Y'—.

The carboxamides of general formula (III)$_H$, diagram 18, in which A, X, Y and Het are as defined above, are prepared by condensation of the amines of general formula (VIII)$_H$, decribed previously, with the carboxylic acids of general formula (X.2)$_H$. The carboxamide bonds are formed under standard conditions of peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1,1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)). The synthesis of the carboxylic acids of general formula (X.2)$_H$ is described below. The intermediates of general formula (XII)$_H$ are then deprotected in an acid medium using, for example, trifluroroacetic acid or an organic solution of HCl.

Diagram 18

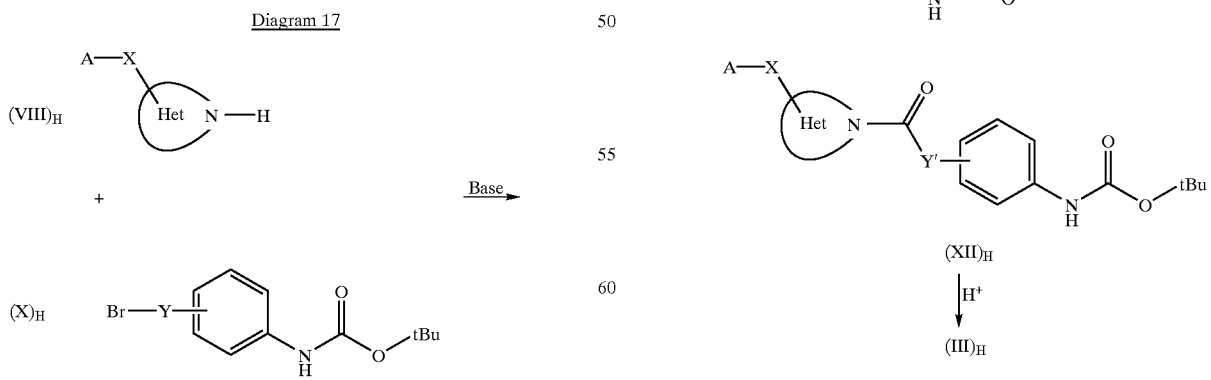

When:
Het=thiazolidine and
Y=—CO—NH—Y'—.

The carboxamides of general formula (V)$_H$, diagram 19, in which A, X, Y and Het are as defined above, are prepared by condensation of carboxylic acids of general formula (XIII)$_H$ with the commercial amines of general formula (XIV)$_H$ under standard conditions for peptide synthesis. The synthesis of the carboxylic acids of general formula (XIII)$_H$ is described below.

Diagram 19

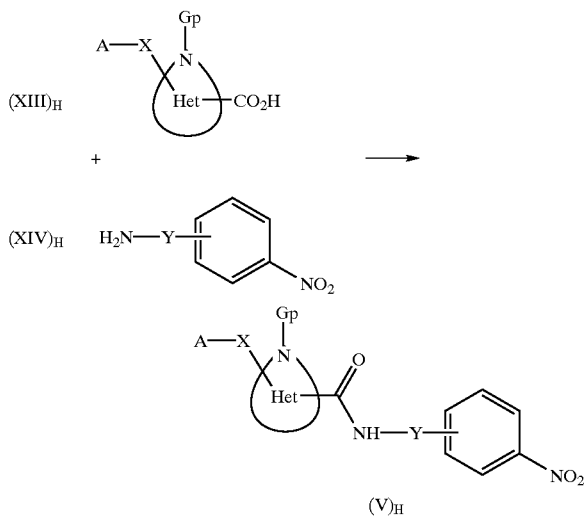

(V)$_H$

When:
Het=thiazole, furan, pyrrole, tetrahydropyridine, pyrrolidine and
X=—NH—CO—X'—.

The carboxamides of general formula (II)$_H$, diagram 20, in which A, X, Y and Het are as defined above, are prepared by condensation of anilines of general formula (XV)$_H$ with the carboxylic acids of general formula (XVI)$_H$ under standard conditions for peptide condensation. The anilines of general formula (XV)$_H$ are obtained by hydrogenation, in the presence of a catalytic quantity of Pd/C, of corresponding nitrobenzene derivatives, themselves synthesized according to a method described in the literature (*J. Org. Chem.* (1968), 33 (1), 223–226). The acids of general formula (XVI)$_H$, diagram 20, which are not commercially available, are prepared according to methods described in the literature.

The synthesis of pyrroles is described in *Chem. Heterocycl. Compd.*, 1982, 18, 375. The substitued prolines are accessible starting from commercial hydroxyprolines and are prepared according to methods described in *J. Org. Chem.*, 1991, 56, 3009. The synthesis of the thiazole and tetrahydropyridine derivatives is described below.

Diagram 20

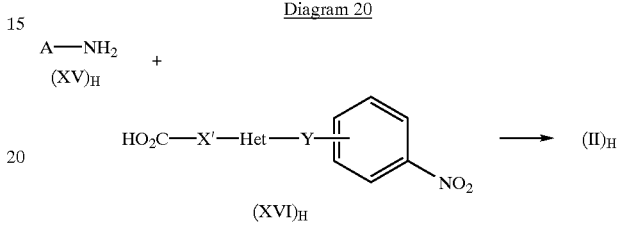

When:
Het hydantoin and
Y=—Y'—.

The hydantoins of general formula (II)$_H$, diagram 21, in which A, X, Y and Het are as defined above, are prepared in 3 stages starting from the anilines of general formula (XV)$_H$ described previously. The substitution of the aniline by ethyl bromoacetate is carried out in the presence of sodium acetate in ethanol at a temperature of approximately 60–70° C. The monosubstitution product of general formula (XVH)$_H$ is then condensed on an isocyanate of general formula (XVIII)$_H$ in an organic solvent such as, for example, dichloromethane, at a temperature of approximately 20° C. The cyclization of urea (XIX)$_H$ is carried out by heating, at 50° C., in ethanol, according to an experimental protocol described in the literature (*J. Heterocyclic Chem.*, (1979), 16, 607–608). The isocyanates of general formula (XVIII)$_H$ are synthesised starting from the corresponding commercial primary amines, triphosgene and a tertiary amine (*J. Org. Chem.* (1994), 59 (7), 1937–1938).

Diagram 21

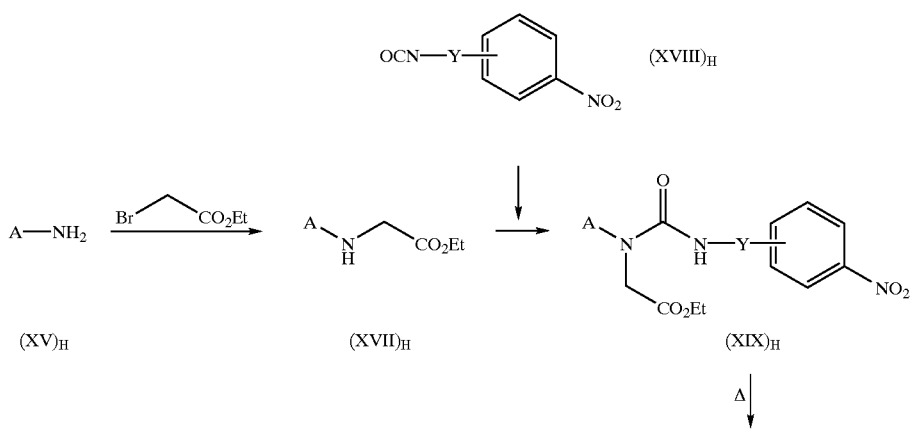

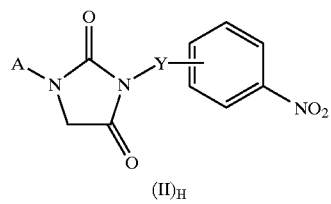

(II)$_H$

When:

Het=thiazolidinone and

Y=—Y'—.

The thiazolidinones of general formula (II)$_H$, diagram 22, in which A, X, Y and Het are as defined above, are prepared starting from commercial amines of general formula (XIV)$_H$ and aldehydes of general formula (XX)$_H$ in the presence of mercaptoacetic acid according to an experimental protocol described in the literature (*J. Med. Chem.*, (1992), 35, 2910–2912).

Diagram 22

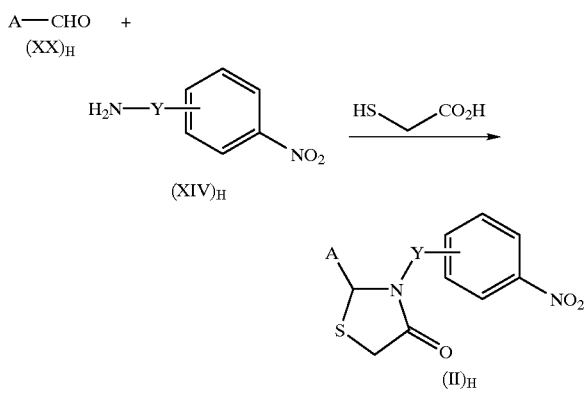

When:

Het=hydantoin

X=—CH= and Y=—Y'—.

The hydantoines of general formula (II)$_H$, diagram 23, in which A, X, Y and Het are as defined above, are prepared in 2 stages starting from the isocyanates of general formula (XVIII)$_H$ described previously. The reaction of the ethyl ester of sarcosine with the isocyanates of general formula (XVIII)$_H$, is carried out according to an experimental protocol described in the literature (*J. Heterocyclic Chem.*, (1979), 16, 607–608), leads to the formation of the heterocycle of the compounds of general formula (XXI)$_H$. The substitution of the hydantoin is carried out in the presence of a weak base, β-alanine, and an aldehyde of general formula (XX)$_H$ according to the experimental conditions described in *J. Med. Chem.*, (1994), 37, 322–328.

Diagram 23

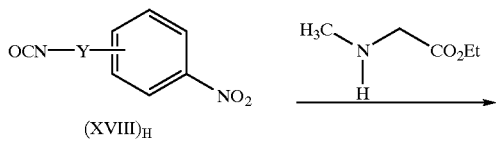

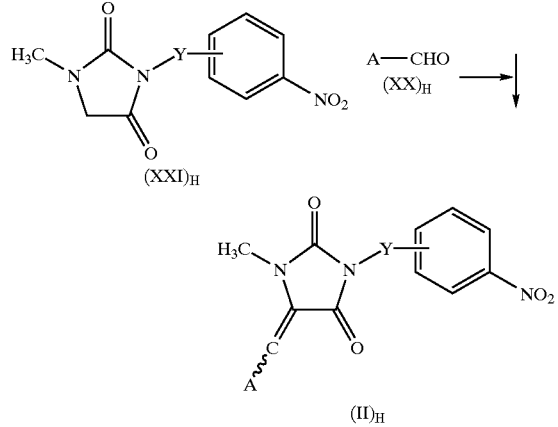

When:

Het=pyrrolidine, thiazolidine

X=—NH—CO—X'— and Y—O—Y'— or —Y'—.

The carboxamides of general formula (V)$_H$, diagram 24, in which A, X, Y and Het are as defined above, are prepared by condensation of the anilines of general formula (XV)$_H$, described previously, with the acids of general formula (XXII)$_H$ under standard conditions for peptide synthesis. The syntheses of carboxylic acids (XXII)$_H$, which are nont commercially available, are described below.

Diagram 24

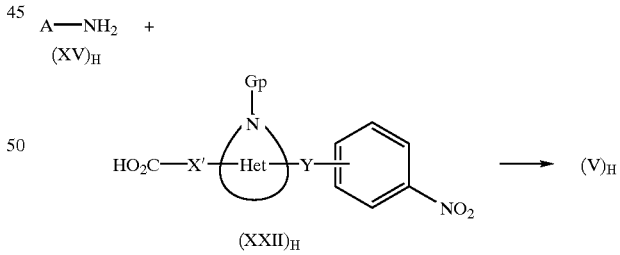

When:

Het=tetrahydropyridine and

Y=—CO—NH—Y'—.

The ureas of general formula (II)$_H$, diagram 25, in which A, X, Y and Het are as defined above, are prepared by condensation of the heterocyclic amines of general formula (VIII)$_H$, described previously, with the isocyanates of general formula (XVIII)$_H$ (cf. above) in a solvent such as dichloromethane, at 20° C., in the presence of a tertiary amine (e.g. diisopropylethylamine).

Diagram 25

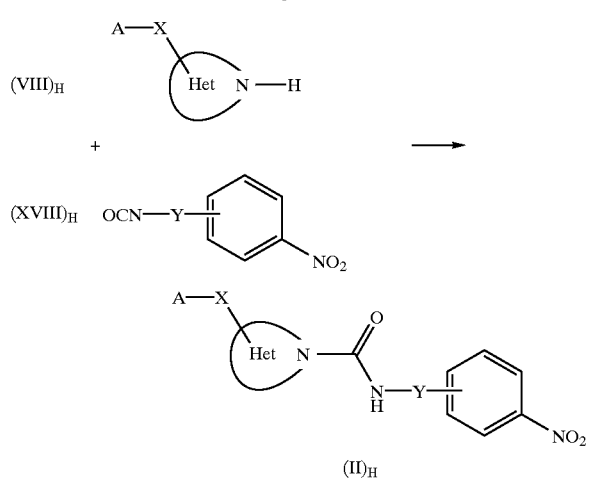

When:

Het=pyrrolidine, thiazole, thiadiazole and

X=—CO—NH—X'—.

The carboxamides of general formula (II)$_H$, diagram 26, in which A, X, Y and Het are as defined above, are prepared by condensation of commercial carboxylic acids of general formula (XXIII)$_H$ with the amines of general formula (XXIV)$_H$ under standard conditions for peptide synthesis. The syntheses of the amines of general formula (XXIV)$_H$, which are not commercially available, are described below.

Diagram 26

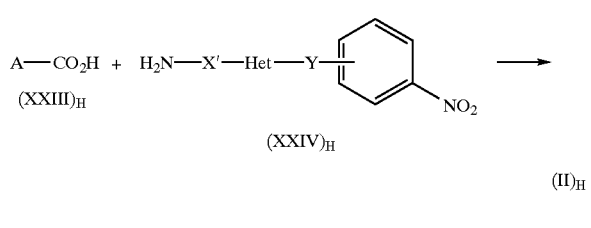

When:

Het=imidazole, oxazole and thiazole and

Y=—CH($R_3$)—N($R_3$)—CO—Y'—.

The carboxamides of general formula (V)$_H$, diagram 27, in which A, X, Y and Het are as defined above, are prepared by condensation of the amines of general formula (XXV)$_H$ with commercial carboxylic acids (or the corresponding acid chlorides) of general formula (XXVI)$_H$ under standard conditions for peptide synthesis. The synthesis of the imidazole derivatives of general formula (XXV)$_H$ is described below.

Diagram 27

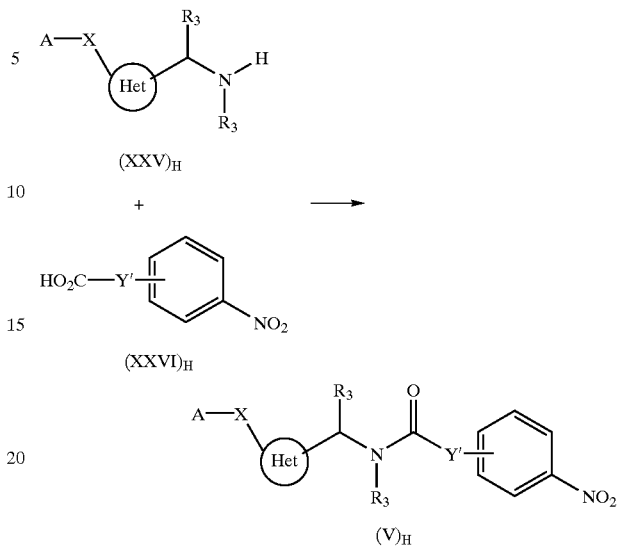

When:

Het=imidazole and

Y=—$CH_2$—N($R_3$)—Y'—.

The amines of general formula (V)$_H$, diagram 28, in which A, X, Y and Het are as defined above, are prepared by condensation of the amines of general formula (XXV)$_H$ (see below) with the commercial halogenated derivatives of general formula (IX)$_H$ under the conditions described previously.

Diagram 28

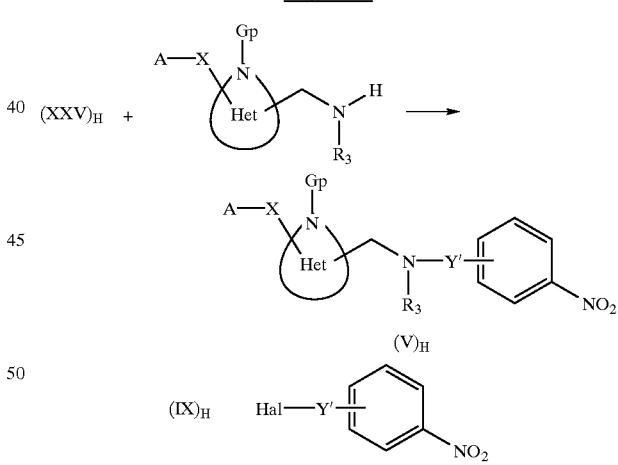

When:

Het=dihydroimidazole-2-one and

Y=—CO—Y'.

The amines of general formula (II)$_H$, diagram 29, in which A, X, Y and Het are as defined above, are prepared by condensation of the amines of general formula (VIII)$_H$ (see below) with the commercial halogenated derivatives of general formula (XXVII)$_H$, for example in an acetonitrile and THF mixture and in the presence of a base such as

Diagram 29

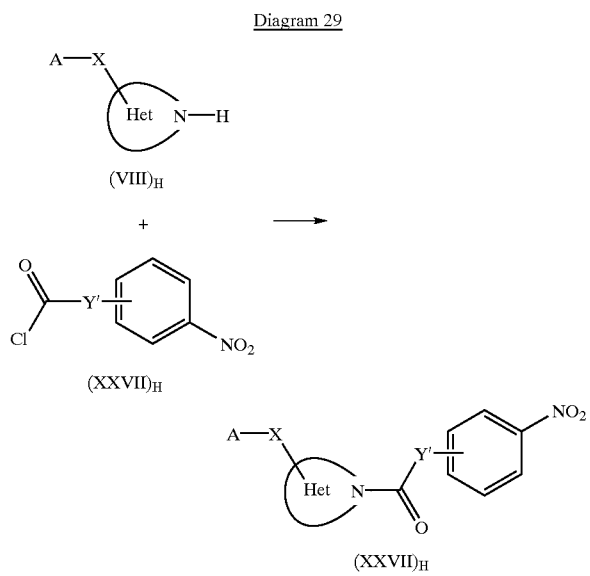

When:
Het=oxazolidinone and
Y=—Y'—O—.

The oxazolidinones of general formula (II)$_H$, diagram 30, are prepared starting from the diols of general formula (XXVII)$_H$ the synthesis of which is described in the literature (Daumas, M., *Tetrahedron*, 1992, 48(12), 2373). The formation of carbonates of general formula (XXVIII)$_H$ is obtained, for example, in the presence of carbonyl di-imidazole (Kutney, J. P., *Synth. Commun.*, 1975, 5(1), 47) or in the presence of triphosgene at low temperature as described in *Synth. Commun.*, 1994, 24(3), 305. The formation of oxazolidinone occurs during heating of the amines of general formula (XV)$_H$ with the carbonates of general formula (XXVIII)$_H$ in the presence of an acid catalyst, such as ZnCl$_2$, to xylene reflux in order to eliminate the water formed during the reaction (Laas, H., *Synthesis*, 1981, 958).

When:
Het=isoxazoline, isoxazole, oxazole, thiazole and
Y=—Y'—CO—NH—Y'—

The carboxamides of general formula (II)$_H$, diagram 31, in which A, X, Y and Het are as defined above, can be prepared starting from the commercial amines of general formula (XIV)$_H$ and the carboxylic acids of general formula (XXVIII)$_H$ by condensation in the presence of isobutyl chloroformate (*Org. Prep. Proced. Int.*, (1975), 7, 215).

The preparation of the oxazoles of general formula (XXVIII)$_H$ is carried out according to an experimental protocol described in *Tetrahedron Lett.*, 1994, 35 (13), 2039. Similarly for the synthesis of the thiazoles of general formula (XXVIII)$_H$: *J. Med. Chem.*, 1983, 26, 884. The preparation of the isoxazolines is described below.

Diagram 31

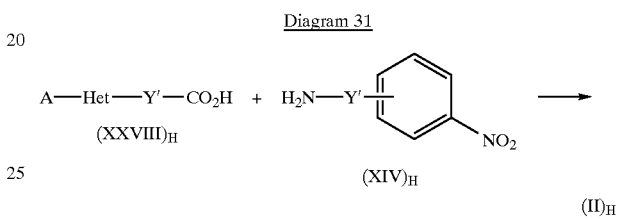

When:
Het=pyrrolidine, piperidine
X=—CO—NH— and
Y=—O—Y'—.

The carboxamides of general formula (II)$_H$, diagram 32, in which A, X, Y and Het are as defined above, can be prepared by condensation of the commercial carboxylic acids of general formula (XXIII)$_H$ with the amines of general formula (XXIX)$_H$ under standard conditions for peptide synthesis. The syntheses of amines of general formula (XXIX)$_H$ are described below.

Diagram 30

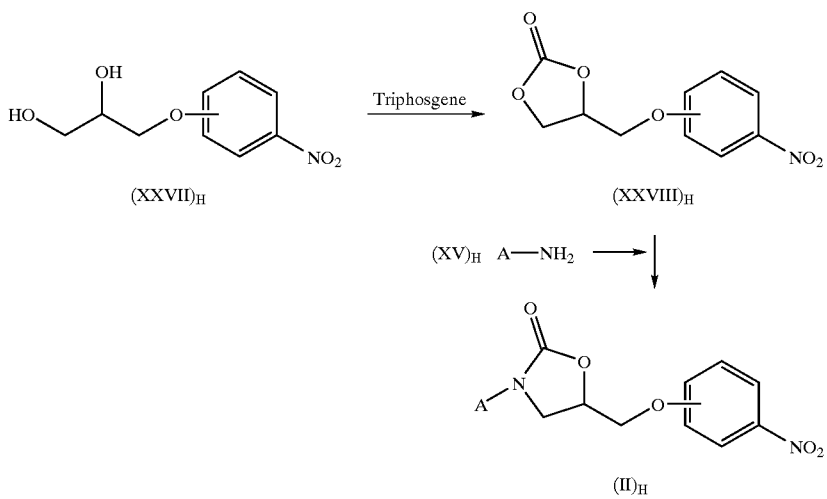

Diagram 32

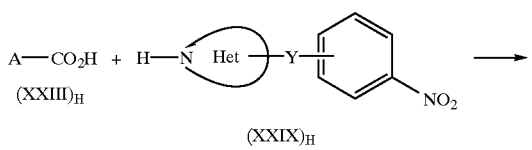

When:

Het isoxazoline, oxazole, thiazole, imidazole and

Y=—Y'—O—Y'— or —Y'—N(R$_3$)—Y'—.

The etheroxides of general formula (II)$_H$, Diagram 33, in which A, X, Y and Het are as defined above, can be prepared starting from the esters of general formula (XXVIII.4)$_H$, diagram 31.1, by reaction with hydrides, for example LiAlH$_4$, in a solvent such as, for example, anhydrous THF. The primary alcohols thus obtained are then condensed on halogenated derivatives of general formula (IX)$_H$ using a base such as for example KOH in an organic medium and in the presence of a phase tranfer catalyst such as for example Aliquat 336.

The primary alcohols (XXXI)$_H$ can also be activated in the form of sulphonate derivatives, by tosyl chloride in the presence of pyridine, in order to produce intermediates of general formula (XXXII)$_H$. The condensation of alcohols of general formula (XXII.2)$_H$ is then carried out in the presence of a strong base, such as, for example, NaH, in an aporotic solvent (THF or DMF) at a temperature comprised between 20° C. and 80° C., in order to obtain the ether oxide of general formula (II)$_H$.

Similarly, the amines of general formula (II)$_H$, diagram 33, are obtained by the substitution of the tosylate function of the intermediates of general formula (XXXII)$_H$, obtained in a standard fashion starting from the alcohols of general formula (XXXI)$_H$ and tosyl chlosride in the presence of pyridine, by the commercial amines of general formula (XXX)$_H$ by reaction in a solvent such as, for example, acetonitrile or DMF, in the presence of a base (K$_2$CO$_3$) at a temperature comprised between 20 and 85° C.

Diagram 33

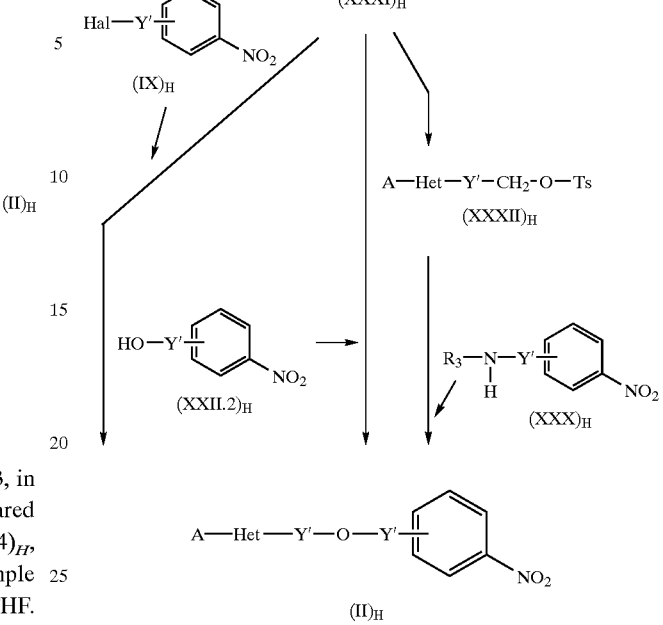

When:

Het=azetidine

X=—CO—NH— and

Y=—O—Y'—.

The carboxamides of general formula (III)$_H$, diagram 34, in which A, X, Y and Het are as defined above, can be prepared by condensation of commercial carboxylic acids of general formula (XXIII)$_H$ with the amines of general formula (XXXII)$_H$ under standard conditions for peptide synthesis. The synthesis of amines of general formula (XXXII)$_H$ is descried below. The deprotection of the aniline is carried out by a strong acid such as, for example, trifluoroacetic acid optionally in the presence of triethylsilane.

Diagram 34

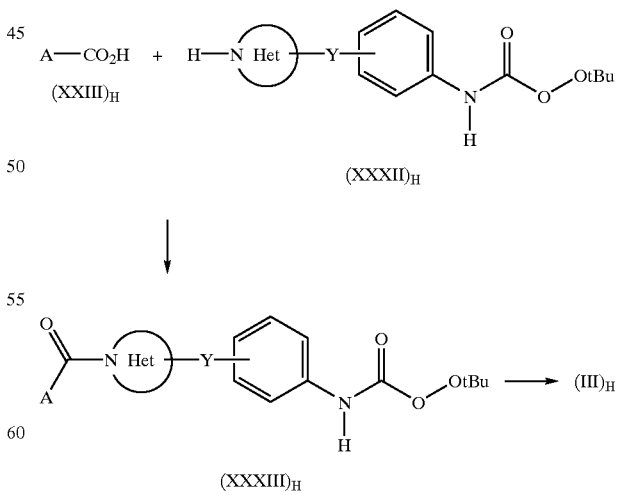

When:

Het=azetidine

X=—NH—CO—X'— and

Y=—O—Y'—.

The ureas of general formula (III)$_H$, diagram 35, in which A, X, Y and Het are as defined above, can be prepared by the addition of the amines of general formula (XXXII)$_H$ on the isocyanates (XXXIV)$_H$ obtained from the reaction of the amines of general formula (XV)$_H$ with triphosgene in the presence of a tertiary anmine such as for example diisopropylethylamine in a neutral solvent such as dichloromethane (*J. Org. Chem.* (1994), 59 (7), 1937–1938). The ureas of general formula (XXXV)$_H$ thus obtained are deprotected by treatment in a strong acid medium as described previously. The synthesis of the aines of general formula (XXXII)$_H$ is described below.

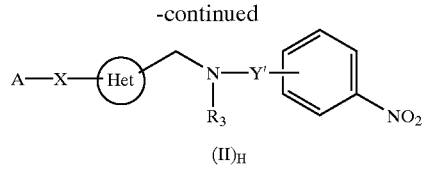

(II)$_H$

Preparation of Different Synthesis Intermediates

Synthesis of Intermediates (VIII)$_H$

The syntheses of the intermediates of general formula (VIII)$_H$ are illustrated in diagrams 16.1 and 16.2.

The intermediates of general formula (VIII)$_H$, diagram 16.1, can be prepared, for example, in 3 stages starting from 4-imidazole carboxylic acid. The protection of the nitrogen Diagram 35

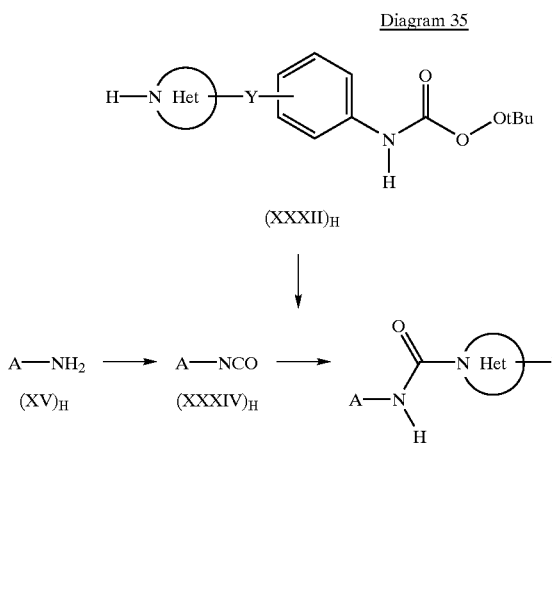

When:

Het=thiazole and

Y=—CH$_2$—N(R$_3$)—Y'—.

The amines of general formula (II)$_H$, diagram 36, in which A, X, Y and Het are as defined above, are prepared by condensation of the amines of general formula (XXV)$_H$ (see below) with the commercial halogenated derivatives of general formula (IX)$_H$ under the conditions described previously.

of the heterocycle is carried out using (Boc)$_2$O in the presence of a base such as K$_2$CO$_3$ in DMF. The condensation with the amines of general formula (XV)$_H$ (see above) is carried out in a standard fashion under the conditions for peptide synthesis in order to produce the intermediates of general formula (VIII.3)$_H$. The amine of the heterocycle is regenerated by treatment in an acid medium and in particular with trifluoroacetic acid in order to produce the intermediates of general formula (VIII)$_H$.

Diagram 16.1

Diagram 36

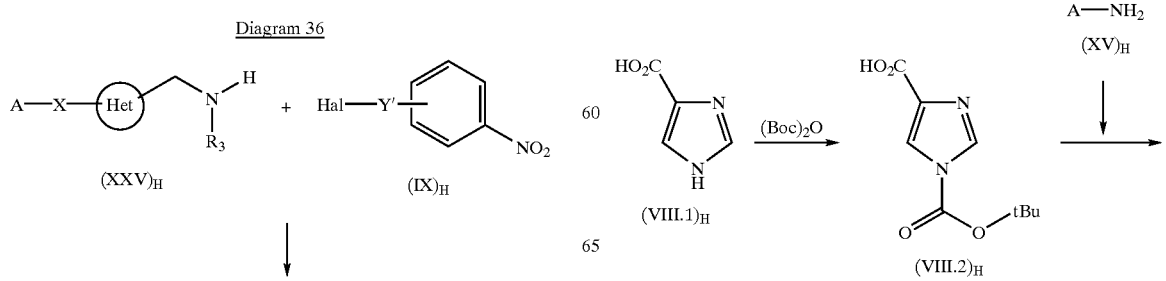

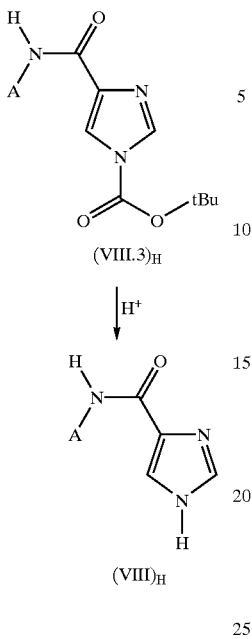

The dihydroimidazole-2-ones of general formula (VIII)$_H$, diagram 16.2, can be prepared, for example, in 2 stages starting from the anilines of general formula (XV)$_H$ (see above) which are condensed on 2-chloroethyl isocyanate in DMF at 20° C. in order to produce the ureas of general formula (VIII.4)$_H$. The cyclization to produce (VIII)$_H$ is then carried out by treatment in a basic medium using, for example, tBuOK in DMF.

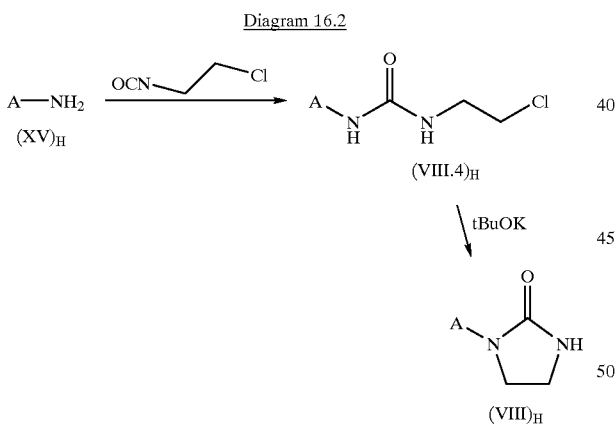

Synthesis of Intermediates (X)$_H$

The intermediates of general formula (X)$_H$, diagram 17.1, can be prepared starting from commercial carboxylic acids of general formula (X.1)$_H$. Protection of the amine function in the form of a carbamate is followed by the selective reduction of the carboxylic acid function by lithium and aluminium hydride in a solvent such as THF, at 20° C. Intermediaite (X.3)$_H$ is then brominated in the presence of carbon tetrabromide and triphenylphosphine in a solvent such as dichloromethane.

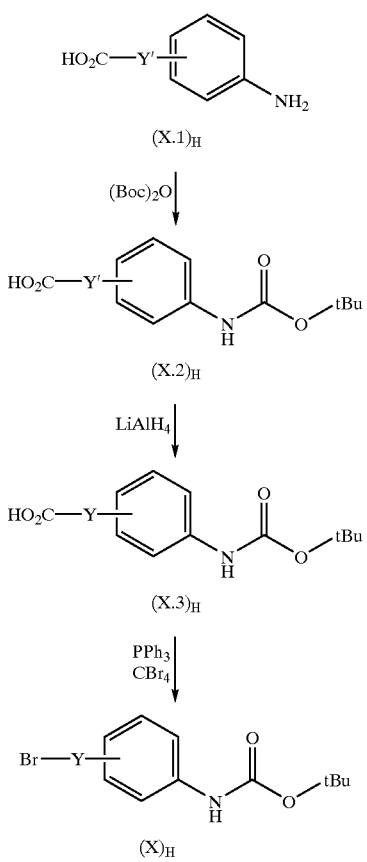

Synthesis of Intermediates (XIII)$_H$

The intermediates of general formula (XIII)$_H$, diagram 19.1, can be prepared starting from (R or S) derivatives of thiazolidine carboxylic acids in the presence of (Boc)$_2$O under standard conditions.

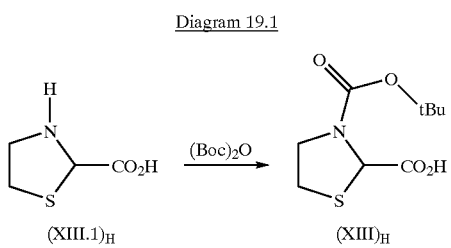

Synthesis of Intermediates (XVI)$_H$

The intermediates of general formula (XVI)$_H$, diagram 20.1, can be prepared starting from commercial carboxamide derivatives of general formula (XVI.1)$_H$. These carboxainides are treated by a Lawesson reagent in a solvent such as 1,4-dioxane for 2 to 3 hours at a temperature which varies from 25° C. to reflux temperature of the mixture. The thiocarboxamides of general formula (XVI.2)$_H$ are then treated by ethyl bromopyruvate, at 20° C. in DMF according to an experimental protocol described in *J. Med. Chem.*, (1983), 26, 884–891, in order to produce the thiazoles of general formula (XVI.3)$_H$. The saponification of the ester is carried out over 15 hours by aqueous potash in solution in acetone.

Diagram 20.1

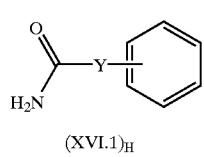
(XVI.1)$_H$

Lawesson's reagent →

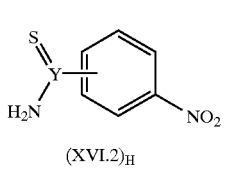
(XVI.2)$_H$

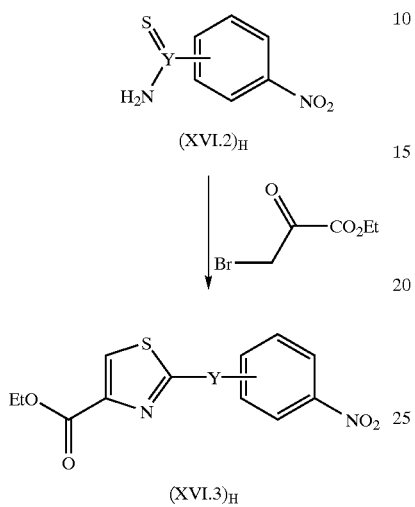

(XVI.3)$_H$

↓ KOH (XVI)$_H$

The tetrahydropyridines of general formula (XVI)$_H$, diagram 20.2, can be prepared starting from commercial tetrahydro-4-pyridine carboxylicacid. Esterification is carried out in a standard fashion in the presence of para-toluene sulphonic acid, in methanol, in order to produce to, the intermediaire (XVI.4)$_H$ which is then condensed on a halogenated derivative of general formula (IX)$_H$ under the conditions described previously. The acid of general formula (XVI)$_H$ is obtained by saponification in the presence of, for example, LiOH or KOH.

Diagram 20.2

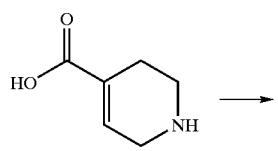

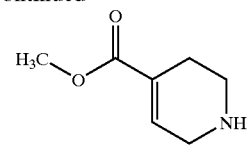
(XVI.4)$_H$

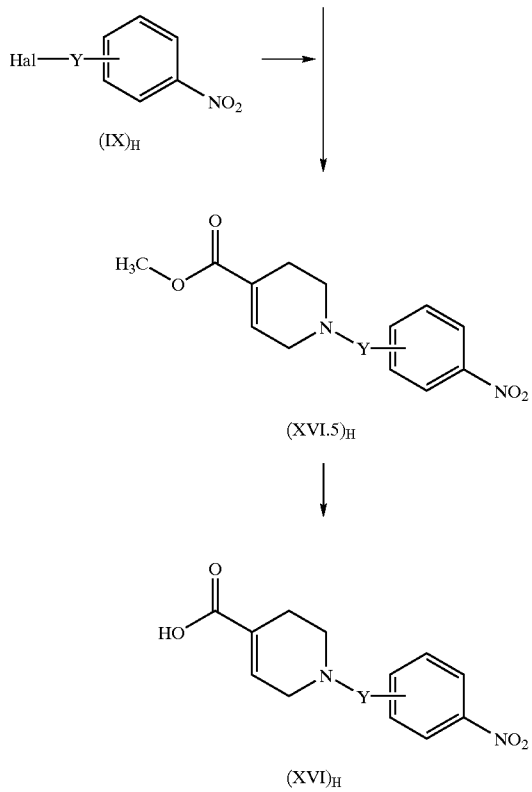
(XVI.5)$_H$ (XVI)$_H$

Synthesis of Intermediates (XXII)$_H$

The syntheses of intermediates of general formula (XXII)$_H$ are described in diagrams 10.1 and 10.2.

The tosyylate function of the (L or D) proline derivatives of general formula (XXII.1)$_H$ (Tetrahedron Lett., (1983), 24 (33), 3517–3520), diagram 24.1, is substituted by the alcoholate of the derivaties of general formula (XXII.2)$_H$, generated in situ by a base such as NaH. The substitution is carried out at 20° C. in a solvent such as N-methylpyrrolidinone which produces the appropriate inversion of the configuration of the carbon seat of the reaction (Tetrahedron Lett., (1983), 24 (33), 3517–3520). The intermediates of general formula (XXII.3)$_H$ thus obtained are then saponified in a standard fashion by alcoholic potash.

Diagram 24.1

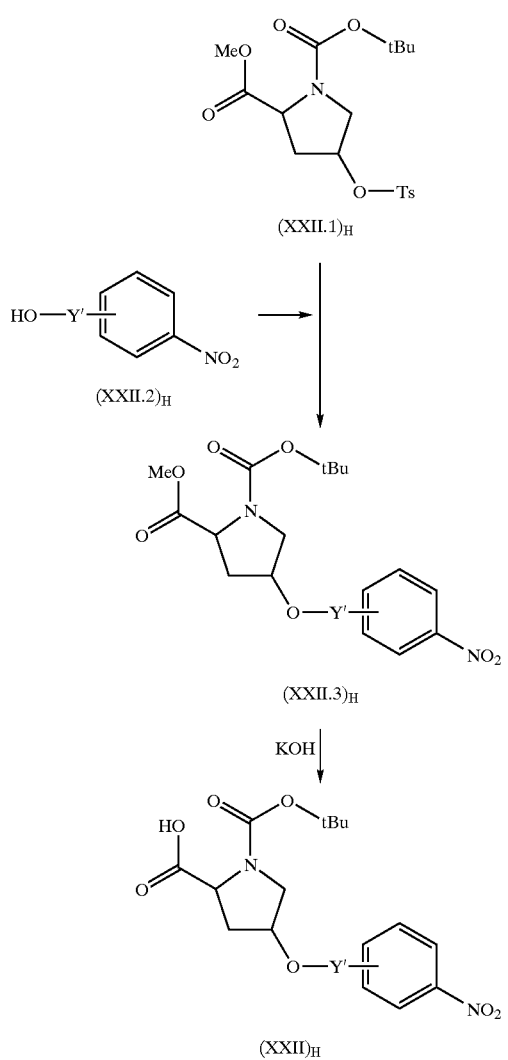

The intermediates of general formula (XXII)$_H$ can also be prepared (diagram 24.2) starting from the condensation of cysteine (L or D) on an aldehyde of general formula (XXII.5)$_H$ according to an experimental protocol described in the literature (*J. Org. Chem.,* (1957), 22, 943–946). The amine of the heterocycle is then protected in the form of a carbamate in order to produce intermediates of general formula (XXII)$_H$. The aldehydes of general formula (XXII.5)$_H$, which are not commercially available, can be prepared according to *J. Chem. Soc., Perkin Trans. I*, 1973, 1, 35.

Diagram 24.2

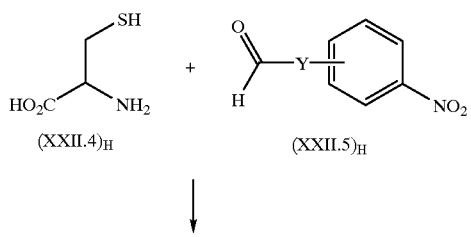

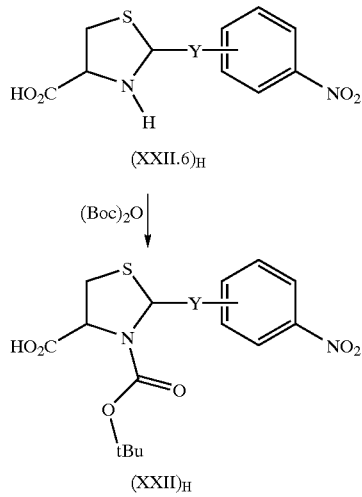

Synthesis of Intermediates (XXIV)$_H$

The synthesis of intermediates of general formula (XXIV)$_H$ is described in diagram 26.1.

The condensation of the amines (R or S) of general formula (XXIV.1)$_H$, diagram 26.1, on the halogenated derivatives of general formula (IX)$_H$ is carried out in the presence of a base such as potassium carbonate in a solvent such as DMF. The condensation product (XXIV.2)$_H$ is then deprotected in an acid medium in order to produce intermediates of general formula (XXIV)$_H$.

Diagram 26.1

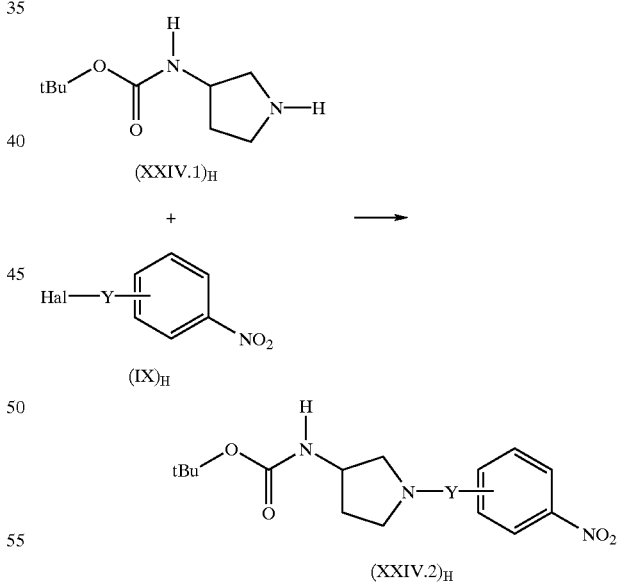

Synthesis of Intermediates $(XXV)_H$

The syntheses of intermediates of general formula $(XXV)_H$ are described in diagrams 27.1, 27.2, 27.3 and 27.4.

The imidazoles of general formula $(XXV)_H$, diagram 27.1, can be prepared in 4 stages starting from the commercial compounds $(XXV.1)_H$ and $(XXV.2)_H$. The condensation between the bromoacetophenones of general formula $(XXV.1)_H$ and the carboxylic acids of general formula $(XXV.2)_H$ is carried out in the presence of Caesium carbonate in DMF. The ketoester obtained $(XXV.3)_H$ is cyclized in the presence of 15 equivalents of ammonium acetate by heating in a mixture of xylenes and simultaneous elimination of the water formed during the reaction in order to produce the imidazoles of general formula $(XXV.4)_H$. The nitrogen of the heterocycle is then protected, for example using 2-(trimethylsilyl)ethoxymethyl (SEM) or by another protective group mentioned in: *Protective groups in organic synthesis*, 2nd ed., (John Wiley & Sons Inc., 1991), in order to produce intermediates of general formula $(XXV.5)_H$. The release of the amine from the chain can be carried out by hydrogenolysis in the presence of Pd/C.

Alternatively, the intermediates of general formula $(XXV.4)_H$ can be alkylated in the presence of a base such as, for example, $K_2CO_3$, and a reagent such as $R_3$—X in a solvent such as DMF or acetonitrile in order to produce the imidazoles of general formula $(XXV.6)_H$. Deprotection of the side chain, as described previously, allows the intermediates of general formula $(XXV)_H$ to be accessed.

Diagram 27.1

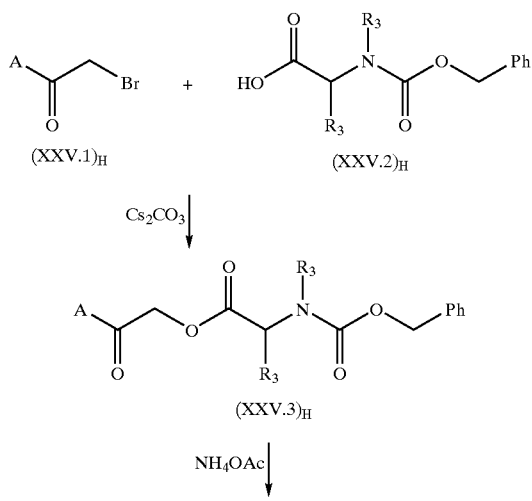

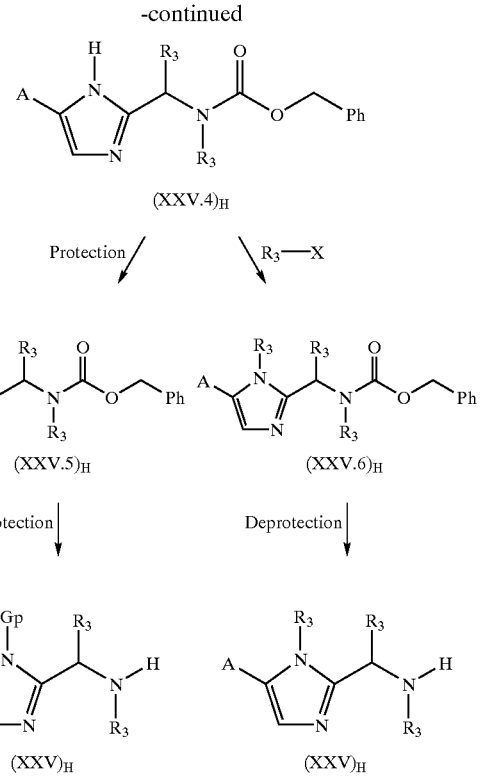

The intermediates of general formula $(XXV)_H$ containing an oxazole, thiazole or an imidazole are also accessible via other synthetic routes such as that described in *Bioorg. and Med. Chem. Lett.*, 1993, 3, 915 or *Tetrahedron Lett.*, 1993, 34, 1901. The intermediates of general formula $(XXV.7)_H$ thus obtained can be modified, diagram 27.2, by saponification followed by decarboxylation, for example thermic, in order to produce disubstituted heterocycles of general formula $(XXV.9)_H$. Release of the amine from the side chain, as described previously, allows the intermediates of general formula $(XXV)_H$ to be accessed.

Diagram 27.2

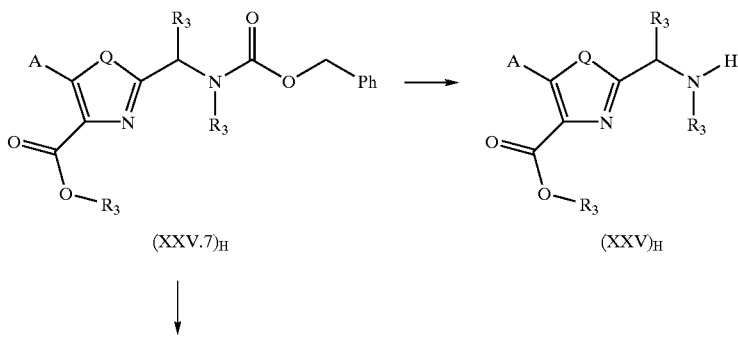

-continued

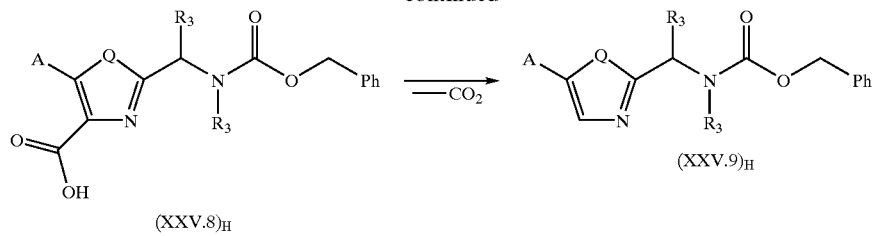

(XXV.8)$_H$   (XXV.9)$_H$

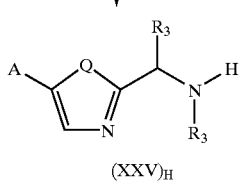

Q = O, N or S (XXV)$_H$

Alternatively, the carboxylic function of the heterocycles of general formula (XXV.7)$_H$, can be reduced, for example by NaBH$_4$, in order to produce alcoholic derivatives of general formula (XXV.10)$_H$, diagram 27.3, which can be alkylated in the presence of R$_3$—X and a base such as K$_2$CO$_3$ in a solvent such as acetonitrile or DMF. Release of the amine from the side chain, as described previously, allows the intermediates of general formula (XXV)$_H$ to be accessed.

Diagram 27.3

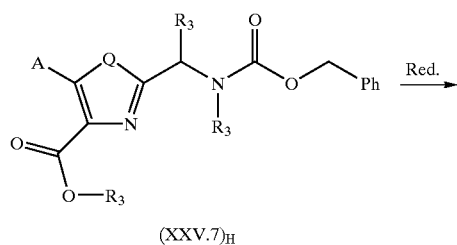

(XXV.7)$_H$

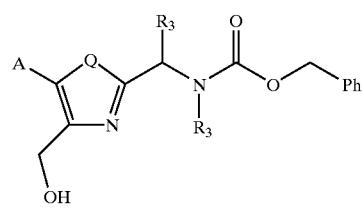

(XXV.10)$_H$

Q = O, N or S

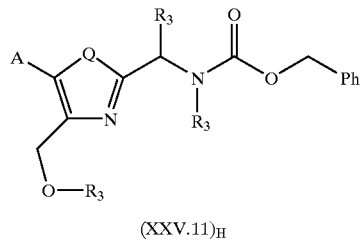

(XXV.11)$_H$

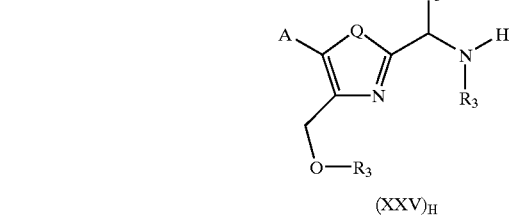

(XXV)$_H$

The thiazoles of general formula (XXV)$_H$, diagram 27.4, can also be prepared in 4 stages starting from commercial sarcosinamide hydrochloride. The amine is first protected in a standard fashion in the form of tBu carbamate and the carboxamide function is converted into thiocarboxamide in the presence of Lawesson reagent. The formation of the thiazole ring is carried out by the reaction of thiocarboxamide with the intermediate of general formula (XXV.1)$_H$ according to an experimental protocol described in the literature (J. Org. Chem., (1995), 60, 5638–5642). The amine function is regenerated by treatment with the intermediate of general formula (XXV.12)$_H$ in a strong acid medium such as, for example, trifluoroacetic acid.

Diagram 27.4

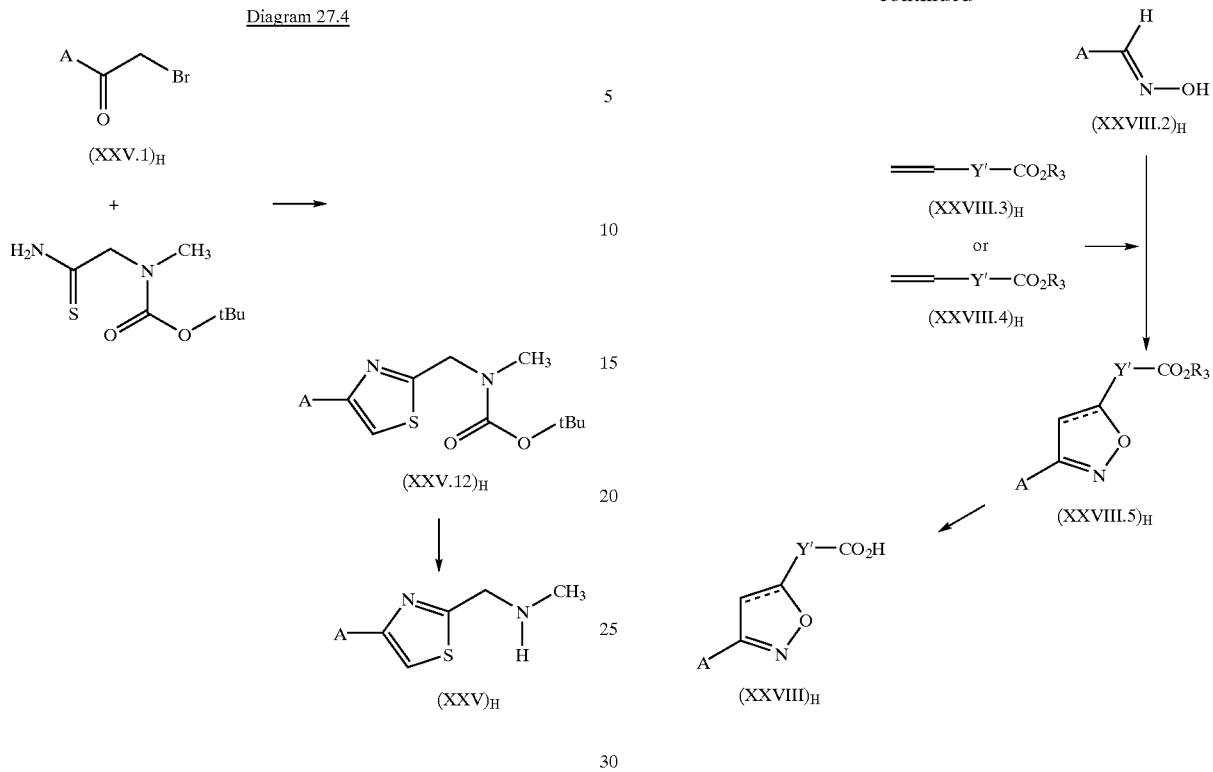

Synthesis of Intermediates $(XXVIII)_H$

The isoxazolines and isoxazoles of general formula $(XXVIII)_H$, Diagram 31.1, are prepared by reaction of commercial aldehydes of general formula $(XX)_H$ with hydroxylamine hydrochloride. The oxime of general formula $(XXVIII.1)_H$ thus obtained is activated in the form of the oxime chloride, of general formula $(XXVIII.2)_H$, by reaction with N-chlorosuccinimide in DMF before reacting with the esters of general formula $(XXVIII.3)_H$ in order to produce isoxazoline derivatives or with the esters of general formula $(XXVIII.4)_H$ in order to produce isoxazole derivatives according to an experimental protocol described in the literature (*Tetrahedron Lett.*, 1996, 37 (26), 4455; *J. Med. Chem.*, 1997, 40, 50–60 and 2064–2084). Saponification of the isoxazolines or isoxazoles of general formula $(XXVIII.5)_H$ is then carried out in a standard fashion under the conditions described previously.

The unsaturated esters of general formula $(XXVIII.3)_H$ and $(XXVIII.4)_H$, which are not commercially available, can be prepared according to methods described in the literature (*J. Med. Chem.*, 1987, 30, 193; *J. Org. Chem.*, 1980, 45, 5017).

Diagram 31.1

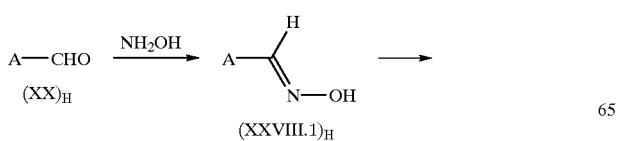

Synthesis of Intermediates $(XXIX)_H$

The syntheses of intermediates of general formula $(XXIX)_H$ are described in diagrams 32.1, 32.2, 32.3 and 32.4.

The intermediates of general formula $(XXIX)_H$ can be prepared, diagram 32.1, starting from the intermediates of general formula $(XXII.3)_H$, described previously, by treatment in a strong acid medium to regenerate the heterocyclic amine function. The selective reduction of the carboxylic function in the presence of, for example, sodium borohydride in a solvent such as, for example, anhydrous THF, allows the intermediate of general formula $(XXIX)_H$ carrying a primary alcohol function to be obtained without touching the nitro group (Rao, A. V. R., *J. Chem. Soc. Chem. Commun.*, 1992, 11, 859).

Diagram 32.1

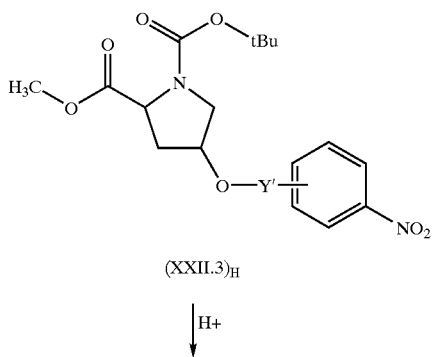

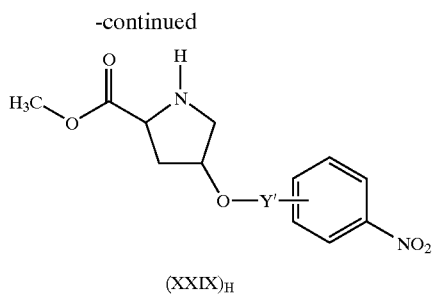

(XXIX)$_H$

↓ red.

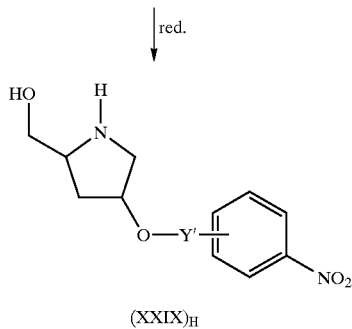

(XXIX)$_H$

The intermediates of general formula (XXIX)$_H$ can also be prepared, diagram 32.2, starting from intermediates of general formula (XXIX.1)$_H$ (R or S) the preparation of which is similar to that of the compounds of general formula (XXII.1)$_H$. Condensation of the alcoholic derivatives of general formula (XXII.2)$_H$ on the intermediates of general formula (XXIX.1)$_H$ is also described above. Release of the heterocyclic amine is carried out in the presence of an organic solution of a strong acid, for example, trifluoroacetic acid.

Diagram 32.2

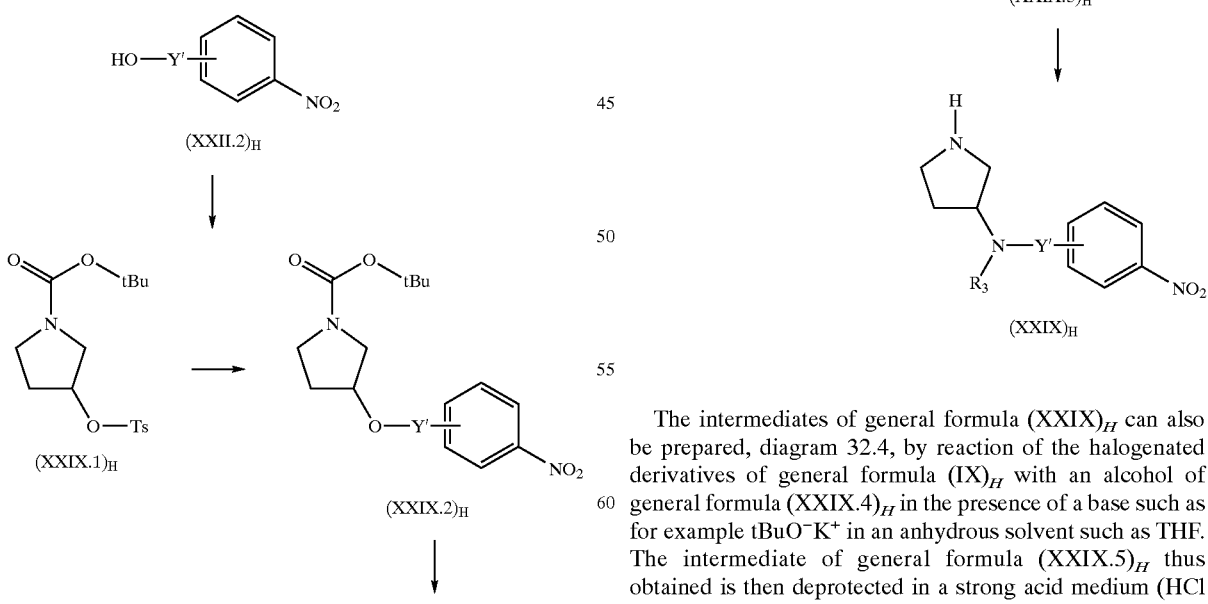

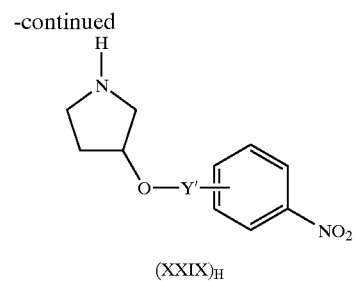

(XXIX)$_H$

The amines of general formula (XXIX)$_H$, diagram 32.3, are also accessible starting from the substitution of tosylated derivatives of general formula (XXIX.1)$_H$ by the commercial amines of general formula (XXX)$_H$. Detachment of the carbamate function from the intermediates of general formula (XXIX.3)$_H$ is carried out as described previously.

Diagram 32.3

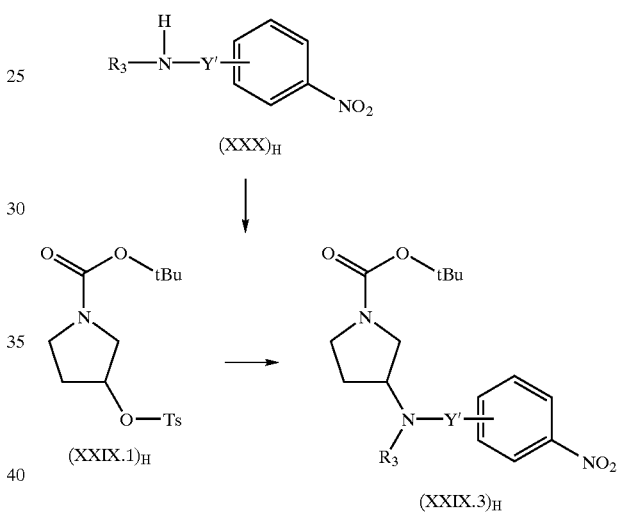

The intermediates of general formula (XXIX)$_H$ can also be prepared, diagram 32.4, by reaction of the halogenated derivatives of general formula (IX)$_H$ with an alcohol of general formula (XXIX.4)$_H$ in the presence of a base such as for example tBuO$^-$K$^+$ in an anhydrous solvent such as THF. The intermediate of general formula (XXIX.5)$_H$ thus obtained is then deprotected in a strong acid medium (HCl or TFA).

Diagram 32.4

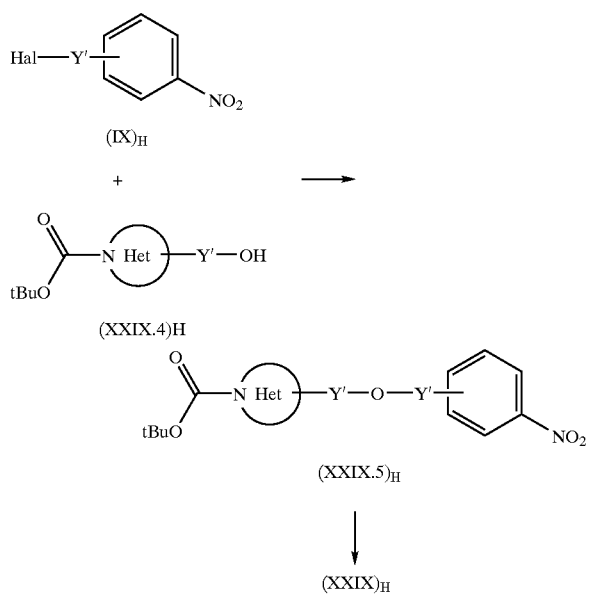

Synthesis of Intermediates (XXXII)$_H$

The intermediates of general formula (XXXII)$_H$ can be prepared, diagram 34.1, by reaction of the halogenated derivatives of general formula (IX)$_H$ with commercial 1-(diphenylmethyl)-3-hydroxyazetidine (XXXII.1)$_H$ in the presence of a base such as for example NaH in an anhydrous solvent such as THF. In this case, the nitro group of the intermediate of general formula (XXXII.2)$_H$ is reduced in the presence of SnCl$_2$, as described previously, in order to produce the intermediate of general formula (XXXII.3)$_H$ the amine of which is then protected in the form of a tButyl carbamate. The detachment of the diphenylmethyl protective group is then carried out in a standard fashion by hydrogenolysis in the presence of Pd(OH)$_2$ in order to produce the intermediate of general formula (XXXII)$_H$.

Diagram 34.1

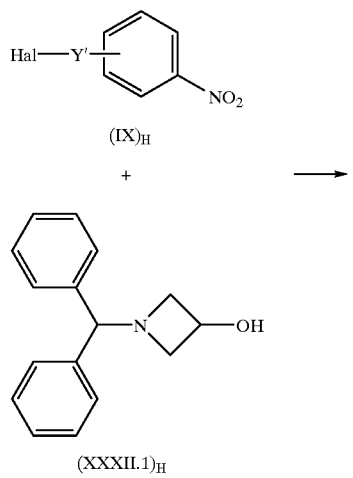

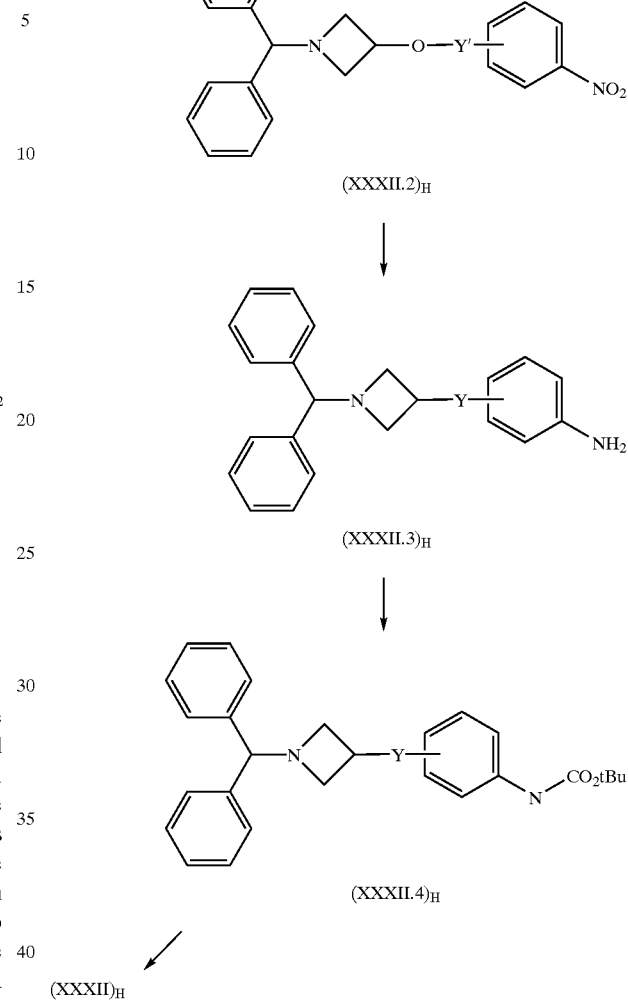

Unless they are defined differently, all the technical and scientific terms used here have the same meaning as that usually understood by an ordinary specialist in the field to which the invention belongs. Similarly, all publications, Patent Applications, Patents and other references mentioned here are incorporated by way of reference.

The following examples are presented to illustrate the above procedures and should in no way be considered as restricting the scope of the invention.

EXAMPLES

Example 1

3,5-bis-(1,1-dimethylethyl)-4-hydroxy-N-{4-[(2-thienyl(imino)methyl)amino]phenyl}-benzamide hydrochloride: 1

1.1) 3,5-bis-(1,1-dimethylethyl)-4-hydroxy-N-(4-nitrophenyl)-benzamide 1.38 g (10 mmoles) of 4-nitroaniline, 2.5 g (10 mmoles) of 3,5-di-tert-butyl-4-hydroxybenzoic acid and 2.26 g (11 mmoles) of dicyclohexylcarbodiimide are introduced into a 250 ml flask containing 20 ml of THF. The reaction medium is agitated for 15 hours at ambient temperature, and the precipitate which appears is filtered out and rinsed with ethyl acetate After the solution is concentrated under reduced pressure, the residue is diluted in 20 ml of ethyl acetate and the insoluble part is filtered out. The solvent is eliminated under vacuum and the residue is precipitated from diethyl ether. The solid is recovered by filtration, rinsed abundantly with diethyl ether in order to produce a white powder with a yield of 65%. Melting point: 277–278° C.

NMR $^1$H (100 MHz, DMSO d6, δ): 10.72 (s, 1H, CONH); 8.30 (m, 4H, Ph—NO$_2$); 7.80 (s, 2H, Ph); 1.60 (s, 18H, 2× tBu).

1.2) 3,5-bis-(1,1-dimethylethyl)-4-hydroxy-N-(4-aminophenyl)-benzamide

In a 250 ml Parr flask, 2.4 g (6.5 mmoles) of 3,5-bis-(1,1-dimethylethyl)-4-hydroxy-N-(4-nitrophenyl)-benzamide is dissolved in 50 ml of an absolute ethanol/dichloromethane mixture (1/1) in the presence of 10% Pd/C. The mixture is agitated under 20 PSI of hydrogen, at 30° C., for one hour. After filtration on celite, the filtrate is concentrated under vacuum. The evaporation residue is taken up in 25 ml of a 1M HCl solution. The precipitate formed is filtered and rinsed with 50 ml of diethyl ether followed by 50 ml of ethyl acetate. The amine is released from its salt by agitation in a mixture of 50 ml of ethyl acetate and 50 ml of 1M NaOH. After decanting, the organic phase is washed with 25 ml of 1M NaOH and 25 ml of brine. The organic solution is dried over sodium sulphate, filtered, rinsed and concentrated to dryness under reduced pressure to produce 1.09 g (49%) of a white powder. Melting point: 220–221° C.

NMR $^1$H (100 MHz, DMSO d6, δ): 9.80 (s, 1H, CONH); 7.78 (s, 2H, Ph); 7.05 (m, 4H, Ph—NH$_2$); 5.02 (s, 2H, OH); 1.60 (s, 18H, 2× tBu).

1.3) 3,5-bis-(1,1-dimethylethyl)-4-hydroxy-N-{4-[(2-thienyl(imino)methyl)-amino]phenyl}-benzamide hydrochloride: 1

880 mg (3.08 mmoles) of S-methyl-2-thiophenethiocarboximide hydriodide (Ann. Chim. (1962), 7, 303–337) is introduced into a 100 ml flask containing a solution of 1.05 g (3.08 mmoles) of 3,5-bis-(1,1-dimethylethyl)-4-hydroxy-N-(4-aminophenyl)-benzamide in 20 ml of 2-propanol. After heating at 50° C. for 15 hours, the reaction medium is concentrated to dryness under vacuum. The residue is taken up in 50 ml of ethyl acetate and 50 ml of a saturated solution of sodium carbonate. After decanting, the organic phase is washed successively with 50 ml of a saturated solution of sodium carbonate, 50 ml of water and 50 ml of brine. The organic solution is dried over sodium sulphate, filtered and evaporated under reduced pressure. The crystals obtained are taken up in diethyl ether, filtered and washed successively with ethyl acetate and acetone. 0.77 g of base is obtained with a yield of 58%.

The hydrochloride is prepared from 0.77 g (1.71 mmole) of base dissolved in 60 ml of methanol and salified in the presence of 3.42 ml (3.42 mmoles) of a molar solution of HCl in anhydrous diethyl ether. After agitating for 30 minutes at ambient temperature, the solvent is evaporated off under vacuum and the residue precipitated in the presence of diethyl ether. The crystals obtained are filtered and rinsed abundantly with diethyl ether in order to finally produce after drying 0.65 g (43%) of a pale yellow powder. Melting point: 290–291° C.

NMR $^1$H (400 MHz, DMSO d6, δ): 11.55 (s, 1H, NH$^+$); 10.40 (s, 1H, CONH); 9.83 (s, 1H, NH$^+$); 8.85 (s, 1H, NH$^+$); 8.21 (m, 2H, thiophene); 7.70 (s, 2H, Ph); 7.67 (m, 4H, Ph—NH); 7.60 (s, 1H, OH); 7.40 (m, 1H, thiophene); 1.42 (s, 18H, 2× tBu).

IR: ν$_{OH}$: 3624 cm$^{-1}$, 3430 cm$^{-1}$; ν$_{C=O}$ (amide): 1653 cm$^{-1}$; ν$_{C=N}$ (amidine): 1587 cm$^{-1}$.

Example 2

3,5-bis-(1,1-dimethylethyl)-4-hydroxy-N-{4-[[(2-thienyl-(imino)methyl)amino]phenyl]methyl}-benzamide hydrochloride: 2

2.1) 3,5-bis-(1,1-dimethylethyl)-4-hydroxy-N-[(4-nitrophenyl)methyl]-benzamide 1.88 g (10 mmoles) of p-nitrobenzylamine hydrochloride, 2.5 g (10 mmoles) of 3,5-di-tert-butyl-4-hydroxybenzoic acid, 1.38 ml (10 mmoles) of triethylamine and 2.26 g (11 mmoles) of dicyclohexylcarbodiimide are introduced into a 250 ml flask containing 25 ml of THF. The reaction medium is agitated for 15 hours at ambient temperature, the precipitate which appears is filtered out and rinsed with the minimum quantity of ethyl acetate. After concentration of the solution under reduced pressure, the residue is precipitated from a mixture of ethyl acetate/diethyl ether (1/4) and filtered. The crystals are washed abundantly with diethyl ether in order to finally produce, after drying, a white powder with a yield of 74% (2.85 g). Melting point: 230–231° C.

NMR $^1$H (100 MHz, CDCl$_3$, δ): 7.85 (m, 4H, Ph—NO$_2$); 7.69 (s, 2H, Ph); 6.82 (m, 1H, NHCO); 5.67 (s, 1H, OH); 4.75 (d, 2H, CH$_2$—NHCO, J=6.5 Hz); 1.49 (s, 18H, 2× tBu).

2.2) 3,5-bis-(1,1-dimethylethyl)-4-hydroxy-N-[(4-aminophenyl)methyl]-benzamide In a 250 ml Parr flask, 2.85 g (7.4 mmoles) of 3,5-bis-(1,1-dimethylethyl)-4-hydroxy-N-[(4-nitrophenyl)methyl]-benzamide is dissolved in 30 ml of an absolute ethanol/dichloromethane mixture (1/1) in the presence of 10% Pd/C. The mixture is agitated under 20 PSI of hydrogen, at 30° C., for one hour. After filtration on celite, the filtrate is concentrated under vacuum. The evaporation residue crystallizes spontaneously. It is left to rest overnight, the crystals are filtered out and rinsed with a mixture of diethyl ether (45 ml) and acetone (5 ml). 1.63 g (62%) of a white powder is obtained. Melting point: 188–189° C.

NMR $^1$H (100 MHz, CDCl$_3$, δ): 7.62 (s, 2H, Ph); 6.95 (m, 4H, Ph—NH$_2$); 6.20 (m, 1H, NHCO); 5.58 (s, 1H, OH); 4.50 (d, 2H, CH$_2$—NHCO, J=6.5 Hz); 3.70 (wide s, 2H, NH$_2$); 1.47 (s, 18H, 2× tBu).

2.3) 3,5-bis-(1,1-dimethylethyl)-4-hydroxy-N-{4-[[(2-thienyl-(imino)methyl)-amino]phenyl]methyl}-benzamide hydrochloride: 2

The experimental protocol used is the same as that described for compound 1, with 3,5-bis-(1,1-dimethylethyl)-4-hydroxy-N-[(4-aminophenyl)methyl]-benzamide replacing the 3,5-bis-(1,1-dimethylethyl)-4-hydroxy-N-(4-aminophenyl)-benzamide. After salification with a molar solution of HCl in anhydrous diethyl ether, a white powder is obtained with a yield of 56%. Melting point: 218–219° C.

NMR $^1$H (400 MHz, DMSO d6, δ): 11.60 (s, 1H, NH$^+$); 9.83 (s, 1H, NH$^+$); 9.02 (s, 1H, CONH); 8.90 (s, 1H, NH$^+$); 8.18 (m, 2H, thiophene); 7.70 (s, 2H, Ph); 7.42 (m, 6H, thiophene, Ph—NH, OH); 4.50 (d, 2H, CH$_2$—NHCO, J=5.7 Hz); 1.40 (s, 18H, 2× tBu).

IR: $v_{OH}$: 3624 cm$^{-1}$, 3424 cm$^{-1}$; $v_{C=O}$ (amide): 1644 cm$^{-1}$; $v_{C=N}$ (amidine): 1568 cm$^{-1}$.

Example 3

4-acetoxy-3,5-dimethoxy-N-{4-[[(2-thienyl(imino) methyl)amino]phenyl]methyl}-benzamide: 3

3.1) 4-acetoxy-3,5-dimethoxy-benzoic acid

In a 100 ml flask, under a nitrogen atmosphere, 1.50 g (7.57 mmoles) of syringic acid is dissolved in 15 ml of dry pyridine. 0.86 ml (9.08 mmoles) of acetic anhydride is added dropwise and the mixture is agitated at ambient temperature for 18 hours. The pyridine is evaporated off under reduced pressure, the residue is taken up in 25 ml of dichloromethane and washed with 10 ml of a molar solution of HCl then with 2×10 ml of water. The organic phase is dried over sodium sulphate, filtered and evaporated under vacuum. 1.72 g (95%) of a beige powder is obtained. Melting point: 181–183° C.

NMR $^1$H (100 MHz, CDCl$_3$, δ): 8.15 (s, 1H, CO$_2$H); 7.40 (s, 2H, Ph); 3.90 (s, 6H, 2× OCH$_3$); 2.40 (s, 3H, CH$_3$).

3.2) 4-acetoxy-3,5-dimethoxy-N-[(4-nitrophenyl) methyl]-benzamide

The experimental protocol used is the same as that described for intermediate 2.1, 4-acetoxy-3,5-dimethoxy-benzoic acid replacing the 3,5-di-tert-butyl-4-hydroxy-benzoic acid. A colourless oil is obtained with a yield of 28%.

NMR $^1$H (100 MHz, DMSO d6, δ): 9.26 (t, 1H, NHCO, J=6.0 Hz); 7.91 (m, 4H, Ph—NO$_2$); 7.31 (s, 2H, Ph); 4.65 (d, 2H, CH$_2$, J=6.0 Hz); 3.83 (s, 6H, 2× OCH$_3$); 2.28 (s, 3H, CH$_3$).

3.3) 4-acetoxy-3,5-dimethoxy-N-[(4-aminophenyl) methyl]-benzamide

The experimental protocol used is the same as that described for intermediate 2.2, 4-acetoxy-3,5-dimethoxy-N-[(4-nitrophenyl)methyl]-benzamide replacing the 3,5-bis-(1,1-dimethylethyl)-4-hydroxy-N-[(4-nitrophenyl)methyl]-benzamide. A colourless oil is obtained with a yield of 82%. The product is used directly in the following stage without additional purification.

3.4) 4-acetoxy-3,5-dimethoxy-N-{4-[[(2-thienyl (imino)methyl)amino]phenyl]methyl}-benzamide: 3

The experimental protocol used is the same as that described for compound 1, with 4-acetoxy-3,5-dimethoxy-N-[(4-aminophenyl)methyl]-benzamide replacing the 3,5-bis-(1,1-dimethylethyl)-4-hydroxy-N-(4-aminophenyl)-benzamide. The base 3 in the form of a beige powder is obtained with a yield of 65%. Melting point: 47–48° C.

NMR $^1$H (400 MHz, DMSO d6, δ): 9.08 (wide s, 1H, CONH); 7.75 (m, 1H, thiophene); 7.62 (m, 1H, thiophene); 7.30 (s, 2H, Ph); 7.10 (m, 1H, thiophene); 7.07 (m, 4H, Ph—N); 6.48 (wide s, 2H, NH$_2$); 4.50 (d, 2H, CH$_2$, J=4.6 Hz); 3.80 (s, 6H, 2× OCH$_3$); 2.30 (s, 3H, CH$_3$).

IR: $v_{C=O}$ (ester): 1760 cm$^{-1}$; $v_{C=O}$ (amide): 1630 cm$^{-1}$; $v_{C=N}$ (amidine): 1540 cm$^{-1}$.

Example 4

3,5-dimethoxy-4-hydroxy-N-{4-[[(2-thienyl(imino) methyl)amino]phenyl]methyl}-benzamide: 4

In a 50 ml flask, 1 ml (2 mmoles) of 2N hydrochloric acid is introduced dropwise into a solution of 0.59 g (1 mmole) of compound 3 in 5 ml of ethanol. The reaction medium is agitated for 18 hours at 50° C. The solvents are evaporated to dryness, the residue is taken up in dichloromethane (5 ml) and washed with molar soda solution (3×5 ml). After drying the organic phase, filtration and concentration to dryness is carried out and the oil obtained is purified by chromatography on a silica gel column (eluant: dichloromethane/methanol: 9/1). The pure fractions are collected and after evaporation under vacuum a beige powder is obtained with a yield of 60%. Melting point: 55–58° C.

NMR $^1$H (400 MHz, DMSO d6, δ): 8.92 (s, 1H, OH); 8.84 (m, 1H, CONH); 7.75 (m, 1H, thiophene); 7.63 (m, 1H, thiophene); 7.26 (s, 2H, Ph); 7.10 (m, 1H, thiophene); 7.05 (m, 4H, Ph—N); 6.50 (s, 2H, NH$_2$); 4.45 (d, 2H, CH$_2$, J=5.7 Hz); 3.81 (s, 6H, 2× OCH$_3$).

IR: $v_{OH}$: 3300 cm$^{-1}$; $v_{C=O}$ (amide): 1630 cm$^{-1}$; $v_{C=N}$ (amidine): 1590 cm$^{-1}$.

Example 5

3,5-bis-(1,1-dimethylethyl)-4-hydroxy-N-{4-[2-[(2-thienyl-(imino)methyl)amino]phenyl]ethyl}-benzamide hydriodide: 5

5.1) 3,5-bis-(1,1-dimethylethyl)-4-hydroxy-N-[2-(4-nitrophenyl)ethyl]-benzamide 2.02 g (10 mmoles) of 4-nitrophenetylamine hydrochloride, 2.5 g (10 mmoles) of 3,5-di-tert-butyl4-hydroxy-benzoic acid, 1.38 ml (10 mmoles) of triethylamine and 2.26 g (11 mmoles) of dicyclohexylcarbodiimide are introduced into a 100 ml flask containing 20 ml of THF. The reaction medium is agitated for 15 hours at ambient temperature, the precipitate which appears is filtered out and rinsed with ethyl acetate. After concentration of the filtrate under reduced pressure, the residue is precipitated from diethyl ether. The solid is recovered by filtration and rinsed with diethyl ether. A white powder is obtained with a yield of 73%. Melting point: 204–206° C.

NMR $^1$H (100 MHz, CDCl$_3$, δ): 7.52 (s, 2H, Ph); 6.85 (m, 4H, Ph—NO$_2$); 6.02 (m, 1H, NHCO); 3.62 (m, 2H, CH$_2$—NHCO); 2.82 (m, 2H, CH$_2$—Ph—NO$_2$); 1.48 (s, 18H, 2× tBu).

5.2) 3,5-bis-(1,1-dimethylethyl)-4-hydroxy-N-[2-(4-aminophenyl)ethyl]-benzamide The experimental protocol used is the same as that described for intermediate 2.2, 3,5-bis-(1,1-dimethylethyl)-4-hydroxy-N-[2-(4-nitrophenyl)ethyl]-benzamide replacing the 3,5-bis-(1,1-dimethylethyl)-4-hydroxy-N-[(4-nitrophenyl)methyl]-benzaniide. A white powder is obtained with a yield of 76%. Melting point: 193–195° C.

NMR $^1$H (100 MHz, CDCl$_3$, δ): 7.80 (m, 4H, Ph—NH$_2$); 7.55 (s, 2H, Ph); 6.10 (m, 1H, NHCO); 5.55 (s, 1H, OH); 3.75 (m, 2H, CH$_2$—NHCO); 3.10 (m, 2H, CH$_2$—Ph—NH$_2$); 1.50 (s, 18H, 2× tBu).

5.3) 3,5-bis-(1,1-dimethylethyl)-4-hydroxy-N-{4-[2-[(2-thienyl(imino)methyl)-amino]phenyl]ethyl}-benzamide hydriodide: 5

0.78 g (2.74 mmoles) of S-methyl-2-thiophene-thiocarboximide hydriodide (Ann. *Chim.* (1962), 7, 303–337) is introduced into a 50 ml flask containing 1.01 g (2.74 mmoles) of 3,5-bis-(1,1-dimethylethyl)-4-hydroxy-N-[2-(4-aminophenyl)ethyl]-benzaride dissolved in 20 ml of 2-propanol. The reaction medium is heated at 40° C. for 4 hours. The solvent is evaporated off under vacuum and the residue is precipitated in the presence of 50 ml of a water/ethyl acetate mixture (1/1). The crystals formed are filtered out and washed successively with ethyl acetate and diethyl ether. After drying, a pale yellow powder is obtained with a yield of 68%. Melting point: 185–186° C.

NMR $^1$H (400 MHz, DMSO d6, δ): 9.80 (s, 1H, NH$^+$); 8.88 (s, 1H, NH$^+$); 8.40 (s, 1H, CONH); 8.12 (m, 2H, thiophene); 7.60 (s, 2H, Ph); 7.42 (m, 6H, thiophene, Ph—NH, OH); 3.52 (d, 2H, CH$_2$—NHCO, J=5.9 Hz); 2.90 (m, 2H, CH$_2$—Ph—NH); 1.40 (s, 18H, 2× tBu).

IR: $\nu_{OH}$: 3624 cm$^{-1}$, 3423 cm$^{-1}$; $\nu_{C=O}$ (amide): 1636 cm$^{-1}$; $\nu_{C=N}$ (amidine): 1569 cm$^{-1}$.

Example 6

4-acetoxy-3,5-dimethoxy-N-{4-[2-[(2-thienyl-(imino)methyl)-amino]phenyl]ethyl}-benzamide fumarate: 6

6.1) 4-acetoxy-3,5-dimethoxy-N-[2-(4-nitrophenyl)ethyl]-benzamide

The experimental protocol used is the same as that described for intermediate 5.1, with 4-acetoxy-3,5-dimethoxy-benzoic acid (intermediate 3.1) replacing the 3,5-di-tert-butyl-4-hydroxy benzoic acid. A colourless oil is obtained with a yield of 70%. The product is used directly in the following stage.

6.2) 4-acetoxy-3,5-dimethoxy-N-[2-(4-aminophenyl)ethyl]-benzamide

The experimental protocol used is the same as that described for intermediate 2.2, with 4-acetoxy-3,5-dimethoxy-N-[2-(4-nitrophenyl)ethyl]-benzamide replacing the 3,5-bis-(1,1-dimethylethyl)-4-hydroxy-N-[(4-nitrophenyl)methyl]-benzamide. A colourless oil is obtained with a quantitative yield. The product is used directly in the following stage without additional purification.

6.3) 4-acetoxy-3,5-dimethoxy-N-{4-[2-[(2-thienyl(imino)methyl)amino]-phenyl]ethyl}-benzamide fumarate: 6

The experimental protocol used to produce the free base is the same as that described for the synthesis of compound 1, with 4-acetoxy-3,5-dimethoxy-N-[2-(4-aminophenyl)ethyl]-benzamide replacing the 3,5-bis-(1,1-dimethylethyl)-4-hydroxy-N-(4-aminophenyl)-benzamide.

The product of the reaction is salified in the presence of an equimolar quantity of fumaric acid in ethanol under reflux. Compound 6 is obtained in the form of a beige powder with a yield of 74%. Melting point: 178–180° C.

NMR $^1$H (400 MHz, DMSO d6, δ): 8.60 (m, 1H, CONH); 7.75 (m, 1H, thiophene); 7.64 (d, 1H, thiophene, J=5.0 Hz); 7.20 (s, 2H, Ph); 7.11 (t, 1H, thiophene, J=9.0 Hz); 7.02 (m, 4H, Ph—N); 6.61 (s, 2H, CH=CH fumarate); 3.81 (s, 6H, 2× OCH$_3$); 3.50 (q, 2H, CH$_2$—N, J=6.5 Hz); 2.82 (t, CH$_2$—Ph, J=7.0 Hz); 2.27 (s, 3H, CH$_3$).

IR: $\nu_{C=O}$ (ester): 1750 cm$^{-1}$; $\nu_{C=O}$ (amide): 1640 cm$^{-1}$; $\nu_{C=N}$ (amidine): 1550 cm$^{-1}$.

Example 7

3,5-dimethoxy-4-hydroxy-N-{4-[2-[(2-thienyl-(imino)methyl)-amino]phenyl]ethyl}-benzamide hydrochloride: 7

In a 50 ml flask, 1.40 ml (2.80 mmoles) of a solution of 2N hydrochloric acid is added dropwise to a solution of 0.64 g (1.37 mmoles) of compound 6 in the form of the free base in 5 ml of ethanol. The reaction medium is agitated for 18 hours at 50° C. The solvents are evaporated to dryness and the evaporation residue is precipitated from a mixture of 5 ml of a 2N solution of soda and 10 ml of dichloromethane. After filtration, the solid is taken up in (4N) hydrochloric ethanol. A light precipitate is then eliminated. The solvent is evaporated under reduced pressure and the residue taken up in acetone. Product 7 precipitated in the form of the hydrochloride is obtained with a yield of 58%. Melting point: 164–167° C.

NMR $^1$H (400 MHz, DMSO d6, δ): 9.80 (wide s, 1H, NH$^+$); 8.90 (s, 2H, NH$^+$, OH); 8.54 (m, 1H, CONH); 8.18 (s, 1H, thiophene); 8.16 (s, 1H, thiophene); 7.40 (m, 4H, Ph—N); 7.21 (s, 2H, Ph); 7.11 (m, 1H, thiophene); 3.81 (s, 6H, 2× OCH$_3$); 3.51 (q, 2H, CH$_2$—N, J=7.0 Hz); 2.92 (t, CH$_2$—Ph, J=7.0 Hz).

IR: $\nu_{OH}$: 3300 cm$^{-1}$; $\nu_{C=O}$ (amide): 1620 cm$^{-1}$; $\nu_{C=N}$ (amidine): 1560 cm$^{-1}$.

Example 8

3,4,5-trihydroxy-N-{4-[2-[(2-thienyl(imino)methyl)-amino]phenyl]ethyl}-benzamide hemi-fumarate: 8

8.1) 3,4,5-trihydroxy-N-[2-(4-nitrophenyl)ethyl]-benzamide 2 g (11.5 mmoles) of gallic acid, 2.5 g (11.5 mmoles) of 4-nitrophenetylamine hydrochloride, 1.8 g (11.5 mmoles) of hydrated 1-hydroxybenzotriazole, 2.25 g (11.5 mmoles) of 1-(3-dimethylaminopropyl)-3-ethylcarbodiimide hydrochloride and 3.3 ml (23 mmoles) of triethylamine are introduced into a 100 ml flask containing 30 ml of anhydrous DMF. The orange-coloured solution obtained is agitated at 20° C. for 20 hours and diluted in a mixture of dichloromethane (50 ml) and water (30 ml). After decanting, the organic phase is washed with a molar solution of hydrochloric acid (20 ml) and with water (3×20 ml) until neutrality is achieved. After drying the organic phase over magnesium sulphate, followed by filtration and concentration under vacuum, the residue is purified on a silica gel column (eluant: dichloromethane/methanol: 9/1). The expected product is obtained in the form of a colourless oil with a yield of 42% (1.57 g).

NMR $^1$H (100 MHz, DMSO d6, δ): 8.95 (m, 3H, 3× OH); 7.85 (m, 4H, Ph—NO$_2$); 6.80 (s, 2H, Ph); 3.36 (m, 2H, CH$_2$—N); 2.97 (t, 2H, CH$_2$—Ph, J=6.0 Hz).

8.2) 3,4,5-trihydroxy-N-[2-(4-aminophenyl)ethyl]-benzamide

The experimental protocol used is the same as that described for intermediate 2.2, with 3,4,5-trihydroxy-N-[2-(4-nitrophenyl)ethyl]-benzamide replacing the 3,5-bis-(1,1-dimethylethyl)-4-hydroxy-N-[(4-nitrophenyl)methyl]-benzamide. A beige powder is obtained with a yield of 89%. Melting point: 167–169° C.

NMR $^1$H (100 MHz, DMSO d6, δ): 8.80 (m, 3H, OH); 8.07 (t, 1H, NHCO, J=5.0 Hz); 6.81 (s, 2H, Ph); 6.68 (m, 4H, Ph—NH$_2$); 3.28 (m, 2H, CH$_2$—N); 2.60 (t, 2H, CH$_2$—Ph, J=7.0 Hz).

8.3) 3,4,5-trihydroxy-N-{4-[2-[(2-thienyl(imino)methyl)amino]-phenyl]ethyl}-benzamide hemi-fumarate: 8

The experimental protocol used is the same as that described for compound 1, with 3,4,5-trihydroxy-N-[2-(4- aminophenyl)ethyl]-benzamide replacing the 3,5-bis-(1,1-dimethylethyl)-4-hydroxy-N-(4-aminophenyl)-benzamide. Base 8 is obtained in the form of a powder which is salified, by heating under reflux with ethanol, in the presence of one equivalent of fumaric acid. The salt crystallizes spontaneously at 20° C. After filtration and washing with ethanol the expected product is obtained in the form of a beige powder with a yield of 53%. Melting point: 245–246° C.

NMR $^1$H (400 MHz, DMSO d6, δ): 8.85 (m, 3H, 3× OH); 8.14 (t, 1H, NHCO, J=5.0 Hz); 7.73 (s, 1H, thiophene); 7.60 (d, 1H, thiophene, J=5.0 Hz); 7.16 (s, 2H, Ph); 7.09 (t, 1H, thiophene, J=4.0 Hz); 6.80 (m, 4H, Ph—N); 6.59 (wide s, 2H, 1/2-CH=CH, NH); 3.41 (m, 3H, CH$_2$—N$^+$NH); 2.76 (t, 2H, CH$_2$, J=7.5 Hz).

IR: $v_{OH}$: 3300 cm$^{-1}$; $v_{C=O}$ (amide): 1620 cm$^{-1}$; $v_{C=N}$ (amidine): 1590 cm$^{-1}$.

Example 9

N-{4-[4-[3,5-bis-(1,1-dimethylethyl)-4-hydroxybenzoyl]-1-piperazinyl]phenyl}-2-thiophenecarboximidamide hydrochloride: 9

9.1) 2,6-bis-(1,1-dimethylethyl)-4-{[4-(4-nitrophenyl)-1-piperazinyl]-carbonyl}-phenol 2.07 g (10 mmoles) of 1-(4-nitrophenyl)piperazine, 2.5 g (10 mmoles) of 3,5-di-tert-butyl-4-hydroxybenzoic acid and 2.26 g (11 mmoles) of dicyclohexylcarbodiimide are introduced into a 100 ml flask containing 25 ml of DMF. The reaction medium is agitated for 15 hours at ambient temperature, the precipitate which appears is filtered out and rinsed with ethyl acetate. After concentration of the filtrate under reduced pressure, the residue is diluted in 20 ml of ethyl acetate and a new insoluble is eliminated by filtration. The solvent is evaporated off under vacuum and the residue is precipitated from diethyl ether. The solid is filtered, rinsed with 2×20 ml of ethyl acetate in order to obtain a yellow powder with a yield of 89%. Melting point: 159.5–160.5° C.

NMR $^1$H (100 MHz, CDCl$_3$, δ): 7.58 (m, 4H, Ph—NO$_2$); 7.30 (s, 2H, Ph); 5.50 (s, 1H, OH); 3.85 (m, 4H, piperazine); 3.55 (m, 4H, piperazine); 1.46 (s, 18H, 2× tBu).

9.2) 2,6-bis-(1,1-dimethylethyl)-4-{[4-(4-aminophenyl)-1-piperazinyl]-carbonyl}-phenol In a 250 ml Parr flask, 2.19 g (5.0 mmoles) of intermediate 9.1 is dissolved in 50 ml of absolute ethanol in the presence of 10% Pd/C. The mixture is agitated under 20 PSI of hydrogen, at 30° C., for one hour. After filtration on celite, the filtrate is concentrated under vacuum. The evaporation residue is taken up in 25 ml of diethyl ether, filtered and rinsed with 2×20 ml of diethyl ether. A pale pink powder is obtained with a yield of 82%. Melting point: 221–222° C.

NMR $^1$H (100 MHz, CDCl$_3$, δ): 7.30 (s, 2H, Ph); 6.75 (m, 4H, Ph—NH$_2$); 5.45 (s, 1H, OH); 3.80 (m, 4H, piperazine); 3.10 (m, 4H, piperazine); 1.49 (s, 18H, 2× tBu).

9.3) N-{4-[4-[3,5-bis-(1,1-dimethylethyl)-4-hydroxybenzoyl]-1-piperazinyl]-phenyl}-2-thiophenecarboximidamide hydrochloride: 9

The experimental protocol used is the same as that described for compound 1, with 2,6-bis-(1,1-dimethylethyl)-4-{[4-(4-aminophenyl)-1-piperazinyl]-carbonyl}-phenol replacing the 3,5-bis-(1,1-dimethylethyl)-4-hydroxy-N-(4-aminophenyl)-benzamide. After treatment with a molar solution of HCl in anhydrous diethyl ether, a beige powder is obtained with a yield of 75%. Melting point: 235–236° C.

NMR $^1$H (400 MHz, DMSO d6, δ): 11.45 (s, 1H, NH$^+$); 9.78 (s, 1H, NH$^+$); 8.75 (s, 1H, NH$^+$); 8.19 (m, 2H, thiophene); 7.29 (m, 5H, Ph—N, thiophene); 7.10 (s, 2H, Ph); 5.60 (wide s, 1H, OH); 3.70 (m, 4H, piperazine); 3.30 (m, 4H, piperazine); 1.40 (s, 18H, 2× tBu).

IR: $v_{OH}$: 3633 cm$^{-1}$, 3433 cm$^{-1}$; $v_{C=O}$ (amide): 1617 cm$^{-1}$; $v_{C=N}$ (amidine): 1590 cm$^{-1}$.

Example 10

N-{4-[4-[3,5-bis-(1,1-dimethylethyl)-4-hydroxybenzyl]-1-piperazinyl]phenyl}-2-thiophenecarboximidamide hydrochloride: 10

10.1) 2,6-bis-(1,1-dimethylethyl)-4-bromomethylphenol

In a 250 ml three-necked flask under a nitrogen atmosphere, 2.36 g (10 mmoles) of 3,5 di-tert-butyl-4-hydroxybenzylic alcohol is dissolved in 25 ml of anhydrous THU. The solution is cooled down using an ice bath before the dropwise addition of 0.95 ml (10 mmoles) of phosphorus tribromide diluted with 25 ml of anhydrous THU. After 15 minutes of agitation at 0° C., the solution is diluted with 100 ml of dichloromethane and washed with 3×30 ml of water followed by 30 ml of brine. The organic phase is dried over sodium sulphate, filtered and concentrated under vacuum to produce a brown oil which is used directly in the following stage.

10.2) 2,6-bis-(1,1-dimethylethyl)-4-{[4-(4-nitrophenyl)-1-piperazinyl]-methyl}-phenol In a 100 ml flask containing a solution of 2.99 g (10 mmoles) of 2,6-bis-(1,1-dimethylethyl)-4-bromomethylphenol in 30 ml of DMF, 1.38 g (10 mmoles) of potassium carbonate and 2.07 g (10 mmoles) of 1-(4-nitrophenyl)piperazine are added successively. After agitation for two hours at ambient temperature, the reaction medium is diluted with 150 ml of dichloromethane and washed successively with 3×40 mnl of water followed by 40 ml of brine. The organic solution is dried over sodium sulphate, filtered and concentrated under reduced pressure. The brown residue obtained is purified on a silica gel column (eluant: petroleum ether (B.p. 40–70° C.)/ethyl acetate: 8/2). After concentration of the pure fractions, 2.31 g (54%) of a brown powder is obtained. Melting point: 177.5–178.5° C.

NMR $^1$H (100 MHz, CDCl$_3$, δ): 7.50 (m, 4H, Ph—NO$_2$); 7.12 (s, 2H, Ph); 5.19 (s, 1H, OH); 3.50 (s, 2H, CH$_2$—Ph); 3.49 (m, 4H, piperazine); 2.60 (m, 4H, piperazine); 1.49 (s, 18H, 2× tBu).

10.3) 2,6-bis-(1,1-dimethylethyl)-4-{[4-(4-aminophenyl)-1-piperazinyl]-methyl}-phenol The experimental protocol used is the same as that described for intermediate 9.2, with 2,6-bis-(1,1-dimethylethyl)-4-{[[4-(4-nitrophenyl)-1-piperazinyl]-carbonyl]-methyl}-phenol replacing the 2,6-bis-(1,1-dimethylethyl)-4-{[4-(4-nitrophenyl)-1-piperazinyl]-carbonyl}-phenol. A pale pink powder is obtained with a yield of 75%. Melting point: 152–154° C.

NMR $^1$H (100 MHz, CDCl$_3$, δ): 7.12 (s, 2H, Ph); 6.78 (m, 4H, Ph—NH$_2$); 3.59 (s, 2H, CH$_2$—Ph); 3.18 (m, 4H, piperazine); 2.70 (m, 4H, piperazine); 1.47 (s, 18H, 2×tBu).

10.4) N-{4-[4-[3,5-bis-(1,1-dimethylethyl)-4-hydroxybenzyl]-1-piperazinyl]-phenyl}-2-thiophenecarboximidamide hydrochloride: 10

0.43 g (1.5 mmole) of S-methyl-2-thiophene-thiocarboximide hydroiodide (Ann. *Chim.* (1962), 7, 303–337) is introduced into a 100 ml flask containing 0.59 g (1.5 mmole) of intermediate 10.3 in 20 ml of 2-propanol. After heating under reflux for 15 hours, the reaction medium is concentrated to dryness under vacuum. The residue is purified on a silica gel column (eluant: dichloromethane/ethanol: 90/10). The pure fractions are concentrated under vacuum and the evaporation residue is salified in the presence of a molar solution of HCl in anhydrous diethyl ether. A pale yellow powder is obtained with a yield of 40%. Melting point: 234–236° C.

NMR $^1$H (400 MHz, DMSO d6, δ): 11.60 (s, 1H, NH$^+$); 11.40 (s, 1H, NH$^+$); 9.75 (s, 1H, NH$^+$); 8.70 (s, 1H, NH$^+$); 8.17 (m, 2H, thiophene); 7.39 (s, 2H, Ph); 7.38 (m, 1H, thiophene); 7.24 (m, 5H, Ph—N, OH); 4.26 (d, 2H, CH$_2$—Ph, J=4.6 Hz); 3.90 (m, 2H, piperazine); 3.35 (m, 4H, piperazine); 3.15 (m, 2H, piperazine); 1.41 (s, 18H, 2× tBu).

IR: $v_{OH}$: 3624 cm$^{-1}$, 3418 cm$^{-1}$; $v_{C=N}$ (amidine): 1610 cm$^{-1}$.

Example 11

N-{4-[4-[3,5-dimethoxy-4-hydroxybenzoyl]-1-piperazinyl]-phenyl}-2-thiophenecarboximidamide hydrochloride: 11

11.1) 2,6-dimethoxy-4-{[4-(4-nitrophenyl)-1-piperazinyl]carbonyl}-phenol

In a 100 ml flask, 0.99 g (5 mmoles) of syringic acid, 0.74 g (5.5 mmoles) of hydroxybenzotriazol, 1.10 g (5.5 mmoles) of dicyclohexylcarbodiimide and 1.04 g (5 mmoles) of 1-(4-nitrophenyl)piperazine are dissolved in 10 ml of DMF. After agitation at ambient temperature for 7 hours, the mixture is filtered and the precipitate rinsed with 20 ml of DMF followed by 100 mnl of chloroform. 2 g of a yellow powder is obtained, containing approximately 20% of dicyclohexylurea. The product is used as it is in the following stage.

NMR $^1$H (100 MHz, DMSO d6, δ): 7.69 (m, 4H, Ph—NO$_2$); 6.88 (s, 2H, Ph); 5.72 (m, 1H, OH); 3.91 (s, 6H, 2× OCH$_3$); 3.75 (m, 4H, piperazine); 3.49 (m, 4H, piperazine).

11.2) 2,6-dimethoxy-4-{[4-(4-aminophenyl)-1-piperazinyl]carbonyl}-phenol

In a 250 ml Parr flask, 2 g of intermediate 11.1 is dissolved in 40 ml of absolute ethanol/DMSO (1/3) in the presence of 10% Pd/C. The mixture is agitated under 20 PSI of hydrogen, at 25° C., for 15 hours. After filtration on celite, the filtrate is concentrated under vacuum. The brown evaporation residue is taken up in 50 ml of ethyl acetate, the precipitate formed is eliminated by filtration, rinsed with 20 ml of ethyl acetate and the filtrate extracted with 2×25 ml of a molar solution of HCl. The aqueous phase is alkalinized by the addition of powdered sodium carbonate and extracted with 2×50 ml of ethyl acetate. The organic solution is dried over sodium sulphate, filtered and concentrated under vacuum. The powder obtained is taken up in 20 ml of diethyl ether containing 3 ml of methanol, filtered and rinsed using diethyl ether. 400 mg (22% over the two stages) of brown crystals are obtained. Melting point: 182–183° C.

NMR $^1$H (100 MHz, DMSO d6, δ): 6.80 (s, 2H, Ph); 6.74 (m, 4H, Ph—NH$_2$); 4.80 (m, 2H, NH$_2$); 3.91 (s, 6H, 2× OCH$_3$); 3.77 (m, 4H, piperazine); 3.08 (m, 4H, piperazine).

11.3) N-{4-[4-[3,5-dimethoxy-4-hydroxybenzoyl]-1-piperazinyl]-phenyl}-2-thiophenecarboximidamide hydrochloride: 11

0.32 g (1.13 mmole) of S-methyl-2-thiophenethiocarboximide hydroiodide (*Ann. Chim.* (1962), 7, 303–337) is introduced into a 100 ml flask containing a solution of 0.4 g (1.13 mmole) of intermediate 11.2 in 10 ml of 2-propanol. After heating at 50° C. for 15 hours, the reaction medium is concentrated to dryness under vacuum. The evaporation residue is then taken up in 100 ml of an ethyl acetate/saturated solution of sodium carbonate mixture (1/1). A precipitate appears which is filtered and rinsed successively with 20 ml of water, 20 ml of ethyl acetate and 50 ml of ether. The base obtained is salified in the presence of a molar solution of HCl in anhydrous diethyl ether. After filtration, rinsing with 10 ml of acetone and drying, 0.12 g (20%) of a pale yellow powder is obtained. Melting point: 184–185° C.

NMR $^1$H (400 MHz, DMSO d6, δ): 11.47 (s, 1H, NH$^+$); 9.78 (s, 1H, NH$^+$); 8.76 (s, 1H, NH$^+$); 8.18 (m, 2H, thiophene); 7.37 (m, 1H, thiophene); 7.28 (m, 4H, Ph—N); 6.74 (s, 2H, Ph); 4.27 (wide s, 1H, OH); 3.80 (s, 6H, 2× OCH$_3$); 3.70 (m, 4H, piperazine); 3.33 (m, 4H, piperazine).

IR: $v_{OH}$: 3423 cm$^{-1}$; $v_{C=O}$ (amide): 1610 cm$^{-1}$; $v_{C=N}$ (amidine): 1587 cm$^{-1}$.

Example 12

3,4-dihydro-6-hydroxy-2,5,7,8-tetramethyl-N-{4-[(2-thienyl(imino)methyl)amino]phenyl}-2H-1-benzopyran-2-carboxamide hydrochloride: 12

12.1) 3,4-dihydro-6-hydroxy-2,5,7,8-tetramethyl-N-(4-nitrophenyl)-2H-1-benzopyran-2-carboxamide In a 100 ml flask, 1.62 g (10 mmoles) of 1,1'-carbonyldiimidazol is added to a solution of 2.5 g (10 mmoles) of Trolox® in 25 ml of THF. After agitation at ambient temperature for one hour, a solution of 4-nitroaniline in 20 ml of THF is added dropwise. Agitation is continued for 15 hours and the solvent is evaporated off under vacuum. The residue is diluted in 50 ml of dichloromethane and washed successively with 25 ml of a molar solution of hydrochloric acid, 25 ml of water and 25 ml of brine. The organic phase is dried over sodium sulphate, filtered and concentrated under reduced pressure. The oil obtained is purified on a silica gel column (eluant: petroleum ether (B.p. 40–70° C.)/ethyl acetate: 7/3). After concentration of the pure fractions, a pale yellow powder is obtained with a yield of 77%. Melting point: 150–151° C.

NMR $^1$H (100 MHz, CDCl$_3$, δ): 8.68 (s, 1H, CONH); 7.91 (m, 4H, Ph); 4.59 (s, 1H, OH); 2.95–0.87 (m, 16H, Trolox®).

12.2) 3,4-dihydro-6-hydroxy-2,5,7,8-tetramethyl-N-(4-aminophenyl)-2H-1-benzopyran-2-carboxamide The experimental protocol used is the same as that described for intermediate 9.2, with 3,4-dihydro-6-hydroxy-2,5,7,8-tetramethyl-N-(4-nitrophenyl)-2H-1-benzopyran-2-carboxamide replacing the 2,6-bis-(1,1-dimethylethyl)-4-{[4-(4-nitrophenyl)-1-piperazinyl]-carbonyl}-phenol. The product of the reaction is purified on a silica gel column (eluant: petroleum ether (B.p. 40–70° C.)/ethyl acetate: 6/4). The pure fractions are collected, after evaporation of the solvent under vacuum, a colourless oil is obtained with a yield of 45%.

NMR $^1$H (100 MHz, CDCl$_3$, δ): 8.19 (s,1H, CONH); 7.00 (m, 4H, Ph); 4.59 (s, 1H, OH); 3.65 (wide s, 2H, NH$_2$); 2.95–0.87 (m, 16H, Trolox®).

12.3) 3,4-dihydro-6-hydroxy-2,5,7,8-tetramethyl-N-{4-[2-thienyl(iminomethyl)amino]phenyl}-2H-1-benzopyran-2-carboxamide hydrochloride: 12

The experimental protocol used is the same as that described for compound 1, with 3,4-dihydro-6-hydroxy-2, 5,7,8-tetramethyl-N-(4-aminophenyl)-2H-1-benzopyran-2-carboxamide replacing the 3,5-bis-(1,1-dimethylethyl)-4-hydroxy-N-(4-aminophenyl)-benzamide. Melting point: 279–280° C.

NMR $^1$H (400 MHz, DMSO d6, δ): 9.80 (s, 1H, NH$^+$); 9.50 (s, 1H, NH$^+$); 8.73 (s, 1H, NHCO); 8.18 (m, 2H, thiophene); 7.60 (s, 1H, OH); 7.59 (m, 4H, Ph); 7.36 (m, 1H, thiophene); 2.60–1.57 (m, 16H, Trolox®).

IR: $v_{OH}$: 3236 cm$^{-1}$; $v_{C=O}$ (amide): 1683 cm$^{-1}$; $v_{C=N}$ (amidine): 1577 cm$^{-1}$.

Example 13

N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 13

13.1) 3,4-dihydro-2,5,7,8-tetramethyl-2-{4-[(4-nitrophenyl)-1-piperazinyl]-carbonyl}-2H-1-benzopyran-6-ol In a 100 ml flask, 1.62 g (10 mmoles) of 1,1'-carbonyldiimidazole is added to a solution of 2.5 g (10 mmoles) of Trolox® in 25 ml of THF. After one hour of agitation at ambient temperature, a solution of 1-(4-nitrophenyl)piperazine in 10 ml of DMF is added dropwise. Agitation is continued for 15 hours, the reaction medium is then concentrated under vacuum. The evaporation residue is dissolved in 50 ml of dichloromethane and washed successively with 3×25 ml of water and 25 ml of brine. The organic phase is dried over sodium sulphate, filtered and concentrated under reduced pressure. The oil obtained is precipitated from 30 ml of a (95/5) ethyl acetate/methanol mixture, the solid is filtered out and washed with 2×20 ml of ethyl acetate. A pale yellow powder is obtained with a yield of 79%. Melting point: 199–200° C.

NMR $^1$H (100 MHz, CDCl$_3$, δ): 7.45 (m, 4H, Ph); 4.41–3.35 (m, 8H, piperazine); 2.95–1.25 (m, 16H, Trolox®).

13.2) 3,4-dihydro-2,5,7,8-tetramethyl-2-{4-[(4-aminophenyl)-1-piperazinyl]-carbonyl}-2H-1-benzopyran-6-ol The experimental protocol used is the same as that described for intermediate 2.2, with 3,4-dihydro-2,5,7,8-tetramethyl-2-{4-[(4-nitrophenyl)-1-piperazinyl]-carbonyl}-2H-1-benzopyran-6-ol replacing the 3,5-bis-(1,1-dimethylethyl)-4-hydroxy-N-[(4-nitrophenyl)methyl]-benzamide. The product of the reaction is purified on a silica gel column (eluant: dichloromethane/methanol: 9/1). The pure fractions are collected to produce, after evaporation of the solvent under vacuum, a brown oil with a yield of 66%.

NMR $^1$H (100 MHz, CDCl$_3$, δ): 6.70 (m, 4H, Ph); 4.15–2.97 (m, 8H, piperazine); 2.80–0.90 (m, 18H, Trolox®).

13.3) N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 13

The experimental protocol used is the same as that described for the compound 1, with 3,4-dihydro-2,5,7,8-tetramethyl-2-{4-[(4-aminophenyl)-1-piperazinyl]-carbonyl}-2H-1-benzopyran-6-ol replacing the 3,5-bis-(1,1-dimethylethyl)-4-hydroxy-N-(4-amino-phenyl)-benzamide.

However, the reaction is slower and requires 15 hours of heating. The base obtained after extraction is purified on a silica gel column (eluant: petroleum ether (B.p. 40–70° C.)/ethyl acetate: 3/7). The pure fractions are concentrated under vacuum and the evaporation residue is salified in the presence of a molar solution of HCl in anhydrous diethyl ether. A yellow powder pale is obtained with a yield of 40%. Melting point: 210–211° C.

NMR $^1$H (400 MHz, DMSO d6, δ): 11.50 (s, 1H, NH$^+$); 9.79 (s, 1H, NH$^+$); 8.69 (s, 1H, NH$^+$); 8.19 (m, 2H, thiophene); 7.38 (m, 1H, thiophene); 7.20 (m, 4H, Ph); 4.58 (wide s, 1H, OH); 4.11 (m, 2H, piperazine); 3.61 (m, 2H, piperazine); 3.19 (m, 4H, piperazine); 2.62–1.55 (m, 16H, Trolox®).

IR: $v_{OH}$: 3410 cm$^{-1}$; $v_{C=O}$ (amide): 1642 cm$^{-1}$; $v_{C=N}$ (amidine): 1613 cm$^{-1}$.

Example 14

N-{4-[4-[(5 methoxy-1H-indol-3-yl)methylcarbonyl]-1-piperazinyl]phenyl}-2-thiophenecarboximidamide: 14

14.1) 1-[(5-methoxy-1H-indol-3-yl)methylcarbonyl]-4-(4-nitrophenyl)-piperazine

In a 100 ml flask, 1.62 g (10 mmoles) of 1,1'-carbonyldiimidazole is added to a solution of 2.05 g (10 mmoles) of 5-methoxyindole-3-acetic acid in 10 ml of THF. After one hour of agitation at ambient temperature, a solution of 1-(4-nitrophenyl)piperazine in 10 ml of DMF is added dropwise. Agitation is continued for 15 hours. The reaction medium is then concentrated under vacuum and the evaporation residue is precipitated from 50 ml of an ethyl acetate/water mixture (1/1). After filtration, the solid is rinsed successively with 50 ml of water, 50 ml of ethyl acetate and 50 ml of dichloromethane. After drying under vacuum, a yellow powder is obtained with a yield of 91%. Melting point: 239–240° C.

NMR $^1$H (100 MHz, DMSO d6, δ): 10.90 (m, 1H, NH); 7.63 (m, 4H, Ph—NO$_2$); 7.40–7.15 (m, 3H, indol); 6.87 (dd, 1H indol, $J_{ortho}$=8.7 Hz, $J_{meta}$=2.8 Hz); 3.90 (s, 2H, CH$_2$—CO); 3.88 (s, 3H, OCH$_3$); 3.79 (m, 4H, piperazine); 3.50 (m, 4H, piperazine).

14.2) 1-[(5 methoxy-1H-indol-3-yl)methylcarbonyl]-4-(4-aminophenyl)-piperazine

In a 250 ml Parr flask, 1 g (2.53 mmoles) of intermediate 14.1 is dissolved in 30 ml of DMSO in the presence of 10%Pd/C. The mixture is agitated under 20 PSI of hydrogen, at 25° C., for 7 hours. After filtration on celite, the filtrate is concentrated under vacuum. The evaporation residue is diluted in 50 ml of ethyl acetate and washed with 3×50 ml of water. The organic phase is then extracted with 2×25 ml of a molar solution of HCl. After the acid solution is washed with 2×25 ml of ethyl acetate, it is alkalinized using sodium carbonate in powder form. Once the product is re-extracted using 2×50 ml of ethyl acetate, the organic solution is dried over sodium sulphate, filtered and the solvent is evaporated off under vacuum. The residue is purified on a silica gel column (eluant: dichloromethane/methanol: 98/2). The pure fractions are collected and after evaporation of the solvent under reduced pressure, 0.39 g of a pale yellow powder is obtained with a yield of 46%. Melting point: 119–120° C.

NMR $^1$H (100 MHz, CDCl$_3$, δ): 8.32 (s, 1H, indolic NH); 7.27–6.80 (m, 4H, indole); 6.69 (m, 4H, Ph—NH$_2$); 3.82 (s, 3H, OCH$_3$); 3.80 (s, 2H, CH$_2$—CO); 3.80 (m, 2H, piperazine); 3.62 (m, 2H, piperazine); 3.48 (s, 2H, NH$_2$); 2.90 (m, 4H, piperazine).

14.3) N-{4-[4-[(5 methoxy-1H-indole-3-yl) methylcarbonyl]-1-piperazinyl]phenyl}-2-thiophenecarboximidamide: 14

The experimental protocol used is the same as that described for the compound 1, with 1-[(5 methoxy-1H-indole-3-yl)methylcarbonyl]-4-(4-aminophenyl)-piperazine replacing the 3,5-bis-(1,1-dimethylethyl)-4-hydroxy-N-(4-aminophenyl)-benzamide. The expected product is isolated in the form of the free base with a yield of 20% (pale yellow powder). Melting point: 221–222° C.

NMR $^1$H (400 MHz, DMSO d6, δ): 10.78 (s, 1H, indolic NH); 7.72 (m, 1H, thiophene); 7.59 (m, 1H, thiophene); 7.22 (d, 1H, indole, J=8.7 Hz); 7.19 (m, 1H, thiophene); 7.09 (m, 2H, indole); 6.82 (m, 4H, Ph); 6.72 (m, 1H indole); 6.35 (s, 2H, NH$_2$); 3.80 (s, 2H, CH$_2$); 3.73 (s, 3H, CH$_3$); 3.62 (m, 4H, piperazine); 2.95 (m, 4H, piperazine).

IR: $\nu_{OH}$: 3414 cm$^{-1}$; $\nu_{C=O}$ (amide): 1628 cm$^{-1}$; $\nu_{C=N}$ (amidine): 1590 cm$^{-1}$.

Example 15

N-[4-[4-[{3-[3,5-bis-(1,1-dimethylethyl)-4-hydroxyphenyl]-1-oxo-2-propenyl}-1-piperazinyl]-phenyl]]-2-thiophenecarboximidamide fumarate: 15

15.1) 2,6-bis-(1,1-dimethylethyl)-4-{3-[4-(4-nitrophenyl)-1-piperazinyl]-3-oxo-2-propenyl}-phenol The experimental protocol used is the same as that described for intermediate 11.1, with 3,5-di-tert-butyl-4-hydroxycinnamic acid replacing the syringic acid. An oil is obtained with a yield of 60%.

NMR $^1$H (100 MHz, CDCl$_3$, δ): 7.71 (d, 1H, C=CH, J=15.0 Hz); 7.51 (m, 4H, Ph—NO$_2$); 7.38 (s, 2H, Ph); 6.69 (d, 1H, HC=C, J=15.0 Hz); 5.50 (s, 1H, OH); 3.88 (m, 4H, piperazine); 3.53 (m, 4H, piperazine); 1.47 (s, 18 H, 2× tBu).

15.2) 2,6-bis-(1,1-dimethylethyl)-4-{3-[4-(4-aminophenyl)-1-piperazinyl]-3-oxo-2-propenyl}-phenol In a 50 ml flask equipped with a refrigerant, 0.5 g (1 mmole) of intermediate 15.1 is dissolved in 5 ml of concentrated hydrochloric acid and 5 ml of absolute ethanol. The mixture is cooled down to 0° C. and 1.69 g (7.5 mmoles) of tin chloride (dihydrate) is added in several portions. After this addition, the reaction medium is heated under reflux for 30 minutes. The solvents are then evaporated off under vacuum, the residue is taken up in 15 ml of water, neutralized with 2N soda and diluted with 20 ml of dichloromethane. The precipitate obtained is filtered on celite and the filtrate is decanted. The organic phase is dried over sodium sulphate, filtered and concentrated under reduced pressure to produce 0.3 g (67%) of a yellow oil.

NMR $^1$H (100 MHz, CDCl$_3$, δ): 7.66 (d, 1H, C=CH, J=15.0 Hz); 7.37 (s, 2H, Ph); 6.75 (m, 4H, Ph—NH$_2$); 6.30 (d, 1H, HC=C, J=15.0 Hz); 5.46 (s, 1H, OH); 3.80 (m, 4H, piperazine); 3.06 (m, 4H, piperazine); 1.46 (s, 18 H, 2× tBu).

15.3) N-[4-[4-[{3-[3,5-bis-(1,1-dimethylethyl)-4-hydroxy-phenyl]-1-oxo-2-propenyl}-1-piperazinyl]-phenyl]]-2-thiophenecarboximidamide fumarate: 15

The experimental protocol used is the same as that described for compound 1, with 2,6-bis-(1,1-dimethylethyl)-4-{3-[4-(4-aminophenyl)-1-piperazinyl]-3-oxo-2-propenyl}-phenol replacing the 3,5-bis-(1,1-dimethylethyl)-4-hydroxy-N-(4-aminophenyl)-benzamide.

The product of the reaction is salified in the presence of an equimolar quantity of fumaric acid in ethanol under reflux. Compound 15 is obtained in the form of a yellow powder with a yield of 22%. Melting point: 170.5–173° C.

NMR $^1$H (400 MHz, DMSO d6, δ): 7.77 (s, 1H, thiophene); 7.67 (d, 1H, thiophene, J=5.0 Hz); 7.48 (d, 1H, C=CH, J=15.0 Hz); 7.39 (s, 2H, Ph); 7.34 (wide s, 1H, OH); 7.13 (t, 1H, thiophene, J=4.0 Hz); 7.05 (d, 1H, HC=C, J=15.0 Hz); 6.92 (m, 4H, Ph—N); 6.60 (s, 2H, CH=CH fumarate); 3.78 (m, 4H, piperazine); 3.13 (m, 4H, piperazine); 1.41 (s, 18 H, 2× tBu).

IR: $\nu_{OH}$: 3619 cm$^{-1}$, 3300 cm$^{-1}$; $\nu_{C=O}$ (amide): 1640 cm$^{-1}$; $\nu_{C=C}$: 1600 cm$^{-1}$; $\nu_{C=N}$ (amidine): 1570 cm$^{-1}$.

Example 16

3,5-bis-(1,1-dimethylethyl)-4-hydroxy-N-{3-[[(2-thienyl-(imino)methyl)amino]phenyl]methyl}-benzamide hydrochloride: 16

16.1) 3,5-bis-(1,1-dimethylethyl)-4-hydroxy-N-[(3-nitrophenyl)methyl]-benzamide The experimental protocol used is the same as that described for intermediate 2.1, with 3-nitrobenzylamine hydrochloride replacing the 4-nitrobenzylamine hydrochloride. A white powder is obtained with a yield of 63%. Melting point: 210–211° C.

NMR $^1$H (100 MHz, DMSO, δ): 9.12 (m, 1H, NH); 8.25 (m, 2H, Ph—NO$_2$); 7.80 (m, 4H, Ph—NO$_2$+Ph—OH); 7.60 (wide s, 1H, OH); 4.68 (d, 2H, CH$_2$, J=6 Hz); 1.55 (s, 18H, 2× tBu).

16.2) 3,5-bis-(1,1-dimethylethyl)-4-hydroxy-N-[(3-aminophenyl)methyl]-benzamide In a 250 ml Parr flask, 2.40 g (6.2 mmoles) of 3,5-bis-(1,1-dimethylethyl)-4-hydroxy-N-[(3-nitrophenyl)methyl]-benzamide is dissolved in 45 ml of an absolute ethanol/THF mixture (1/2) in the presence of 10% Pd/C. The mixture is agitated under 20 PSI of hydrogen, at 30° C., for three hours. After filtration on celite, the filtrate is concentrated to dryness and the residue is purified on a silica column (eluant: heptane/ethyl acetate: 60/40). The pure fractions are collected and concentrated under reduced pressure to produce 0.94 g (45%) of a white powder. Melting point: 171–172° C.

NMR $^1$H (100 MHz, CDCl$_3$, δ): 7.20 (m, 2H, Ph—NH$_2$); 6.70 (m, 4H, Ph—NH$_2$+Ph—OH); 6.34 (m, 1H, NH); 5.55 (s, 1H, OH); 4.56 (d, 2H, CH$_2$, J=6 Hz); 3.70 (wide s, 2H, NH$_2$); 1.49 (s, 18H, 2× tBu).

6.3) 3,5-bis-(1,1-dimethylethyl)-4-hydroxy-N-{3-[[(2-thienyl-(imino)methyl)-amino]phenyl]methyl}-benzamide hydrochloride: 16

The experimental protocol used is the same as that described for compound 1, with 3,5-bis-(1,1-dimethylethyl)-4-hydroxy-N-[(3-aminophenyl)methyl]-benzamide replacing the 3,5-bis-(1,1-dimethylethyl)-4-hydroxy-N-(4-aminophenyl)-benzamide. After salification with a molar solution of HCl in an acetone/anhydrous methanol mixture, a pale yellow powder is obtained with a yield of 50%. Melting point: 226–227° C.

NMR $^1$H (400 MHz, DMSO d6, δ): 11.71 (s, 1H, NH$^+$); 9.93 (s, 1H, NH$^+$); 9.10 (s, 1H, CONH); 9.00 (s, 1H, NH$^+$);

8.18 (m, 2H, thiophene); 7.70 (s, 2H, Ph); 7.42 (m, 6H, thiophene, Ph—NH, OH); 4.50 (d, 2H, CH$_2$—NHCO, J=5.4 Hz); 1.40 (s, 18H, 2× tBu).

IR: $v_{OH}$: 3420 cm$^{-1}$; $v_{C=O}$ (amide): 1639 cm$^{-1}$; $v_{C=N}$ (amidine): 1578 cm$^{-1}$.

Example 17

N-[3,5-bis-(1,1-dimethylethyl)-4-hydroxyphenyl]-N'-{{4-[(2-thienyl(imino)methyl)amino]phenyl}methyl}-urea hydrochloride: 17

17.1) 4-amino-2,6-bis-(1,1-dimethylethyl)-phenol

In a 250 ml Parr flask, 3.6 g (14 mmoles) of 4-nitro-2,6-bis-(1,1-dimethylethyl)-phenol (*J. Org. Chem.* (1968), 33 (1), 223–226) is dissolved in 60 ml of a (2/1) mixture of ethanol and dichloromethane in the presence of a catalytic quantity of 10% Pd/C. The mixture is agitated for 2 hours, at 20° C., under 20 PSI of hydrogen. After filtration on celite, the filtrate is concentrated to dryness under reduced pressure. The reddish-brown powder obtained is suspended in heptane (30 ml), filtered and rinsed with the same volume of heptane. The expected product is obtained in the form of an salmon pink powder with a yield of 50% (1.56 g). Melting point: 123–124° C.

NMR $^1$H (100 MHz, CDCl$_3$, δ): 6.60 (s, 2H, Ph); 4.65 (wide s, 1H, OH); 3.15 (wide s, 2H, NH$_2$); 1.42 (s, 18H, 2× tBu).

17.2) 4-nitrophenylacetic acid chloride 3.75 ml (7.5 mmoles) of a 2M solution of oxalyl chloride in dichloromethane is added at 20° C. to a solution of 0.9 g (5 mmoles) of 4-nitrophenylacetic acid in a mixture composed of 10 ml of dichloromethane and 0.5 ml of DMF. After agitation for 30 minutes, the solution is concentrated under vacuum. The yellow oil obtained is used without additional purification in the following stage.

17.3) 4-nitrobenzylisocyanate

The chloride of 4-nitrophenylacetic acid in solution in dry acetone (7.5 ml) is slowly added to an aqueous solution of 0.75 g (11.5 mmoles) of sodium azide, cooled down to 0° C. Agitation of the medium is maintained for one hour after the addition is completed, at 0–5° C. The reaction medium is then diluted with 30 ml of chloroform, decanted and the organic phase washed with water (20 ml) followed by a saturated solution of sodium chloride (20 ml). After drying over sodium sulphate, the organic solution is filtered and partly concentrated (≈20 ml) under vacuum. This solution of the acylazide in chloroform is then heated, under reflux, for one hour. The isocyanate obtained is used directly, in solution, in the following stage.

17.4) N-[3,5-bis-(1,1-dimethylethyl)-4-hydroxyphenyl]-N'-[(4-nitrophenyl)methyl]-urea 1.1 g (5 mmoles) of 4-amino-2,6-bis-(1,1-dimethylethyl)-phenol is added in one portion to the isocyanate solution (intermediate 17.3) (theoretically 5 mmoles) in 20 ml of chloroform. After agitation for 2 hours at 20° C., the precipitate which appears is filtered out and rinsed with chloroform (2×20 ml). A yellow powder is obtained with a yield of 72%. Melting point: 240–241° C.

NMR $^1$H (100 MHz, DMSO d6, δ): 8.60 (s, 1H, NH—Ph); 8.01 (m, 4H, Ph—NO$_2$); 7.30 (s, 2H, Ph—OH); 6.77 (m, 1H, NH—CH$_2$); 6.71 (s, 1H, OH); 4.52 (d, 2H, CH$_2$, J=5.5 Hz); 1.49 (s, 18H, 2× tBu).

17.5) N-[(4-aminophenyl)methyl]-N'-[3,5-bis-(1,1-dimethylethyl)-4-hydroxyphenyl]-urea In a 100 ml autoclave, 0.55 g (1.38 mmole) of N-[3,5-bis-(1,1-dimethylethyl)-4-hydroxyphenyl]-N'-[(4-nitrophenyl)methyl]-urea is dissolved in a 2/1 mixture of ethanol and ethyl acetate, in the presence of 10% Pd/C. After hydrogenation for one and a half hours at 20° C., under 20 PSI, the mixture is filtered on celite and the filtrate is concentrated under vacuum. The evaporation residue is diluted in 20 ml of diethyl ether and the expected product crystallizes spontaneously. The crystals are filtered out and rinsed with 20 ml of diethyl ether. A white powder is obtained with a yield of 60% (0.31 g). Melting point: 194–195° C.

NMR $^1$H (100 MHz, CDCl$_3$, δ): 7.08 (s, 2H, Ph—OH); 6.87 (m, 4H, Ph—NH$_2$); 6.15 (s, 1H, NH—Ph); 5.14 (s, 1H, OH); 4.89 (m, 1H, NH—CH$_2$); 4.41 (d, 2H, CH$_2$, J=5.5 Hz); 3.65 (wide s, 2H, NH$_2$); 1.40 (s, 18H, 2× tBu).

17.6) N-[3,5-bis-(1,1-dimethylethyl)-4-hydroxyphenyl]-N'-{{4-[2-thienyl(imino-methyl)amino]phenyl}methyl}-urea hydrochloride: 17

The experimental protocol used is the same as that described for compound 1, with N-[(4-amninophenyl)methyl]-N'-[3,5-bis-(1,1-dimethylethyl)-4-hydroxyphenyl]-urea replacing the 3,5-bis-(1,1-dimethylethyl)-4-hydroxy-N-(4-aminophenyl)-benzamide. After salification with a molar solution of HCl in anhydrous diethyl ether, a white powder is obtained with a yield of 45%. Melting point: 236–237° C.

NMR $^1$H (400 MHz, DMSO d6, δ): 11.42 (wide s, 1H, NH$^+$); 9.77 (wide s, 1H, NH$^+$); 8.92 (wide s, 1H, NH$^+$); 8.54 (s, 1H, NH—Ph); 8.11 (m, 2H, thiophene); 7.41 (m, 5H, Ph—N, thiophene); 7.19 (s, 2H, Ph); 6.70 (m, 1H, NH—CH$_2$); 6.60 (s, 1H, OH); 4.35 (d, 2H, CH$_2$, J=5.5 Hz); 1.34 (s, 18H, 2× tBu).

IR: $v_{OH}$: 3624 cm$^{-1}$; $v_{C=O}$ (urea): 1644 cm$^{-1}$; $v_{C=N}$ (amidine): 1569 cm$^{-1}$.

Example 18

N-[5-[{3-(3,5-bis-(1,1-dimethylethyl)-4-hydroxyphenyl)-1-oxo-2-propenyl}-amino]-2-hydroxyphenyl]-2-thiophenecarboximidamide hydrochloride: 18

18.1) 3-[(3,5-bis-(1,1-dimethylethyl)-4-hydroxyphenyl]-N-(4-hydroxy-3-nitrophenyl)-2-propenamide 1.78 g (6.4 mmoles) of 3,5-di-tert-butyl-4-hydroxycinnamic acid, 0.99 g (6.4 mmoles) of 4-amino-2-nitrophenol, previously diluted in 10 ml of DMF, 0.86 g (6.4 mmoles) of hydroxybenzotriazol and 1.32 g (6.4 mmoles) of dicyclobexylcarbodiimide are introduced into a 50 ml flask containing 10 ml of THF. The reaction medium is agitated for 15 hours at ambient temperature, the precipitate which appears is filtered and rinsed with ethyl acetate. After concentration of the solution under reduced pressure, the residue is diluted in 20 ml of ethyl acetate and the insoluble part is filtered again. The filtrate is washed with 20 ml of a saturated solution of sodium carbonate followed by 20 ml of water and 20 ml of a saturated solution of sodium chloride. After drying over sodium sulphate, the organic solution is filtered and concentrated to dryness under reduced pressure. The residue is purified on a silica column (eluant: heptane/ ethyl acetate: 8/2). The pure fractions are collected and concentrated under vacuum to produce 1.95 g (47%) of the expected compound in the form of a yellow-orange powder. Melting point: 231–232° C.

NMR $^1$H (100 MHz, CDCl$_3$, δ): 10.45 (s, 1H, NH); 8.45 (d, 1H, Ph—NO$_2$, J=1.7 Hz); 7.98 (dd, 1H, Ph—NO$_2$, J=1.7 Hz and J=6.8 Hz); 7.78 (d, 1H, —CH=CH—, J=10.5 Hz); 7.75 (s, 1 H, OH); 7.40 (s, 2H, Ph—OH); 7.20 (d, 1H, Ph—NO$_2$); 6.48 (d, 1H, —CH=CH—); 5.51 (s, 1H, OH); 1.50 (s, 18H, 2× tBu).

18.2) 3-[(3,5-bis-(1,1-dimethylethyl)-4-hydroxyphenyl]-N-(4-hydroxy-3-aminophenyl)-2-propenamide In a 100 ml flask equipped with a refrigerant, 0.9 g (2.18 mmoles) of 3-[(3,5-bis-(1,1-dimethylethyl)-4-hydroxyphenyl]-N-(4-hydroxy-3-nitrophenyl)-2-propenamide is dissolved in 20 ml of ethyl acetate, 2.46 g (10.9 mmoles) of tin chloride (dihydrate) is added and the mixture is heated at 70° C. for three hours. After returning to ambient temperature, the reaction medium is poured onto an agitated solution of sodium bicarbonate (0.1 M), a precipitate forms, which is eliminated by filtration on celite. The filtrate is decanted and the aqueous phase is extracted with 20 ml of ethyl acetate. The organic phases are collected together and washed with 20 ml of water followed by 20 ml of a saturated solution of sodium chloride. After drying over sodium sulphate and filtration, the organic solution is concentrated to dryness, under partial vacuum. The evaporation residue is suspended in a heptane/ethyl acetate mixture (1/1) and filtered to produce a yellowish powder with a yield of 53%. The product is used as it is in the following stage.

18.3) N-[5-[{3-(3,5-bis-(1,1-dimethylethyl)-4-hydroxyphenyl)-1-oxo-2-propenyl}amino]-2-hydroxyphenyl]-2-thiophenecarboximidamide hydrochloride: 18

The experimental protocol used is the same as that described for compound 1, with 3-[(3,5-bis-(1,1-dimethylethyl)-4-hydroxyphenyl]-N-(4-hydroxy-3-aminophenyl)-2-propenamide replacing the 3,5-bis-(1,1-dimethylethyl)-4-hydroxy-N-(4-aminophenyl)-benzamide. The free base is purified on a silica column (eluant: heptane/ethyl acetate: 35/65). The pure fractions are collected and concentrated under reduced pressure. The evaporation residue is diluted in 10 ml of acetone and salified with a molar solution of HCl in anhydrous ether, as described previously. 0.35 g (62%) of a yellow powder is obtained. Melting point: 199–200° C.

NMR $^1$H (400 MHz, DMSO, δ): 11.11 (s, 1H, NH$^+$); 10.29 (s, 1H, NH$^+$); 10.17 (s, 1H, NH$^+$); 9.71 (s, 1H, CONH); 8.61 (wide s, 1H, OH); 8.14 (m, 2H, thiophene); 7.79 (s, 1H, Ph—N); 7.53 (m, 1H, Ph—N); 7.48 (d, 1H, —CH=CH—, J=14.7 Hz); 7.37 (m, 4H, Ph—tBu+OH+Ph—N); 7.05 (m, 1H, thiophene); 6.68 (d, 1H, —CH=CH—); 1.41 (s, 18H, 2× tBu).

IR: $\sigma_{OH}$: 3624 cm$^{-1}$, 3415 cm$^{-1}$; $\nu_{C=O}$ (amide): 1656 cm$^{-1}$; $\nu_{C=C}$: 1616 cm$^{-1}$; $\nu_{C=N}$ (amidine): 1587 cm$^{-1}$.

Example 19

N-[3-[{3-(3,5-bis-(1,1-dimethylethyl)-4-hydroxyphenyl)-1-oxo-2-propenyl}-amino]-4-hydroxyphenyl]-2-thiophenecarboximidamide hydrochloride: 19

19.1) 3-[(3,5-bis-(1,1-dimethylethyl)-4-hydroxyphenyl]-N-(2-hydroxy-5-nitrophenyl)-2-propenamide The experimental protocol used is the same as that described for intermediate 18.1, with 2-amino-4-nitrophenol replacing the 4-amino-2-nitrophenol. A light yellow powder is obtained with a yield of 25%. Melting point: 256–257° C.

NMR $^1$H (400 MHz, DMSO, δ): 11.79 (wide s, 1H, OH); 9.59 (s, 1H, NH); 9.21 (wide s, 1H, Ph—NO$_2$);,7.90 (badly resolved dd, 1H, Ph—NO$_2$, J=8.1 Hz); 7.52 (d, 1H, —CH=CH—, J=15.5 Hz); 7.47 (s, 1H, OH); 7.42 (s, 2H, Ph—OH); 7.15 (d, 1H, —CH=CH—); 7.04 (d, 1H, Ph—NO$_2$); 1.42 (s, 18H, 2× tBu).

19.2) 3-[(3,5-bis-(1,1-dimethylethyl)-4-hydroxyphenyl]-N-(2-hydroxy-5-aminophenyl)-2-propenamide The experimental protocol used is the same as that described for intermediate 18.2, with 3-[(3,5-bis-(1,1-dimethylethyl)-4-hydroxyphenyl]-N-(2-hydroxy-5-nitrophenyl)-2-propenamide replacing the 3-[(3,5-bis-(1,1-dimethylethyl)-4-hydroxyphenyl]-N-(4-hydroxy-3-nitrophenyl)-2-propenamide. A yellow powder is obtained with a yield of 74%. The product is used without additional purification in the following stage.

19.3) N-[5-[{3-(3,5-bis-(1,1-dimethylethyl)-4-hydroxyphenyl)-1-oxo-2-propenyl}-amino]-2-hydroxyphenyl]-2-thiophenecarboximidamide hydrochloride: 19

The experimental protocol used is the same as that described for compound 1, with 3-[(3,5-bis-(1,1-dimethylethyl)-4-hydroxyphenyl]-N-(2-hydroxy-5-aminophenyl)-2-propenamide replacing the 3,5-bis-(1,1-dimethylethyl)-4-hydroxy-N-(4-amninophenyl)-benzamide. After salification with a molar solution of HCl in anhydrous diethyl ether, a yellow powder is obtained with a yield of 54%. Melting point: 256–257° C.

NMR $^1$H (400 MHz, DMSO d6, δ): 11.32 (s, 1H, NH$^+$); 10.67 (s, 1H, NH$^+$); 9.69 (s, 1H, NH$^+$); 9.55 (s, 1H, CONH); 8.70 (wide s, 1H, OH); 8.19 (m, 2H, thiophene); 7.48 (d, 1H, —CH=CH—, J=15.5 Hz); 7.40 (s, 2H, Ph—tBu); 7.37 (m, 2H, Ph—N); 7.34 (s, 1H, OH); 7.13 (d, 1H, —CH=CH—); 7.10 (m, 1H, Ph—N); 6.99 (m, 1H, thiophene); 1.41 (s, 18H, 2× tBu).

IR: $\nu_{OH}$: 3623 cm$^{-1}$, 3410 cm$^{-1}$; $\nu_{C=O}$ (amide): 1652 cm$^{-1}$; $\nu_{C=C}$: 1616 cm$^{-1}$; $\nu_{C=N}$ (amidine): 1587 cm$^{-1}$.

Example 20

N-{4-[4-[3,4,5-trihydroxybenzoyl]-1-piperazinyl]phenyl}-2-thiophenecarboximidamide hydrochloride: 20

20.1) 5-{[4-(4-nitrophenyl)-1-piperazinyl]carbonyl}-benzene-1,2,3-triol

The experimental protocol is the same as that described for intermediate 8.1, with 1-(4-nitrophenyl)piperazine replacing the 4-nitrophenetylamine. A yellow powder still containing traces of impurities is obtained with a yield of 43%.

NMR $^1$H (100 MHz, DMSO, δ): 9.17 (wide s, 2H, 2× —OH); 8.55 (wide s, 1H, —OH); 7.57 (m, 4H, Ph—NO$_2$); 6.40 (s, 2H, Ph—OH); 3.59 (badly resolved m, 8 H, piperazine).

20.2) 5-{[4-(4-aminophenyl)-1-piperazinyl]carbonyl}-benzene-1,2,3-triol

The experimental protocol used is the same as that described for intermediate 2.2, with 5-{[4-(4-nitrophenyl)-

1-piperazinyl]carbonyl}-benzene-1,2,3-triol replacing the 3,5-bis-(1,1-dimethylethyl)-4-hydroxy-N-[(4-nitrophenyl) methyl]-benzamide. A beige powder is obtained with a yield of 61%. This is used directly in the following stage without additional purification.

NMR $^1$H (100 MHz, DMSO, δ): 9.12 (wide s, 2H, 2× —OH); 8.55 (wide s, 1H, —OH); 6.61 (m, 4H, Ph—NH$_2$); 6.34 (s, 2H, Ph—OH); 3.59 (m, 4H, piperazine); 2.89 (m, 4H, piperazine).

20.3) N-{4-[4-[3,4,5-trihydroxybenzoyl]-1-piperazinyl]phenyl}-2-thiophenecarboximidamide hydrochloride: 20

The experimental protocol used is the same as that described for compound 1, with 5-{[4-(4-amninophenyl)-1-piperazinyl]carbonyl}-benzene-1,2,3-triol replacing the 3,5-bis-(1,1-dimethylethyl)-4-hydroxy-N-(4-aminophenyl)-benzamide. After treatment with a molar solution of HCl in anhydrous diethyl ether, a brown powder is obtained with a yield of 25%. Melting point: 198–205° C.

NMR $^1$H (400 MHz, DMSO d6, δ): 11.38 (s, 1H, NH$^+$); 9.75 (s, 1H, NH$^+$); 9.00 (wide s, 1H, OH); 8.75 (s, 1H, NH$^+$); 8.15 (m, 2H, thiophene); 7.39 (m, 1H, thiophene); 7.22 (m, 4H, Ph—N); 6.40 (s, 2H, Ph); 5.11 (wide s, 2H, 2× OH); 3.65 (m, 4H, piperazine); 3.29 (m, 4H, piperazine).

IR: ν$_{OH}$: 3399 cm$^{-1}$; ν$_{C=O}$ (amide): 1696 cm$^{-1}$; ν$_{C=N}$ (amidine): 1588 cm$^{-1}$.

Example 21

N-[3,5-bis-(1,1-dimethylethyl)-4-hydroxyphenyl]-N'-{{4-[(2-thienyl(imino)methyl)amino]phenyl}carbonylamino}-urea hydrochloride: 21

21.1) N-[3,5-bis-(1,1-dimethylethyl)-4-hydroxyphenyl]-N'-[(4-nitrophenyl)-carbonylamino]-urea 0.22 g (0.73 mmole) of triphosgene at 20° C. is dissolved in a 50 ml three-necked flask equipped with an addition funnel, under an argon atmosphere. Over one hour, a solution of 0.44 g (2 mmoles) of 4-amino-2,6-bis-(1,1-dimethylethyl)-phenol (intermediate 17.1) and 0.38 ml (2.2 mmoles) of diisopropylethylamine in 7 ml of anhydrous dichloromethane is added dropwise to this mixture. Five minutes after the end of this addition, a solution of 0.36 g (2 mmoles) of 4-nitrobenzoyl-hydrazide and 0.38 ml (2.2 mmoles) of diisopropylethylamine in 4 ml of anhydrous DMF is added in a single portion. After agitation for four hours at 20° C., the reaction medium is concentrated to dryness under reduced pressure. The evaporation residue is diluted in 40 ml of ethyl acetate and the organic solution is washed successively with 3 times 20 ml of water and 20 ml of a saturated solution of sodium chloride. After drying over sodium sulphate, the organic solution is filtered and the filtrate concentrated to dryness under reduced pressure. The residue obtained is suspended in heptane, agitated and filtered to produce a yellow powder with a yield of 86%. Melting point: 163–164° C.

NMR $^1$H (100 MHz, DMSO d6, δ): 10.65 (wide s, 1H, NH amide); 8.72 (s, 1H, NH—Ph); 8.38 (m, 4H, Ph—NO$_2$); 8.20 (s, 1H, CO—NH—NH); 7.36 (s, 2H, Ph—OH); 6.78 (s, 1H, OH); 1.50 (s, 18H, 2× tBu).

21.2) N-[(4-aminophenyl)carbonylamino]-N'-[3,5-bis-(1,1-dimethylethyl)-4-hydroxyphenyl]-urea In a 250 ml Parr flask, 0.72 g (1.68 mmoles) of N-[3,5-bis-(1,1-dimethylethyl)-4-hydroxyphenyl]-N'-[(4-nitrophenyl)carbonylamino]-urea is dissolved in 30 ml of absolute ethanol in the presence of 10% Pd/C. The mixture is agitated under 20 PSI of hydrogen, at 30° C., for two hours. After filtration on celite, the filtrate is concentrated under vacuum. The evaporation residue is suspended in diethyl ether (20 ml), agitated and filtered to produce a pale yellow powder with a yield of 75%. Melting point: 245–246° C.

NMR $^1$H (100 MHz, DMSO d6, δ): 9.84 (wide s, 1H, NH amide); 8.56 (s, 1H, NH—Ph); 7.85 (m, 2H, Ph—NH$_2$); 7.74 (s, 1H, CO—NH—NH); 7.38 (s, 2H, Ph—OH); 6.78 (s, 1H, OH); 6.60 (m, 2H, Ph—NH$_2$); 5.80 (wide s, 2H, NH$_2$); 1.50 (s, 18H, 2× tBu).

21.3) N-[3,5-bis-(1,1-dimethylethyl)-4-hydroxyphenyl]-N'-{{4-[(2-thienyl(imino)methyl)amino]phenyl}carbonylamino}-urea hydrochloride: 21

The experimental protocol used is the same as that described for compound 1, with N-[(4-aminophenyl)carbonylamino]-N'-[3,5-bis-(1,1-dimethylethyl)-4-hydroxyphenyl]-urea replacing the 3,5-bis-(1,1-dimethylethyl)-4-hydroxy-N-(4-aminophenyl)-benzamide. The free base is purified on a silica column (eluant: heptane/ethyl acetate: 1/1). The pure fractions are collected and concentrated under reduced pressure. The evaporation residue is diluted in 15 ml of acetone and salified with a molar solution of HCl in anhydrous ether, as described previously. 0.40 g (58%) of a yellow powder is obtained. Melting point: 254–255° C.

NMR $^1$H (400 MHz, DMSO, δ): 11.68 (wide s, 1H, NH$^+$); 10.32 (s, 1H, NH amide); 9.94 (wide s, 1H, NH$^+$); 9.13 (wide s, 1H, NH$^+$); 8.68 (s, 1H, NH—CO); 8.18 (m, 2H, thiophene); 8.07 (m, 3H, CO—NH—NH+Ph—NH); 7.58 (m, 2H, Ph—NH); 7.39 (m, 1H, thiophene); 7.22 (s, 2H, Ph—OH); 6.60 (s, 1H, OH); 1.36 (s, 18H, 2× tBu).

IR: ν$_{OH}$: 3627 cm$^{-1}$; ν$_{C=O}$ (amide), ν$_{C=O}$ (urea): 1654 cm$^{-1}$, 1602 cm$^{-1}$; ν$_{C=N}$ (amidine): 1559 cm$^{-1}$.

Example 22

N-[3,5-bis-(1,1-dimethylethyl)-4-hydroxyphenyl]-N'-{{4-[(2-thienyl(imino)methyl)amino]phenyl}methyl}-thiourea hydrochloride: 22

22.1) N-[3,5-bis-(1,1-dimethylethyl)-4-hydroxyphenyl]-N'-[(4-nitrophenyl)methyl]-thiourea Compound 22.1 is obtained by the action of Lawesson's reagent on intermediate 17.4 according to an experimental protocol described in the literature (J. Med. Chem. (1995), 38 (18), 3558–3565). A light yellow powder is obtained with a yield of 80%. Melting point: 218–220° C.

NMR $^1$H (100 MHz, CDCl$_3$, δ): 7.85 (m, 4H, Ph—NO$_2$); 7.70$^-$ (s, 1H, NH—Ph); 7.05 (s, 2H, Ph—OH); 6.21 (m, 1H, NH—CH$_2$); 5.40 (s, 1H, OH); 5.00 (d, 2H, CH$_2$, J=6.5 Hz); 1.41 (s, 18H, 2× tBu).

22.2) N-[(4-aminophenyl)methyl]-N'-[3,5-bis-(1,1-dimethylethyl)-4-hydroxyphenyl]-thiourea The experimental protocol used is the same as that described for intermediate 18.2, with intermediate 22.1 replacing the 3-[(3,5-bis-(1,1-dimethylethyl)-4-hydroxyphenyl]-N-(4-hydroxy-3-nitrophenyl)-2-propenamide. A beige powder is obtained with a yield of 70%. Melting point: 167–169° C.

NMR $^1$H (100 MHz, CDCl$_3$, δ): 7.48 (wide s, 1H, NH—Ph); 6.95 (s, 2H, Ph—OH); 6.81 (m, 4H, Ph—NH$_2$); 5.98 (m, 1H, NH—CH$_2$); 5.28 (s, 1H, OH); 4.69 (d, 2H, CH$_2$, J=5.5 Hz); 3.62 (wide s, 2H, NH$_2$); 1.40 (s, 18H, 2× tBu).

22.3) N-[3,5-bis-(1,1-dimethylethyl)-4-hydroxyphenyl]-N'-{{4-[(2-thienyl(imino)methyl)amino]phenyl}methyl}-thiourea hydrochloride: 22

The experimental protocol used is the same as that described for intermediate 17.6, with intermediate 22.2 replacing the N-[(4-aminophenyl)methyl]-N'-[3,5-bis-(1,1-dimethylethyl)-4-hydroxyphenyl]-urea. A pale yellow powder is obtained with a yield of 15%. Melting point: 203–205° C.

NMR $^1$H (400 MHz, DMSO d6, δ): 11.52 (wide s, 1H, NH$^+$); 9.86 (wide s, 1H, NH$^+$); 8.98 (wide s, 1H, NH$^+$); 8.39 (s, 1H, NH—Ph); 8.16 (m, 2H, thiophene); 7.46 (m, 6H, Ph—N, thiophene, NH—CH$_2$); 7.18 (s, 2H, Ph); 6.92 (s, 1H, OH); 4.80 (wide s, 2H, CH$_2$); 1.35 (s, 18H, 2× tBu).

IR: $\nu_{OH}$: 3630 cm$^{-1}$; $\nu_{C=O}$ (urea): 1649 cm$^{-1}$; $\nu_{C=N}$ (amidine): 1600 cm$^{-1}$.

Example 23

N-[3,5-bis-(1,1-dimethylethyl)-4-hydroxyphenyl]-N'-{2-{4-[(2-thienyl(imino)methyl)amino]phenyl}ethyl}-urea hydrochloride: 23

23.1) N-[3,5-bis-(1,1-dimethylethyl)-4-hydroxyphenyl]-N'-[2-(4nitrophenyl)ethyl]-urea The experimental protocol used is the same as that described for intermediate 21.1, with 4-nitrophenetylamine replacing the 4-nitrobenzoyl-hydrazide. A beige powder is obtained with a yield of 80%. Melting point: 185–187° C.

NMR $^1$H (100 MHz, CDCl$_3$, δ): 7.75 (m, 4H, Ph—NO$_2$); 7.00 (s, 2H, Ph—OH); 6.05 (s, 1H, OH); 5.18 (s, 1H, NH); 4.68 (m, 1H, NH—CH$_2$); 3.50 (m, 2H, NH—CH$_2$); 2.92 (m, 2H, CH$_2$); 1.40 (s, 18H, 2× tBu).

23.2) N-[2-(4-aminophenyl)ethyl]-N'-[3,5-bis-(1,1-dimethylethyl)-4-hydroxyphenyl]-urea The experimental protocol used is the same as that described for intermediate 21.2, with intermediate 23.1 replacing the N-[3,5-bis-(1,1-dimethylethyl)-4-hydroxyphenyl]-N'-[(4-nitrophenyl)-carbonylamino]-urea. A white powder is obtained with a yield of 56%. Melting point: 192–194° C.

NMR $^1$H (100 MHz, DMSO d6, δ): 8.25 (wide s, 1H, Ph—NH—CO); 7.22 (s, 2H, Ph—OH); 6.79 (m, 4H, Ph—NH$_2$); 6.65 (s, 1H, OH); 5.92 (m, 1H; NH—CH$_2$); 4.98 (wide s, 2H, —NH$_2$); 3.31 (m, 2H, NH—CH$_2$); 2.65 (m, 2H, CH$_2$); 1.48 (s, 18H, 2× tBu).

23.3) N-[3,5-bis-(1,1-dimethylethyl)-4-hydroxyphenyl]-N'-{2-{4-[(2-thienyl(imino)methyl)amino]phenyl}ethyl}-urea hydrochloride: 23

The experimental protocol used is the same as that described for compound 1, with intermediate 23.2 replacing the 3,5-bis-(1,1-dimethylethyl)-4-hydroxy-N-(4-aminophenyl)-benzamide. The free base is purified on a silica column (eluant: heptane/ethyl acetate: 1/1). The pure fractions are collected and concentrated under reduced pressure. The evaporation residue is diluted in 15 ml of acetone and salified with a molar solution of HCl in anhydrous ether, as described previously. Finally, 0.25 g (24%) of a pale yellow powder is obtained. Melting point: 207–210° C.

NMR $^1$H (400 MHz, DMSO d6, δ): 11.48 (wide s, 1H, NH$^+$); 9.83 (wide s, 1H, NH$^+$); 8.95 (wide s, 1H, NH$^+$); 8.50 (s, 1H, NH—CO); 8.18 (m, 2H, thiophene); 7.38 (m, 5H, Ph—NH+thiophene); 7.18 (s, 2H, Ph—OH); 6.55 (s, 1H, OH); 6.21 (m, 1H, CO—NH—CH$_2$); 3.35 (m, 2H, NH—CH$_2$); 2.78 (m, 2H, CH$_2$); 1.36 (s, 18H, 2× tBu).

IR: $\nu_{OH}$: 3631 cm$^{-1}$; $\nu_{C=O}$ (urea): 1654 cm$^{-1}$, 1600 cm$^{-1}$; $\nu_{C=N}$ (amidine): 1560 cm$^{-1}$.

Example 24

N-(4-{4-[(3,4-dihydro-6-methoxy-2,5,7,8-tetramethyl-2H-1-benzopyran-2-yl)carbonyl]-1-piperazinyl}phenyl)-2-thiophenecarboximidamide hydrochloride: 24

24.1) 1-{[3,4-dihydro-6-methoxy-2,5,7,8-tetramethyl-2H-1-benzopyran-2-yl]carbonyl}-4-(4-nitrophenyl)piperazine The experimental protocol is identical to that described for intermediate 13.1, with (±)-3,4-dihydro-6-methoxy-2,5,7,8-tetramethyl-2H-1-benzopyran-2-carboxylique acid (prepared according to CHIMIA (1991), 45 (4), 121–3) replacing the (±)-Trolox®. A yellow powder is obtained.

NMR $^1$H (100 MHz, CDCl$_3$, δ): 7.45 (m, 4H, Ph); 3.60 (s, 3H, CH$_3$O); 3.40 (m, 4H, piperazine); 3.00 (m, 4H, piperazine); 2.50–1.60 (m, 16H, Trolox®).

24.2) 1-{[3,4-dihydro-6-methoxy-2,5,7,8-tetramethyl-2H-1-benzopyran-2-yl]carbonyl}-4-(4-aminophenyl)piperazine The experimental protocol is identical to that described for intermediate 13.2, with intermediate 24.1 replacing the 3,4-dihydro-2,5,7,8-tetramethyl-2-{4-[(4-nitrophenyl)-1-piperazinyl]-carbonyl}-2H-1-benzopyran-6-ol. An oil is obtained which is used directly in the following stage.

NMR $^1$H (100 MHz, CDCl$_3$, δ): 6.70 (m, 4H, Ph); 3.90 (wide d, 4H, piperazine); 3.60 (s, 3H, CH$_3$O); 3.45 (wide s, 2H, NH$_2$); 2.90 (m, 4H, piperazine); 2.60–1.60 (m, 18H, Trolox®).

24.3) N-(4-{4-[(3,4-dihydro-6-methoxy-2,5,7,8-tetramethyl-2H-1-benzopyran-2-yl)carbonyl]-1-piperazinyl}phenyl)-2-thiophenecarboximidamide hydrochloride: 24

The experimental protocol is the same as that described for compound 13, with intermediate 24.2 replacing the 3,4-dihydro-2,5,7,8-tetramethyl-2-{4-[(4-aminophenyl)-1-piperazinyl]-carbonyl}-2H-1-benzopyran-6-ol. A pale yellow powder is obtained. Melting point: 190–195° C.

NMR $^1$H (400 MHz, DMSO, δ): 11.35 (wide s, 1H, NH$^+$); 9.70 (wide s, 1H, NH$^+$); 8.70 (wide s, 1H, NH$^+$); 8.15 (wide s, 2H, thiophene); 7.35 (wide s, 1H, thiophene); 7.17 (m, 4H, Ph); 3.90 (wide d, 4H, piperazine); 3.50 (s, 3H, CH$_3$O); 3.15 (m, 4H, piperazine); 2.55–1.55 (m, 16H, Trolox®).

IR: $\nu_{C=O}$ (amide): 1642 cm$^{-1}$; $\nu_{C=N}$ (amidine): 1618 cm$^{-1}$.

Example 25

N-[4-{4-[(3,4-dihydro-6-hydroxy-2,5,7,8-tetramethyl-2H-1-benzopyran-2-yl)carbonyl]-1H-1,4-diazepin-1-yl}phenyl]-2-thiophenecarboximidamide hydrochloride: 25

25.1) hexahydro-4-(4-nitrophenyl)-1H-1,4-diazepine 3.37 g (24.4 mmoles) of potassium carbonate and 1.89 g (13.4 mmoles) of 4-nitrofluorobenzene are added to a solution of 2.44 g (12.2 mmoles) of (1,1-dimethyl)ethyl hexahydro-1H-1,4-diazepine-1-carboxylate in 50 ml of DMF. The reaction medium is heated at 100° C. for 16 hours. After cooling down, 25 ml of ethyl acetate and 50 ml of water are added. The organic solution is decanted and the aqueous phase extracted with 3 times 50 ml of ethyl acetate. The organic phases are collected together and washed with 50 ml of brine, dried over sodium sulphate, filtered and concentrated under vacuum. 3.7 g of a bright yellow solid is obtained with a yield of 95%. This solid is then dissolved in 100 ml of a mixture of solvents (dichloromethane/ethyl acetate 1:1) to which 20 ml of a 6N aqueous solution of hydrochloric acid is added dropwise at 0° C. After vigorous agitation at 20° C. for 1 hour, the reaction medium is decanted. The aqueous phase is basified to pH=11 with 4N soda and extracted with 3 times 50 ml of dichloromethane. The organic phases are collected, washed with 50 ml of water followed by 50 ml of brine, dried over sodium sulphate and finally filtered and concentrated under vacuum. 1.78 g of a bright yellow powder is obtained with a yield of 66%. The product is used directly in the following stage without additional purification.

NMR $^1$H (100 MHz, CDCl$_3$, δ): 8.10 (m, 2H, Ph); 6.65 (m, 2H, Ph); 3.70 (q, 4H, CH$_2$N, J=5.2 Hz); 3.10 (t, 2H, CH$_2$N); 2.85 (t, 2H, CH$_2$N); 1.95 (q, 2H, C—CH$_2$—C); 1.65 (wide s, 1H NH).

25.2) 1-[(3,4-dihydro-6-hydroxy-2,5,7,8-tetramethyl-2H-1-benzopyran-2-yl)carbonyl]hexahydro-4-(4-nitrophenyl)-1H-1,4-diazepine In a 50 ml flask, 0.71 g (4.4 mmoles) of 1,1'-carbonyldiimidazole is added to a solution of 1.07 g (4.3 mmoles) of (±)-Trolox® in 8 ml of anhydrous THF. After agitation for one hour at 20° C., a solution of 0.95 g (4.3 mmoles) of intermediate 25.1 in 4 ml of DMF is added dropwise. The reaction medium is agitated for 16 hours at 20° C. After evaporation of the solvents under vacuum, the residue is taken up in 30 ml of a mixture of solvents (dichloromethane/water 1:2). After decanting, the organic phase is washed with 2 times 20 ml of water, dried over sodium sulphate and concentrated under vacuum. A pale yellow powder is obtained with a gross yield of 97%. The product is used directly in the following stage without additional purification.

NMR $^1$H (100 MHz, CDCl$_3$, δ): 8.10 (m, 2H, Ph); 6.60 (m, 2H, Ph); 4.40 (wide s, 1H, OH); 3.50 (m, 8H, CH$_2$N); 2.50–1.50 (m, 18H, Trolox®+CH$_2$).

25.3) 1-(4-aminophenyl)-4-[(3,4-dihydro-6-hydroxy-2,5,7,8-tetramethyl-2H-1-benzopyran-2-yl)carbonyl]hexahydro-1H-1,4-diazepine The experimental protocol used is the same as that described for intermediate 13.2, with intermediate 25.2 replacing the 3,4-dihydro-2,5,7,8-tetramethyl-2-{4-[(4-nitrophenyl)-1-piperazinyl]-carbonyl}-2H-1-benzopyran-6-ol. The product of the reaction is purified on a silica gel column (eluant: ethyl acetate/petroleum ether 3:2). An oil is obtained with a yield of 57%.

25.4) N-[4-{4-[(3,4-dihydro-6-hydroxy-2,5,7,8-tetramethyl-2H-1-benzopyran-2-yl)carbonyl]-1H-1, 4-diazepin-1-yl}phenyl]-2-thiophenecarboximidamide hydrochloride A mixture of 0.52 g (1.22 mmole) of intermediate 25.3 and 0.35 g (1.22 mmole) of S-methyl-2-thiophene thiocarboximide hydroiodide in 4 ml of isopropanol is heated at 50° C. for 40 hours. The reaction medium is then filtered and the solid obtained is taken up in 4 ml of a saturated aqueous solution of sodium carbonate and 4 ml of ethyl acetate. The mixture is heated at 50° C. for 30 minutes, then decanted. The organic phase is washed twice with 10 ml of water followed by 10 ml of brine. The organic phases are collected, dried over sodium sulphate, filtered and concentrated under reduced pressure. The solid obtained is purified on a silica gel column (eluant: ethyl acetate/petroleum ether 5:1). 0.5 g of product is obtained with a yield of 77%. 0.15 g (0.29 mmole) of this product is then dissolved in 2 ml of acetone. 0.84 ml (0.84 mmole) of a 1N hydrochloric acid solution in anhydrous ethyl ether is added dropwise. The whole is agitated at ambient temperature for 30 minutes. A yellow precipitate forms which is filtered. The precipitate is triturated and washed successively with 3 times 5 ml of ethyl ether and 5 ml of acetone. The dark yellow powder is dried under vacuum at 70° C. for 48 hours. The yield obtained is 80%. Melting point: 180–185° C.

NMR $^1$H (400 MHz, DMSO, δ): 11.15 (wide s, 1H, NH$^+$); 9.60 (wide s, 1H, NH$^+$); 8.55 (wide s, 1H, NH$^+$); 8.10 (wide s, 2H, thiophene); 7.35 (wide s, 1H, thiophene); 7.02 (m, 4H, Ph); 4.80 (wide s, 1H, OH); 3.70 (m, 8H, CH$_2$N); 2.50–1.40 (m, 18H, Trolox®+CH$_2$).

IR: $\nu_{OH}$: 3412 cm$^{-1}$; $\nu_{C=O}$ (amide): 1613 cm$^{-1}$; $\nu_{C=N}$ (amidine): 1613 cm$^{-1}$.

Example 26

(R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 26

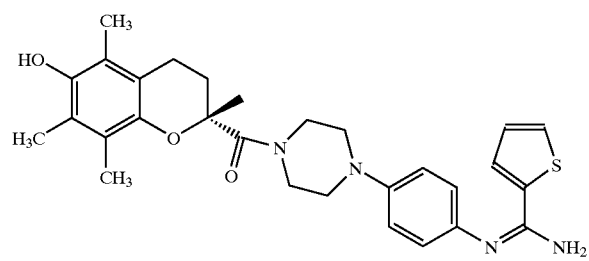

26.1) (R)-3,4-dihydro-2,5,7,8-tetramethyl-2-{4-[(4-nitrophenyl)-1-piperazinyl]-carbonyl}-2H-1-benzopyran-6-ol The experimental protocol used is the same as that described for compound 13.1, with (R)-Trolox® replacing the (±)Trolox®. A bright yellow powder is obtained with a yield of 98%. Melting point: 102–105° C.

26.2) (R)-3,4-dihydro-2,5,7,8-tetramethyl-2-{4-[(4-aminophenyl)-1-piperazinyl]-carbonyl}-2H-1-benzopyran-6-ol The experimental protocol used is the same as that described for intermediate 2.2, with intermediate 26.1 replacing the 3,5-bis-(1,1-dimethylethyl)-4-hydroxy-N-[(4-nitrophenyl)methyl]-benzamide. A pink powder is obtained with a yield of 75%. The product is used as it is in the following stage. Melting point: 103–105° C.

26.3) (R)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide hydrochloride: 26

The experimental protocol used is the same as that described for compound 13, with intermediate 26.2 replacing the 3,4-dihydro-2,5,7,8-tetramethyl-2-{4-[(4-aminophenyl)-1-piperazinyl]-carbonyl}-2H-1-benzopyran-6-ol. The product is obtained in the form of a pale yellow powder which hydrates in air. Melting point: 195–197° C.

The NMR and IR analyses are identical to compound 13. [α]$^{20}_D$=−43.5° (c=0.11; DMSO)

Example 27

(S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide dihydrochloride: 27

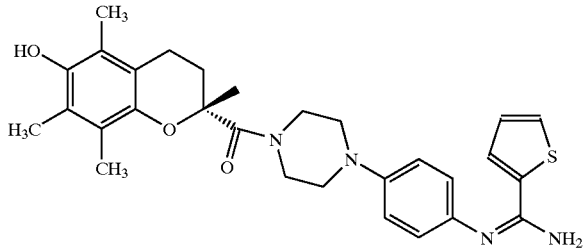

27.1) (S)-3,4-dihydro-2,5,7,8-tetramethyl-2-{4-[(4-nitrophenyl)-1-piperazinyl]-carbonyl}-2H-1-benzopyran-6-ol The experimental protocol used is the same as that described for compound 13.1, with (S)-Trolox® replacing the (±)Trolox®. A yellow powder is obtained with a yield of 73%. Melting point: 110–111° C.

27.2) (S)-3,4-dihydro-2,5,7,8-tetramethyl-2-{4-[(4-aminophenyl)-1-piperazinyl]-carbonyl}-2H-1-benzopyran-6-ol The experimental protocol used is the same as that described for intermediate 2.2, with intermediate 27.1 replacing the 3,5-bis-(1,1-dimethylethyl)-4-hydroxy-N-[(4-nitrophenyl)methyl]-benzamide. After purification on a silica gel column (heptane/ethyl acetate: 2/8), collection and evaporation under vacuum of the pure fractions, a beige powder is obtained with a yield of 54%. Melting point: 109–111° C.

27.3) (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide dihydrochloride: 27

The experimental protocol used is the same as that described for compound 13, with intermediate 27.2 replacing the 3,4-dihydro-2,5,7,8-tetramethyl-2-{4-[(4-aminophenyl)-1-piperazinyl]-carbonyl}-2H-1-benzopyran-6-ol. The product is obtained in the form of a pale yellow powder which hydrates in air. Melting point: 210.6–211.8° C.

The NMR and IR analyses are identical to compound 13. [α]$^{20}_D$=+76.2° (c=0.17; DMSO)

Alternatively, compound 27 can be prepared according to the following protocol:

27.4) methyl 2-thiophene carboximidate 10.91 g (0.1 mole) of 2-thiophene carbonitrile, 100 ml of anhydrous ethyl ether and 4.5 ml (0.11 mole) of methanol are introduced into a 250 ml erlen meyer flask purged with argon. The solution is cooled down to 0° C. using an ice bath and saturated with a stream of anhydrous gaseous HCl for 45 minutes. The reaction medium is agitated for an additional hour at 0° C. and overnight at 20° C. The precipitate formed is filtered out, washed with ethyl ether and dried. The hydrochloride obtained is partitioned into a mixture of 100 ml of water and 150 ml of ethyl ether. The medium is neutralized by adding 8.4 g (0.1 mole) of dry NaHCO$_3$. After decanting and separation, the organic phase is washed successively with 2×30 mnl of water and 30 ml of brine. After drying over magnesium sulphate, the organic solution is filtered and concentrated under vacuum. A colourless oil is obtained with a yield of 66%.

NMR $^1$H (400 MHz, CDCl$_3$, δ): 7.58 (wide s, 1H, =N—H); 7.42 (m, 1H, thiophene); 7.37 (m, 1H, thiophene); 7.01 (m, 1H, thiophene); 3.86 (s, 3H, OCH$_3$).

IR: ν$_{C=N}$ (carboximidate): 1630 cm$^{-1}$.

27.5) (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide dihydrochloride: 27

In a 150 ml erlen meyer flask, under a stream of argon, 8.2 g (20 mmoles) of (S)-3,4-dihydro-2,5,7,8-tetramethyl-2-{4 [(4-aminophenyl)-1-piperazinyl]-carbonyl]-2H-1-benzopyran-6-ol (obtained as intermediate 13.2 but from (S)-Trolox®), is dissolved in 60 ml of methanol and 4.2 g (30 mmoles) of methyl 2-thiophene carboximidate is added. The reaction medium is heated for 18 hours under reflux. The methanol is evaporated under vacuum and the oily brown residue is purified on a silica gel column (eluant: dichloromethane/ethanol: 95/5). The pure fractions are collected and concentrated under vacuum to produce a brown oil with a yield of 68%. This oil is taken up in 22 ml of an ethanolic solution of HCl (1.3N) and diluted with 180 ml of anhydrous acetone. The reaction medium is agitated for 1 hour at 0° C. The precipitate formed is filtered and washed successively with acetone and ethyl ether. After drying, the dihydrochloride is obtained in the form of a pale yellow powder with a yield of 53%.

Example 28

3,5-bis-(1,1-dimethylethyl)-4-hydroxy-N-{2-[3-[(2-thienyl(imino)methyl)amino]phenyl]ethyl}-benzamide hydrochloride: 28

28.1) 3,5-bis-(1,1-dimethylethyl)-4-hydroxy-N-[2-(3-nitrophenyl)ethyl]-benzamide The experimental protocol used is the same as that described for intermediate 5.1, with 3-nitrophenetylamine (J. Med. Chem. (1968), 11 (1), 21–26) replacing the 4-nitrophenetylamine. A white powder is obtained with a yield of 50%. Melting point: 195–197° C.

NMR $^1$H (100 MHz, CDCl$_3$, δ): 7.86 (m, 4H, Ph—NO$_2$); 7.50 (s, 2H, Ph); 6.10 (m, 1H, NHCO); 5.54 (s, 1H, OH); 3.75 (m, 2H, CH$_2$—NHCO); 3.08 (m, 2H, CH$_2$—Ph—NO$_2$); 1.42 (s, 18H, 2× tBu).

28.2) 3,5-bis-(1,1-dimethylethyl)-4-hydroxy-N-[2-(3-aminophenyl)ethyl]-benzamide The experimental protocol used is the same as that described for intermediate 5.2, with intermediate 28.1 replacing the 3,5-bis-(1,1-dimethylethyl)-4-hydroxy-N-[2-(4-nitrophenyl)ethyl]-benzamide. A white powder is obtained (yield of 40%) which is sufficiently pure to be used directly in the following stage.

28.3) 3,5-bis-(1,1-dimethylethyl)-4-hydroxy-N-{2-[3-[(2-thienyl-(imino)methyl)-amino]phenyl]ethyl}-benzamide hydrochloride: 28

The experimental protocol used is the same as that described for intermediate 1.3, with intermediate 28.2 replacing the 3,5-bis-(1,1-dimethylethyl)-4-hydroxy-N-(4-aminophenyl)-benzamide. A pale yellow powder is obtained with a yield of 35%. Melting point: 205–207° C.

NMR $^1$H (400 MHz, DMSO d6, δ): 11.59 (wide s, 1H, NH$^+$); 9.89 (s, 1H, NH$^+$); 8.95 (s, 1H, NH$^+$); 8.46 (s, 1H, CONH); 8.17 (m, 2H, thiophene); 7.54 (s, 2H, Ph—OH); 7.39 (m, 6H, thiophene, Ph—NH, OH); 3.51 (m, 2H, CH$_2$—NHCO); 2.89 (m, 2H, CH$_2$—Ph—NH); 1.38 (s, 18H, 2× tBu).

IR: $\nu_{OH}$: 3624 cm$^{-1}$; $\nu_{C=O}$ (amide): 1631 cm$^{-1}$; $\nu_{C=N}$ (amidine): 1577 cm$^{-1}$.

Example 29

N-{4-(4-[2-(3,5-bis-(1,1-dimethylethyl)-4-hydroxyphenyl)-1-oxo-ethyl]-1-piperazinyl)phenyl}-2-thiophene-carboximidamide hydrochloride: 29

The experimental protocol used is the same as that described for the compound 9, with 3,5-di-tert-butyl-4-hydroxyphenylacetic acid replacing the 3,5-di-tert-butyl-4-hydroxybenzoic acid in the first stage of synthesis. Yellow powder. Melting point: 176–180° C.

NMR $^1$H (400 MHz, DMSO d6, δ): 11.30 (wide s, 1H, NH$^+$); 9.70 (wide s, 1H, NH$^+$); 8.65 (wide s, 1H, NH$^+$); 8.10 (wide s, 2H, thiophene); 7.35 (wide s, 1H, thiophene); 7.12 (m, 4H, Ph—N); 6.95 (s, 2H, Ph—OH); 6.80 (wide s, 1H, OH); 3.60 (wide s, 6H, piperazine, CH$_2$CO); 3.10 (m, 4H, piperazine); 1.35 (s, 18H, 2× tBu).

IR: $\nu_{OH}$: 3620 cm$^{-1}$; $\nu_{C=O}$ (ester): 1638 cm$^{-1}$; $\nu_{C=N}$ (amidine): 1612 cm$^{-1}$.

Example 30

2-{4-[(2-thienyl(imino)methyl)amino]phenyl}ethyl 3,5-bis-(1,1-dimethylethyl)-4-hydroxy-benzoate hydrochloride: 30

30.1) 2-(4-nitrophenyl)ethyl 3,5-bis-(1,1-dimethylethyl)-4-hydroxybenzoate

In a 250 ml flask containing 80 ml of THF, under an argon atmosphere, 2.45 g (9.8 mmoles) of 3,5-di-tert-butyl-4-hydroxybenzoic acid, 1.8 g (10.8 mmoles) of 4-nitrobenzene-ethanol and 2.2 g (10.8 mmoles) of dicyclohexylcarbodiimide are introduced successively, under agitation. The reaction medium is agitated for 15 hours at 20° C. and the precipitate which appears is filtered out. The filtrate is washed with 2×30 ml of a saturated NaCl solution, the organic phase is dried over magnesium sulphate, filtered and concentrated under vacuum. The residue is then crystallized using di-isopropyl ether. The solid is recovered by filtration and 2.4 g (62%) of white crystals are obtained after drying. Melting point: 123.5–124.5° C.

NMR $^1$H (100 MHz, CDCl$_3$, δ): 7.85 (m, 4H, Ph—NO$_2$); 7.80 (s, 2H, Ph—OH); 5.70 (s, 1H, OH); 4.50 (m, 2H, O—CH$_2$); 3.20 (m, 2H, CH$_2$); 1.40 (s, 18H, 2× tBu).

30.2) 2-(4-aminophenyl)ethyl 3,5-bis-(1,1-dimethylethyl)-4-hydroxy-benzoate

The experimental protocol is the same as that described for intermediate 2.2, with intermediate 30.1 replacing the 3,5-bis-(1,1-dimethylethyl)-4-hydroxy-N-[(4-nitrophenyl)-methyl]-benzamide. A white powder is obtained with a yield of 50%. Melting point: 135–136° C.

NMR $^1$H (400 MHz, DMSO d6, δ): 7.75 (s, 2H, Ph—OH); 6.70 (m, 4H, Ph—N); 4.90 (wide s, 1H, OH); 4.25 (m, 2H, O—CH$_2$); 3.30 (wide s, 2H, NH$_2$); 2.80 (m, 2H, CH$_2$); 1.40 (s, 18H, 2× tBu).

0.3) 2-{4-[(2-thienyl(imino)methyl)amino]phenyl}ethyl 3,5-bis-(1,1-dimethylethyl)-4-hydroxy-benzoate hydrochloride: 30

The experimental protocol is the same as that described for intermediate 1.3, with intermediate 30.2 replacing the 3,5-bis-(1,1-dimethylethyl)-4-hydroxy-N-(4-aminophenyl)-benzamide. A white solid is obtained with a yield of 26%. Melting point: 145–150° C.

NMR $^1$H (400 MHz, DMSO d6, δ): 11.50 (wide s, 1H, NH$^+$); 9.80 (wide s, 1H, NH$^+$); 8.90 (wide s, 1H, NH$^+$); 8.20 (wide s, 2H, thiophene); 7.85 (s, 1H, OH); 7.75 (s, 2H, Ph—OH); 7.47 (m, 5H, Ph—N, thiophene); 4.41 (m, 2H, O—CH$_2$); 3.08 (m, 2H, CH$_2$); 1.40 (s, 18H, 2× tBu).

IR: $\nu_{C=O}$ (ester): 1700 cm$^{-1}$; $\nu_{C=N}$ (amidine): 1592 cm$^{-1}$.

Example 31

2-{3-[(2-thienyl(imino)methyl)amino]phenyl}ethyl 3,5-bis-(1,1-dimethylethyl)-4-hydroxy-benzoate hydrochloride: 31

The experimental protocol used is the same as that described for the compound 30, with 3-nitrobenzene-ethanol replacing the 4-nitrobenzene-ethanol in the first stage of synthesis. Pale yellow powder. Melting point: 145–148° C.

NMR $^1$H (400 MHz, DMSO d6, δ): 11.50 (wide s, 1H, NH$^+$); 9.82 (wide s, 1H, NH$^+$); 8.99 (wide s, 1H, NH$^+$); 8.15 (m, 2H, thiophene); 7.81 (s, 1H, OH); 7.75 (s, 2H, Ph—OH); 7.41 (m, 5H, Ph—N, thiophene); 4.41 (m, 2H, O—CH$_2$); 3.08 (m, 2H, CH$_2$); 1.38 (s, 18H, 2× tBu).

IR: $\nu_{OH}$: 3620 cm$^{-1}$; $\nu_{C=O}$ (ester): 1707 cm$^{-1}$; $\nu_{C=N}$ (amidine): 1654 cm$^{-1}$.

Example 32

2-{2-[(2-thienyl(imino)methyl)amino]phenyl}ethyl 3,5-bis-(1,1-dimethylethyl)-4-hydroxy-benzoate hydrochloride: 32

The experimental protocol used is the same as that described for compound 30, with 2-nitrobenzene-ethanol replacing the 4-nitrobenzene-ethanol in the first stage of synthesis. Beige powder. Melting point: 139–145° C.

NMR $^1$H (400 MHz, DMSO d6, δ): 11.50 (wide s, 1H, NH$^+$); 9.80 (wide s, 1H, NH$^+$); 8.65 (wide s, 1H, NH$^+$); 8.15 (m, 2H, thiophene); 7.80 (s, 1H, OH); 7.70 (s, 2H, Ph—OH); 7.60 (m, 1H, Ph); 7.45 (m, 3H, Ph); 7.35 (s, 1H; thiophene); 4.40 (m, 2H, O—CH$_2$); 3.00 (m, 2H, CH$_2$); 1.35 (s, 18H, 2× tBu).

IR: $\nu_{C=O}$ (ester): 1728 cm$^{-1}$; $\nu_{C=N}$ (amidine): 1649 cm$^{-1}$.

Example 33

N-[4-(1H-imidazol-1-yl)phenyl]-2-thiophenecarboximidamide hydroiodide (33)

33.1 1-(4-nitrophenyl)-1H-imidazole 9 g (64.5 mmoles) of potassium carbonate and 5 g (3.75 ml; 35.2 mmol) of 1-fluoro-4-nitrobenzene are added to a solution of 2 g of imidazole (29.4 mmol) in 14 ml of DMF. The reaction mixture is agitated for 1.5 hours at 110° C. Ethyl acetate (50 ml) is added to the medium which is washed 3 times with 50 ml of water. The organic phases are dried over magnesium sulphate and concentrated under vacuum. 4.4 g of product are thus obtained (yield =80%) in the form of a clear oil and used without further purification in the following stages.

NMR $^1$H (CDCl$_3$, 100 MHz, δ): 6.92 (t, 1H, Arom. H imidazole), 7.16 (s, 1H, Arom. H imidazole), 7.24–7.32–8.18–8.27 (4s, 4H, Arom. H), 7.59 (s, 1H, Arom. H imidazole).

33.2 1-(4-aminophenyl)-1H-imidazole 1-(4-nitrophenyl)-1H-imidazole (4.4 g; 23.5 mmoles) is put in solution in anhydrous methanol (140 ml) and palladium on carbon (0.44 g) is added to the medium. The reaction medium is placed under hydrogen for 4 hours. The catalyst is filtered off and the solvent is evapored to dryness. The expected product is obtained in a virtually pure state with a yield of 89% (3.3 g).

NMR $^1$H (CDCl$_3$, 100 MHz, δ): 6.61–6.69–6.95–7.05 (4s, 4H, Arom. H), 6.88 (t, 1H, Arom. H imidazole), 7.07 (s, 1H, Arom. H imidazole), 7.52 (s, 1H, Arom. H imidazole).

33.3 N-[4-(1H-imidazol-1-yl)phenyl]-2-thiophenecarboximidamide hydroiodide (33)

1-(4-aminophenyl)-1H-imidazole (0.3 g; 1.7 mmoles) and S-methyl-2-thiophenethiocarboximide hydroiodide (0.5 g; 1.75 mmoles) are put into solution in 1 ml isopropanol and 1 ml of DMF and the reaction mixture is agitated for 18 hours at 25° C. The precipitate formed is filtered and washed with 15 ml of dichloromethane and 15 ml of ethanol. The expected product is thus obtained (0.48 g; 73%) in salified form (hydroiodide). Melting point: 252–253° C. (decomposition).

NMR $^1$H (DMSO, 400 MHz, δ): 7.24 (s, 1H, arom. H). 7.38 (t, 1H, arom. H). 7.55–7.57–7.85–7.87 (4s, 4H, arom. H), 7.89 (s, 1H, arom. H), 8.10 (m. 2H, arom. H), 8.50 (s, 1H, arom. H).

IR: ν$_{C=N}$ (amidine): 1585 cm$^{-1}$.

Example 34

N-[4-(3-thiazolidinylmethyl)phenyl]-2-thiophenecarboximidamide (34)

34.1 1-bromomethyl-4-nitrobenzene 4-nitrobenzyl alcohol (6 g, 39 mmoles) is put into solution in dichloromethane (100 ml) and carbon tetrabromide (14.9 g, 45 mmoles) is added. Triphenylphosphine (11.8 g, 45 mmoles) is added in portions to the medium at 0° C. Then the mixture is agitated for 2 hours at ambient temperature. The solvent is evaporated off and the product obtained is purified on silica gel in an ethyl acetate/heptane mixture (1/2). It is obtained in the form of white needle-shaped crystals (7.2 g; 85%). Melting point: 97–98° C.

NMR $^1$H (CDCl$_3$, 100 MHz, δ): 4.53 (s, 2H, CH$_2$). 7.53–7.61–8.18–8.27 (4 s, 4H, Arom. H).

34.2 3-(4-nitrobenzyl)-thiazolidine

A mixture of thiazolidine (0.9 g, 10 mmoles) and potassium carbonate (2.5 g, 18 mmoles) in acetonitrile (10 ml) is heated to 70° C. 1-bromomethyl-4-nitrobenzene (2 g, 9.2 mmoles) in solution in acetonitrile (25 ml) is added dropwise and the reaction is maintained under reflux for 2 hours.

The precipitate formed is filtered, the mother liquors are evaporated and the residue is taken up in 50 ml of dichloromethane and washed 3 times with 50 ml of water. The organic phases are dried, evaporated and purified over silica gel in an ethyl acetate/heptane mixture (1/2). The expected product is obtained in the form of a colourless oil (1.5 g, 72%).

NMR $^1$H (CDCl$_3$, 100 MHz, δ): 3.05 (m, 4H, 2CH$_2$), 3.68 (s, 2H, CH$_2$—S), 4.04 (s, 2H, CH$_2$), 7.53–7.62–8.17–8.26 (4s, 4H, Arom. H).

34.3 3-(4-aminobenzyl)-thiazolidine 3-(4-nitrobenzyl)-thiazolidine (1.1 g, 5 mmoles) is put into solution in 10 ml concentrated hydrochloric acid at 0° C. Dihydrated tin chloride (7.7 g, 34 mmoles) is added in portions, the mixture is heated for 2 hours under reflux and the acid is evaporated off under reduced pressure. The residue is then taken up in 20 ml of water and neutralized with a 2N soda solution (approximately 100 ml). 100 ml of dichloromethane is added to the medium and the whole is filtered on celite in order to eliminate the salts in suspension. The organic phase is extracted, washed 3 times with 50 ml of water, dried, filtered and evaporated to dryness under reduced pressure. The expected product is purified on silica gel in a dichloromethane/methanol (98/2) mixture and is obtained in the form of of a beige powder (0.6 g, 63%). Melting point: 73–74° C.

NMR $^1$H (CDCl$_3$, 100 MHz, δ): 3.02 (m, 4H, 2CH$_2$), 3.44 (s, 2H, CH$_2$) 3.66 (wide s, 2H, NH$_2$), 4.07 (s, 2H, CH$_2$), 6.62–6.71–7.10–7.27 (4 s, 4H, arom. H).

34.4 [4-(3-thiazolidinylmethyl)phenyl]-2-thiophenecarboximidamide (34)

3-(4-aminobenzyl)-thiazolidine (0.6 g, 3 mmoles) and S-methyl-2-thiophenethiocarboximide hydroiodide (1.14 g, 4 mmoles) are put into solution in 7 ml of an isopropaiiol/DMF mixture (2/5). The reaction medium is agitated for 18 hours at ambient temperature. Then 10 ml of ethyl acetate is added to the medium and the reaction product is extracted 3 times with 10 mnl of water. The aqueous phase is collected and basified with a saturated solution of sodium hydrogen carbonate, then the product is extracted 3 times with 10 ml of ethyl acetate. It is purified on silica gel in a dichloromethane/methanol mixture (95/5) and is obtained in the form of a white powder (0.6 g, 65%). Melting point: 161.5–163.5° C.

NMR $^1$H (CDCl$_3$, 400 MHz, δ): 2.98 (t, 2H, CH$_2$), 3.14 (t, 2H, CH$_2$), 3.54 (s, 2H, CH$_2$), 4.10 (s, 2H, CH$_2$), 4.85 (wide s, 2H, NH$_2$), 6.98 (s, 1H, arom. H), 7.00 (s, 1H, arom. H), 7.10 (t, 1H, thiophene), 7.34 (s, 1H, arom. H), 7.36 (s, 1H, arom. H), 7.42 (t, 1H, thiophene), 7.45 (m, 1H, thiophene).

IR: ν$_{C=N}$ (amidine): 1593 cm$^{-1}$.

Example 35

N-[4-(1,2,3,6-tetrahydropyridin-1-yl)phenyl]-2-thiophenecarboximidamide fumarate (35)

35.1 1-(4-nitrophenyl)-1,2,3,6-tetrahydropyridine

The experimental protocol used is the same as that described for intermediate 33.1. 1,2,3,6-tetrahydropyridine replacing imidazole. Colourless oil.

NMR $^1$H (CDCl$_3$, 100 MHz, δ): 2.33 (m, 2H, CH$_2$), 3.59 (t, 2H, CH$_2$), 3.90 (m, 2H, CH$_2$), 5.90 (m, 2H, CH═CH), 6.75–6.82–8.07–8.18 (m, 4H, arom. H).

35.2 1-(4-aminophenyl)-1,2,3,6-tetrahydropyridine

The experimental protocol used is the same as that described for intermediate 34.3, 1-(4-nitrophenyl)-1,2,3,6-tetrahydropyridine replacing 3-(4-nitrobenzyl)-thiazolidine. Colourless oil.

NMR $^1$H (CDCl$_3$, 100 MHz, δ): 2.31 (m, 2H, CH$_2$), 3.21 (t, 2H, CH$_2$), 3.43 (m, 2H, NH$_2$), 3.56 (m, 2H, CH$_2$), 5.84 (m, 2H, CH=CH), 6.75 (m, 4H, arom. H).

35.3 N-[4-(1,2,3,6-tetrahydropyridin-1-yl)phenyl]-2-thiophenecarboximidamide fumarate (35)

The experimental protocol used is the same as that described for intermediate 33.3. 1-(4-aminophenyl)-1,2,3,6-tetrahydropyridine replacing 1-(4-aminophenyl)-1H-imidazole. Beige powder. Melting point: 193–194° C.

NMR $^1$H (DMSO, 400 MHz, δ): 2.23 (m, 2H, CH$_2$), 3.29 (m, 2H, CH$_2$), 3.61 (m, 2H, CH$_2$), 5.84 (m, 2H, CH=CH), 6.56 (s, 1H, fumaric acid), 6.89 (m, 4H, arom. H), 7.13 (m, 1H, arom. H), 7.67 (m, 1H, arom. H), 7.77 (m, 1H, arom. H).

IR: $v_{C=N}$ (amidine): 1560 cm$^{-1}$.

Example 36

N-[4-(1H-imidazol-1-yl methyl)phenyl]-2-thiophenecarboximidamide hydrochloride (36)

36.1 1-(4-nitrobenzyl)-1H-imidazole

The experimental protocol used is the same as that described for intermediate 33.1, 1-bromomethyl-4-nitrobenzene replacing 1-fluoro-4-nitrobenzene. Colourless oil.

NMR $^1$H (CDCl$_3$, 100 MHz, δ): 5.26 (s, 2H, CH$_2$), 6.92 (m, 1H, H imidazole), 7.16 (m, 1H, H imidazole), 7.59 (m, 1H, H imidazole), 7.24–7.32–8.18–8.27 (4s, 4H, arom. H).

36.2 1-(4-aminobenzyl)-1H-imidazole

The experimental protocol used is the same as that described for intermediate 33.2, 1-(4-nitrobenzyl)-1H-imidazole replacing 1-(4-aminophenyl)-1H-imidazole. Pale yellow powder. Melting point: 121–122° C.

NMR $^1$H (CDCl$_3$, 100 MHz, δ): 2.87 (wide s, 2H, NH$_2$), 4.98 (s, 2H, CH$_2$), 6.88 (m, 1H, H imidazole), 7.06 (m, 1H, H imidazole), 7.52 (m, 1H, H imidazole), 6.60–6.69–6.95–7.05 (4s, 4H, arom. H).

36.3 N-[4-(1H-imidazol-1-yl methyl)phenyl]-2-thiophenecarboximidamide hydrochloride (36)

The experimental protocol used is the same as that described for intermediate 34.4, 1-(4-aminobenzyl)-1H-imidazole replacing 3-(4-aminobenzyl)-thiazolidine. After salification by a molar solution of HCl in anhydrous diethyl ether, a beige powder is obtained. Melting point: 261–263° C.

NMR $^1$H (DMSO, 400 MHz, δ): 5.12 (s, 2H, CH$_2$), 6.46. (wide s, 2H, NH$_2$), 6.83–6.85–7.22–7.24 (4s, 4H, arom. H), 6.90 (s, 1H, arom. H), 7.09 (t, 1H, arom. H), 7.20 (s, 1H, arom. H), 7.60 (d. 1H, arom. H), 7.74 (s, 2H, arom. H).

IR: $v_{C=N}$ (amidine): 1599 cm$^{-1}$.

Example 37

N-[4-{2-(3-thiazolidinyl)ethyl}phenyl]-2-thiophenecarboximidamide (37)

37.1 4-(t-butoxycarbonylamino)-benzeneacetic acid

Para-aminophenylacetic acid (3 g, 20 mmoles) is dissolved in 60 ml of a THF/H$_2$O mixture (2/1). 11 ml of 10% soda is added then 6 g of di-t-butyl-dicarbonate (28 mmol) in solution in 50 ml of a THF/H$_2$O mixture (2/1). Agitation is carried out for 18 hours at ambient temperature. Then the THF is evaporated off under reduced pressure. The medium is then acidified (pH 2) with a 10% solution of potassium acid sulphate (approximately 45 ml) and the reaction product is extracted with 3 washings with ethyl acetate (3 times 50 ml). The organic phases are dried and evaporated in order to produce 4.32 g (87%) of pure 4-(t-butoxycarbonylamino)-benzeneacetic acid in the form of a beige powder. Melting point: 149–150° C.

NMR $^1$H (CDCl$_3$, 100 MHz, δ): 1.52 (s, 9H, tBu), 3.60 (s, 2H, CH$_2$), 4.12 (wide s, 1H, COOH), 6.55 (s, 1H, NH), 7.21 (m, 4H, arom. H).

37.2 (t-butoxycarbonylamino)-benzene ethanol 4-(t-butoxycarbonylamino)-benzeneacetic acid (2.9 g, 11.4 mmoles) is dissolved in 10 ml of anhydrous THF at 0° C. and added to a suspension of LiAlH$_4$ (0.52 g, 13.6 mmoles) in 30 ml of THF. The reaction mixture is agitated at ambient temperature for 1.5 hours. 50 ml of ethyl acetate then 20 ml of 2N soda are added to the medium. The expected product is extracted from the organic phase, which is then washed with 3 times 15 ml of water. The organic phase is dried and the solvent evaporated off under reduced pressure. Then the reaction product is purified on silica gel in a dichloromethane/methanol mixture (95/5). 1.1 g (40%) is thus obtained in the form of a colourless oil.

NMR $^1$H (CDCl$_3$, 100 MHz, δ): 1.53 (s, 9H, tBu), 2.82 (t, 2H, CH$_2$), 3.83 (q, 2H, <u>CH$_2$</u>—OH), 6.47 (s, 1H, NH), 7.23 (m, 4H, arom. H).

37.3 (2-bromoethyl-4-t-butoxycarbonylamino) benzene 4-(t-butoxycarbonylamino)-benzene ethanol (0.75 g, 3.1 mmoles) and carbon tetrabromide (1.2 g, 3.6 mmoles) are dissolved in 20 ml of dichloromethane at 0° C. Triphenylphosphine (0.94 g, 3.6 mmoles) is added in portions and the whole is agitated for 1 hour at ambient temperature. The solvent is evaporated off under reduced pressure and the product obtained is purified on silica gel in an ethyl acetate/heptane mixture (1/2), 1-(2-bromoethyl-4-t-butoxycarbonylamino)benzene is obtained in the form of a white powder (0.8 g, 84%). Melting point: 129–130° C.

NMR $^1$H (CDCl$_3$, 100 MHz, δ): 1.52 (s, 9H, tBu), 3.11 (t, 2H, CH$_2$), 3.54 (t, 2H, CH$_2$Br), 6.45 (s, 1H, NH), 7.22 (m, 4H, arom. H).

37.4 3-{2-[4-(t-butoxycarbonylamino)phenyl]ethyl}thiazolidine

The experimental protocol used is the same as that described for intermediate 34.2, (2-bromoethyl-4-t-butoxycarbonylamino)benzene replacing 1-bromomethyl-4-nitrobenzene. Colourless oil.

NMR $^1$H (CDCl$_3$, 100 MHz, δ): 1.52 (s, 9H, tBu), 2.90 (m, 8H, 4CH$_2$), 4.10 (s, 2H, N—CH$_2$—S), 6.46 (s, 1H, NH), 7.25 (m, 4H, arom. H).

37.5 3-{2-[4-aminophenyl]ethyl}thiazolidine 2.3 g (20 mmoles) of trifluoroacetic acid is added to a 100 ml flask containing a solution of 616 mg (2 mmoles) of intermediate 5.4 in 10 ml of dichloromethane. After agitation for one hour at 20° C. the reaction mixture is concentrated to dryness under vacuum. The residue is diluted with a mixture of 20 ml of dichloromethane and 20 ml of 4N soda. After decantation, the organic phase is washed successively with 3×20 ml of water followed by 20 ml of salt water. The organic solution is dried over sodium sulphate, filtered and the solvent is evaporated off under reduced pressure in order to obtain a colourless oil with a yield of 72%.

NMR $^1$H (CDCl$_3$, 100 MHz, δ): 2.85 (m, 8H, 4CH$_2$), 4.15 (s, 2H, N—CH$_2$—S), 7.25 (m, 4H, arom. H).

37.6 [4-{2-(3-thiazolidinyl)ethyl}phenyl]-2-thiophenecarboximidamide (37)

The experimental protocol used is the same as that described for intermediate 2.4, 3-{2-[4-aminophenyl]ethyl}thiazolidine replacing 3-(4-aminobenzyl)-thiazolidine. Beige powder. Melting point: 60.5–61.5° C.

NMR 1H (DMSO, 400 MHz, δ): 2.65 (t, 2H, CH$_2$), 2.82 (t, 2H, CH$_2$), 2.91 (t, 2H, CH$_2$), 3.13 (t, 2H CH$_2$), 4.13 (s, 2H, N—CH$_2$—S), 6.93–6.95–7.19–7.21 (4s, 4H, arom. H), 7.09 (t, 1H, H thiophene), 7.44 (m, 2H, H thiophene).

IR: ν$_{C=N}$ (amidine): 1591 cm$^{-1}$.

Example 38

N-{4-[2-(1H-imidazol-1-yl)ethyl]phenyl}-2-thiophenecarboximidamide hydroiodide (38)

38.1 1-{2-[4-(t-butoxycarbonylamino)phenyl]ethyl}-1H-imidazole 2.5 g (18 mmoles) of K$_2$CO$_3$ is mixed together in a 100 ml flask with 680 mg (10 mmoles) of imidazole diluted in 10 ml of acetonitrile. The reaction mixture is heated at 70° C. before the dropwise addition of a solution of 2 g (9.2 mmoles) of 1-bromomethyl-4-nitrobenzene in solution in 25 ml of acetonitrile. After agitation for 2 hours at this temperature, the reaction mixture is cooled down and filtered in order to eliminate the insoluble part. The filtrate is concentrated under vacuum and the residue is diluted in 50 ml of dichloromethane. The organic solution is successively washed with 3×50 ml of water and 50 ml of salt water. After drying over Na$_2$SO$_4$, filtration, the organic phase is concentrated under vacuum and the residue purified on a silica column (eluant: dichloromethane/methanol: 95/5). Brown oil.

NMR $^1$H (CDCl$_3$, 100 MHz, δ): 1.50 (s, 9H, tBu), 2.90 (t, 2H, CH$_2$), 4.10 (t, 2H, CH$_2$), 6.50 (s, 1H, NH), 7.05 (m, 4H, arom. H), 6.85 (m, 1H, H imidazole), 7.03 (s, 1H, H imidazole), 7.32 (m, 1H, H imidazole).

38.2 1-[2-(4-aminophenyl)ethyl]-1H-imidazole

The experimental protocol used is the same as that described for intermediate 37.5, 1-{2-[4-(t-butoxycarbonylamino)phenyl]ethyl}-1H-imidazole replacing 3-{2-[4-(t-butoxycarbonylamino)phenyl]ethyl}thiazolidine. Colourless oil.

NMR $^1$H (CDCl$_3$, 100 MHz, δ): 2.90 (t, 2H, CH$_2$), 3.35 (wide s, 2H, NH$_2$), 4.10 (t, 2H, CH$_2$), 6.70 (m, 4H, arom. H), 6.85 (m, 1H, H imidazole.), 7.03 (s, 1H, H imidazole.), 7.32 (m, 1H, H imidazole).

38.3 N-{4-[2-(1H-imidazol-1-yl)ethyl]phenyl}-2-thiophenecarboximidamide hydroiodide (38)

The experimental protocol used is the same as that described for intermediate 33.3, 1-[2-(4-aminophenyl)ethyl]-1H-imidazole replacing 1-(4-aminophenyl)-1H-imidazole. Beige powder. Melting point: 214–215° C.

NMR $^1$H (DMSO, 400 MHz, δ): 3.11 (t, 2H, CH$_2$), 4.33 (t, 2H, CH$_2$), 7.29 (m, 6H. arom. H), 7.99 (m, 1H, arom. H), 8.70 (wide s, 2H, NH$_2$).

IR: ν$_{C=N}$ (amidine): 1597 cm$^{-1}$.

Example 39

N-{4-[2-(1,2,3,6-tetrahydropyridin-1-yl)ethyl]phenyl}-2-thiophenecarboximidamide fumarate (39)

39.1 1-{2-[4-(t-butoxycarbonylamino)phenyl]ethyl}-1,2,3,6-tetrahydropyridine The experimental protocol used is the same as that described for intermediate 38.1, 1,2,3,6-tetrahydropyridine replacing thiazolidine. Colourless oil.

NMR $^1$H (CDCl$_3$, 100 MHz, δ): 1.57 (s, 9H, tBu), 2.10 (m, 2H, CH$_2$), 2.70 (m, 6H, 3CH$_2$), 3.00 (m, 2H, CH$_2$), 5.72 (m, 2H, CH=CH), 6.48 (s, 1H, NH), 7.10 (m, 4H, arom. H).

39.2 1-[2-(4-aminophenyl)ethyl]-1,2,3,6-tetrahydropyridine

The experimental protocol used is the same as that described for intermediate 37.5, 1-{2-[4-(t-butoxycarbonylamino)phenyl]ethyl}-1,2,3,6-tetrahydropyridine replacing 3-{2-[4-aminophenyl]ethyl}thiazolidine. Colourless oil.

NMR $^1$H (CDCl$_3$, 100 MHz, δ): 3.20 (m, 2H, CH$_2$), 3.80 (m, 6H, 3CH$_2$), 4.10 (m, 2H, CH$_2$), 4.57 (wide s, 2H, NH$_2$), 6.90 (m, 2H, CH=CH), 8.00 (m, 4H, arom. H).

39.3 N-{4-[2-(1,2,3,6-tetrahydropyridin-1-yl)ethyl]phenyl}-2-thiophenecarboximidamide fumarate (39)

The experimental protocol used is same as that described for intermediate 33.3. 1-[2-(4-aminophenyl)ethyl]-1,2,3,6-tetrahydropyridine replacing 1-(4-aminophenyl)-1H-imidazole. White powder. Melting point: 128–129° C.

NMR $^1$H (DMSO, 400 MHz, δ): 2.19 (m, 2H, CH$_2$), 2.83 (m, 6H, 3CH$_2$), 3.25 (m, 2H, CH$_2$), 5.72 (m, 2H, CH=CH), 6.58 (s, 3H. fumaric acid), 6.81–6.83–7.18–7.20 (4s, 4H, arom. H), 7.10 (t, 1H, H thiophene), 7.63 (m, 1H, H thiophene), 7.75 (m, 1H, H thiophene).

IR: ν$_{C=N}$ (amidine): 1620 cm$^{-1}$.

Example 40

N-[4-(3-thiazolidinylcarbonylmethyl)phenyl]-2-thiophenecarboximidamide (40)

40.1 3-[{4-(t-butoxycarbonylamino)phenyl}methylcarbonyl]thiazolidine 4-(t-butoxycarbonylamino)-benzeneacetic acid (1.4 g, 5.6 mmoles). intermediate 37.1. and carbonyldiimidazole (0.9 g, 5.6 mmoles) are dissolved in 15 ml of THF. The reaction is maintained at ambient temperature for 1 hour. Then thiazolidine (0.5 g, 5.6 mmol). in solution in THF (5 ml), is added to the medium. The whole is agitated again for 2 hours at ambient temperature. The solvents are evaporated off under reduced pressure. Then the residue is taken up in 25 ml of dichloromethane and washed 3 times with 15 ml of water. The organic phase is dried and concentrated under reduced pressure. 3-[{4-(t-butoxycarbonylamino)phenyl}methylcarbonyl]thiazolidine is obtained in the form of a white powder (1.43 g, 79%) and will be used without further purification in the following stages. Melting point: 223–224° C.

NMR $^1$H (CDCl$_3$, 100 MHz, δ): 1.51 (s, 9H, tBu), 3.00 (m, 2H, CH$_2$—S), 3.67 (s, 2H, N—CH$_2$—S), 3.88 (m, 2H, CH$_2$—N), 4.52 (d, J=16 Hz, 2H, CH$_2$—CO), 6.52 (wide s, 1H, NH), 7.26 (m, 4H, arom. H).

40.2 3-[(4-aminophenyl)methylcarbonyl]thiazolidine

3-[(4-aminophenyl)methylcarbonyl]thiazolidine is obtained in the form of a colourless oil with a yield of 44% by following the operating method described for intermediate 37.5.

NMR $^1$H (CDCl$_3$, 100 MHz, δ): 1.62 (wide s, 2H, NH$_2$), 2.98 (m, 2H, CH$_2$—S), 3.61 (s, 2H, N—CH$_2$—S), 3.80 (m, 2H, CH$_2$—N), 4.52 (d. J=16 Hz. 2H, CH$_2$—CO), 6.61–6.69–7.01–7.09 (4 s, 4H, arom. H).

40.3 [4-(3-thiazolidinylcarbonylmethyl)phenyl]-2-thiophenecarboximidamide (40)

The operating method used is the same as that described for intermediate 34.4, 3-[(4-aminophenyl)methylcarbonyl] thiazolidine replacing 3-(4-aminobenzyl)-thiazolidine. The free base is obtained with a yield of 64%. Melting point: 163.0–163.5° C.

NMR $^1$H (CDCl$_3$, 400 MHz, δ): 3.01 (m, 2H, CH$_2$—S), 3.69 (d, J=6 Hz. 2H, N—CH$_2$—S), 3.75–3.88 (2 t, 2H, CH$_2$—N), 4.55 (d, 2H, CH$_2$—CO), 4.87 (s, 2H, NH$_2$), 6.95–6.97–7.22–7.24 (4 s, 4H, arom. H), 7.08 (t, 1H, thiophene), 7.43 (m, 2H, thiophene).

IR: $v_{C=O}$ (amide): 1630 cm$^{-1}$; $v_{C=N}$ (amidine): 1577 cm$^{-1}$.

Example 41

N-(4-{[2-thiazolidinyl]carbonylaminomethyl}phenyl)-2-thiophenecarboximidamide fumarate (41)

41.1 3-(t-butoxycarbonyl)thiazolidine-2-carboxylic acid

Thiazolidine-2-carboxylic acid (2 g, 15 mmoles) is agitated in the presence of di-t-butyl dicarbonate according to the operating method described for intermediate 37.1. 3-(t-butoxycarbonyl)thiazolidine-2-carboxylic acid is obtained in the form of a pale yellow oil with a yield of 97% (3.4 g) and will be used as is in the following stages.

NMR $^1$H (CDCl$_3$, 100 MHz, δ): 1.46 (s, 9H, tBu), 3.10 (m, 3H. CH$_2$—S, CH—S), 3.85 (m, 2H, CH$_2$—N).

41.2 (4-nitrobenzyl)-3-(t-butoxycarbonyl)thiazolidine-2-carboxamide 3-(t-butoxycarbonyl)thiazolidine-2-carboxylic acid (1 g, 4.3 mmol) and carbonyldiimidazole (0.7 g, 4.3 mmol) are dissolved in THF (10 ml). The mixture is agitated for 1 hour at ambient temperature. 4-nitrobenzylamine (0.81 g, 4.3 mmoles) and triethylamine (0.6 ml. 0.43 g, 4.3 mmoles) in suspension in 10 ml of a THF and DMF mixture (1/1) are added to the preceding solution and the whole is heated under reflux for 5 hours. The solvents are then evaporated off under reduced pressure. The residue is taken up in 25 ml of ethyl acetate and washed 3 times with 15 ml of water. The organic phase is dried and the solvent is evaporated off under reduced pressure. The product obtained is purified on silica gel in a dichloromethane/methanol mixture (95/5). N-(4-nitrobenzyl)-3-(t-butoxycarbonyl)thiazolidine-2-carboxamide is obtained in the form of a pale yellow oil with a yield of 80% (1.25 g).

NMR $^1$H (CDCl$_3$, 100 MHz, δ): 1.45 (s, 9H, tBu), 3.09 (m, 3H, CH$_2$—S, CH—S), 3.86 (m, 2H, CH$_2$—CH$_2$—N), 4.57 (m, 2H, CH$_2$—NH), 6.60 (wide s, 1H, NH), 7.41–7.50–8.14–8.23 (4s, 4H, arom. H).

41.3 (4-aminobenzyl)-3-(t-butoxycarbonyl)thiazolidine-2-carboxamide

A spatula tip's worth of Nickel of Raney is added to a solution of 1.25 g (3.4 mmoles) of N-(4-nitrobenzyl)-3-(t-butoxycarbonyl)thiazolidine-2-carboxamide in 2.5 ml of methanol. The whole is taken to reflux and hydrazine hydrate (1.75 ml) is added dropwise to the medium. The reaction is maintained for 1 hour under reflux, then returned to ambient temperature. The catalyst is filtered off and abundantly rinsed with methanol. The solvent is evaporated off under reduced pressure. Then the residue is taken up in dichloromethane (20 ml) and washed 3 times with 15 ml of water. The organic phase is dried and the solvent is evaporated off under reduced pressure. N-(4-aminobenzyl)-3-(t-butoxycarbonyl)thiazolidine-2-carboxamide is obtained in the form of an inert yellow solid (0.815 g, 71%); it will be used in following stages without further purification.

NMR $^1$H (CDCl$_3$, 100 MHz, δ): 1.43 (s, 9H, tBu), 3.08 (m, 2H, CH$_2$—S), 3.67 (m, 3H, CH$_2$—CH$_2$—N, CH—S), 4.36 (m, 2H, CH$_2$—NH), 6.05 (wide s, 1H, NH), 6.60–6.69–7.04–7.12 (4 s, 4H, arom. H).

41.4 [4-{[3-(t-butoxycarbonyl)-2-thiazolidinyl]carbonylaminomethyl}phenyl]-2-thiophenecarboximidamide The experimental protocol used is the same as that described for intermediate 34.4, N-(4-aminobenzyl)-3-(t-butoxycarbonyl)thiazolidine-2-carboxamide replacing 3-(4-aminobenzyl)-thiazolidine. The expected compound is obtained with a yield of 77%.

NMR $^1$H (CDCl$_3$, 100 MHz, δ): 1.45 (s, 9H, tBu), 3.14 (m, 3H, CH$_2$—S, CH—S), 3.84 (m, 2H, CH$_2$—CH$_2$—N), 4.46 (m, 2H, CH$_2$—NH), 4.83 (wide s, 2H, NH$_2$), 6.27 (wide s, 1H, NH), 7.22 (m, 7H, arom. H).

41.5 N-(4-{[2-thiazolidinyl]carbonylaminomethyl}phenyl)-2-thiophenecarboximidamide fumarate (41)

The experimental protocol used is the same as that described for intermediate 37.5. [4-{[3-(t-butoxycarbonyl)-2-thiazolidinyl]carbonylaminomethyl}phenyl]-2-thiophenecarboximidamide replacing 3-{2-[4-aminophenyl]ethyl}thiazolidine. The expected compound is obtained in the form of the free base with a yield of 34%. It is salified with an equivalent of fumaric acid in ethanol under reflux. Melting point: 167–168° C.

NMR $^1$H (DMSO, 400 MHz, δ): 2.78 (t, 2H, CH$_2$—S), 3.06 (m, 2H, CH$_2$—CH$_2$—N), 3.28 (wide s, 1H, CH—S), 4.26 (m, 2H, CH$_2$—NH), 4.86 (wide s, 1H, NH), 6.45 (wide s, 2H, NH$_2$), 6.81–6.83–7.19–7.21 (4 s, 4H, arom. H), 7.10 (t, 1H, thiophene); 7.61 (d. 1H, thiophene), 7.74 (m, 1H, thiophene), 8.53 (t, 1H, NH—CO).

IR: $v_{C=O}$ (amide): 1624 cm$^{-1}$; $v_{C=N}$ (amidine): 1584 cm$^{-1}$.

Example 42

N-(3,5-di-t-butyl-4-hydroxyphenyl)-5-[4-{imino(2-thienyl)-methylamino}phenyl]-2-furan carboxamide hydroiodide (42)

42.1 2,6-di-t-buty-4-nitrophenol 2,6-di-t-butylphenol (8 g, 39 mmoles) is dissolved in 25 ml of cyclohexane at 10° C. A (1/1) mixture of nitric acid/acetic acid (5 ml) is added dropwise to the reaction medium maintained at this temperature. Agitation is then carried out for 15 minutes at ambient temperature. Then the precipitate formed is filtered off, rinsed with water and pentane. The 2,6-di-t-butyl-4-nitrophenol obtained (6.34 g, 65%) is dried in an oven and will be used without further purification in the following stages. Pale yellow powder. Melting point: 167–168° C.

NMR $^1$H (CDCl$_3$, 100 MHz, δ): 1.48 (s, 18H, 2tBu), 5.93 (s, 1H, OH), 8.13 (s, 2H, arom. H).

42.2 2,6-di-t-butyl-4-aminophenol 2,6-di-t-butyl-4-nitrophenol (6.3 g, 25 mmoles) is dissolved in methanol (100 ml), 0.6 g of palladium on carbon (10 %) is added and the reaction medium is placed under a hydrogen atmosphere under 2 bars of pressure. The catalyst is filtered out and the solvent is evaporated off under reduced pressure. The residue is taken up in heptane and filtered. In this way 2,6-di-t-butyl-4-aminophenol (2.7 g, 48%) is obtained which will be used without further purification in the following stages. Pink powder. Melting point: 123–124° C.

NMR $^1$H (CDCl$_3$, 100 MHz, δ): 6.60 (s, 2H, Ph); 4.65 (wide s, 1H, OH); 3.15 (wide s, 2H, NH$_2$); 1.42 (s, 18H, 2 tBu).

42.3 N-(3,5-di-t-butyl-4-hydroxyphenyl)-5-(4-nitrophenyt)-2-furan carboxamide

The experimental protocol used is the same as that described for intermediate 40.1, 2,6-di-t-butyl-4-aminophenol and 5-(4-nitrophenyl)-2-furan carboxylic acid replacing thiazolidine and 4-(t-butoxycarbonylamino)-benzeneacetic acid respectively. The expected compound is obtained in the form of a colourless oil with a yield of 56%.

RMN $^1$H (DMSO, 100 MHz, δ): 1.41 (s, 18H, 2tBu), 6.91 (s, 1H, OH), 7.42 (m, 4H, arom. H), 7.54 (s, 2H, arom. H), 8.30 (m, 4H, arom. H), 10.11 (s, 1H, NH).

42.4 N-(3,5-di-t-butyl-4-hydroxyphenyl)-5-(4-aminophenyl)-2-furan carboxamide

The experimental protocol used is the same as that described for intermediate 1.2. N-(3,5-di-t-butyl-4-hydroxyphenyl)-5-(4-nitrophenyl)-2-furan carboxamide replacing 1-(4-nitrophenyl)-1H-imidazole. The expected compound is obtained in the form of a colourless oil with a yield of 59%.

NMR $^1$H (DMSO, 100 MHz, δ): 1.41 (s, 18H, 2 tBu), 4.70 (wide s, 2H, NH$_2$), 6.91 (s, 1H, OH), 7.50 (m, 4H, arom. H), 7.54 (s, 2H, arom. H), 8.20 (m, 4H, arom. H).

42.5 N-(3,5-di-t-butyl-4-hydroxyphenyl)-5-[4-{imino(2-thienyl)-methylamino}phenyl]-2-furan carboxamide hydroiodide (42)

The experimental protocol used is the same as that described for intermediate 33.3, N-(3,5-di-t-butyl-4-hydroxyphenyl)-5-(4-aminophenyl)-2-furan carboxamide replacing 1-(4-aminophenyl)-1H-imidazole. The expected product is obtained in salified form with a yield of 27%. Melting point: 273–274° C.

NMR $^1$H (DMSO, 400 MHz, δ): 1.40 (s, 18H, 2tBu), 6.90 (s, 1H, OH), 7.45 (m, 5H, arom. H), 7.54 (s, 2H, arom. H), 8.15 (m, 4H, arom. H), 9.05–9.90 (wide 2s's, 2H, NH$_2$), 10.01 (s, 1H, NH—CO), 11.57 (s, 1H, HI).

IR: $v_{OH}$: 3423–3242 cm$^{-1}$; $v_{C=O}$ (amide): 1646 cm$^{-1}$; $v_{C=N}$ (amidine): 1554 cm$^{-1}$.

Example 43

3-(3,5-di-t-butyl-4-hydroxyphenyl)-1-[4-{imino(2-thienyl)-methylamino}phenyl]-2,5-imidazolidinedione hydrochloride (43)

43.1 Ethyl (3,5-di-t-butyl-4-hydroxyphenyl)amino acetate 1 g (4.5 mmol) of 2,6-di-t-butyl-4-aminophenol (intermediate 10.2) and 0.65 g of sodium acetate (7.9 mmol) are put into suspension in 1 ml of ethanol. Then bromoethyl acetate (0.94 g, 5.65 mmol) is added to the medium and the reaction medium is heated at 65° C. for 2 hours. The reaction mixture is poured into 20 ml of ice-cooled water and the reaction product is extracted with dichloromethane (3 times 15 ml). The organic phases are dried and the solvent is evaporated off under reduced pressure. The residue is passed over silica gel in dichloromethane. A colourless oil is obtained constituted by a mixture of 2 compounds: the product of mono- and di-substitution. The mixture of these 2 compounds is used without further purification in the following stage.

43.2 Ethyl (3,5-di-t-butyl-4-hydroxyphenyl)-(4-nitrophenylcarbamoyl)amino acetate 1.13 g (4.2 mmoles) of intermediate 43.1 and 0.69 g (4.23 mmoles) of 4-nitrophenylisocyanate are dissolved in 9 ml of dichloromethane. The reaction mixture is agitated for 2.5 hours at ambient temperature. The solvent is evaporated off under reduced pressure and the residue is passed over silica gel in dichloromethane. In this way 0.66 g of pure (3,5-di-t-butyl-4-hydroxyphenyl)-(4-nitrophenylcarbamoyl)aminoethyl acetate is isolated in the form of a colourless oil. (Yield over 2 stages: 31%).

NMR $^1$H (CDCl$_3$, 100 MHz, δ): 1.30 (t, 3H, CH$_3$), 1.46 (s, 18H, 2tBu), 4.23 (q, 2H, CH$_2$—CH$_3$), 4.38 (s, 2H, CH$_2$—CO), 5.50 (s, 1H, OH), 6.75 (wide s, 1H, NH), 7.28 (s, 2H, arom. H), 7.40–7.50–8.10–8.20 (4s, 4H, arom. H).

43.3 (3,5-di-t-butyl-4-hydroxyphenyl)-1-(4-nitrophenyl)-2,5-imidazolidinedione 0.66 g (1.4 mmole) of intermediate 43.2 is dissolved in 10 ml of ethanol at 50° C. and the whole is heated at this temperature for 2 hours. The precipitate formed is filtered off and washed with cold ethanol. The compound obtained is used directly in the following stage without additional purification.

NMR $^1$H (CDCl$_3$, 100 MHz, δ): 1.47 (s, 18H, 2tBu), 4.51 (s, 2H, N—CH$_2$—CO), 5.27 (s, 1H, OH), 7.33 (s, 2H, arom. H), 7.77–7.86–8.32–8.41 (4s, 4H, arom. H).

43.4 (3,5-di-t-butyl-4-hydroxyphenyl)-1-(4-aminophenyl)-2,5-imidazolidinedione

The experimental protocol used is the same as that described for intermediate 33.2, 3-(3,5-di-t-butyl-4-hydroxyphenyl)-1-(4-nitrophenyl)-2,5-imidazolidinedione replacing 1-(4-nitrophenyl)-1H-imidazole. The expected compound is obtained in the form of a white precipitate with a yield of 87%. It is used without additional purification in the following stage.

NMR $^1$H (CDCl$_3$, 100 MHz): 1.47 (s, 18H, 2tBu), 4.45 (s, 2H, N—CH$_2$—CO), 5.18 (s, 1H, OH), 6.70–6.80–7.16–7.23 (4s, 4H, arom. H), 7.39 (s, 2H, arom. H).

43.5 3-(3,5-di-t-butyl-4-hydroxyphenyl)-1-[4-{imino (2-thienyl)-methylamino}phenyl]-2,5-imidazolidinedione hydrochloride (43)

The experimental protocol used is the same as that described for intermediate 34.4, 3-(3,5-di-t-butyl-4- hydroxyphenyl)-1-(4-aminophenyl)-2,5-imidazolidinedione replacing 3-(4-aminobenzyl)-thiazolidine. The free base is salified by treatment with a 1N solution of hydrochloric ether. The hydrochloride is obtained with a yield of 53%. Melting point: 258–265° C.

NMR $^1$H (DMSO, 400 MHz, δ): 1.40 (s, 18H, 2 tBu), 4.65 (s, 2H, CH$_2$), 7.08 (s, 1H, OH), 7.40 (m, 3H, arom. H), 7.61 (s, 4H, arom. H), 8.21 (m, 2H, arom. H), 9.20–9.95 (wide 2s's, 2H, NH$_2$), 11.75 (s, 1H, HCl).

IR: $v_{OH}$: 3637–3437 cm$^{-1}$; $v_{C=O}$ (imidazolidinedione): 1712 cm$^{-1}$; $v_{C=O}$ (amidine): 1598 cm$^{-1}$.

Example 44

2-(3,5-di-t-butyl-4-hydroxyphenyl)-3-[4-{imino(2-thienyl)-methylamino}phenyl]-4-thiazolidinone hydrochloride (44)

44.1 2-(3,5-di-t-butyl-4-hydroxyphenyl)-3-(4-nitrophenyl)-4-thiazolidinone 5 g of 3,5-di-t-butyl-4-hydroxybenzaldehyde (21 mmol) and 2.95 g of para-nitroaniline (21 mmol) are dissolved in 50 ml of anhydrous toluene. 0.5 ml of glacial acetic acid is added and the whole is taken to reflux for 24 hours. Then 1.96 g of mercaptoacetic acid (21 mmol) is added to the medium and reflux is continued for another 24 hours. After the reaction mixture has returned to ambient temperature, it is washed with water (3 times 30 ml). After decantation. the organic phase is dried over sodium sulphate and the solvent is evaporated off under reduced pressure. The residue is purified on silica gel in an ethyl acetate/heptane mixture (1/4) and 1.33 g of pure 2-(3,5-di-t-butyl-4-hydroxyphenyl)-3-(4-nitrophenyl)-4-thiazolidinone is obtained in the form of a colourless oil (15%).

NMR $^1$H (CDCl$_3$, 100 MHz, δ): 1.36 (s, 18H, 2tBu), 3.91 (s, 2H, CH—S), 5.28 (s, 1H, CH—S), 6.20 (s, 1H, OH), 7.03 (s, 2H, arom. H), 7.38–7.48–8.11–8.20 (4 s, 4H, arom. H).

44.2 2-(3,5-di-t-butyl-4-hydroxyphenyl)-3-(4-aminophenyl)-4-thiazolidinone 1.3 g of 2-(3,5-di-t-butyl-4-hydroxyphenyl)-3-(4-nitrophenyl)-4-thiazolidinone (3 mmol) and 3.4 g (15 mmol) of dihydrated tin chloride are dissolved in 25 ml of ethyl acetate. The reaction is maintained for 2 hours at 70° C. After the mixture has returned to ambient temperature, it is poured into a saturated solution of sodium hydrogen carbonate. The expected product is then extracted from the organic phase then it is washed 3 times with 10 ml of water. The 2-(3,5-di-t-butyl-4-hydroxyphenyl)-3-(4-aminophenyl)-4-thiazolidinone is purified on silica gel in an ethyl acetatelheptane mixture (1/1) and is obtained in the form of a beige oil with a yield of 69% (0.82 g).

NMR $^1$H (CDCl$_3$, 100 MHz, δ): 1.37 (s, 18H, 2tBu), 3.64 (wide s, 2H, NH$_2$), 3.89 (s, 2H, CH$_2$—S), 5.22 (s, 1H, CH—S), 5.91 (s, 1H, OH), 6.51–6.59–6.78–6.86 (4 s, 4H, arom. H), 7.04 (s, 2H, arom. H).

44.3 2-(3,5-di-t-butyl-4-hydroxyphenyl)-3-[4-{imino (2-thienyl)-methylamino}phenyl]-4-thiazolidinone hydrochloride (44)

The experimental protocol used is the same as that described for intermediate 34.4, 2-(3,5-di-t-butyl-4-hydroxyphenyl)-3-(4-aminophenyl)-4-thiazolidinone replacing 3-(4-aminobenzyl)-thiazolidine. The expected compound is obtained in salified form (hydrochloride) by treatment of the free base with a 1N solution of hydrochloric ether with a yield of 43%. Melting point: 58–61° C.

NMR $^1$H (DMSO, 400 MHz, δ): 1.32 (s, 18H, 2tBu), 3.93 (m, 2H, CH—S), 6.57 (s, 1H, CH—S), 7.08 (s, 2H, arom. H), 7.41 (m, 5H, arom. H), 8.15 (m, 2H, arom. H), 9.10–9.90 (wide 2s's, 2H, NH$_2$), 11.45 (wide s, 1H, HCl).

IR: $v_{OH}$: 3624–3423 cm$^{-1}$; $v_{C=O}$ (thiazolidinone): 1679–1658 cm$^{-1}$; $v_{C=N}$ (amidine): 1568 cm$^{-1}$.

Example 45

5-[(3,5-di-t-butyl-4-hydroxyphenyl)methylene]-1-methyl-3-[4-{imino(2-thienyl) methylamino}phenyl]-2,4-imidazolidinedione fumarate (45)

45.1 1-Methyl-3-(4-nitrophenyl)-2,4-imidazolidinedione 0.47 g of the ethyl ester of sarcosine, HCl (3 mmoles) is dissolved in 5 ml of dichloromethane and 0.42 ml (3 mmoles) of triethylamine is added. 0.5 g of 4-nitrophenylisocyanate (3 mmoles) in solution in 5 ml of dichloromethane is added dropwise in the preceding mixture and the reaction mixture is maintained for 30 minutes at ambient temperature. The organic solution is then washed with water (3 times 10 ml) then dried and the solvent is evaporated off under reduced pressure. The residue is taken up in 10 ml of ethanol and the reaction medium is heated under reflux for 2 hours, After the reaction medium has returned to ambient temperature, the precipitate formed is filtered. In this way 1-methyl-3-(4-nitrophenyl)-2,4-imidazolidinedione is obtained with a yield of 72% (0.5 g) and will be used without further purification in the following stage.

NMR $^1$H (CDCl$_3$, 100 MHz, δ): 3.11 (s, 3H, CH$_3$), 4.09 (s, 2H, CH$_2$), 7.70–7.79–8.27–8.37 (4 s, 4H, arom. H).

45.2 5-[(3,5-di-t-butyl-4-hydroxyphenyl)methylene]-1-methyl-3-(4-nitrophenyl)-2,4-imidazolidinedione Intermediate 45.1 (0.5 g, 2.13 mmol), 3,5-di-t-butyl-4-hydroxybenzaldehyde (0.5 g, 2.13 mmol) and β-alanine (0.123 g, 1.4 mmol) are dissolved in acetic acid (10 ml). The reaction is maintained under reflux for 24 hours. After the reaction medium has returned to ambient temperature, 40 ml of water is added to the medium and the whole is agitated for 1 hour. The precipitate formed is filtered and washed with water. The filtrate is concentrated under vacuum and the evaporation residue is purified on silica gel (eluant: heptane/ ethyl acetate: 4/1). The pure fractions are collected and concentrated to dryness in order to produce the expected product with a yield of 32% (0.3 g).

NMR $^1$H (CDCl$_3$, 100 MHz, δ): 1.49 (s, 18H, 2tBu), 3.35 (s, 3H, CH$_3$), 5.59 (s, 1H, OH), 6.40 (s, 1H, CH=C), 7.75–7.84–8.31–8.40 (4 s, 4H, arom. H), 7.92 (s, 2H, arom. H).

45.3 5-[(3,5-di-t-butyl-4-hydroxyphenyl)methylene]-1-methyl-3-(4-aminophenyl)-2,4-imidazolidinedione The experimental protocol used is the same as that described for intermediate 44.2, 5-[(3,5-di-t-butyl-4-hydroxyphenyl)methylene]-1-methyl-3-(4-nitrophenyl)-2,4-imidazolidinedione replacing 2-(3,5-di-t-butyl-4-hydroxyphenyl)-3-(4-nitrophenyl)-4-thiazolidinone. The expected compound is obtained with a yield of 45%.

NMR $^1$H (CDCl$_3$, 100 MHz, δ): 1.47 (s, 18H, 2tBu), 3.30 (s, 3H, CH$_3$), 5.51 (s, 1H, OH), 6.28 (s, 1H, CH=C), 6.69–6.78–7.12–7.21 (4 s, 4H, arom. H), 7.91 (s, 2H, arom. H).

45.4 5-[(3,5-di-t-butyl-4-hydroxyphenyl)methylene]-1-methyl-3-[4-{imino(2-thienyl)methylamino}phenyl]-2,4-imidazolidinedione fumarate (45)

The experimental protocol used is the same as that described for intermediate 34.4, 5-[(3,5-di-t-butyl-4-hydroxyphenyl)methylene]-1-methyl-3-(4-aminophenyl)-2,4-imidazolidinedione replacing 3-(4-aminobenzyl)-thiazolidine. The expected compound is obtained in salified form (fumarate) by treatment of the free base with an equivalent of fumaric acid in ethanol while warm with a yield of 35%. Melting point: 54.5–57.5° C.

NMR $^1$H (DMSO, 400 MHz, δ): 1.40 (s, 18H, 2tBu), 3.22 (s, 3H, CH$_3$), 6.59 (s, 1H, CH=C), 6.61 (s, fumaric acid), 6.97–6.99, 7.30–7.32 (4 s, 4H, arom. H), 7.11 (t, 1H, thiophene), 7.64 (d, 1H, thiophene), 7.79 (m, 1H, thiophene), 7.96 (s, 2H, arom. H).

IR: $v_{OH}$: 3618–3433 cm$^{-1}$; $v_{C=O}$ (imidazolidinedione): 1711 cm$^{-1}$; $v_{C=N}$ (amidine): 1585 cm$^{-1}$.

Example 46

2-(S)-4-(S)-N-[4-hydroxy-3,5-bis-(1,1-dimethylethyl)-phenyl]-4-{4-[(imino(2-thienyl)methyl)amino]phenoxy}-prolinamide hydrochloride (46)

46.1 Methyl ester of 2-(S)-4-(S)-1-[(1,1-dimethylethoxy)carbonyl]-4-(4-nitrophenoxy)-proline A solution of 4.37 g (30.7 mmoles) of 4-nitrophenol in 30 ml of anhydrous N-methyl-2-pyrrolidinone is added slowly to a suspension, cooled down to 0° C., of 1.23 g (30.7 mmol) of NaH at 60% in suspension in 30 ml of anhydrous N-methyl-2-pyrrolidinone, under an inert atmosphere. After agitation for one hour at 0° C., the proline derivative (6 g, 15 mmol) is added in one go. The reaction mixture is agitated at 20° C. for 15 hours followed by heating at 80° C. for 2 hours in order to complete the reaction. After the reaction mixture has returned to 20° C., 200 ml of ethyl acetate and 100 ml of 1N soda are added to the medium. After decantation, the organic phase is washed successively with dilute solutions of 1N soda until complete extraction of the unreacted phenolic derivative, 2×100 ml of water and 100 ml of salt water. The organic solution is dried over sodium sulphate, filtered and concentrated to dryness under reduced pressure, in order to produce a light yellow oil which crystallizes spontaneously in air. The crystals are collected and washed with 3×50 ml of ethyl ether. After drying, colourless crystals are obtained with a yield of 63%. Melting point: 155–157° C.

NMR $^1$H (DMSO, 400 MHz, δ): 1.34–1.40 (2s, 9H, tBu); 2.45 (m, 2H, CH$_2$); 3.60 (m, 2H, CH$_2$—N); 3.58–3.63 (2s, 3H, O—CH$_3$); 4.40 (m, 1H, CH—CO$_2$); 5.22 (m, 1H, HC—O); 7.63 (m, 4H, Ph).

46.2 2-(S)-4-(S)-1-[(1,1-dimethylethoxy)carbonyl]-4-(4-nitrophenoxy)-proline 730 mg (approximately 16 mmol) of potash diluted in 5 ml of water is added at 20° C. to a 100 ml flask containing 2.87 g (7.84 mmol) of compound 46.1 in 40 ml of ethanol. After agitation for 15 hours, the reaction mixture is diluted with 100 ml of ethyl acetate, acidified at 0° C. with a 12N solution of HCl and decanted. The organic phase is washed with 50 ml of water followed by 50 ml of salt water. After drying over sodium sulphate, the organic solution is filtered and concentrated to dryness under vacuum. 2.67 g of a white powder is obtained which is used directly in the following stage without additional purification.

NMR $^1$H (CDCl$_3$, 100 MHz, δ): 1.50 (s, 9H, tBu); 2.60 (m, 2H, CH$_2$); 3.80 (m, 2H, CH$_2$—N); 4.60 (m, 1H, CH—CO$_2$); 5.07 (m, 1H, HC—O); 7.58 (m, 4H, Ph); 8.95 (wide s, 1H, CO$_2$H).

46.3 2-(S)-4-(S)-1-[(1,1-dimethylethoxy)carbonyl]-N-[4-hydroxy-3,5-bis-(1,1-dimethylethyl)phenyl]-4-(4-nitrophenoxy)-prolinamide 1.28 g (6.20 mmol) of dicyclohexylcarbodiimide is added at 0° C. to a solution of 1.99 g (5.64 mmol) of intermediate 46.2, 1.25 g (5.64 mmol) of intermediate 42.2 and 845 mg (6.20 mmol) of hydroxybenzotriazole in 25 ml of DMF. After agitation for 24 hours at 20° C., the reaction mixture is filtered and the precipitate is washed with ethyl acetate. The filtrate is diluted with 100 ml of ethyl acetate and washed successively with 2×40 ml of 1N soda, 2×40 ml of water and 40 ml of salt water. After drying over sodium sulphate, the organic solution is filtered and concentrated to dryness under vacuum in order to produce a brown oil which is purified on a silica column (eluant heptane/ethyl acetate: 1/1). The pure fractions are collected and after concentration under vacuum, 1.35 g (43%) of a beige powder is obtained. Melting point: 117–120° C.

NMR $^1$H (CDCl$_3$, 100 MHz, δ): 1.20–1.70 (m, 27 H, 3×tBu); 2.68 (m, 2H, CH$_2$); 3.80 (m, 2H, CH$_2$—N); 4.58 (m, 1H, CH—CO$_2$); 5.10 (m, 2H, OH, HC—O); 7.25–7.28 (2s, 2H, Ph—OH); 7.51 (m, 4H, Ph—NO$_2$); 8.00 (wide s, 1H, NHCO).

46.4 2-(S)-4-(S)-1-[(1,1-dimethylethoxy)carbonyl]-N-[4-hydroxy-3,5-bis-(1,1-dimethylethyl)phenyl]-4-(4-aminophenoxy)-prolinamide 1.35 g (2.4 mmol) of intermediate 46.3 in 30 ml of ethanol is dissolved in an autoclave equipped with a magnetic stirrer in the presence of 1/2 a spatula's worth of Pd/C at 10%. The reaction mixture is agitated under 1.5 bar of hydrogen for 3 hours. After filtration on celite, the filtrate is concentrated under vacuum. The residue is taken up in a 1/1 ethyl ether/heptane mixture and after crystallization, it is filtered and rinsed using heptane. A beige powder is obtained with a yield of 60%. Melting point: 112–113° C.

NMR $^1$H (CDCl$_3$, 100 MHz, δ): 1.20–1.70 (m, 27 H, 3×tBu); 2.55 (m, 2H, CH$_2$); 3.50 (wide s, 2H, NH$_2$); 3.75 (m, 2H, CH$_2$—N); 4.48 (m, 1H, CH—CO$_2$); 4.80 (m, 1H, HC—O); 5.10 (s, 1H, OH); 6.65 (m, 4H, Ph—NH$_2$); 7.28 (m, 2H, Ph—OH); 8.00 (wide s, 1H, NHCO).

46.5 2-(S)-4-(S)-N-[4-hydroxy-3,5-bis-(1,1-dimethylethyl)phenyl]-4-{4-[(imino(2-thienyl)methyl)amino]phenoxy}-prolinamide hydrochloride (46)

A mixture of 694 mg (1.32 mmol) of intermediate 46.4 is heated at 50° C. for 48 hours in the presence of 376 mg (1.32 mmol) of S-methyl-2-thiophenethiocarboximide hydroiodide in solution in 15 ml of isopropanol. The reaction mixture is then concentrated to dryness under vacuum and the evaporation residue is suspended in 50 ml of ethyl acetate. After the addition of 50 ml of a saturated solution of Na$_2$CO$_3$ the organic phase is decanted and successively washed with 25 ml of a saturated solution of Na$_2$CO$_3$, 50 ml of water and 50 ml of salt water. After drying over sodium sulphate, the organic solution is filtered and concentrated to dryness under vacuum in order to produce a yellow powder which is purified on a silica column (eluant: ethyl acetate). The pure fractions are collected and after concentration under vacuum. 686 mg (82%) of a beige powder is obtained which is immediately dissolved in 5 ml of a 4M solution of HCl in 1,4-dioxan. After agitation for 15 hours at 20° C., 20 ml of dry ethyl ether is added to the reaction mixture. The precipitate which appears is then filtered off, rinsed with 2×25 ml of dry ethyl ether and dried in an oven in order to produce 270 mg of a beige powder. Melting point: 233, 5–235° C.

NMR ¹H (DMSO, 400 MHz, δ): 1.37 (s, 18H, 2×tBu); 2.61 (m, 2H, $CH_2$); 3.60 (m, 2H, $CH_2$—N); 4.56 (m, 1H, CH—$CO_2$); 5.25 (m, 1H, HC—O); 6.92 (s, 1H, OH); 7.21 (m, 4H, Ph—N); 7.38 (m, 1H, thiophene); 7.45 (s, 2H, Ph—OH); 8.18 (m, 2H, thiophene); 8.78 (wide s, 1H, $NH^+$); 9.09 (wide s, 1H, $NH^+$); 9.80 (wide s, 1H, $NH^+$); 10.68 (c. 1H, CONH); 11.42 (wide s, 1H, $NH^+$).

IR: $v_{OH}$: 3624–3420 $cm^{-1}$; $v_{C=O}$ (amide): 1653 $cm^{-1}$; $n_{C=N\ (amidine)}$: 1610 $cm^{-1}$.

Example 47

5,6-dihydro-N-{4-[(imino(2-thienyl)methyl)amino] phenyl}-1-(2H)-pyridine carboxanide hydrochloride (47)

47.1 5,6-dihydro-N-(4-nitrophenyl)-1-(2H)-pyridine carboxamide 900 mg (5 mmol) of 4-nitrophenylisocyanate is dissolved, under an argon atmosphere, in a 100 ml three-necked flask in 17 ml of dry DMF. 0.45 ml (5 mmol) of 1,2,3,6-tetrahydropyridine is added to this solution in one go, and agitation is maintained for 15 hours. The reaction mixture is then concentrated to dryness under vacuum and the evaporation residue placed on a silica gel column. After elution with a heptane/ethyl acetate mixture: 4/6, the pure fractions are collected and concentrated under reduced pressure in order to produce 860 mg (70%) of a bright yellow powder. Melting point: 169–170° C.

NMR ¹H (DMSO, 100 MHz, δ): 2.29 (m, 2H, =CH—$CH_2$); 3.69 (m, 2H, $CH_2$—N); 4.10 (m, 2H, =CH—$CH_2$—N); 5.91 (m, 2H, CH=CH); 8.09 (m, 4H, Ph); 9.32 (wide s, 1H, NHCO).

47.2 N-(4-aminophenyl)-5,6-dihydro-1-(2H)-pyridine carboxamide

The experimental protocol used is the same as that described for intermediate 44.2, 5,6-dihydro-N-(4-nitrophenyl)-1-(2H)-pyridine carboxamide replacing 2-(3,5-di-t-butyl-4-hydroxyphenyl)-3-(4-nitrophenyl)-4-thiazolidinone. A brown oil is obtained with a yield of 36%.

NMR ¹H ($CDCl_3$+$D_2O$, 400 MHz, δ): 2.20 (m, 2H, =CH—$CH_2$); 3.59 (m, 2H, $CH_2$—N); 3.95 (m, 2H, =CH—$CH_2$—N); 5.84 (m, 2H, CH=CH); 6.90 (m, 4H, Ph); 9.32 (wide s, 1H, NHCO).

47.3 5,6-dihydro-N-{4-[(imino(2-thienyl)methyl) amino]phenyl}-1-(2H)-pyridine carboxamide hydrochloride (47)

The experimental protocol used is the same as that described for intermediate 46.5, N-(4-aminophenyl)-5,6-dihydro-1-(2H)-pyridine carboxamide replacing 2-(S)-4-(S)-1-[(1,1-dimethylethoxy)carbonyl]-N-[4-hydroxy-3,5-bis-(1,1-dimethylethyl)phenyl]-4-(4-aminophenoxy)-prolinamide. After salification, using a solution of 1M HCl in ethyl ether, a pale yellow powder is obtained with a yield of 55%. Melting point: 230–231° C.

NMR ¹H (DMSO, 400 MHz, δ). 2.16 (m, 2H, =CH—$CH_2$); 3.59 (m, 2H, $CH_2$—N); 3.98 (m, 2H, =CH—$CH_2$—N); 5.80 (m, 2H, CH=CH); 7.52 (m, 4H, Ph); 7.38 (s, 1H, thiophene); 8.16 (m, 2H, thiophene); 8.78 (wide s, 1H, $NH^+$); 8.81 (s, 1H, CONH); 9.73 (wide s, 1H, $NH^+$); 11.41 (wide s, 1H, $NH^+$).

IR: $v_{C=O}$ (urea): 1637 $cm^{-1}$; $v_{C=N}$ (amidine): 1583 $cm^{-1}$.

Example 48

N-[4-hydroxy-3,5-bis-(1,1-dimethylethyl)phenyl]-2-(R,S)-{4-[(imino(2-thienyl)methyl)amino]phenyl}-4-(R)-thiazolidine carboxamide fumarate (48)

48.1 2-(R,S)-(4-nitrophenyl)-4-(R)-thiazolidine carboxylic acid 3 g (17.08 mmoles) of L-Cysteine hydrochloride and 2.18 g (22.2 mmoles) of sodium acetate are dissolved in 75 ml of water. The solution is agitated vigorously during the addition. by portions, of 3.10 g (20.5 mmoles) of 4-nitrobenzaldehyde in solution in 80 ml of 95% ethanol. A white precipitate rapidly appears in this pale yellow solution which forms abundantly. Agitation is maintained for one hour, the reaction mixture is then cooled down to 0° C. and filtered. The precipitate is successively rinsed with 200 ml of water, 100 ml of cold ethanol and 100 ml of ethyl ether. After drying, a white powder is obtained with a yield of 87%. Melting point: 120–121° C.

NMR ¹H (Acetone D6, 100 MHz, δ): 3.50 (m, 2H, $CH_2$—S); 4.25 (m, 1H, CH—CO); 4.75 (hump, 2H, $CO_2H$+NH); 5.86 (s, 1H, N—CH—S); 8.20 (m, 4H, Ph).

48.2 3-[(1,1-dimethylethoxy)carbonyl]-2-(R,S)-(4-nitrophenyl)-4-(R)-thiazolidine carboxylic acid The experimental protocol used is the same as that described for intermediate 47.1, 2-(R,S)-(4-nitrophenyl)-4-(R)-thiazolidine carboxylic acid replacing 4-(t-butoxycarbonylamino)-benzeneacetic acid. A pale yellow powder is obtained with a yield of 59%. Melting point: 145–146° C.

NMR ¹H ($CDCl_3$, 100 MHz, δ): 1.35 (m, 9H, tBu); 3.40 (m, 2H, $CH_2$—S); 4.95 (m, 1H, CH—CO); 6.10 (m, 1H, N—CH—S); 8.00 (m, 4H, Ph); 10.00 (wide s, 1H, $CO_2H$).

48.3 3-[(1,1-dimethylethoxy)carbonyl]-N-[4-hydroxy-3,5-bis(1,1-dimethylethyl)phenyl]-2-(R,S)-(4-nitrophenyl)-4-(R)-thiazolidine carboxamide The experimental protocol used is the same as that described for intermediate 46.3, 3-[(1,1-dimethylethoxy)carbonyl]-2-(R,S)-(4-nitrophenyl)-4-(R)-thiazolidine carboxylic acid replacing 2-(S)-4-(S)-1-[(1,1-dimethylethoxy)carbonyl]-4-(4-nitrophenoxy)-proline. A white powder is obtained with a yield of 41%. Melting point: 226–227° C.

NMR ¹H ($CDCl_3$, 100 MHz, δ): 1.45 (m, 27H, 3×tBu); 3.52 (m, 2H, $CH_2$—S); 5.00 (m, 1H, CH—CO); 5.15 (s, 1H, OH); 6.10 (wide s, 1H, N—CH—S); 7.30 (s, 2H, Ph—OH); 7.92 (m, 4H, Ph—$NO_2$); 8.60 (wide s, 1H, CONH).

48.4 3-[(1,1-dimethylethoxy)carbonyl]-N-[4-hydroxy-3,5-bis-(1,1-dimethylethyl)phenyl]-2-(R,S)-(4-aminophenyl)-4-(R)-thiazolidine carboxamide The experimental protocol used is the same as that described for intermediate 44.2, 3-[(1,1-dimethylethoxy)

carbonyl]-N-[4-hydroxy-3,5-bis-(1,1-dimethylethyl) phenyl]-2-(R,S)-(4-nitrophenyl)-4-(R)-thiazolidine carboxamide replacing 2-(3,5-di-t-butyl-4-hydroxyphenyl)-3-(4-nitrophenyl)-4-thiazolidinone. The expected product is obtained in the form of a pale yellow powder with a yield of 21%. Melting point: 196–198° C.

NMR $^1$H (CDCl$_3$, 100 MHz, δ): 1.40 (m, 27H, 3×tBu); 3.50 (m, 4H, CH$_2$—S+NH$_2$); 5.00 (m, 1H, CH—CO); 5.10 (s, 1H, OH); 6.01 (wide s, 1H, N—CH—S); 6.98 (m, 4H, Ph—NH$_2$); 7.25 (s, 2H, Ph—OH); 8.50 (wide s, 1H, CONH).

48.5 N-[4-hydroxy-3,5-bis-(1,1-dimethylethyl) phenyl]-2-(R,S)-{4-[(imino(2-thienyl)methyl)amino]phenyl}-4-(R)-thiazolidine carboxamide fumarate (48)

The experimental protocol used is the same as that described for intermediate 46.5, intermediate 48.4 replacing 2-(S)-4-(S)-1-[(1,1-dimethylethoxy)carbonyl]-N-[4-hydroxy-3,5-bis-(1,1-dimethylethyl)phenyl]4-(4-aminophenoxy)-prolinamide. Compound 48.5 obtained in the form of the free base is then salified in the presence of fumaric acid under reflux of ethanol for 30 minutes. A yellow powder is obtained with an overall yield of 30%. Melting point: 201–204° C.

NMR $^1$H (DMSO, 400 MHz, δ): 1.37 (s, 18H, 2×tBu); 3.17 (m, 2H, CH$_2$—S); 3.29 (wide s, 1H, NH thiazolidine); 3.91 (m, _H, CH—CO); 4.31 (m, _H, CH—CO); 5.59 (s, _H, N—CH—S); 5.67 (s, _H, N—CH—S); 6.61 (s, 2H, fum,); 6.74 (m, 2H, NH$_2$ amidine); 7.11 (m, 1H, thiophene); 7.19 (m, 4H, Ph—N); 7.42 (s, 2H, Ph—OH); 7.62 (m, 1H, thiophene); 7.73 (wide s, 1H, thiophene); 9.69 (s, _H, CONH); 9.95 (s, _H, CONH).

IR: $v_{OH}$: 3625–3421 cm$^{-1}$; $v_{C=O}$ (amide): 1652 cm$^{-1}$; $v_{C=N}$ (amidine): 1604 cm$^{-1}$.

Example 49

N-[3,5-bis(1,1-dimethylethyl)-4-hydroxyphenyl]-2-{4-[(imino(2-thienyl)methyl)amino]phenyl}-4-thiazolecarboxamide hydroiodide (49)

49.1 4-nitrobenzene-carbothioamide 6.06 g (15 mmol) of Lawesson reagent is added to a solution of 4.15 g (25 mmol) of 4-nitrobenzamide in 100 ml of 1,4-dioxan. The reaction mixture is heated under reflux for two hours. After the solution has returned to ambient temperature, it is poured into 150 ml of water and extracted with 5 times 100 ml of ethyl acetate. The organic solution is dried over magnesium sulphate, filtered and concentrated under vacuum in order to produce a yellow oil which is purified on a silica gel column (eluant: heptane/ethyl acetate 1/1). The pure fractions are collected and concentrated under vacuum. 3.26 g of a yellow powder is obtained with a yield of 72%. Melting point: 165–167° C.

49.2 Ethyl 2-(4-nitrophenyl)-4-thiazolecarboxylate 3.26 g (17.9 mmol) of intermediate 49.1 and 2.26 ml (18 mmol) of ethyl bromopyruvate are introduced successively into a flask containing 100 ml of DMF. After agitating the reaction mixture at 23° C., for 1 hour, the solution is concentrated under vacuum. The evaporation residue is dissolved in 150 ml of dichloromethane and washed successively with 100 ml of water and 100 ml of salt water. After drying over magnesium sulphate and filtration, the organic solution is concentrated under vacuum. The powder obtained is then agitated in the presence of 100 ml of a (3/1) mixture of toluene and ethanol, filtered and rinsed with 25 ml of the same mixture of solvents. 3.2 g (60%) of a beige powder is obtained. Melting point: 156–158° C.

49.3 2-(4-nitrophenyl)-4-thiazolecarboxylic acid

A solution of 0.82 g (14.5 mmol) of KOH in 5 ml of water is added dropwise at 23° C. to a solution of intermediate 49.2 (2.15 g, 7.25 mmol) in 100 ml of acetone. After agitation overnight, the precipitate formed is filtered off and rinsed with 10 ml of acetone. This precipitate is taken up in a mixture of 100 ml of ethyl acetate and 100 ml of a 1M solution of HCl. After decantation, the aqueous phase is reextracted with 25 ml of ethyl acetate. The organic phases are collected and washed successively with 25 ml of water and 50 ml of salt water. The organic solution is dried over sodium sulphate, filtered and concentrated under vacuum in order to produce a yellow powder with a yield of 93%. Melting point: 250–252° C.

49.4 N-[3,5-bis(1,1-dimethylethyl)-4-hydroxyphenyl]-2-(4-nitrophenyl)-4-thiazolecarboxamide The experimental protocol used is the same as that described for intermediate 46.3, intermediate 49.3 replacing intermediate 46.2. The expected compound is obtained in the form of a yellow powder with a yield of 51%. Melting point: 262–264° C.

NMR $^1$H (acetone d6, 100 MHz, δ): 1.60 (s, 18H, 2 tBu), 6.12 (s, 1H, OH), 8.21 (m, 2H, arom. H), 8.50 (s, 4H, arom. H), 8.60 (s, 1H, thiazole), 9.93 (wide s, 1H, CO—NH).

49.5 N-[3,5-bis(1,1-dimethylethyl)-4-hydroxyphenyl]-2-(4-aminophenyl)-4-thiazolecarboxamide 3.59 g (16 mmol) of SnCl$_2$.2H$_2$O is introduced into a solution of intermediate 49.4 (1.50 g, 3.18 mmol) in 50 ml of an ethyl acetate/ethanol/acetone mixture (2/1/2). The reaction mixture is heated under reflux for 5 hours and finally after cooling down, concentration to one half is carried out under vacuum. The evaporation residue is then poured into 50 ml of cold water, the precipitate which forms is diluted with 100 ml of ethyl acetate and 25 ml of a saturated solution of NaHCO$_3$. The cloudy mixture is filtered on celite and the filtrate is decanted. The organic phase is washed successively with 50 ml of water and 50 ml of salt water. After drying over magnesium suphate and filtration, the organic solution is concentrated under vacuum in order to produce a bright yellow powder which is purified by washing with an Et$_2$O/heptane mixture (90/10). The expected compound is obtained in the form of a pale yellow powder with a yield of 55%. Melting point: 267–268° C.

NMR $^1$H (CDCl$_3$, 100 MHz, δ): 1.49 (s, 18H, 2 tBu), 4.00 (wide s, 2H, NH$_2$), 5.11 (s, 1H, OH), 6.72 (m, 2H, arom. H), 7.60 (s, 2H, arom. H), 7.81 (m, 2H, arom. H), 8.05 (s, 1H, thiazole), 9.10 (wide s, 1H, CO—NH).

49.6 N-[3,5-bis(1,1-dimethylethyl)-4-hydroxyphenyl]-2-{4-[(imino(2-thienyl)methyl) amino]phenyl}-4-thiazolecarboxamide hydroiodide (49)

The experimental protocol used is the same as that described for intermediate 33.3, intermediate 49.5 replacing intermediate 33.2. A yellow powder is obtained with a yield of 27%. Melting point: 270–272° C.

NMR $^1$H (DMSO d6, 400 MHz, δ): 1.40 (s, 18H, 2 tBu), 6.89 (s, 1H, OH), 7.41 (m, 1H, arom. H), 7.63 (m, 4H, arom. H), 8.11 (m, 1H, arom. H), 8.20 (m, 1H, arom. H), 8.36 (m, 2H, arom. H), 8.48 (s, 1H, arom. H), 9.19 (wide s, 1H, NH$^+$), 9.90 (wide s, 1H, NH$^+$), 10.02 (s, 1H, CO—NH), 11.50 (s, 1H, NH$^+$).

IR: $v_{C=O}$ (amide): 1660 cm$^{-1}$; $v_{C=N}$ (amidine): 1646 cm$^{-1}$.

Example 50

N-[3,5-bis(1,1-dimethylethyl)-4-hydroxyphenyl]-4-(S)-{4-[(imino(2-thienyl)methyl)amino]phenoxy}-pyrrolidine-2-(R)-carboxamide dihydrochloride (50)

50.1 1-(1,1-dimethylethyl) and 2-methyl 4-(S)-(4-nitrophenoxy)-1,2-(R)-pyrrolidinedicarboxylate 4.38 g (31.5 mmoles) of 4-nitrophenol in solution in 40 ml of anhydrous N-methyl-2-pyrrolidinone is added dropwise to a suspension of 1.26 g (31.5 mmoles) of NaH at 60% in 60 ml of anhydrous N-methyl-2-pyrrolidinone in a three-necked flask cooled down to 0° C. under an inert atmosphere. The reaction is accompanied by a significant release of hydrogen. After agitation for one hour at 0° C. 6 g (15 mmoles) of 1-(1,1-dimethylethyl) and 2-methyl 4-(R)-{[(4-methylphenyl)sulphonyl]oxy}-1,2-(R)-pyrrolidinedicarboxylate is added in one go, agitation is maintained for another 15 hours at 23° C. and the reaction is completed by 5 hours of reflux. After the reaction mixture is returned to 23° C., it is diluted with 150 ml of ethyl acetate and 100 ml of a 1M solution of soda. After decantation, the aqueous phase is reextracted twice with 50 ml of ethyl acetate. The organic phases are collecteed and washed successively with 1N soda (until the excess of 4-nitrophenol of the organic phase disappears), with water until neutrality is achieved and finally with 100 ml of salt water. After drying over magnesium sulphate and filtration, the organic solution is concentrated under vacuum in order to produce an oily brown residue which is purified on a silica column (eluant: heptane/ethyl acetate: 8/2). The pure fractions are collected and concentrated under vacuum in order to produce a pale yellow oil with a yield of 83%.

NMR $^1$H (CDCl$_3$, 100 MHz, δ): 1.41 (s, 9H, tBu), 2.40 (m, 2H, CH$_2$), 3.80 (s, 5H, CH$_3$+CH$_2$), 4.50 (m, 1H, CH—N), 5.03 (m, 1H, CH—O), 6.95 (m, 2H, arom. H), 8.22 (m, 2H, arom. H).

50.2 1,1-dimethylethyl 2-(R)-carboxy-4-(S)-(4-nitrophenoxy)-1-pyrrolidinecarboxylate A solution of 2.14 g (38 mmoles) of KOH in 15 ml of water is added dropwise at 0° C. to a solution of 7 g (19 mmoles) of intermediate 50.1 in 100 ml of methanol. The reaction mixture is agitated at 23° C. for 15 hours and finally concentrated to one half under vacuum. After dilution with 50 ml of ethyl acetate and 50 ml of 1N soda, the mixture is decanted. The organic phase is eliminated and the aqueous phase is acidified cold with 1M HCl, the product is then extracted with 100 ml of ethyl acetate. The organic solution is then washed with 50 ml of water and 50 ml of salt water. After drying over magnesium sulphate and filtration, the solution is concentrated under vacuum. A pale yellow oil is obtained with a yield of 66%.

NMR $^1$H (CDCl$_3$, 100 MHz, δ): 1.45 (s, 9H, tBu), 2.52 (m, 2H, CH$_2$), 3.80 (m, 2H, CH$_2$), 4.48 (m, 1H, CH—N), 5.03 (m, 1H, CH—O), 5.92 (wide s, CO$_2$H), 6.92 (m, 2H, arom. H), 8.20 (m, 2H, arom. H).

50.3 1,1-dimethylethyl 2-(R)-{[[3,5-bis(1,1-dimethylethyl)-4-hydroxyphenyl]amino]carbonyl}-4-(S)-(4-nitrophenoxy)-pyrrolidine-1-carboxylate The experimental protocol used is the same as that described for intermediate 46.3, intermediate 50.2 replacing intermediate 46.2. A beige powder is obtained with a yield of 43%. Melting point: 140–142° C.

NMR $^1$H (CDCl$_3$, 100 MHz, δ): 1.45 (s, 18H, 2 tBu), 1.50 (s, 9H, tBu), 2.30 (m, 1H, 1/2 CH$_2$), 2.95 (m, 1H, 1/2 CH$_2$), 3.75 (m, 2H, CH$_2$), 4.65 (m, 1H, CH—N), 5.10 (m, 2H, CH—O+OH), 6.98 (m, 2H, arom. H), 7.31 (s, 2H, arom. H), 8.22 (m, 2H, arom. H), 9.10 (wide s, 1H, CO—NH).

50.4 1,1-dimethylethyl 2-(R)-{[[3,5-bis(1,1-dimethylethyl)-4-hydroxyphenyl]amino]carbonyl}-4-(S)-(4-aminophenoxy)-pyrrolidine-1-carboxylate The experimental protocol used is the same as that described for intermediate 46.4, intermediate 50.3 replacing intermediate 46.3. After purification on a silica column (eluant: heptane/ethyl acetate: 1/1) and concentration of the pure fractions, the expected compound is obtained in the form of a beige powder with a yield of 70%. Melting point: 104–106° C. NMR $^1$H (CDCl$_3$, 100 MHz, δ): 1.45 (s, 18H, 2 tBu), 1.50 (s, 9H, tBu), 1.60 (s, 2H, NH$_2$), 2.10 (m, 1H, 1/2 CH$_2$), 2.80 (m, 1H, 1/2 CH$_2$), 3.60 (m, 2H, CH$_2$), 4.60 (m, 1H, CH—N), 4.85 (m, 1H, CH—O), 5.04 (s, 1H, OH), 6.70 (m, 4H, arom. H), 7.34 (s, 2H, arom. H), 9.10 (wide s, 1H, CO—NH).

50.5 N-[3,5-bis(1,1-dimethylethyl)-4-hydroxyphenyl]-4-(S)-{4-[(imino(2-thienyl)methyl)amino]phenoxy}-pyrrolidine-2-(R)-carboxamide dihydrochloride (50)

The experimental protocol used is the same as that described for intermediate 34.4, intermediate 50.4 replacing 3-(4-amninobenzyl)-thiazolidine. The free base, obtained in the form of a light yellow powder, is directly deprotected in the presence of 10 equivalents of a 4M solution of anhydrous HCl in 1,4-dioxan. After agitation for 15 hours, the precipitate formed is filtered, the crystals are washed with acetone followed by ethyl ether. The expected product is obtained in the form of a pale yellow powder with a yield of 53%. Melting point: 245–247° C.

NMR $^1$H (DMSO d6, 400 MHz, δ): 1.36 (s, 18H, 2 tBu), 2.29 (m, 1H, 1/2 CH$_2$), 2.71 (m, 1H, 1/2 CH$_2$), 3.42 (m, 1H, 1/2 CH$_2$), 3.77 (m, 1H, 1/2 CH$_2$), 4.57 (m, 1H, CH—N), 5.26 (m, 1H, CH—O), 6.93 (s, 1H, OH), 7.17 (m, 2H, arom. H), 7.37 (m, 1H, arom. H), 7.42 (m, 2H, arom. H), 7.48 (s, 2H, arom. H), 8.17 (m, 2H, arom. H), 8.81 (wide s, 1H, NH$^+$), 9.03(wide s, 1H, NH$^+$), 9.78 (wide s, 1H, NH$^+$), 10.70 (s, 1H, CO—NH), 10.84 (wide s, 1H, NH$^+$), 11.50 (wide s, 1H, NH$^+$).

IR: $v_{C=O}$ (amide): 1681 cm$^{-1}$; $v_{C=N}$ (amidine): 1652 cm$^{-1}$.

Example 51 methyl 1-[(3,4-dihydro-6-hydroxy-2,5,7,8-tetramethyl-2-H-[1]-benzopyran-2-yl)carbonyl]-4-(S)-{4-[(imino(2-thienyl)methyl)amino]-phenoxy}-pyrrolidine-2-(S)-carboxylate hydrochloride (51)

51.1 1-(1,1-dimethylethyl) and 2-methyl 4-(S)-(4-nitrophenoxy)-1,2-(S)-pyrrolidinedicarboxylate The experimental protocol used is the same as that described for intermediate 50.1, the 1-(1,1-dimethylethyl)

and 2-methyl 4-(S)-{[(4-methylphenyl)sulphonyl]oxy}-1,2-(R)-pyrrolidinedicarboxylate derivatives being used instead of the 1-(1,1-dimethylethyl) and 2-methyl 4-(R)-{[(4-methylphenyl)sulphonyl]oxy}-1,2-(R)-pyrrolidinedicarboxylate derivatives. The expected product is obtained in the form of a white powder with a yield of 63%. Melting point: 155–157° C.

NMR $^1$H (DMSO d6, 400 MHz, δ): 1.37 (2 s, 9H, tBu), 2.22 (m, 1H, 1/2 $CH_2$), 2.62 (m, 1H, 1/2 $CH_2$), 3.45 (m, 1H, 1/2 $CH_2$), 3.62 (2 s, 3H, $OCH_3$), 3.78 (m, 1H, 1/2 $CH_2$), 4.42 (m, 1H, CH—N), 5.20 (m, 1H, CH—O), 7.07 (m, 2H, arom. H), 8.20 (m, 2H, arom. H).

51.2 Methyl 4-(S)-(4-nitrophenoxy)-pyrrolidine-2-(S)-carboxylate 10 ml (94 mmol) of trifluoroacetic acetic diluted with 10 ml of dichloromethane is added at 0° C. to a a solution of 3.45 g (9.4 mmol) of intermediate 51.1 in 15 ml of dichloromethane. The reaction mixture is then agitated for 2 hours at 23° C. and finally it is concentrated under vacuum. The evaporation residue is diluted with 100 ml of dichloromethane and the organic solution is washed successively 3 times with 20 ml of a saturated solution of $Na_2CO_3$, twice with 20 ml of water and finally with 20 ml of salt water. After drying over magnesium sulphate and filtration, the organic solution is concentrated under vacuum in order to produce a pale yellow oil with a yield of 78%.

51.3 Methyl 1-[(3,4-dihydro-6-hydroxy-2,5,7,8-tetramethyl-2-H-[1]-benzopyran-2-yl)carbonyl]-4-(S)-(4-nitrophenoxy)-pyrrolidine-2-(S)-carboxylate 1.3 g (8.06 mmol) of 1,1'-carbonyldiimidazole is added to a solution of 1.83 g (7.33 mmol) of Trolox in 20 ml of dry THF. After agitation for one hour at 23° C., a solution of 1.95 g (7.33 mmoles) of intermediate 51.2 diluted in 10 ml of dry THF is added dropwise. The reaction mixture is agitated at 23° C. for 15 hours and finally concentrated to dryness under vacuum. The residue is diluted with 100 ml of ethyl acetate and the organic solution is washed twice with 50 ml of water and 50 ml of salt water. After drying over magnesium sulphate and filtration, the organic solution is concentrated under vacuum. The evaporation residue is purified on a silica gel column (eluant: heptane/ethyl acetate: 6/4). The pure fractions are collected and evaporated under vacuum in order to produce a yellow powder with a yield of 61%. Melting point: 103–105° C.

NMR $^1$H ($CDCl_3$, 400 MHz, δ): 1.55–2.50 (m, 16H, Trolox), 2.63 (m, 2H, $CH_2$), 3.60–3.71 (2 s, 3H, $OCH_3$), 3.85 (m, 2H, $CH_2$), 4.70–4.88 (2 m, 1H, CH—N), 5.02 (m, 1H, CH—O), 6.82 (m, 2H, arom. H), 8.20 (m, 2H, arom. H).

51.4 Methyl 1-[(3,4-dihydro-6-hydroxy-2,5,7,8-tetramethyl-2-H-[1]-benzopyran-2-yl)carbonyl]-4-(S)-(4-aminophenoxy)-pyrrolidine-2-(S)-carborylate The protocol used is the same as that described for intermediate 46.4, intermediate 51.3 replacing intermediate 46.3. The expected product is obtained in the form of a white powder with a yield of 95%. Melting point: 110–112° C.

51.5 Methyl 1-[(3,4-dihydro-6-hydroxy-2,5,7,8-tetramethyl-2-H-[1]-benzopyran-2-yl)carbonyl]-4-(S)-{4-[(imino(2-thienyl)methyl)amino]phenoxy}-pyrrolidine-2-(S)-carboxylate hydrochloride (51)

The protocol used is the same as that described for intermediate 34.4, intermediate 51.4 replacing intermediate 34.3. The condensation reaction is carried out in 2-propanol only. After salification, the expected product is obtained in the form of a pale yellow powder with a yield of 75%. Melting point: 203–206° C.

NMR $^1$H (DMSO d6, 400 MHz, δ): 1.55–2.50 (m, 16H, Trolox), 2.45 (m, 2H, $CH_2$), 3.45–3.60 (2 s, 3H, $OCH_3$), 3.70 (m, 2H, $CH_2$), 4.51 (m, 1H, CH—N), 5.02 (m, 1H, CH—O), 7.00 (m, 2H, arom. H), 7.39 (m, 3H, arom. H), 8.16 (m, 2H, arom. H), 8.80 (wide s, 1H, $NH^+$), 9.75 (wide s, 1H, $NH^+$), 11.36 (wide s, 1H, $NH^+$). IR: $v_{C=O}$ (amide): 1650 $cm^{-1}$; $v_{C=N}$ (amidine): 1611 $cm^{-1}$.

Example 52

1-[(3,4-dihydro-6-hydroxy-2,5,7,8-tetramethyl-2H-[1]-benzopyran-2-yl)carbonyl]-3-(S)-{4-[(imino(2-thienyl)methyl)amino]phenoxy}-pyrrolidine hydrochloride (52)

52.1 1,1-dimethylethyl:3-(R)-{[(4-methylphenyl)sulphonyl]oxy}-1-pyrrolidinecarboxylate 21.6 g (114 mmol) of p-toluenesulphonyl chloride is added to a solution of 10 g (57 mmol) of (R)-N-Boc-3-pyrrolidinol (prepared in a standard fashion starting from commercial (R)-3-pyrrolidinol) and 13.7 ml (171 mmoles) of pyridine in 150 ml of dichloromethane). After agitation for 24 hours at 23° C., the reaction mixture is washed with 3 times 50 ml of a 1M solution of HCl. After decantation, the organic phase is washed with 50 ml of water followed by 50 ml of salt water and finally dried over magnesium sulphate, filtered and concentrated under vacuum. The evaporation residue is purified rapidly on a silica column (eluant: heptane/ethyl acetate: 8/2) in order to produce a pale yellow oil with a yield of 67%.

52.2 1,1-dimethylethyl 3-(S)-(4-nitrophenoxy)-1-pyrrolidine-carboxylate

The experimental protocol used is the same as that described for intermediate 50.1, intermediate 52.1 replacing the 1-(1,1-dimethylethyl) 2-methyl 4-(R)-{[(4-methylphenyl)sulphonyl]oxy}-1,2-(R)-pyrrolidinedicarboxylate derivative. The expected product is obtained in the form of a light yellow powder with a yield of 77%. Melting point: 112–114° C.

NMR $^1$H ($CDCl_3$, 100 MHz, δ): 1.45 (s, 9H, tBu), 2.20 (m, 2H, $CH_2$), 3.60 (m, 4H, $CH_2$—$CH_2$), 5.00 (m, 1H, CH—O), 6.94 (m, 2H, arom. H), 8.20 (m, 2H, arom. H).

52.3 3-(S)-(4-nitrophenoxy)pyrrolidine

The experimental protocol used is the same as that described for intermediate 51.2, intermediate 52.2 replacing intermediate 51.1. A brown oil is obtained with a quantitative yield.

52.4 1-[(3,4-dihydro-6-hydroxy-2,5,7,8-tetramethyl-2H-[1]-benzopyran-2-yl)carbonyl]-3-(S)-(4-nitrophenoxy)pyrrolidine The experimental protocol used is the same as that described for intermediate 51.3, intermediate 52.3 replacing intermediate 51.2. The expected product is obtained after chromatography on a silica column (eluant: heptane/ethyl acetate: 7/3). The pure fractions, after evaporation, produce a beige powder with a yield of 23%. Melting point: 176–178° C.

NMR $^1$H ($CDCl_3$, 400 MHz, δ): 1.52–2.60 (m, 16H, Trolox), 2.62 (m, 2H, $CH_2$), 3.50–4.40 (m, 4H, $CH_2$—$CH_2$), 4.80 (m, 1H, CH—O), 6.89 (m, 2H, arom. H), 8.20 (m, 2H, arom. H).

52.5 1-[(3,4-dihydro-6-hydroxy-2,5,7,8-tetramethyl-2H-[1]-benzopyran-2-yl)carbonyl]-3-(S)-(4-aminophenoxy)pyrrolidine The experimental protocol used is the same as that described for intermediate 46.4, intermediate 52.4 replacing intermediate 46.3. A white powder is obtained with a yield of 78%. Melting point: 98–100° C.

52.6 1-[(3,4-dihydro-6-hydroxy-2,5,7,8-tetramethyl-2H-[1]-benzopyran-2-yl)carbonyl]-3-(S)-{4-[(imino(2-thienyl)methyl)amino]phenoxy}prrolidine hydrochloride (52)

The protocol used is the same as that described for intermediate 34.4, intermediate 52.5 replacing intermediate 34.3. The condensation reaction is carried out in 2-propanol only. After salification, the expected product is obtained in the form of a pale yellow powder with a yield of 85%. Melting point: 195–197° C.

NMR $^1$H (pyridine d5, 400 MHz, δ): 1.52–2.48 (m, 16H, Trolox), 2.60–3.05 (m, 2H, $CH_2$), 3.58–4.42 (m, 4H, $CH_2$—$CH_2$), 4.59–4.90 (m, 1H, CH—O), 6.65 (m, 1H, arom. H), 6.89 (m, 2H, arom. H), 7.01 (m, 1H, arom. H), 7.15 (m, 1H, arom. H), 7.30 (m, 1H, $NH^+$), 7.41 (m, 1H, $NH^+$), 7.74 (m, 2H, arom. H), 8.95 (m, 1H, $NH^+$).

IR: $v_{C=O}$ (amide): 1650 $cm^{-1}$; $v_{C=N}$ (amidine): 1610 $cm^{-1}$

Example 53

3-{[(3,4-dihydro-6-hydroxy-2,5,7,8-tetramethyl-2H-[1]-benzopyran-2-yl)-carbonyl]amino}-1-{4-[(imino(2-thienyl)methyl)amino]phenyl}pyrrolidine (53)

53.1 3-{[(1,1-dimethylethoxy)carbonyl]amino}-1-(4-nitrophenyl)pyrrolidine

The experimental protocol used is the same as that described for intermediate 33.1, 3-(tert-butoxycarbonylamino)pyrrolidine replacing imidazole.

NMR $^1$H (CDCl$_3$, 100 MHz, δ): 1.45 (s, 9H, tBu), 2.20 (m, 2H, $CH_2$), 3.50 (m, 4H, 2×$CH_2$—N), 4.35 (m, 1H, CH—N), 4.75 (m, 1H, NH), 6.45 (m, 2H, arom. H), 8.10 (m, 2H, arom. H).

53.2 3-amino-1-(4-nitrophenyl)pyrrolidine

The experimental protocol used is the same as that described for intermediate 51.2, intermediate 53.1 replacing intermediate 51.1.

NMR $^1$H (CDCl$_3$, 100 MHz, δ): 1.50 (wide s, 2H, $NH_2$), 2.10 (m, 2H, $CH_2$), 3.10 (m, 1H, CH), 3.50 (m, 4H, 2×$CH_2$), 6.40 (m, 2H, arom. H), 8.10 (m, 2H, arom. H).

53.3 3-{[(3,4-dihydro-6-hydroxy-2,5,7,8-tetramethyl-2H-[1]-benzopyran-2-yl)carbonyl]amino}-1-(4-nitrophenyl)pyrrolidine The experimental protocol used is the same as that described for intermediate 51.3, intermediate 53.2 replacing intermediate 51.2. A yellow solid is obtained which is used directly in the following stgae without further purification.

NMR $^1$H (CDCl$_3$, 100 MHz, δ): 1.50–2.20 (m, 18H, Trolox+$CH_2$), 3.45 (m, 4H, 2×$CH_2$), 4.40 (m, 1H, CH), 4.50 (wide s, 1H, NH), 8.15 (m, 2H, arom. H), 8.35 (m, 2H, arom. H).

53.4 3-{[(3,4-dihydro-6-hydroxy-2,5,7,8-tetramethyl-2H-[1]-benzopyran-2-yl)carbonyl]amino}-1-(4-aminophenyl)pyrrolidine The experimental protocol used is the same as that described for intermediate 46.4, intermediate 53.3 replacing intermediate 46.3.

NMR $^1$H (CDCl$_3$, 100 MHz, δ): 1.50–2.50 (m, 18H, Trolox+$CH_2$), 3.15 (m, 4H, 2×$CH_2$), 4.50 (m, 2H, CH+NH), 6.40 (m, 4H, arom. H).

53.5 3-{[(3,4-dihydro-6-hydroxy-2,5,7,8-tetramethyl-2H-[1]-benzopyran-2-yl)carbonyl]amino}-1-{4-[(imino(2-thienyl)methyl)amino]phenyl}pyrrolidine (53)

The experimental protocol used is the same as that described for intermediate 34.4, intermediate 53.4 replacing intermediate 34.3. The expected product is obtained in the form of a yellow powder (free base) with a yield of 81%. Melting point: 135–138° C.

NMR $^1$H (DMSO d6, 400 MHz, δ): 1.39–2.50 (m, 18H, Trolox+$CH_2$), 2.85–3.43 (m, 4H, 2×$CH_2$), 4.37 (m, 1H, CH), 6.23 (wide s, 2H, $NH_2$), 6.46 (m, 2H, arom. H), 6.73 (m, 2H, arom. H), 7.07 (m, 1H, arom. H), 7.17 (d. 1/2H, 1/2 CONH. J=7.6 Hz), 7.34 (d. 1/2H, 1/2 CONH. J=7.6 Hz), 7.56 (m, 1H, arom. H), 7.68 (m, 1H, arom. H).

IR: $v_{C=O}$ (amide): 1657 $cm^{-1}$; $v_{C=N}$ (amidine): 1626 $cm^{-1}$.

Example 54

4-[3,5-bis-(1,1-dimethylethyl)-4-hydroxyphenyl]-N-{4-[(imino(2-thienyl)methyl)amino]benzoyl}-N-methyl-1H-imidazole-2-methanamine hydrochloride (54)

54.1 {[3,5-bis-(1,1-dimethylethyl)-4-hydroxyphenyl]carbonyl}methyl N-methyl-N-[(phenylmethoxy)carbonyl]glycinate This intermediate is obtained in a standard fashion starting from Cbz-Sarcosine and 1-[3,5-bis(1,1-dimethylethyl)-4-hydroxyphenyl]-2-bromo-ethanone in the presence of caesium carbonate in DMF.

NMR $^1$H (CDCl$_3$, 100 MHz, d): 1.46 (s, 18H, 2 tBu), 3.00 (s, 3H, N—$CH_3$), 4.20 (m, 2H, O—$CH_2$—Ph), 5.10–5.40 (m, 4H, $\underline{CH_2}$—N($CH_3$)+CO—$\underline{CH_2}$—O—CO), 5.80 (s, 1H, OH), 7.30 (m, 5H, arom. H), 7.70 (s, 2H, arom. H).

54.2 4-[3,5-bis-(1,1-dimethylethyl)-4-hydroxyphenyl]-N-methyl-N-[(phenylmethoxy)carbonyl]-1H-imidazole-2-methanamine This intermediate is obtained, starting from intermediate 54.1, using the same experimental protocol as that described in *Tetrahedron Lett,*. 1993. 34. 1901. A pale green powder is obtained with a yield of 81%. Melting point: 200–207° C.

NMR $^1$H (CDCl$_3$, 400 MHz, δ): 1.40 (s, 18H, 2 tBu), 3.00 (s, 3H, N—$CH_3$), 4.50 (m, 2H, O—$CH_2$—Ph), 5.10 (s, 2H, $\underline{CH_2}$—N—COO), 5.20 (s, 1H, OH), 7.00 (s, 1H, imidazole), 7.20–7.50 (m, 7H, arom. H), 9.90 (s, 1H, NH).

54.3 4-[3,5-bis-(1,1-dimethylethyl)-4-hydroxyphenyl]-N-methyl-N-[(phenylmethoxy)carbonyl]-1-{[2-(trimethylsilyl)ethoxy]methyl}-1H-imidazole-2-methanamine 7.1 g (51.2 mmol) of potassium carbonate is added by portions to a mixture of 9.96 ml (56.3 mmol) of 2-(trimethylsilyl)ethoxymethyl chloride and 23 g (51.2 ml) of intermediate 54.2 in 200 ml of DMF. When the addition is finished, the reaction mixture is agitated for 3 hours at 50° C. The solvent is then eliminated under vacuum and the residue is diluted with 200 ml of ethyl acetate. The organic solution is washed twice with 100 ml of salt water, dried over magnesium sulphate, filtered and concentrated under vacuum. The evaporation residue is purified on a silica gel column (eluant heptane/ethyl acetate: 1/1). The pure fractions are evaporated in order to produce a green oil with a yield of 53%.

NMR $^1$H (CDCl$_3$, 400 MHz, δ): 0.0 (s, 9H, Si(CH$_3$)$_3$), 0.9 (m, 2H, CH$_2$—Si), 1.50 (s, 18H, 2 tBu), 3.00 (s, 3H, N—CH$_3$), 3.30–3.50 (m, 2H, O—CH$_2$—CH$_2$—Si), 4.70 (s, 2H, CH$_2$—N—COO), 5.10 (s, 2H, O—CH$_2$—Ph), 5.20 (s, 2H, imidazole-CH$_2$-OSEM), 5.30 (s, 1H, OH), 7.20 (s, 1H, imidazole), 7.35 (m, 5H, arom. H), 7.60 (s, 2H, arom. H).

54.4 4-[3,5-bis-(1,1-dimethylethyl)-4-hydroxyphenyl]-N-methyl-1,1[2-(trimethylsilyl)ethoxy]-methyl]-1H-imidazole-2-methanamine The experimental protocol used is the same as that described for intermediate 46.4, intermediate 54.3 replacing intermediate 46.3. A brown oil is obtained with a yield of 98%.

NMR $^1$H (CDCl$_3$, 100 MHz, δ): 0.0 (s, 9H, Si(CH$_3$)$_3$), 0.9 (m, 2H, CH$_2$—Si), 1.50 (s, 18H, 2 tBu), 2.50 (s, 3H, N—CH$_3$), 3.50 (m, 2H, O—CH$_2$—CH$_2$—Si), 4.00 (s, 2H, N—CH$_2$-imidazole), 5.20 (s, 1H, OH), 5.40 (s, 2H, imidazole-CH$_2$-OSEM), 7.10 (s, 1H, imidazole), 7.50 (s, 2H, arom. H).

54.5 4-[3,5-bis-(1,1-dimethylethyl)-4-hydroxyphenyl]-N-methyl-N-(4-nitrobenzoyl)-1-{[2-(trimethylsilyl)ethoxy]methyl}-]H-imidazole-2-methanamine A solution of 2.67 g (14.4 mmol) of 4-nitrobenzoic acid chloride in 50 ml of dry THF is added dropwise to a solution of 5.34 g (11.9 mmol) of intermediate 54.4 and 2 ml (14.4 mmol) of triethylamine in 50 ml of dichloromethane. After agitation for 2 hours at 23° C., the mixture is diluted with 100 ml of dichloromethane and the organic solution is washed with twice 100 ml of salt water. After drying over magnesium sulphate, the organic phase is filtered and concentrated under vacuum in order to produce a yellow oil which is used as it is in the following stage.

NMR $^1$H (CDCl$_3$, 400 MHz, δ): 0.0 (s, 9H, Si(CH$_3$)$_3$), 0.9 (m, 2H, CH$_2$—Si), 1.50 (s, 18H, 2 tBu), 3.15 (s, 3H, N—CH$_3$), 3.50 (m, 2H, O—CH$_2$—CH$_2$—Si), 4.80 (s, 2H, N—CH$_2$-imidazole), 5.20 (s, 2H, imidazole-CH$_2$-OSEM), 5.30 (s, 1H, OH), 6.90 (m, 2H, arom. H), 7.15 (s, 1H, imidazole), 7.60 (s, 2H, arom. H), 8.10 (m, 2H, arom. H).

54.6 4-[3,5-bis-(1,1-dimethylethyl)-4-hydroxyphenyl]-N-methyl-N-(4-nitrobenzoyl)-1H-imidazole-2-methanamine Intermediate 54.5 (7.42 g, 12.5 mmol) is dissolved in 62.4 ml (62.4 mmol) of a 1M solution of tetrabutylammonium fluoride in the presence of 1.12 g (18.7 mmol) of ethylenediamine. The reaction mixture is heated under reflux for 5 hours and finally poured directly into 200 ml of salt water and diluted with 200 ml of ethyl acetate. The organic phase is decanted, washed with 100 ml of salt water and finally dried over magnesium sulphate, filtered and concentrated under vacuum. The evaporation residue is purified on a silica column (eluant: dichloromethane+5% of ethanol). The expected product is obtained in the form of a red foam with a yield of 37%.

NMR $^1$H (CDCl$_3$, 400 MHz, d): 1.50 (s, 18H, 2 tBu), 3.00 (s, 3H, N—CH$_3$), 4.70 (s, 2H, N—CH$_2$-imidazole), 5.20 (s, 1H, OH), 7.10 (s, 1H, imidazole), 7.40–7.60 (m, 4H, arom. H), 8.30 (m, 2H, arom. H), 10.10 (wide s, 1H, NH).

54.7 4-[3,5-bis-(1,1-dimethylethyl)-4-hydroxyphenyl]-N-methyl-N-(4-aminobenzoyl)-1H-imidazole-2-methanamine The experimental protocol used is the same as that described for intermediate 46.4, intermediate 54.6 replacing intermediate 46.3. An orange solid is obtained with a yield of 52%. Melting point: 129–131° C.

NMR $^1$H (CDCl$_3$, 400 MHz, δ): 1.50 (s, 18H, 2 tBu), 3.10 (s, 3H, N—CH$_3$), 3.90 (s, 2H, N—CH$_2$-imidazole), 4.70 (s, 2H, NH$_2$), 5.20 (s, 1H, OH), 6.60 (m, 2H, arom. H), 7.10 (s, 1H, Imidazole), 7.30–7.60 (m, 4H, arom. H), 10.30 (wide s, 1H, NH).

54.8 4-[3,5-bis-(1,1-dimethylethyl)-4-hydroxyphenyl]-N-{4-[(imino(2-thienyl)methyl)amino]benzoyl}-N-methyl-1H-imidazole-2-methanamine hydrochloride (54)

The experimental protocol used is the same as that described for intermediate 36.3, intermediate 54.7 replacing intermediate 36.2. A light beige solid is obtained with a yield of 54%. Melting point: 250–260° C.

NMR $^1$H (DMSO d6, 400 MHz, δ): 1.50 (s, 18H, 2 tBu), 3.20 (s, 3H, N—CH$_3$), 5.00 (s, 2H, N—CH$_2$-imidazole), 7.30 (s, 1H, OH), 7.35 (m, 1H, thiophene), 7.50 (m, 4H, arom. H), 7.70 (s, 2H,a. H), 8.00 (s, 1H, Imidazole), 8.20 (m, 2H, thiophene), 9.20 (s, 1H, NH$^+$), 10.00 (s, 1H, NH$^+$), 11.8 (s, 1H, NH$^+$), 14.8 (s, 1H, NH$^+$), 15.2 (s, 1H, NH$^+$).

IR: $v_{C=O}$ (amide): 1635 cm$^{-1}$; $v_{C=N}$ (amidine): 1601 cm$^{-1}$.

Example 55

N-[3,5-bis-(1,1-dimethylethyl)-4-hydroxyphenyl]-1-{4-[(imino(2-thienyl)methyl)amino]phenyl}-1H-pyrrole-2-carboxamide hydroiodide (55)

55.1 Ethyl 1-(4-nitrophenyl)-1H-pyrrole-2-carboxylate 0.9 g (7.2 mmol) of the methyl ester of pyrrole-2-carboxylic acid (prepared in a standard fashion by the esterification of commercial pyrrole-2-carboxylic acid) diluted with 10 ml of dry DMF is added dropwise at 0° C., under an inert atmosphere, to a suspension of 0.3 g (7.4 mmol) of NaH at 60% in 15 ml of dry DMF. After agitation for one hour at 23° C., a solution of 1.01 g (7.2 mmol) of 4-fluoronitrobenzene in 10 ml of dry DMF is added dropwise. The reaction mixture is then heated for 3 hours at 80° C. After the reaction medium has returned to 23° C., it is poured into 100 ml of an ice+water mixture and finally diluted with 200 ml of ethyl acetate. After decantation, the organic phase is washed with 3 times 100 ml of water followed by 100 ml of salt water. The organic solution is dried over magnesium sulphate, filtered and concentrated under vacuum. The evaporation residue is purified on a silica column (eluant: heptane/ethyl acetate: 9/1). The pure fractions are collected and evaporated under vacuum in order to produce a pale yellow powder with a yield of 49%.

55.2 1-(4-nitrophenyl)-1H-pyrrole-2-carboxylic acid

A solution of 0.5 g (7.1 mmol) of KOH in 5 ml of water is added to a flask containing a solution of 0.87 g (3.5 mmol) of intermediate 55.1 in 20 ml of THF cooled down to 0° C. The reaction mixture is agitated for 24 hours at 55° C. and finally diluted with 100 ml of ethyl acetate. After decantation, the organic phase is eliminated and the aqueous phase is cooled down using an ice bath before acidification with a solution of concentrated HCl. The precipitate formed is then filtered and washed twice with 20 ml of water. After drying. the expected product is obtained with a yield of 66%.

55.3 N-[3,5-bis-(1,1-dimethylethyl)-4-hydroxyphenyl]-1-(4-nitrophenyl)-1H-pyrrole-2-carbocamide The experimental protocol used is the same as that described for intermediate 46.3, intermediate 55.2 replacing intermediate 46.2. The expected compound is obtained in the form of a greenish powder with a crude yield of 25%. The product is used such as it is in the following stage.

55.4 N-[3,5-bis-(1,1-dimethylethyl)-4-hydroxyphenyl]-1-(4-aminophenyl)-1H-pyrrole-2-carboxamide The experimental protocol used is sirnilar to that described for intermediate 46.4, intermediate 55.3 replacing intermediate 46.3. The reaction is carried out in a dichloromethane/ethanol mixture (1/1). A white powder is obtained with a yield of 61%. Melting point: 218–219° C.

55.5 N-[3,5-bis-(1,1-dimethylethyl)-4-hydroxyphenyl]-1-{4-[(imino(2-thienyl)methyl)amino]phenyl}-1H-pyrrole-2-carboxamide hydroiodide (55)

The experimental protocol used is similar to that described for intermediate 33.3, intermediate 55.4 replacing intermediate 33.2. A pale yellow powder is obtained with a yield of 73%. Melting point: 271–272° C.

NMR $^1$H (DMSO d6, 400 MHz, δ): 1.35 (s, 18H, 2 tBu), 6.36 (s, 1H, OH), 6.78 (s, 1H, arom. H), 7.01 (s, 1H, arom. H), 7.16 (s, 1H, arom. H), 7.45 (m, 7H, arom. H), 8.10 (m, 1H, arom. H), 8.19,(m, 1H, arom. H), 9.16 (wide s, 1H, NH$^+$), 9.89 (wide s, 2H, CONH+NH$^+$), 11.39 (wide s, 1H, NH$^+$).

IR: $v_{C=O}$ (amide): 1633 cm$^{-1}$; $v_{C=N}$ (amidine): 1609 cm$^{-1}$.

Example 56

1-[3,5-bis(1,1-dimethylethyl)-4-hydroxyphenyl]-3-{[4-[[imino(2-thienyl)methyl]amino]phenyl]carbonyl}-2-imidazolidinone hydroiodide (56)

56.1 N-[3,5-bis(1,1-dimethylethyl)-4-hydroxyphenyl]-N'-(2-chloroethyl)urea 0.17 ml (2 mmol) of chloroethylisocyanate is added to a flask containing a solution of 0.5 g (2 mmol) of intermediate 10.2 in 5 ml of DMF. The reaction mixture is agitated for 2 hours at 23° C. and finally diluted with 100 ml of ethyl acetate and 25 ml of water. After decantation, the organic solution is washed with 25 ml of water, twice with 25 ml of salt water and finally dried over magnesium sulphate. After filtration and evaporation, the residue is taken up in isopentane in order to finally produce the expected product, in the form of a pink solid, with a yield of 83%. Melting point: 169–171° C.

NMR $^1$H (DMSO d6, 400 MHz, δ): 1.30 (s, 18H, 2 tBu), 3.35 (t, 2H, CH$_2$—NH, J=6.0 Hz), 3.60 (t, 2H, CH$_2$—Cl, J=6.0 Hz), 6.20 (t, 1H, NH—CH$_2$, J=5.6 Hz), 6.60 (s, 1H, OH), 7.10 (s, 2H, arom. H), 8.30 (s, 1H, NH—Ph).

56.2 1-[3,5-bis(1,1-dimethylethyl)-4-hydroxyphenyl]-2-imidazolidinone

A solution of 0.22 g (1.93 mmol) of tBuO$^-$K$^+$ in 2 ml of dry DMF is added to a solution of 0.56 g (1.93 mmol) of intermediate 56.1 in 10 ml of dry DMF. After agitation for 3 hours at 23° C., the reaction mixture is diluted with 50 ml of water and 100 ml of ethyl acetate. The organic phase is decanted, washed successively with 50 ml of water and 50 ml of salt water, dried over magnesium sulphate, filtered and finally concentrated under vacuum. The brown oil thus obtained is taken up in isopropyl ether in order to produce a white powder with a yield of 51%. Melting point: 205–207° C.

NMR $^1$H (DMSO d6, 100 MHz, δ): 1.40 (s, 18H, 2 tBu), 4.60 (m, 2H, CH$_2$), 4.90 (m, 2H, CH$_2$), 4.90 (wide s, 1H, NH), 5.00 (s, 1H, OH), 7.15 (s, 2H, arom. H).

56.3 1-[3,5-bis(1,1-dimethylethyl)-4-hydroxyphenyl]-3-[(4-nitrophenyl)carbonyl]-2-imidazolidinone 1.28 g (6.9 mmol) of 4-nitrobenzoic acid chloride is added by portions to a solution of 1.0 g (3.45 imnol) of intermediate 56.2 in a mixture of 20 ml of acetonitrile and 10 ml of THF, followed by 0.71 g (5.15 mmol) of potassium carbonate. After agitation for 3 hours at 23° C., the reaction mixture is diluted with 100 ml of dichloromethane and 50 ml of salt water. The organic phase,after decantation. is washed with 50 ml of salt water and dried over magnesium sulphate. After filtration and concentration under vacuum, the evaporation residue taken up in isopropyl ether in order to produce a yellow solid with a yield of 83% after drying. Melting point>260° C.

NMR $^1$H (CDCl$_3$, 400 MHz, δ): 1.40 (s, 18H, 2 tBu), 3.95–4.20 (m, 4H, 2 CH$_2$), 5.20 (s, 1H, OH), 7.20 (s, 2H, arom. H), 7.80 (m, 2H, arom. H), 8.25 (m, 2H, arom. H).

56.4 1-[3,5-bis(1,1-dimethylethyl)-4-hydroxyphenyl]-3-[(4-aminophenyl)carbonyl]-2-imidazolidinone The experimental protocol used is similar to that described for intermediate 46.4, intermediate 56.3 replacing intermediate 46.3. The expected product is obtained in the form of a white powder with a yield of 45%. Melting point>260° C.

NMR $^1$H (CDCl$_3$, 400 MHz, δ): 1.40 (s, 18H, 2 tBu), 3.90–4.00 (m, 4H, 2 CH$_2$), 5.15 (s, 1H, OH), 6.60 (m, 2H, arom. H), 7.13 (s, 2H, arom. H), 7.60 (m, 2H, arom. H).

56.5 1-[3,5-bis(1,1-dimethylethyl)-4-hydroxyphenyl]-3-{[4-[[imino(2-thienyl)methyl]amino]phenyl]carbonyl}-2-imidazolidinone hydroiodide (56)

The experimental protocol used is identical to that described for intermediate 33.3, intermediate 56.4 replacing intermediate 33.2. The expected product is obtained in the form of a light beige solid with a yield of 79%. Melting point: 220–260° C.

NMR $^1$H (DMSO d6, 400 MHz, d): 1.30 (s, 18H, 2 tBu), 4.00 (m, 4H, 2 CH$_2$), 6.95 (s, 1H, OH), 7.20 (s, 2H, arom. H), 7.40 (m, 1H thiophene), 7.50 (m, 2H, arom. H), 7.70 (m, 2H, arom. H), 8.20 (m, 2H, thiophene), 9.20 (wide s, 1H, NH$^+$), 9.90 (wide s, 1H, NH$^+$), 11.60 (wide s, 1H, NH$^+$).

IR: $v_{C=O}$ (urea): 1735 cm$^{-1}$; $v_{C=O}$ (amide): 1649 cm$^{-1}$; $v_{C=N}$ (amidine): 1595 cm$^1$.

Example 57

3-[3,5-bis(1,1-dimethylethyl)-4-hydroxyphenyl]-4,5-dihydro-N-{4-[(imino(2-thienyl)methyl)amino]phenyl}-5-isoxazoleacetamide hydroiodide (57)

57.1 3,5-bis-(1,1-dimethylethyl)-N,4-dihydroxy-benzene carboxime

This intermediate is prepared according to an experimental protocol described in *J. Med. Chem,*. 1997, 40, 50–60, starting from commercial 3,5-di-tert-butyl-4-hydroxybenzaldehyde. A red foam is obtained with a quantitative yield.

57.2 3,5-bis-(1,1-dimethylethyl)-N,4-dihydroxy-benzene carboximidoyl chloride The experimental protocol used is the same as that described in *Tetrahedron Lett,*. 1996, 37 (26), 4455, starting from intermediate 57.1. A beige solid is obtained with a crude yield of 77%. The product is used directly in the following stage without additional purification.

57.3 Methyl 3-[3,5-bis(1,1-dimethylethyl)-4-hydroxyphenyl]-4,5-dihydro-5-isoxazoleacetate The reaction of intermediate 57.2 with the methyl ester of 3-butenoic acid is carried out under the same conditions as those described in *Tetrahedron Lett.* 1996, 37 (26), 4455. The expected compound is obtained in the form of a brown oil with a yield of 49%.

NMR $^1$H (CDCl$_3$, 400 MHz, δ): 1.50 (s, 18H, 2 tBu), 2.60 (dd. 1H, 1/2 CH$_2$—C=N, J=16.0 Hz and J=7.8 Hz), 2.90 (dd. 1H, 1/2 CH$_2$—C=N, J=16.0 Hz and J=5.8 Hz), 3.10 (dd, 1H, 1/2 CH$_2$—C=O, J=16.6 Hz and J=6.9 Hz), 3.60 (dd. 1H, 1/2 CH$_2$—C=O, J=16.6 Hz and J=10.2 Hz), 5.10 (m, 1H, CH), 5.50 (s, 1H, OH), 7.50 (s, 2H, arom. H).

57.4 3-[3,5-bis(1,1-dimethylethyl)-4-hydroxyphenyl]-4,5-dihydro-5-isoxazoleacetic acid This intermediate is obtained by the saponification of intermediate 57.3 according to an experimental protocol described in *J. Med. Chem.* 1997, 40, 50–60. A white solid is obtained with a yield of 74%. Melting point: 229–231° C.

NMR $^1$H (CDCl$_3$, Hz), 2.90 (dd, 1H, 1/2 CH$_2$—C=N, J=16.3 Hz and J=6.0 Hz), 3.10 (dd. 1H, 1/2 CH$_2$—C=O, J=16.6 Hz and J=6.9 Hz), 3.50 (dd, 1H, 1/2 CH$_2$—C=O, J=16.6 Hz and J=10.2 Hz), 5.05 (m, 1H, CH), 5.50 (s, 1H, OH), 7.45 (s, 2H, arom. H).

57.5 3-[3,5-bis(1,1-dimethylethyl)-4-hydroxyphenyl]-4,5-dihydro-N-(4-nitrophenyl)-5-isoxazoleacetamide The experimental protocol used is the same as that described in *Org. Prep. Proced. Int.* (1975), 7. 215 starting from intermediate 57.4 and 4-nitroaniline. A white solid is obtained with a yield of 45%. Melting point: 149–151° C.

NMR $^1$H (CDCl$_3$, 400 MHz, δ): 1.50 (s, 18H, 2 tBu), 2.70 (m, 1H, 1/2 CH$_2$—C=N), 2.85 (dd, 1H, 1/2 CH$_2$—C=N, J=15.1 Hz and J=7.5 Hz), 3.20 (dd, 1H, 1/2 CH$_2$—C=O, J=16.7 Hz and J=7.0 Hz), 3.70 (dd, 1H, 1/2 CH$_2$—C=O, J=16.7 Hz and J=10.1 Hz), 5.05 (m, 1H, CH), 5.50 (s, 1H, OH), 7.45 (s, 2H, arom. H), 7.70 (m, 2H, arom. H), 8.20 (m, 2H, arom. H), 8.50 (s, 1H, NH—CO).

57.6 3-[3,5-bis(1,1-dimethylethyl)-4-hydroxyphenyl]-4,5-dihydro-N-(4-aminophenyl)-5-isoxazoleacetamide The experimental protocol used is the same as that described for intermediate 49.5, intermediate 57.5 replacing intermediate 49.4. A colourless oil is obtained with a yield of 80%.

NMR $^1$H (CDCl$_3$, 400 MHz, δ): 1.40 (s, 18H, 2 tBu), 2.60 (dd, 1H, 1/2 CH$_2$—C=N, J=15.0 Hz and J=5.7 Hz), 2.80 (dd, 1H, 1/2 CH$_2$—C=N, J=15.0 Hz and J=6.7 Hz), 3.15 (dd, 1H, 1/2 CH$_2$—C=O, J=16.7 Hz and J=7.2 Hz), 3.50 (dd, 1H, 1/2 CH$_2$—C=O, J=16.7 Hz and J=10.1 Hz), 3.70 (2H, NH$_2$), 5.10 (m, 1H, CH), 5.60 (s, 1H, OH), 6.60 (m, 2H, arom. H), 7.20 (m, 2H, arom. H), 7.50 (s, 2H, arom. H), 8.10 (s, 1H, NH—CO).

57.7 3-[3,5-bis(1,1-dimethylethyl)-4-hydroxyphenyl]-4,5-dihydro-N-{4-[(imino(2-thienyl)methyl)amino]phenyl}-5-isoxazoleacetamide hydroiodide (57)

The experimental protocol used is identical to that described for intermediate 33.3, intermediate 57.6 replacing intermediate 33.2. The expected product is obtained in the form of a pale yellow powder with a yield of 72%. Melting point>260° C.

NMR $^1$H (DMSO d6, 400 MHz, δ): 1.40 (s, 18H, 2 tBu), 2.70 (m, 2H, CH$_2$—C=N), 3.20 (dd. 1H, 1/2 CH$_2$—C=O, J=16.8 Hz and J=6.8 Hz), 3.60 (dd, 1H, 1/2 CH$_2$—C=O, J=16.8 Hz and J=10.2 Hz), 5.00 (m, 1H, CH), 7.35 (m, 6H, arom. H+OH), 7.80 (m, 2H, arom. H), 8.20 (m, 2H, thiophene), 8.70 (wide s, 1H, NH$^+$), 9.70 (wide s, 1H, NH$^+$), 10.30 (s, 1H, NH—CO), 11.20 (wide s, 1H, NH$^+$).

IR: $\nu_{C=O}$ (amide): 1650 cm$^{-1}$; $\nu_{C=N}$ (amidine): 1603 cm$^{-1}$.

Example 58

4-[3,5-bis(1,1-dimethylethyl)-4-hydroxyphenyl]-N-{4-[(imino(2-thienyl)methyl)amino]phenyl}-N-methyl-2-thiazolemethanamine hydrochloride (58)

58.1 2-{[(1,1-dimethylethoxy)carbonyl]methyl}amino-ethanethioamide

The experimental protocol used is identical to that described for intermediate 49.1, N-Boc sarcosinamide (obtained in a standard fashion starting from commercial sarcosinamide and BocOBoc) is used as starting -product in place of 4-nitrobenzamide. A white paste is obtained which is used directly in the following stage.

58.2 4-[3,5-bis(1,1-dimethylethyl)-4-hydroxyphenyl]-N-[(1,1-dimethylethoxy)carbonyl]-N-methyl-2-thiazolemethanamine The experimental protocol used is the same as that described in *J. Org. Chem.* (1995), 60, 5638–5642, starting from intermediate 58.1 and 1-[3,5-bis(1,1-dimethylethyl)-4-hydroxyphenyl]-2-bromo-ethanone. A brown oil is obtained.

NMR $^1$H (CDCl$_3$, 400 MHz, δ): 1.50 (m, 27H, 3 tBu), 3.00 (s, 3H, N—CH$_3$), 4.70 (s, 2H, CH$_2$), 5.30 (s, 1H, OH), 7.25 (s, 1H, thiazole), 7.70 (s, 2H, arom. H).

58.3 4-[3,5-bis(1,1-dimethylethyl)-4-hydroxyphenyl]-N-methyl-2-thiazolemethanamine 2.3 ml (29 mmol) of TFA is added dropwise at 0° C. to a solution of 2.5 g (5.8 mmol) of intermediate 58.2 and 2 ml (1.6 mmol) of triethylsilane in 50 ml of dichloromethane. After agitation for one hour, the reaction mixture is concentrated under vacuum and the residue is diluted with 100 ml of ethyl acetate and 50 ml of a saturated solution of NaHCO$_3$. After agitation and decantation, the organic phase is dried over magnesium sulphate, filtered and concentrated under vacuum. The residue is taken up in heptane in order to produce a white solid, after drying, with a yield of 73%. Melting point: 136° C.

NMR $^1$H (CDCl$_3$, 400 MHz, δ): 1.50 (s, 18H, 2 tBu), 2.60 (s, 3H, N—CH$_3$), 4.20 (s, 2H, CH$_2$), 5.30 (s, 1H, OH), 7.20 (s, 1H, thiazole), 7.70 (s, 2H, arom. H).

58.4 4-[3,5-bis(1,1-dimethylethyl)-4-hydroxyphenyl]-N-methyl-N-(4-nitrophenyl)-2-thiazolemethanamine The experimental protocol used is the same as that described for intermediate 33.1, intermediate 58.3 replacing imidazole. A yellow solid is obtained with a yield of 23%. Melting point: 199–201° C.

NMR $^1$H (DMSO d6, 400 MHz, δ): 1.40 (s, 18H, 2 tBu), 3.25 (s, 3H, N—CH$_3$), 5.10 (s, 2H, CH$_2$), 6.95 (m, 2H, arom. H), 7.10 (s, 1H, OH), 7.60 (s, 2H, arom. H), 7.80 (s, 1H, thiazole), 8.05 (m, 2H, arom. H).

58.5 4-[3,5-bis(1,1-dimethylethyl)-4-hydroxyphenyl]-N-methyl-N-(4-aminophenyl)-2-thiazolemethanamine The experimental protocol used is the same as that described for intermediate 49.5, intermediate 58.4 replacing intermediate 49.4. The expected product is obtained in the form of a beige foam with a yield of 71%.

NMR $^1$H (DMSO d6, 400 MHz, δ): 1.40 (s, 18H, 2 tBu), 2.90 (s, 3H, N—CH$_3$), 4.50 (wide s, 2H, NH$_2$), 4.60 (s, 2H, CH$_2$), 6.50 (m, 2H, arom. H), 6.60 (m, 2H, arom. H), 7.10 (s, 1H, OH), 7.60 (s, 2H, arom. H), 7.70 (s, 1H, thiazole).

58.6 4-[3,5-bis(1,1-dimethylethyl)-4-hydroxyphenyl]-N-{4-[(imino(2-thienyl)methyl)amino]phenyl}-N-methyl-2-thiazolemethanamine hydrochloride (58)

The experimental protocol used is the same as that described for intermediate 36.3, intermediate 58.5 replacing intermediate 36.2. A white powder is obtained with a yield of 67%. Melting point: 157–160° C.

NMR $^1$H (DMSO d6, 400 MHz, δ): 1.50 (s, 18H, 2 tBu), 3.15 (s, 3H, N—CH$_3$), 5.00 (s, 2H, CH$_2$), 6.95 (m, 2H, arom. H), 7.15 (s, 1H, OH), 7.20 (m, 2H, arom. H), 7.40 (m, 1H, thiophene), 7.65 (s, 2H, arom. H), 7.75 (s, 1H, thiazole), 8.15 (m, 2H, thiophene), 8.70 (wide s, 1H, NH$^+$), 9.70 (wide s, 1H, NH$^+$), 11.30 (wide s, 1H, NH$^+$).

IR: $v_{C=O}$ (amide): 1648 cm$^{-1}$; $v_{C=N}$ (amidine): 1611 cm$^{-1}$.

Example 59

4-[3,5-bis(1,1-dimethylethyl)-4-hydroxyphenyl]-N-{4-[(imino(2-thienyl)methyl)amino]phenyl}-N-methyl-1H-imidazole-2-methanamine hydrochloride (59)

59.1 4-[3,5-bis(1,1-dimethylethyl)-4-hydroxyphenyl]-N-methyl-N-(4-nitrophenyl)-1-{[2-(trimethylsilyl)ethoxy]methyl}-1H-imidazole-2-methanamine The experimental protocol used is the same as that described for intermediate 33.1, intermediate 54.4 replacing imidazole. A yellow solid is obtained with a yield of 53%. Melting point: 149–151° C.

NMR $^1$H (CDCl$_3$, 400 MHz, δ): 0.0 (s, 9H, Si(CH$_3$)$_3$), 0.9 (t, 2H, CH$_2$—Si, J=8.4 Hz), 1.50 (s, 18H, 2 tBu), 3.15 (s, 3H, N—CH$_3$), 3.50 (t, 2H, O—CH$_2$—CH$_2$—Si, J=8.4 Hz), 4.80 (s, 2H, N—CH$_2$-imidazole), 5.20 (s, 2H, imidazole-CH$_2$-OSEM), 5.25 (s, 1H, OH), 6.90 (m, 2H, arom. H), 7.10 (s, 1H, imidazole). 7.60 (s, 2H, arom. H), 8.15 (m, 2H, arom. H).

59.2 4-[3,5-bis(1,1-dimethylethyl)-4-hydroxyphenyl]-N-methyl-N-(4-nitrophenyl)-1H-imidazole-2-methanamine The experimental protocol used is the same as that described for intermediate 54.6, intermediate 59.1 replacing intermediate 54.5. A yellow solid is obtained with a yield of 44%. Melting point: 209–21°° C.

NMR $^1$H (CDCl$_3$, 400 MHz, δ): 1.40 (s, 18H, 2 tBu), 3.20 (s, 3H, N—CH$_3$), 4.70 (s, 2H, CH$_2$), 6.80–7.10 (m, 3H, arom. H), 7.20–7.60 (m, 3H, arom. H+OH), 8.10 (m, 2H, arom. H), 12.00 (s, 1H, NH).

59.3 4-[3,5-bis(1,1-dimethylethyl)-4-hydroxyphenyl]-N-methyl-N-(4-aminophenyl)-1H-imidazole-2-methanamine The experimental protocol used is the same as that described for intermediate 46.4, intermediate 59.2 replacing intermediate 46.3. A beige foam is obtained with a yield of 67%.

NMR $^1$H (CDCl$_3$, 400 MHz, δ): 1.40 (s, 18H, 2 tBu), 2.80 (s, 3H, N—CH$_3$), 4.20 (s, 2H, CH$_2$), 4.30–4.70 (m, 3H, NH$_2$+NH imidazole), 5.00 (s, 1H, OH), 6.50 (m, 2H, arom. H), 6.70 (m, 2H, arom. H), 6.80 (s, 1H, imidazole), 7.40 (s, 2H, arom. H).

59.4 4-[3,5-bis(1,1-dimethylethyl)-4-hydroxyphenyl]-N-{4-[(imino(2-thienyl)methyl)amino]phenyl}-N-methyl-1H-imidazole-2-methanamine hydrochloride (59)

The experimental protocol used is the same as that described for intermediate 36.3, intermediate 59.3 replacing intermediate 36.2. A yellow powder is obtained with a yield of 86%. Melting point: 195–200° C.

NMR $^1$H (DMSO d6, 400 MHz, δ): 1.50 (s, 18H, 2 tBu), 3.20 (s, 3H, N—CH$_3$), 5.00 (s, 2H, CH$_2$), 7.00 (m, 2H, arom. H), 7.20 (m, 2H, arom. H), 7.40 (m, 2H, thiophene+OH), 7.60 (s, 2H, arom. H), 7.90 (s, 1H, imidazole), 8.20 (m, 2H, thiophene), 8.70 (wide s, 1H, NH$^+$), 9.70 (wide s, 1H, NH$^+$), 11.40 (wide s, 1H, NH$^+$), 14.60 (wide s, 1H, NH$^+$), 15.60 (wide s, 1H, NH$^+$).

IR: $v_{C=O}$ (amide): 1646 cm$^{-1}$; $v_{C=N}$ (amidine): 1612 cm$^{-1}$.

Example 60

3-[3,5-bis(1,1-dimethylethyl)-4-hydroxyphenyl]-4,5-dihydro-5-{2-{4-[(imino(2-thienyl)methyl)amino]phenoxy}ethyl}isoxazole (60)

60.1 3-[3,5-bis(1,1-dimethylethyl)-4-hydroxyphenyl]-4,5-dihydro-5-isoxazoleethanol 0.09 g (2.4 mmol) of LiAlH$_4$ is added in small portions to a solution of 0.69 g (2.1 mmol) of intermediate 25.3 in 15 ml of dry THF, cooled down to 0° C. After agitation for one hour at 23° C., the reaction mixture is cooled down using an ice bath and the excess hydride is destroyed by the addition of water (5 ml). The product is extracted using twice 25 ml of ethyl ether. The organic phase is washed twice with 10 ml of salt water, dried over magnesium sulphate, filtered and concentrated under vacuum. The residue is purified on silica (eluant: heptane/ethyl acetate: 1/1). A white foam is obtained with a yield of 58%.

NMR $^1$H (DMSO d6, 100 MHz, δ): 1.40 (s, 18H, 2 tBu), 1.60–1.80 (m, 2H, CH$_2$—CH$_2$—O), 3.05 (m, 1H, 1/2 CH$_2$ isoxazoline), 3.40 (m, 1H, 1/2 CH$_2$ isoxazoline), 3.50 (m, 2H, CH$_2$—CH$_2$—O), 4.60 (s, 1H, OH), 4.70 (m, 1H, CH isoxazoline), 7.40 (wide s, 3H, arom. H+OH).

60.2 3-[3,5-bis(1,1-dimethylethyl)-4-hydroxyphenyl]-4,5-dihydro-5-[2-(4-nitrophenoxy)ethyl]isoxazole A mixture composed of 0.37 g (1.58 mmol) of intermediate 60.1, 0.5 ml of Aliquat 336, 0.18 g (1.27 mmol) of 4-fluoronitrobenzene and 0.071 g (1.27 mmol) of KOH in 2 ml of toluene is heated at 80° C. for 2 hours. After the reaction mixture has returned to 23° C., it is divided between 50 ml of dichloromethane and 20 ml of water. After decantation, the organic phase is washed with 20 ml of water followed by 20 ml of salt water. The organic solution is then dried over magnesium sulphate, filtered and concentrated under vacuum. The evaporation residue is purified on a silica column (eluant: heptane/ethyl acetate: gradient 10/0 up to 0/10). A white powder is obtained with a yield of 60%. Melting point: 151–153° C.

NMR $^1$H (CDCl$_3$, 400 MHz, d): 1.50 (s, 18H, 2 tBu), 2.15 (m, 2H, $\underline{CH_2}$—CH$_2$—O), 3.10 (dd, 1H, 1/2 CH$_2$ isoxazoline, J=16.3 Hz and J=6.65 Hz), 3.50 (dd, 1H, 1/2 CH$_2$ isoxazoline, J=16.3 Hz and J=10.4 Hz), 4.10–4.30 (m, 2H, CH$_2$—$\underline{CH_2}$—O), 5.00 (m, 1H, CH isoxazoline), 5.50 (s, 1H, OH), 6.90 (m, 2H, arom. H), 7.50 (s, 2H, arom. H), 8.20 (m, 2H, arom. H).

60.3 3-[3,5-bis(1,1-dimethylethyl)-4-hydroxyphenyl]-4,5-dihydro-5-[2-(4-aminophenoxy)ethyl]isoxazole The experimental protocol used is the same as that described for intermediate 49.5, intermediate 60.2 replacing intermediate 49.4. A white powder is obtained with a yield of 60%. Melting point: 129–131° C.

NMR $^1$H (DMSO d6, 400 MHz, δ): 1.35 (s, 18H, 2 tBu), 2.00 (m, 2H, $\underline{CH_2}$—CH$_2$—O), 3.15 (dd, 1H, 1/2 CH$_2$ isoxazoline, J=16.7 Hz and J=7.5 Hz), 3.40 (dd, 1H, 1/2 CH$_2$ isoxazoline, J=16.7 Hz and J=10.5 Hz), 3.90 (m, 2H, CH$_2$—$\underline{CH_2}$—O), 4.60 (s, 2H, NH$_2$), 4.70 (m, 1H, CH isoxazoline), 6.50 (m, 2H, arom. H), 6.70 (m, 2H, arom. H), 7.40 (s, 3H, arom. H+OH).

60.4 3-[3,5-bis(1,1-dimethylethyl)-4-hydroxyphenyl]-4,5-dihydro-5-{2-{4-[(imino(2-thienyl)methyl)amino]phenoxy}ethyl}isoxazole (60)

The experimental protocol used is the same as that described for intermediate 36.3, intermediate 60.3 replacing intermediate 36.2. A white solid is obtained with a yield of 32%. Melting point: 240–245° C.

NMR $^1$H (DMSO d6, 400 MHz, δ): 1.40 (s, 18H, 2 tBu), 2.15 (m, 2H, $\underline{CH_2}$13 CH$_2$—O), 3.20 (dd, 1H, 1/2 CH$_2$ isoxazoline, J=16.65 Hz and J=7.35 Hz), 3.50 (dd, 1H, 1/2 CH$_2$ isoxazoline, J=16.65 Hz and J=10.3 Hz), 4.20 (wide s, 2H, CH$_2$—$\underline{CH_2}$—O), 4.90 (m, 1H, CH isoxazoline), 7.20 (m, 2H, arom. H), 7.40 (m, 6H, arom. H+OH), 8.20 (m, 2H, thiophene), 8.80 (wide s, 1H, NH$^+$), 9.80 (wide s, 1H, NH$^+$), 11.40 (wide s, 1H, NH$^+$).

IR: $\nu_{C=O}$ (amide): 1655 cm$^{-1}$; $\nu_{C=N}$ (amidine): 1618 cm$^{-1}$.

Example 61

1-{[3,5-bis(1,1-dimethylethyl)-4-hydroxyphenyl]amino}-carbonyl}-3-{4-[(imino(2-thienyl)methyl)amino]phenoxy}azetidine hydrochloride (61)

61.1 1-(diphenylmethyl)-3-(4-nitrophenoxy)azetidine 0.5 g (2 mmol) of 1-(diphenylmethyl)-3-hydroxyazetidine is added under an argon atmosphere to a suspension of 0.06 g (2.3 mmol) of NaH in 20 ml of dry THF. After agitation for one hour at 23° C., a solution of 0.29 g (2.1 mmol) of 4-fluoronitrobenzene in 5 ml of dry THF is added dropwise to the reaction mixture. Agitation is maintained for another 2 hours at 23° C. and the whole is finally poured into 25 ml of water. The product is extracted twice with 25 ml of ethyl acetate, the organic phase is then washed twice with 25 ml of salt water, dried over magnesium sulphate, filtered and concentrated under vacuum. The product is purified on a silica column (eluant: 12% of ethyl acetate in heptane). The pure fractions are evaporated in order to produce a colourless oil with a yield of 40%.

NMR $^1$H (CDCl$_3$, 400 MHz, d): 3.20 (m, 2H, azetidine), 4.50 (s, 1H, CH—(Ph)$_2$), 4.80 (m, 2H, azetidine), 4.90 (m, 1H, CH—O), 6.80 (m, 2H, arom. H), 7.20–7.50 (m, 10H, arom. H), 8.20 (m, 2H, arom. H).

61.2 1-(diphenylmethyl)-3-(4-aminophenoxy)azetidine

The experimental protocol used is the same as that described for intermediate 49.5, intermediate 61.1 replacing intermediate 49.4. A colourless oil is obtained with a yield of 75%.

NMR $^1$H (CDCl$_3$, 400 MHz, 8): 3.10 (m, 2H, azetidine), 3.40 (wide s, 2H, NH$_2$), 4.40 (s, 1H, CH—(Ph)$_2$), 4.70 (m, 2H, azetidine), 4.75 (m, 1H, CH—O), 6.60 (s, 4H, arom. H), 7.10–7.40 (m, 10H, arom. H).

61.3 1-(diphenylmethyl)-3-{4-[(1,1-dimethylethoxy)carbonyl]aminophenoxy}azetidine Protection of the amine is carried out in a standard fashion with BocOBoc in the presence of triethylamine in dichloromethane. A white solid is obtained with a yield of 77%. Melting point: 149–151° C.

NMR $^1$H (DMSO d6, 400 MHz, δ): 1.40 (s, 9H, tBu), 2.90 (wide s, 2H, azetidine), 3.60 (wide s, 2H, azetidine), 4.50 (s, 1H, CH—(Ph)$_2$), 4.70 (m, 1H, CH—O), 6.70 (m, 2H, arom. H), 7.10–7.60 (m, 12H, arom. H), 9.10 (s, 1H, NH).

61.4 3-{4-[(1,1-dimethylethoxy)carbonyl]aminophenoxy}azetidine

The experimental protocol used is the same as that described for intermediate 46.4 except for the hydrogenation catalyst which is replaced by Pd(OH)$_2$. A white solid is obtained with a yield of 78%. Melting point 184–186° C.

NMR $^1$H (DMSO d6, 400 MHz, δ): 1.50 (s, 9H, tBu), 3.50 (m, 2H, azetidine), 3.70 (m, 2H, azetidine), 4.90 (m, 1H, CH—O), 6.70 (m, 2H, arom. H), 7.30 (m, 2H, arom. H), 9.10 (s, 1H, NH).

61.5 1-{[3,5-bis(1,1-dimethylethyl)-4-hydroxyphenyl]amino}carbonyl}-3-{4-[(1,1-dimethylethoxy)carbonyl]aminophenoxy}azetidine A solution of 0.6 g (2.7 mmol) of intermediate 42.2 in 10 ml of dichloromethane is added dropwise, over one hour, to a solution of 0.27 g (0.9 mmol) of triphosgene in 6 ml of dichloromethane. After agitation for 5 minutes at 23° C., a solution of 0.72 g (2.7 mmol) of intermediate 61.4 and 0.52 ml (3 mmol) of diisopropylethylamine in 6 ml of dichloromethane is added in one go. The reaction mixture is agitated for 2 hours at 23° C. and finally evaporated to dryness under vacuum. The residue is diluted in 50 ml of ethyl acetate and this organic solution is washed twice with 25 ml of water followed by 25 ml of salt water. After drying over magnesium sulphate and filtration, the organic solution is concentrated under vacuum. The residue is purified on a silica column (eluant:heptane/ethyl acetate:7/3). A white solid is obtained with a yield of 61%. Melting point: 224–226° C.

NMR ¹H (DMSO d6, 400 MHz, δ): 1.35 (s, 18H, 2 tBu), 1.45 (s, 9H, tBu), 3.80 (m, 2H, azetidine), 4.30 (m, 2H, azetidine), 4.90 (m, 1H, CH—O), 6.60 (s, 1H, OH), 6.70 (m, 2H, arom. H), 7.20 (s, 2H, arom. H), 7.35 (m, 2H, arom. H), 8.20 (s, 1H, NH urea), 9.10 (s, 1H, NH).

61.6 1-{[3,5-bis(1,1-dimethylethyl)-4-hydroxyphenyl]amino}carbonyl}-3-(4-aminophenoxy)azetidine The experimental protocol used is the same as that described for intermediate 58.3, intermediate 61.5 replacing intermediate 58.2. A white solid is obtained with a yield of 93%. Melting point: 225–227° C.

NMR ¹H (DMSO d6, 400 MHz, δ): 1.30 (s, 18H, 2 tBu), 3.80 (m, 2H, azetidine), 4.30 (m, 2H, azetidine), 4.70 (wide s, 2H, NH$_2$), 4.85 (m, 1H, CH—O), 6.40–6.70 (m, 5H, arom. H+OH), 7.25 (s, 2H, arom. H), 8.20 (s, 1H, NH urea).

61.7 1-{[3,5-bis(1,1-dimethylethyl)-4-hydroxyphenyl]amino}carbonyl}-3-{4-[(imino(2-thienyl)methyl)amino]phenoxy}azetidine hydrochloride (61)

The experimental protocol used is the same as that described for intermediate 36.3, intermediate 61.6 replacing intermediate 36.2. A white solid is obtained with a yield of 16%. Melting point: 235–240° C.

NMR ¹H (DMSO d6, 400 MHz, δ): 1.30 (s, 18H, 2 tBu), 3.90 (m, 2H, azetidine), 4.40 (m, 2H, azetidine), 5.10 (m, 1H, CH—O), 6.60 (s, 1H, OH), 6.90–7.50 (m, 7H, arom. H), 8.20 (m, 2H, thiophene), 8.30 (s, 1H, NH urea), 8.80 (s, 1H, NH$^+$), 9.80 (s, 1H, NH$^+$), 11.50 (s, 1H, NH$^+$).

IR: $v_{C=O}$ (urea): 1660 cm$^{-1}$; $v_{C=N}$ (amidine): 1640 cm$^{-1}$.

Example 62

1-(2-hydroxy-5-methoxybenzoyl)-3-{4-[(imino(2-thienyl)methyl)amino]phenoxy}azetidine hydrochloride (62)

62.1 1-(2-hydroxy-5-methoxybenzoyl)-3-{4-[(1,1-dimethylethoxy)carbonyl]aminophenoxy}azetidine Condensation of 2-hydroxy 5-methoxybenzoic acid and of intermediate 61.4 is carried out under the same experimental conditions as those described for intermediate 40.1. A white solid is obtained with a yield of 62%. Melting point: 152–153° C.

NMR ¹H (DMSO d6, 400 MHz, δ): 1.50 (s, 9H, tBu), 3.70 (s, 3H, OCH$_3$), 4.00–4.80 (m, 4H, azetidine), 5.00 (m, 1H, CH—O), 6.70–6.90 (m, 5H, arom. H), 7.30 (m, 2H, arom. H), 9.1 (s, 1H, OH), 10.65 (s, 1H, NH).

62.2 1-(2-hydroxy-5-methoxybenzoyl)-3-aminophenoxy-azetidine

The experimental protocol used is the same as that described for intermediate 58.3, intermediate 62.1 replacing intermediate 58.2. A yellow oil is obtained with a yield of 90%.

NMR ¹H (DMSO d6, 400 MHz, δ): 3.25 (wide s, 2H, NH$_2$), 3.80 (s, 3H, OCH$_3$), 4.20–4.90 (m, 4H, azetidine), 4.95 (m, 1H, CH—O), 6.60–7.00 (m, 7H, arom. H), 11.35 (wide s, 1H, OH).

62.3 1-(2-hydroxy-5-methoxybenzoyl)-3-{4-[(imino(2-thienyl)methyl)amino]phenoxy}azetidine hydrochloride (62)

The experimental protocol used is the same as that described for intermediate 36.3, intermediate 62.2 replacing intermediate 36.2. A white powder is obtained with a yield of 44%. Melting point: 165–166° C.

NMR ¹H (DMSO d6, 400 MHz, δ): 3.70 (s, 3H, OCH$_3$), 4.00–4.80 (m, 4H, azetidine), 5.15 (m, 1H, CH—O), 6.80–7.10 (m, 5H. arom. H), 7.40 (m, 3H, arom. H), 8.20 (m, 2H, thiophene), 8.75 (wide s, 1H, NH$^+$), 9.80 (wide s, 1H, NH$^+$), 10.60 (s, 1H, OH), 11.50 (wide s, 1H, NH$^+$).

IR: $v_{C=O}$ (amide): 1655 cm$^{-1}$; $v_{C=N}$ (amidine): 1612 cm$^{-1}$.

Example 63

1-[(3,4-dihydro-6-hydroxy-2,5,7,8-tetramethyl-2H-[1]-benzopyran-2-yl)carbonyl]-4-[4-[(imino(2-thienyl)methyl)amino]phenoxy}-piperidine hydrochloride (63)

63.1 1,1-dimethylethyl 4-(4-nitrophenoxy)-1-piperidinecarboxylate

A solution of 2.01 g (10 mmol) of N-Boc-4-hydroxypiperidine (prepared in a standard fashion starting from commercial 4-hydroxypiperidine) in 10 ml of dry THF is added dropwise to a solution of 1.23 g (11 mmol) of tBuO$^-$K$^+$ in 10 ml of dry THF in a three necked flask, under an inert atmosphere, cooled by an ice bath. After agitation for 30 minutes at 0° C., a solution of 1.06 ml (10 mmol) of 4-fluoronitrobenzene in 10 ml of dry THF is added dropwise. The reaction mixture is agitated for 5 hours at 23° C. and finally poured into 25 ml of a water+ice mixture. The product is extracted using 50 ml of ethyl acetate. After decantation, the organic phase is washed twice with 25 ml of water and 25 ml of salt water. The organic solution is dried over magnesium sulphate, followed by filtration and concentration of the filtrate under vacuum to produce a residue which is purified on a silica column (eluant:heptane/ethyl acetate:8/2). The pure fractions are collected and evaporated under vacuum. The expected product is obtained in the form of a pale yellow powder with a yield of 47%. Melting point: 97–98° C.

63.2 4-(4-nitrophenoxy)piperidine

The experimental protocol used is the same as that described for intermediate 51.2, intermediate 63.1 replacing intermediate 51.1. A yellow oil is obtained with a yield of 87%.

NMR ¹H (CDCl$_3$, 100 MHz, δ): 1.58 (s, 1H, NH), 1.59–2.19 (m, 4H, CH$_2$—CH$_2$), 2.65–3.30 (m, 4H, CH$_2$—CH$_2$), 4.51 (m, 1H, CH—O), 6.98 (m, 2H, arom. H), 8.21 (m, 2H, arom. H).

63.3 1-[(3,4-dihydro-6-hydroxy-2,5,7,8-tetramethyl-2H-[1]-benzopyran-2-yl)carbonyl]-4-(4-nitrophenyl)piperidine The experimental protocol used is the same as that described for intermediate 51.3, intermediate 63.2 replacing intermediate 51.2. A pale yellow powder is obtained with a crude yield of 83%. The product is sufficiently pure to be used directly in the following stage.

63.4 1-[(3,4-dihydro-6-hydroxy-2,5,7,8-tetramethyl-2H-[1]-benzopyran-2-yl)carbonyl]-4-(4-aminophenyl)piperidine The experimental protocol used is similar to that described for intermediate 46.4, intermediate 63.3 replacing intermediate 46.3. The reaction is carried out in a dichloromethane/ethanol mixture (1/1). A white powder is obtained with a yield of 77%. Melting point: 153–154° C.

NMR $^1$H (CDCl$_3$+D$_2$O, 400 MHz, δ): 1.60–2.18 (m, 18H, CH$_2$+Trolox), 2.52–2.81 (m, 2H, CH$_2$), 3.41–4.28 (m, 5H, 2×CH$_2$+CH—O), 6.63 (m, 2H, arom. 6.74 (m, 2H, arom. H).

63.5 1-[(3,4-dihydro-6-hydroxy-2,5,7,8-tetramethyl-2H-[1]-benzopyran-2-yl)carbonyl]-4-[4-[(imino(2-thienyl)methyl)amino]phenoxy}piperidine hydrochloride (63)

The protocol used is the same as that described for intermediate 34.4, intermediate 63.4 replacing intermediate 34.3. The condensation reaction is carried out in 2-propanol only. After salification, the expected product is obtained in the form of a yellow powder with a yield of 25%. Melting point: decomposition from 170° C.

NMR $^1$H (DMSO d6, 400 MHz, δ): 1.50–2.10 (m, 18H, CH$_2$+Trolox), 2.40–2.65 (m, 2H, CH$_2$), 3.13–4.37 (m, 4H, 2×CH$_2$), 4.64 (m, 1H, CH—O), 7.11 (m, 2H, arom. H), 7.35 (m, 2H, arom. H), 7.57 (s, 1H, arom. H), 8.17 (m, 2H, arom. H), 8.74 (wide s, 1H, NH$^+$), 9.76 (wide s, 1H, NH$^+$), 11.42 (wide s, 1H, NH$^+$).

IR: $v_{C=O}$ (amidine): 1611 cm$^{-1}$.

Example 64

1-[(3,4-dihydro-6-hydroxy-2,5,7,8-tetramethyl-2H-[1]-benzopyran-2-yl)carbonyl]-3-{4-[(imino(2-thienyl)methyl)amino]-phenoxy}azetidine hydrochloride (64)

64.1 1-[(3,4-dihydro-6-hydroxy-2,5,7,8-tetramethyl-2H-[1]-benzopyran-2-yl)carbonyl]-3-{4-[(1,1-dimethylethoxy)carbonyl]aminophenoxy}azetidine The condensation of Trolox and intermediate 51.4 is carried out under the same experimental conditions as those described for intermediate 40.1. A white solid is obtained with a yield of 98%. Melting point: 182–183° C.

NMR $^1$H (CDCl$_3$, 400 MHz, δ): 1.50 (s, 9H, tBu), 1.60–2.60 (m, 16H, Trolox), 3.90–4.90 (m, 5H, azetidine), 6.40 (s, 1H, OH), 6.65 (m, 2H, arom. H), 7.20–7.30 (m, 3H, arom. H+NH).

64.2 1-[(3,4-dihydro-6-hydroxy-2,5,7,8-tetramethyl-2H-[1]-benzopyran-2-yl)carbonyl]-3-aminophenoxy-azetidine The experimental protocol used is the same as that described for intermediate 58.3, intermediate 64.1 replacing intermediate 58.2. A white foam is obtained with a yield of 43%.

NMR $^1$H (CDCl$_3$, 400 MHz, δ): 1.60–2.60 (m, 16H, Trolox), 3.50 (wide s, 2H, NH$_2$), 3.90–4.90 (m, 5H, azetidine), 6.50–6.70 (m, 4H, arom. H).

64.3 1-[(3,4-dihydro-6-hydroxy-2,5,7,8-tetramethyl-2H-[1]-benzopyran-2-yl)carbonyl]-3-{4-[(imino(2-thienyl)methyl)amino]phenoxy}azetidine hydrochloride (64)

The experimental protocol used is the same as that described for intermediate 36.3, intermediate 64.2 replacing intermediate 36.2. A white powder is obtained with a yield of 56%. Melting point: 190–195° C.

NMR $^1$H (DMSO d6, 400 MHz, δ): 1.60–2.50 (m, 16H, Trolox), 3.60–5.00 (m, 5H, azetidine), 6.90 (m, 2H, arom. H), 7.30 (m, 3H, arom. H), 8.15 (m, 2H, thiophene), 8.80 (wide s, 1H, NH$^+$), 9.80 (wide s, 1H, NH$^+$), 11.50 (wide s, 1H, NH$^+$).

IR: $v_{C=O}$ (amide): 1647 cm$^{-1}$; $v_{C=N}$ (amidine): 1611 cm$^{-1}$.

Pharmacological Study of the Products of the Invention

Study of the Effects on Neuronal Constitutive NO Synthase of a Rat's Cerebellum

The inhibitory activity of the products of the invention is determined by measuring their effects on the conversion by the NO synthase of the [$^3$H]L-arginine in [$^3$H]L-citrulline according to the modified method of Bredt and Snyder (*Proc. Natl. Acad. Sci. USA,* (1990) 87: 682–685). The cerebellums of Sprague-Dawley rats (300 g—Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 μl of incubation buffer containing 100 mM of HEPES (pH 7.4), 2 mM of EDTA, 2.5 mM of CaCl$_2$, 2 mM of dithiotreitol, 2 mM of reduced NADPH and 10 μg/ml of calmodulin are distributed. 25 μl of a solution containing 100 nM of [$^3$H]L-arginine (Specific activity: 56.4 Ci/mmole, Amersham) and 40 μM of non-radioactive L-arginine is added. The reaction is initiated by adding 50 μl of homogenate, the final volume being 200 μl (the missing 25 μl are either water or the tested product). After 15 min, the reaction is stopped with 2 ml of stopping buffer (20 mM of HEPES, pH 5.5, 2 mM of EDTA). After placing the samples on a 1 ml column of DOWEX resin, the radioactivity is quantified by a liquid scintillation spectrometer. The compounds of examples 6, 7, 13, 14, 33 and 38 to 40 described above show an IC$_{50}$ lower than 3.5 μM. Compound of Example 35 shows an IC$_{50}$ lower than 5 μM.

Study of the Effects on Lipidic Peroxidation of the Cerebral Cortex of a Rat

The inhibitory activity of the products of the invention is determined by measuring their effects on the degree of lipidic peroxidation, determined by the concentration of malondialdehyde (MDA). The MDA produced by peroxidation of unsaturated fatty acids is a good indication of lipidic peroxidation (H Esterbauer and K H Cheeseman, *Meth. Enzymol.* (1990) 186: 407–421). Male Sprague Dawley rats of 200 to 250 g (Charles River) were sacrificed by decapitation. The cerebral cortex is removed, then homogenized using a Thomas potter in a 20 mM Tris-HCl buffer, pH=7.4. The homogenate was centrifuged twice at 50000 g for 10 minutes at 4° C. The pellet is maintained at −80° C. On the day of the experiment, the pellet is replaced in suspension at a concentration of 1 g/15 ml and centrifuged at 515 g for 10 minutes at 4° C. The supernatant is used immediately to determine the lipidic peroxidation. The homogenate of rat's cerebral cortex (500 μl) is incubated at 37° C. for 15 minutes in the presence of the compounds to be tested or of solvent (10 μl). The lipidic peroxidation reaction is initiated by adding 50 μl of FeCl$_2$ at 1 mM, EDTA at 1 mM and ascorbic acid at 4 mM. After 30 minutes of incubation at 37° C., the reaction is stopped by adding 50 μl of a solution of hydroxylated di tertio butyl toluene (BHT, 0.2%). The MDA is quantified using a calorimetric test, by reacting a chromogenic reagent (R), N-methyl-2-phenylindol (650 μl) with 200 μl of the homogenate for 1 hour at 45° C. The condensation of an MDA molecule with two molecules of reagent R produce a stable chromophore the maximum absorbence wavelength of which is equal to 586 nm. (Caldwell et al. *European J. Pharmacol.* (1995)

285, 203–206). The compounds of Examples 5, 8 to 10, 12 to 14, 16 to 21, 26, 27, 35 and 43 to 47 described above all show an $IC_{50}$ lower than 30 μM.

What is claimed is:

1. A compound of the formula

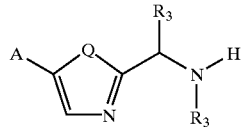

(XXV)$_H$ wherein Q is oxygen or sulfur, A is selected from the group consisting of

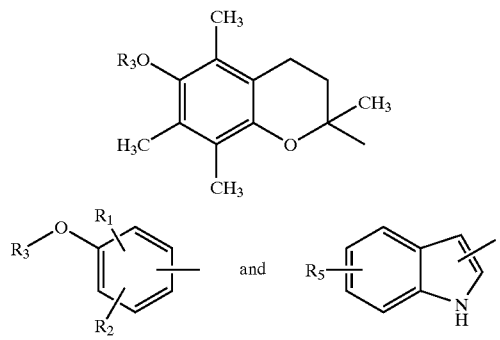

and $R_1$ and $R_2$ are individually selected from the group consisting of hydrogen, halogen, —OH and alkyl and alkoxy of 1 to 6 carbon atoms, $R_3$ is selected from the groups consisting of hydrogen, alkyl of 1 to 6 carbon atoms and —$COR_4$, $R_4$ is alkyl of 1 to 6 carbon atoms and $R_5$ is selected from the group consisting of hydrogen, —OH and alkyl and alkoxy of 1 to 6 carbon atoms.

2. A compound of claim 1 having the formula

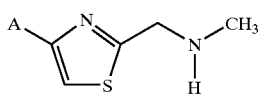

(XXV)$_H$

3. A compound of claim 1 wherein Q is sulfur, $R_3$ are hydrogen and A is

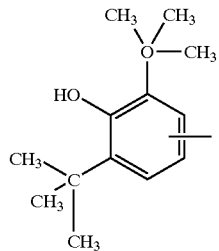

4. A compound of claim 1 which is 4-[3,5-bis(1,1-dimethyl-ethyl)-4-hydroxy-phenyl]-N-methyl-2-thiazolemethanamine.

5. A compound of claim 1 wherein Q is sulfur, $R_3$ are hydrogen and A is

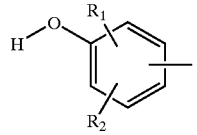

6. A compound of the formula

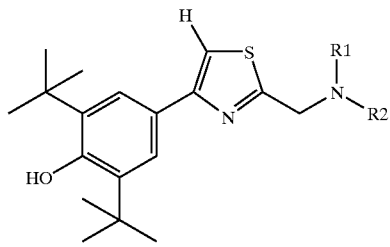

wherein $R_1$ and $R_2$ are individually hydrogen or alkyl of 1 to 6 carbon atoms.

7. A compound of claim 6 wherein $R_1$ is methyl.

* * * * *